US010111967B2

(12) United States Patent
Fotin-Mleczek et al.

(10) Patent No.: US 10,111,967 B2
(45) Date of Patent: Oct. 30, 2018

(54) COMPLEXES OF RNA AND CATIONIC PEPTIDES FOR TRANSFECTION AND FOR IMMUNOSTIMULATION

(71) Applicant: CureVac AG, Tübingen (DE)

(72) Inventors: Mariola Fotin-Mleczek, Sindelfingen (DE); Patrick Baumhof, Dusslingen (DE)

(73) Assignee: CureVac AG, Tübingen (DE)

( * ) Notice: Subject to any disclaimer, the term of this patent is extended or adjusted under 35 U.S.C. 154(b) by 334 days.

(21) Appl. No.: 13/904,868

(22) Filed: May 29, 2013

(65) Prior Publication Data

US 2014/0037660 A1 Feb. 6, 2014

Related U.S. Application Data

(63) Continuation of application No. 12/676,015, filed as application No. PCT/EP2008/007244 on Sep. 4, 2008, now abandoned.

(30) Foreign Application Priority Data

Sep. 4, 2007 (WO) .................. PCT/EP2007/007702

(51) Int. Cl.
| | | |
|---|---|---|
| *A61K 48/00* | (2006.01) | |
| *A61K 38/00* | (2006.01) | |
| *C07K 19/00* | (2006.01) | |
| *C12N 15/87* | (2006.01) | |
| *A61K 47/48* | (2006.01) | |
| *A61K 38/45* | (2006.01) | |
| *C12N 9/02* | (2006.01) | |
| *A61K 39/00* | (2006.01) | |

(52) U.S. Cl.
CPC .......... *A61K 48/005* (2013.01); *A61K 38/45* (2013.01); *A61K 39/00* (2013.01); *A61K 47/48323* (2013.01); *A61K 48/0033* (2013.01); *A61K 48/0041* (2013.01); *A61K 48/0066* (2013.01); *A61K 48/0075* (2013.01); *C07K 19/00* (2013.01); *C12N 9/0069* (2013.01); *C12N 15/87* (2013.01); *C12Y 113/12007* (2013.01); *C12Y 204/01007* (2013.01); *A61K 2039/53* (2013.01)

(58) Field of Classification Search
CPC .............. A61K 48/005; A61K 48/0041; A61K 47/48323; A61K 38/45; A61K 48/0033; A61K 48/0075; A61K 48/0066; A61K 39/00; A61K 2039/53; C12N 15/87; C12N 9/0069; C07K 19/00; C12Y 204/01007; C12Y 113/12007
See application file for complete search history.

(56) References Cited

U.S. PATENT DOCUMENTS

| | | | |
|---|---|---|---|
| 3,906,092 A | 9/1975 | Hilleman et al. | |
| 4,373,071 A | 2/1983 | Itakura | |
| 4,401,796 A | 8/1983 | Itakura | |
| 4,415,732 A | 11/1983 | Caruthers et al. | |
| 4,578,399 A | 3/1986 | Schorlemmer et al. | |
| 5,516,652 A | 5/1996 | Abramovitz et al. | |
| 5,646,120 A * | 7/1997 | Sumner-Smith et al. | ..... 514/3.8 |
| 5,663,153 A | 9/1997 | Hutcherson et al. | |
| 5,663,163 A | 9/1997 | Takaya et al. | |
| 5,844,075 A | 12/1998 | Kawakami et al. | |
| 5,965,720 A | 10/1999 | Gryaznov et al. | |
| 6,096,307 A | 8/2000 | Braswell et al. | |
| 6,218,371 B1 | 4/2001 | Krieg et al. | |
| 6,239,116 B1 | 5/2001 | Krieg et al. | |
| 6,322,967 B1 | 11/2001 | Parkin | |
| 6,387,700 B1 | 5/2002 | Rice et al. | |
| 6,406,705 B1 | 6/2002 | Davis et al. | |
| 6,498,148 B1 | 12/2002 | Raz | |
| 6,514,948 B1 | 2/2003 | Raz et al. | |
| 6,552,006 B2 | 4/2003 | Raz et al. | |
| 6,589,940 B1 | 7/2003 | Raz et al. | |
| 6,610,661 B1 | 8/2003 | Carson et al. | |
| 6,689,757 B1 | 2/2004 | Jacob et al. | |
| 6,716,434 B1 | 4/2004 | Ansley et al. | |
| 7,001,890 B1 | 2/2006 | Wagner et al. | |
| 7,208,478 B2 | 4/2007 | Carson et al. | |
| 7,407,944 B2 | 8/2008 | Agrawal et al. | |
| 7,470,674 B2 | 12/2008 | Agrawal et al. | |
| 7,517,862 B2 | 4/2009 | Agrawal et al. | |
| 8,703,906 B2 | 4/2014 | Baumhof et al. | |

(Continued)

FOREIGN PATENT DOCUMENTS

| | | |
|---|---|---|
| AU | 776268 | 12/2000 |
| DE | 10148886 | 4/2003 |

(Continued)

OTHER PUBLICATIONS

Andreu et al., "Formation of disulfide bonds in synethetic peptides and proteins," Chapter 7, *Methods in Molecular Biology*, vol. 35, Peptide Synthesis Protocols, Pennington and Dunn, 1994.

(Continued)

*Primary Examiner* — Julie Ha
*Assistant Examiner* — Li N Komatsu
(74) *Attorney, Agent, or Firm* — Parker Highlander PLLC

(57) ABSTRACT

The present invention relates to a complexed RNA, comprising at least one RNA complexed with one or more oligopeptides, wherein the oligopeptide, which has the function of cell-penetrating peptide (CPP), has a length of 8 to 15 amino acids and has the empirical formula $(Arg)_l$; $(Lys)_m$; $(His)_n$; $(Orn)_o$; $(Xaa)_x$ with the majority of residues being selected from Arg, Lys, His, Orn. The invention further relates to a method for transfecting a cell or an organism, thereby applying the inventive complexed RNA. Additionally, pharmaceutical compositions and kits comprising the inventive complexed RNA, as well as the use of the inventive complexed RNA for transfecting a cell, tissue or an organism and/or for modulating, preferably inducing or enhancing, an immune response are disclosed herein.

Figure 5:
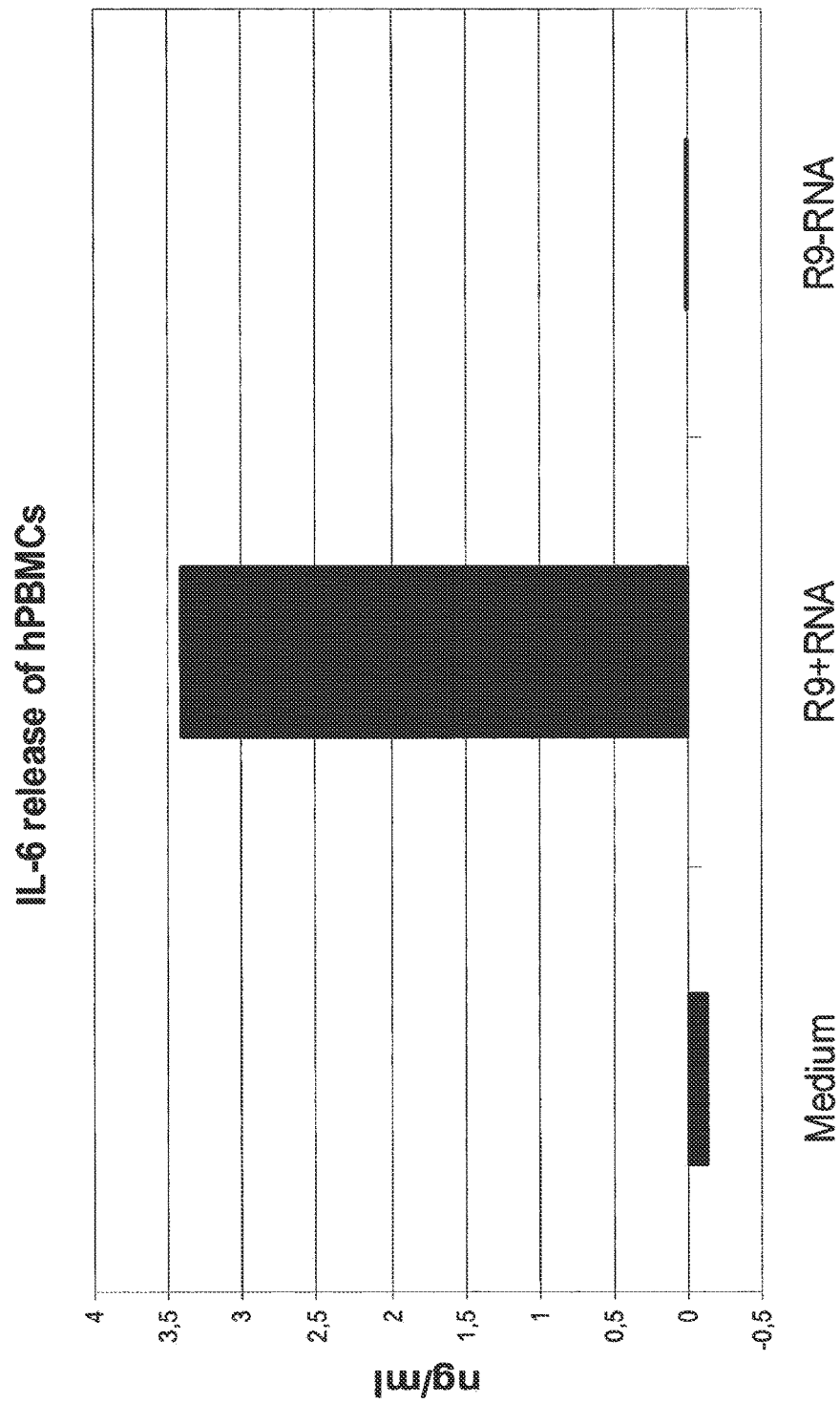

25 Claims, 22 Drawing Sheets
Specification includes a Sequence Listing.

(56) References Cited

U.S. PATENT DOCUMENTS

| | | | |
|---|---|---|---|
| 2003/0083272 A1 | 5/2003 | Wiederholt et al. | |
| 2003/0104622 A1* | 6/2003 | Robbins et al. | 435/455 |
| 2003/0133942 A1 | 7/2003 | Segal | |
| 2003/0225016 A1 | 12/2003 | Fearon et al. | |
| 2004/0006010 A1 | 1/2004 | Carson et al. | |
| 2004/0006034 A1 | 1/2004 | Raz et al. | |
| 2004/0019007 A1 | 1/2004 | Monahan et al. | |
| 2004/0047869 A1 | 3/2004 | Garcon et al. | |
| 2004/0052763 A1 | 3/2004 | Mond et al. | |
| 2005/0032730 A1 | 2/2005 | Von Der Mulbe et al. | |
| 2005/0037494 A1 | 2/2005 | Hecker et al. | |
| 2005/0059624 A1 | 3/2005 | Hoerr et al. | |
| 2005/0130918 A1 | 6/2005 | Agrawal et al. | |
| 2005/0250723 A1 | 11/2005 | Hoerr et al. | |
| 2006/0018841 A1 | 1/2006 | Arbetman et al. | |
| 2006/0172966 A1 | 8/2006 | Lipford et al. | |
| 2006/0188490 A1 | 8/2006 | Hoerr et al. | |
| 2006/0251623 A1 | 11/2006 | Bachmann et al. | |
| 2007/0142315 A1* | 6/2007 | Forsbach et al. | 514/44 |
| 2007/0280929 A1 | 12/2007 | Hoerr et al. | |
| 2008/0025944 A1 | 1/2008 | Hoerr et al. | |
| 2008/0171711 A1 | 7/2008 | Hoerr et al. | |
| 2008/0248067 A1 | 10/2008 | Frazer et al. | |
| 2008/0267873 A1 | 10/2008 | Hoerr et al. | |
| 2008/0279891 A1* | 11/2008 | Johnston et al. | 424/205.1 |
| 2009/0169529 A1* | 7/2009 | Hartmann et al. | 424/93.21 |
| 2009/0286280 A1 | 11/2009 | Roubos et al. | |
| 2009/0324584 A1 | 12/2009 | Hoerr et al. | |
| 2010/0048883 A1 | 2/2010 | Ketterer et al. | |
| 2010/0189729 A1 | 7/2010 | Hoerr et al. | |
| 2010/0203076 A1 | 8/2010 | Fotin-Mleczek et al. | |
| 2010/0291156 A1 | 11/2010 | Banner et al. | |
| 2010/0305196 A1 | 12/2010 | Probst et al. | |
| 2011/0053829 A1 | 3/2011 | Baumhof | |
| 2011/0250225 A1 | 10/2011 | Fotin-Mleczek et al. | |
| 2011/0311472 A1 | 12/2011 | Hoerr et al. | |
| 2012/0021043 A1 | 1/2012 | Kramps et al. | |
| 2012/0258046 A1 | 10/2012 | Mutzke | |
| 2013/0142818 A1 | 6/2013 | Baumhof et al. | |

FOREIGN PATENT DOCUMENTS

| | | |
|---|---|---|
| DE | 69819150 | 7/2004 |
| EP | 0347501 | 12/1989 |
| EP | 0772619 | 5/1997 |
| EP | 0839912 | 5/1998 |
| EP | 1063232 | 3/2001 |
| EP | 1083232 | 3/2001 |
| EP | 1167379 | 1/2002 |
| EP | 1374894 | 1/2004 |
| EP | 1393745 | 3/2004 |
| EP | 1564291 | 8/2005 |
| JP | 2005-521749 | 7/2005 |
| JP | 2008-542500 | 11/2008 |
| KR | 10-1003622 | 9/2003 |
| KR | 10-1051785 | 1/2005 |
| KR | 10-1032853 | 4/2005 |
| WO | WO 1991/005560 | 5/1991 |
| WO | WO 1994/017093 | 8/1994 |
| WO | WO 1994/017792 | 8/1994 |
| WO | WO 98/019710 | 5/1998 |
| WO | WO 98/047913 | 10/1998 |
| WO | WO 1999/053961 | 10/1999 |
| WO | WO 2000/075304 | 12/2000 |
| WO | WO 2001/004135 | 1/2001 |
| WO | WO 2001/054720 | 8/2001 |
| WO | WO 2001/075164 | 10/2001 |
| WO | WO 2001/093902 | 12/2001 |
| WO | WO 2001/097843 | 12/2001 |
| WO | WO 2002/000594 | 1/2002 |
| WO | WO 2002/000694 | 1/2002 |
| WO | WO 2002/078614 | 10/2002 |
| WO | WO 2002/098443 | 12/2002 |
| WO | WO 2003-000227 | 1/2003 |
| WO | WO 2003/028656 | 4/2003 |
| WO | WO 03/059381 | 7/2003 |
| WO | WO 2003/057822 | 7/2003 |
| WO | WO 03/068942 | 8/2003 |
| WO | WO 2003/066649 | 8/2003 |
| WO | WO 2003/086280 | 10/2003 |
| WO | WO 2004/004743 | 1/2004 |
| WO | WO 2004/058159 | 7/2004 |
| WO | WO 2004/064782 | 8/2004 |
| WO | WO 2004/092329 | 10/2004 |
| WO | WO 2005/001022 | 1/2005 |
| WO | WO 2005/030259 | 4/2005 |
| WO | WO 2005/062947 | 7/2005 |
| WO | WO 2005/097993 | 10/2005 |
| WO | WO 2006/029223 | 3/2006 |
| WO | WO 06/046978 | 5/2006 |
| WO | WO 2006/080946 | 8/2006 |
| WO | WO 2006/116458 | 11/2006 |
| WO | WO 2007/008300 | 1/2007 |
| WO | WO 07/031319 | 3/2007 |
| WO | WO 2007/031322 | 3/2007 |
| WO | WO 2007/042554 | 4/2007 |
| WO | WO 2007/051303 | 5/2007 |
| WO | WO 2007/062107 | 5/2007 |
| WO | WO 07/069068 | 6/2007 |
| WO | WO 2007/124755 | 11/2007 |
| WO | WO 08/014979 | 2/2008 |
| WO | WO 08/022046 | 2/2008 |
| WO | WO 2008/052770 | 5/2008 |
| WO | WO 09/030254 | 3/2009 |
| WO | WO 2009/030481 | 3/2009 |
| WO | WO 2009/053700 | 4/2009 |
| WO | WO 2009/086640 | 7/2009 |
| WO | WO 2010/037408 | 4/2010 |
| WO | WO 2010/037539 | 4/2010 |
| WO | WO 11/026641 | 3/2011 |
| WO | WO 2012/013326 | 2/2012 |
| WO | WO 2012-113413 | 8/2012 |
| WO | WO 2013/113326 | 8/2013 |
| WO | WO 2013/113501 | 8/2013 |
| WO | WO 2013/113502 | 8/2013 |
| WO | WO 2013/174409 | 11/2013 |
| WO | WO 2016/077125 | 5/2016 |

OTHER PUBLICATIONS

Devi et al.,"siRNA-based approaches in cancer therapy," *Cancer Gene Therapy*, 13:819-829, 2006.

Hamm et al., "Immunostimulatory RNA is a potent inducer of antigen-specific cytotoxic and humoral immune response in vivo," *International Immunology*, 19(3):297-304, 2007.

Hwang et al.,"A brain-targeted rabies virus glycoprotein-disulfide linked PEI nanocarrier for delivery of neurogenic microRNA," *Biomaterials*, 32:4968-4975, 2011.

Wei et al., "Hybridization properties of oligodeoxynucleotide pairs bridged by polyarginine peptides," *Nucl. Acids Res.*, 24:655-661, 1996.

Weide et al., "Direct injection of protamine-protected mRNA: results of a phase 1/2 vaccination trial in metastatic melanoma patients," *J Immunother.*, 32(5):498-507, 2009.

Zhao et al.,"N/P ratio significantly influences the transfection efficiency and cytotoxicity of a polyethylenimine/chitosan/DNA complex," *Biol. Pharin. Bull.*, 32(4):706-710, 2009.

Bettinger et al., "Peptide-mediated RNA delivery: a novel approach for enhanced transfection of primary and post-mitotic cells", *Nucleic Acids Research*, 29(18):3882-3891, 2001.

Bolhassani et al., "Improvement of different vaccine delivery systems for cancer therapy", *Molecular Cancer*, 10(1):3, 2011.

Bot et al., "Enhanced protection against influenza virus of mice immunized as newborns with a mixture of plasmids expressing hemagglutinin and nucleoprotein", *Vaccine*, 16(17):1675-1682, 1998.

Bot et al., "Genetic immunization of neonates", *Microbes and Infection*, 4(4):511-520, 2002.

Bot et al., "Induction of humoral and cellular immunity against influenza virus by immunization of newborn mice with a plasmid bearing a hemagglutinin gene", *International Immunology*, 9(11):1641-1650, 1997.

(56) References Cited

OTHER PUBLICATIONS

Burke et al., "Extracellular barriers to in vivo PEI and PEGylated PEI polyplex-mediated gene delivery to the liver", *Bioconjug Chem.*, 19(3):693-704, 2008.
Carralot et al., "Polarization of immunity induced by direct injection of naked sequence-stabilized mRNA vaccines", *CMLS Cellular and Molecular Life Sciences*, 61(18):2418-2424, 2004.
Deshayes et al., "Cell-penetrating peptides: tools for intracellular delivery of therapeutics", *Cellular and Molecular Life Sciences*, 62(16):1839-1849, 2005.
Fajac et al., "Histidylated polylysine as a synthetic vector for gene transfer into immortalized cystic fibrosis airway surface and airway gland serous cells", *J Gene Med.*, 2(5):368-378, 2000.
Foerg et al., "On the biomedical promise of cell penetrating peptides: limits versus prospecis", *J Pharm Sci.*, 97(1):144-162, 2008.
Fotin-Mleczek et al., "Messenger RNA-based vaccines with dual activity induce balanced TLR-7 dependent adaptive immune responses and provide antitumor activity", *Journal of Immunotherapy*, 34(1):1-16, 2011.
Fujita et al., "Calcium enhanced delivery of tetraarginine-PEG-lipid-coated DNA/protamine complexes", *International Journal of Pharmaceutics*, 368(1-2):186-192, 2009.
Gao et al., "Nonviral gene delivery: what we know and what is next", *AAPS J.*, 9(1):E92-E104, 2007.
Garinot et al., "PEGylated PLGA-based nanoparticles targeting M cells for oral vaccination", *Journal of Controlled Release*, 120(3):195-204, 2007.
Giel-Pietraszuk et al., "Interaction of HIV Tat model peptides with tRNA and 5S rRNA", *Database Biosis*, Database Accession No. Prev199800116011. (Abstract—1 page).
Gravekamp et al., "Cancer vaccines in old age", *Experimental Gerontology*, 42(5):441-450, 2007.
Hamidi et al., "Pharmacokinetic consequences of pegylation", *Drug Deliv.*, 13(6):399-409, 2006.
Heil et al., "Species-specific recognition of single-stranded RNA via toll-like receptor 7 and 8", *Science*, 303:1526-1529, 2004.
Kovarik et al., "Optimization of vaccine responses in early life: the role of delivery systems and immunomodulators", *Immunology and Cell Biology*, 76(3):222-236, 1998.
Kwok et al., "Formulation of highly soluble poly(ethylene glycol)-peptide DNA condensates", *J Pharm Sci.*, 88(10):996-1003, 1999.
Lochmann et al., "Drug delivery of oligonucleotides by peptides", *European Journal of Pharmaceutics and Biopharmaceutics*, 58(2):237-251, 2004.
Martin et al., "Peptide-guided gene delivery", *AAPS J.*, 9(1):E18-E29, 2007.
Nakamura et al., "Octaarginine-modified multifunctional envelope-type nano device for siRNA", *Journal of Controlled Release*, 119(3):360-367, 2007.
Neu et al., "Recent advances in rational gene transfer vector design based on poly(ethylene imine) and its derivatives", *J Gene Med.*, 7(8):992-1009, 2005.
Oupicky et al., "Importance of lateral and steric stabilization of polyelectrolyte gene delivery vectors for extended systemic circulation", *Mol Ther.*, 5(4):463-472, 2002.
Oupicky et al., "Laterally stabilized complexes of DNA with linear reducible polycations: strategy for triggered intracellular activation of DNA delivery vectors", *J Am Chem Soc.*, 124(1):8-9, 2002.
Parker et al., "Enhanced gene transfer activity of peptide-targeted gene-delivery vectors", *J Drug Target.*, 13(1):39-51, 2005.
Pichon et al., "Poly[Lys-(AEDTP)] a cationic polymer that allows dissociation of pDNA/cationic polymer complexes in a reductive medium and enhances polyfection", *Bioconjug Chem.*, 13(1):76-82, 2002.
Pomroy et al., "Solubilization of hydrophobic peptides by reversible cysteine PEGylation", *Biochem Biophys Res Commun.*, 245(2):618-21, 1998.
Radu et al., "Plasmid expressing the influenza HA gene protects old mice from lethal challenge with influenza virus", *Viral Immunology*, 12(3):217-226, 1999.
Read et al., "A versatile reducible polycation-based system for efficient delivery of a broad range of nucleic acids", *Nucleic Acids Res.*, 33(9):e86, 2005.
Read et al., "RNA-based therapeutic strategies for cancer", *Expert Opinion on Therapeutic Patents*, 13(5):627-638, 2003.
Read et al., "Vectors based on reducible polycations facilitate intracellular release of nucleic acids", *The Journal of Gene Medicine*, 5(3):232-245, 2003.
Sakae et al., "Highly efficient in vivo gene transfection by plasmid/PEI complexes coated by anionic PEG derivatives bearing carboxyl groups and RGD peptide", *Biomedicine and Pharmacotherapy*, 62(7):448-453, 2008.
Scheel et al., "Therapeutic anti-tumor immunity triggered by injections of immunostimulating single-stranded RNA", *Eur J Immunol.*, 36(10):2807-16, 2006.
Scheel et al., "Toll-like receptor-dependent activation of several human blood cell types by protamine-condensed mRNA", *Eur J Immunol.*, 35(5):1557-1566, 2005.
Takae et al., "PEG-detachable polyplex micelles based on disulfide-linked block catiomers as bioresponsive nonviral gene vectors", *J Am Chem Soc.*, 130(18):6001-6009, 2008.
Tönges et al., "Stearylated octaarginine and artificial virus-like particles for transfection of siRNA into primary rat neurons", *Cold Spring Harbor Laboratory Press RNA*, 12(7):1431-1438, 2006.
Unnamalai et al., "Cationic oligopeptide-mediated delivery of dsRNA for post-transcriptional gene silencing in plant cells", *FEBS Letters*, 566(1-3):307-310, 2004.
Vivés et al., "A truncated HIV-1 Tat protein basic domain rapidly translocates through the plasma membrane and accumulates in the cell nucleus", *J Biol Chem.*, 272(25):16010-16017, 1997.
Wang et al., "An intracellular delivery method for siRNA by an arginine-rich peptide", *Journal of Biochemical and Biophysical Methods*, 70(4):579-586, 2007.
Brito et al., "Non-viral eNOS gene delivery and transfection with stents for the treatment of restenosis", *Biomed Eng Online*, 9:56, 2010.
Casciato, "Preface", *Manual of Clinical Oncology*. 6$^{th}$ ed. Philadelphia: Lippincott Williams & Wilkins, 2009. ix. Print, 2 pages.
Danhier et al., "PLGA-based nanoparticles: an overview of biomedical applications", *J Control Release*, 161(2):505-522, 2012.
Mattner et al., "Vaccination with poly-L-arginine as immunostimulant for peptide vaccines: induction of potent and long-lasting T-cell responses against cancer antigens", *Cancer Research*, 62:1477-1480, 2002.
Office Action issued in U.S. Appl. No. 12/676,015, dated Aug. 8, 2012, 9 pages.
Office Action issued in U.S. Appl. No. 12/676,015, dated Nov. 30, 2012, 27 pages.
PCT International Preliminary Report on Patentability issued in International Application No. PCT/EP2008/007244, dated Mar. 9, 2010, 11 pages.
PCT International Search Report issued in International Application No. PCT/EP2008/007244, dated Jan. 5, 2009, 4 pages.
Shiffman et al., "Protein dissociation from DNA in model systems and chromatin", Nucleic Acids Res., 5(9):3409-3426, 1978.
Yoshitomi et al., "Design of core shell-type nanoparticles carrying stable radicals in the core", Biomacromolecules, 10(3):596-601, 2009.
Zhang et al., "Delivery of telomerase reverse transcriptase small interfering RNA in complex with positively charged single-walled carbon nanotubes suppresses tumor growth", *Clin Cancer Res.*, 12(16):4933-4939, 2006.
Zohra et al., "Effective delivery with enhanced translational activity synergistically accelerates mRNA-based transfection", *Biochem Biophys Res Commun.*, 358(1):373-378, 2007.
"Cell-penetrating peptide," *Wikipedia*, located at http://en.wikipedia.org/wiki/Cell-penetrating_peptide, downloaded Dec. 11, 2012, 13 pages.
"DOC/Alum Complex," Violin: Vaccine investigation and online information network, located at http://www.violinet.org/vaxjo/vaxjo_detail.php?c_vaxjo_id=49, downloaded on Aug. 28, 2012, 1 page.
"QS21," Wikipedia, located at http://en.wikipedia.org/wiki/QS21, downloaded on Dec. 11, 2012, 1 page.

(56) References Cited

OTHER PUBLICATIONS

"Ribi vaccine adjuvant," Violin: Vaccine investigation and online information network, located at http://www.violinet.org/vaxjo/vaxjo_detail.php?c_vaxjo_id=21, downloaded on Dec. 17, 2012, 2 pages.
"SPT (Antigen Formulation)," Violin: Vaccine investigation and online information network, located at http://www.violinet.org/vaxjo/vaxjo_detail.php?c_vaxjo_id=72, downloaded on Aug. 21, 2012, 1 page.
"Virus-like particle," Wikipedia, located at http://en.wikipedia.org/wiki/virus-like_particle, downloaded on Sep. 3, 2012, 3 pages.
Adams et al., "Preparation and hybridization properties of oligonucleotides containing 1-alpha-D-arabinofuranosylthymine", *Nucleic Acids Res.*, 19(13):3647-3651, 1991.
Agrawal, "Antisense oligonucleotides: towards clinical trials", *Trends Biotechnol.*, 14(10):376-387, 1996.
Ara et al., "Zymosan enhances the immune response to DNA vaccine for human immunodeficiency virus type-1 through the activation of complement system", *Immunology*, 103(1):98-105, 2001.
Bayard et al., "Antiviral activity in L1210 cells of liposome-encapsulated (2'5')oligo(adenylate)analogues", *Eur J Biochem.*, 151(2):319-326, 1985.
Berzofsky et al., "Progress on new vaccine strategies against chronic viral infections", *J Clin Invest.*, 114(4):450-462, 2004.
Blaxter et al., "The *Brugia malayi* genome project: expressed sequence tags and gene discovery", *Transactions of the Royal Society of Tropical Medicine and Hygiene*, 96(1):1-17, 2002.
Bocchia et al., "Antitumor vaccination: where we stand", *Heamatologica*, 85(11):1172-1206, 2000.
Buteau et al., "Challenges in the development of effective peptide vaccines for cancer", *Mayo Clin Proc.*, 77:339-349, 2002.
Caplus accession No. 190686-49-8; *Brugia malayi* strain TRS Labs conic RRAMCA1537 EST; *Chemical Abstracts Services*; Database Caplus; Jun. 2009, 1 page.
Cooper et al., "CPG 7909 adjuvant improves hepatitis B virus vaccine seroprotection in antiretroviral-treated HIV-infected adults," *AIDS*, 19:1473-1479, 2005.
Dmitriev, "Bactenecin 7 peptide fragment as a tool for intracellular delivery of a phosphorescent oxygen sensor," *FEBS Journal*, 277:4651-4661, 2010.
EBI Database accession No. BP836659; *Arabidopsis thaliana* clone RAFL22-17-C17 EST; Database EMBL; Jan. 2005, 1 page.
EBI Database accession No. CZ193289; PST12107-MICB1 *Mus musculus* genomic clone PST12107-NR; Database EMBL; Feb. 2005, 1 page.
EBI Database accession No. DN868844; NEIBank analysis of Dog lens; Wistow, G., Database EMBL; Apr. 2005, 2 pages.
Eliyahu et al., "Polymers for DNA delivery," *Molecules*, 10:34-64, 2005.
EMBL accession No. AA430815; Brugia malayi strain TRS Labs clone RRAMCA1537 EST; Database EMBL; May 1997, 2 pages.
Feroze-Merzoug et al., "Molecular profiling in prostate cancer", *Cancer and Metastasis Reviews*, 20:165-171, 2001.
Fire et al., "Potent and specific genetic interferences by double-stranded RNA in *Caenorhabditis elegans*", 391:806-811, 1998.
Fox, "Squalene emulsions for parenteral vaccine and drug delivery," *Molecules*, 14:3286-3312, 2009.
Galbraith et al., "Complement activation and hemodynamic changes following intravenous administration of phosphorothioate oligonucleotides in the monkey", *Antisense Research and Development*, 4:201-206, 1994.
GenBank Accession No. JK489756.1, GI; 346421249, publicly available Sep. 2011, 2 pages.
Gerogieva et al., "Comparative study on the changes in photosynthetic activity of the homoiochlorophyllous desiccation-tolerant *Haberlea rhodopensis* and desiccation-sensitive spinach leaves during desiccation and rehydration", *Photosynthesis Research*, 65:191-203, 2005.
Gryaznov, "Oligonucleotide N3'-P5'phosphoramidates as potential therapeutic agents", *Biochimica et Biophysica Acta*, 1489:131-140, 1999.
Hardy et al., "Synergistic effects of gene delivery—co-formulation of small disulfide-linked dendritic polycations with Lipofectamine 2000", *Organic and Biomolecular Chemistry*, 7(4):789-793, 2009.
Hausch et al., "A novel carboxy-functionalized photocleavable dinucleotide analog for the selection to RNA catalysts", *Tetrahedron Letters*, 39(34):6157-6158, 1998.
Heffernan et al.,"Disulfide-crosslinke plyion micelles for delivery of protein therapeutics", *Annals of Biomedical Engineering*, 37(10):1993-2002, 2009.
Heidenreich et al., "Chemically modified RNA: approaches and applications", *The FASEB Journal*, 7(1):90-6, 1993.
Herbert et al., "Lipid modification of GRN163, an N3'-P5' thio-phosphoramidate oligonucleotide enhances the potency telomerase inhibition", *Oncogene*, 24:5262-5268, 2005.
Herbert et al., *The Dictionary of Immunology*, Academic Press: San Diego, 4$^{th}$ ed. 1995. Print, 3 pages.
Heyman, "The immune complex: possible ways of regulating the antibody response", *Immunology Today*, 11(9):310-313, 1990.
Hoerr et al., "In vivo application of RNA leads to induction of specific cytotoxic T lymphocytes and antibodies", *Eur J Immunol.*, 30(1):1-7, 2000.
Huang et al., "Recent development of therapeutics for chronic HCV infection", *Antiviral Res.*, 71:351-362, 2006.
Huget et al., "Adjuvant and suppressor activity of the polycation protamine hydrochloride in the primary immune response of mice", *Z Immunitatsforsch Immunobiol.*, 152(3):190-9, 1976. (English Abstract), 1 page. Abstract only.
Janssens et al., "Role of toll-like receptors in pathogen recognition", *Clinical Microbiology Reviews*, 16(4):637-646, 2003.
Kilk, "Cell-penetrating peptides and bioactive cargoes. Strategies and mechanisms," *Department of Neurochemistry and Neurotoxicology*, Stockholm University, Doctoral dissertation, 2004.
Kim et al., "VeGF siRNA delivery system using arginine-grafted bioreducible poly(disulfide amine)", *Molecular Pharmaceutics*, 6(3):718-726, 2009.
Koziel et al., "Hepatitis C virus (HCV)-specific cytotoxic T lymphocytes recognize epitopes in the core and envelope proteins of HCV", *J Virol.*, 67(12):7522-7532, 1993.
Kwiatkowski et al., "The 9-(4-Octadecyloxyphenylxanthen)-9-yl-Group. A new Acid-labile Hydroxyl Protective Group and Its Application in the Preparative Reverse-phase Chromatographic Separation of Oligoribonucleotides", *Acta Chemica Scandinavica*, 38b:657-671, 1984.
Lo et al., "An endosomolytic Tat peptide produced by incorporation of histidine and cysteine residues as a nonviral vector for DNA transfection", *Biomaterials*, 29(15):2408-2414, 2008.
Mateo et al., "An HLA-A2 polyepitope vaccine for melanoma immunotheraphy", *J Immunol.*, 163:4058-4063, 1999.
Matray and Gryaznov., "Synthesis and properties of RNA analogs-oligoribonucleotide N3'-P5' phosphoramidates", *Nucleic Acids Research*, 27(20):3976-3985, 1999.
McKenzie et al., "A potent new class of reductively activated peptide gene delivery agents", *Journal of Biological Chemistry*, 275(14):9970-9977, 2000.
McKenzie et al., "Low molecular weight disulfide cross-linking peptides as nonviral gene discovery carriers", *Bioconjugate Chemistry*, 11(6):901-909, 2000.
Milich et al., "The hepatitis B virus core and e antigens elicit different Th cell subsets: antigen structure can affect Th cell phenotype", *J Virol.*, 71(3):2192-2201, 1997.
Minks et al., "Structural requirements of double-stranded RNA for the activation of 2',5'-oligo(A)polymerase and protein kinase of interferon-treated HeLa cells", *The Journal of Biological Chemistry*, 254(20):10180-10183, 1979.
Miyata et al., "Block catiomer polyplexes with regulated densities of charge and disulfide cross-linking directed to enhance gene expression", *Journal of the American Chemical Society*, 126(8):2355-2361, 2004.

(56) References Cited

OTHER PUBLICATIONS

Nicholson et al., "Accurate in vitro cleavage by RNase III of phosphorothioate-substituted RNA processing signals in bacteriophage T7 early mRNA", *Nucleic Acids Res.*, 16(4):1577-1591, 1988.

Racanelli et al., "Presentation of HCV antigens to naïve CD8+T cells: why the where, when, what and how are important for virus control and infection outcome", *Clin Immunol.*, 124(1):5-12, 2007.

Ramazeilles et al., "Antisense phosphorothioate oligonucleotides: selective killing of the intracellular parasite *Leishmania amazonensis*", *Proc Natl Acad Sci USA*, 91(17):7859-7863, 1994.

Riedl et al., "Priming Th1 immunity to viral core particles is facilitated by trace amounts of RNA bound to its arginine-rich domain", *J Immunol.*, 168(10):4951-4959, 2002.

Rittner et al., "New basic membrane-destabilizing peptides for plasmid-based gene delivery in Vitro and in Vivo," *Molecular Therapy*, 5(2)104-114, 2002.

Rollier et al., "Control of heterologous hepatitis C virus infection in chimpanzees is associated with the quality of vaccine-induced peripheral t-helper immune response", *J Virol.*, 78(1):187-196, 2004.

Romagne et al., "Current and future drugs targeting one class of innate immunity receptors: the toll-like receptors", *Drug Discov Today*, 12(1-2):80-7, 2007.

Rozenfeld et al., "Stable assemblies of cationic bilayer fragments and CpG oligonucleotide with enhanced immunoadjuvant activity in vivo", *Journal of Controlled Release*, 160(2):367-373, 2011.

Saenz-Badillos et al., "RNA as a tumor vaccine: a review of the literature", *Exp Dermatol.*, 10(3):143-154, 2001.

Scheel et al., "Immunostimulating capacities of stabilized RNA molecules", *Eur J Immunol.*, 24:537-547, 2004.

Scheel et al., "mRNA as immunostimulatory molecule", Krebsimmuntherapie Annual Meeting, Oral Presentation May 9, 2003. (Abstract), 6 pages.

Schirrmacher et al., "Intra-pinna anti-tumor vaccinaton with self-replicating infectious RNA or with DNA encoding a model tumor antigen and a cytokine", *Gene Therapy*, 7(13):1137-1147, 2000.

Shea et al., "Synthesis, hybridization properties and antiviral activity of lipid-oligodeoxynucleotide conjugates", *Nucleic Acids Research*, 18(13):3777-3783, 1990.

Shirai et al., "An epitope in hepatitis C virus core region recognized by cytotoxic T cells in mice and humans", *J Virol.*, 68(5):3334-3342, 1994.

Stephens et al., "Sequence analysis of the major outer membrane protein gene from *Chlamydia trachomatis* serovar L2", *Journal of Bacteriology*, 168(3):1277-1282, 1986.

Sun et al., "Advances in saponin-based adjuvants," *Vaccine*, 27:1787-1796, 2009.

Tan et al., "Strategies for hepatitis C therapeutic intervention: now and next", *Curr Opin in Pharmacology*, 4:465-470, 2004.

Teplova et al., "Crystal structure and improved antisense properties of 2'-O-(2-methoxyethyl)-RNA", *Nature Structural Biology*, 6(6):535-539, 1999.

Tokunaga et al., "Effect of oligopeptides on gene expression: comparison of DNA/peptide and DNA/peptide/liposome complexes", *International Journal of Pharmaceutics*, 269(1):71-80, 2004.

Trinchieri et al., "Cooperation of toll-like receptor signals in innate immune defence", *Nature Reviews Immunology*, 7:179-190, 2007.

Tse et al., "Update on toll-like receptor-directed therapies for human disease", *Ann Rheum Dis.*, 66 Suppl 3:iii77-80, 2007.

Wyman et al., "Design, synthesis, and characterization of a cationic peptide that binds to nucleic acids and permeabilizes bilayers," *Biochemistry*, 36:3008-3017, 1997.

Xiong et al., "pH-responsive multi-PEGylated dual cationic nanoparticles enable charge modulations for safe gene delivery," *Chem Med Chem*, 2:1321-1327, 2007.

Zhou et al., "RNA melanoma vaccine: induction of antitumor immunity by human glycoprotein 100 mRNA immunization", *Human Gene Therapy*, 10:2719-2724, 1999.

Zimmermann et al., "Immunostimulatory DNA as adjuvant: efficacay of phosphodiester CpG oligonucleotides is enhanced by 3' sequence modifications", *Vaccine*, 21(9-10):990-995, 2003. (abstract only), 1 page.

Diebold et al., "Innate antiviral responses by means of TLR7-mediated recognition of single-stranded RNA", *Science*, 1529-1531, 2004.

Holcik et al., "Four highly stable eukaryotic mRNAs assemble 3' untranslated region RNA-protein complexes sharing cis and trans components," *Proc. Natl. Acad. Sci.*, 94:2410-2414, 1997.

Karikó et al., "Suppression of RNA recognition by toll-like receptors: the impact of nucleoside modification and the evolutionary origin of RNA," *Immunity*, 23:165-175, 2005.

Kay et al., "Evidence for gene transfer and expression of factor IX in haemophilia B patients treated with an AAV vector," *Nature Genetics*, 24:257-261, 2000.

Makeyev et al., "The poly(C)-binding proteins: a multiplicity of functions and a search for mechanisms," RNA, 8:265-278, 2002.

Office Action issued in U.S. Appl. No. 15/065,741, dated Jan. 11, 2017.

Office Action issued in U.S. Appl. No. 15/065,741, dated May 18, 2017.

Office Action issued in U.S. Appl. No. 15/065,741, dated Sep. 7, 2017.

Office Action issued in U.S. Appl. No. 15/350,560, dated Feb. 16, 2018.

Office Action issued in U.S. Appl. No. 15/408,320, dated Mar. 9, 2018.

Office Action issued in U.S. Appl. No. 15/850,845, dated Mar. 30, 2018.

Ren et al., "Structural basis of DOTMA for its high intravenous transfection activity in mouse," *Gene Therapy*, 7:764-768, 2000.

\* cited by examiner

|      |            |            |            |            |            |
|-----:|------------|------------|------------|------------|------------|
|    1 | GGGAGAAAGC | UUGGCAUUCC | GGUACUGUUG | GUAAAGCCAC | CAUGGAAGAC |
|   51 | GCCAAAAACA | UAAAGAAAGG | CCCGGCGCCA | UUCUAUCCGC | UGGAAGAUGG |
|  101 | AACCGCUGGA | GAGCAACUGC | AUAAGGCUAU | GAAGAGAUAC | GCCCUGGUUC |
|  151 | CUGGAACAAU | UGCUUUUACA | GAUGCACAUA | UCGAGGUGGA | CAUCACUUAC |
|  201 | GCUGAGUACU | UCGAAAUGUC | CGUUCGGUUG | GCAGAAGCUA | UGAAACGAUA |
|  251 | UGGGCUGAAU | ACAAAUCACA | GAAUCGUCGU | AUGCAGUGAA | AACUCUCUUC |
|  301 | AAUUCUUUAU | GCCGGUGUUG | GGCGCGUUAU | UUAUCGGAGU | UGCAGUUGCG |
|  351 | CCCGCGAACG | ACAUUUAUAA | UGAACGUGAA | UUGCUCAACA | GUAUGGGCAU |
|  401 | UUCGCAGCCU | ACCGUGGUGU | UCGUUCCAA  | AAAGGGGUUG | CAAAAAAUUU |
|  451 | UGAACGUGCA | AAAAAAGCUC | CCAAUCAUCC | AAAAAAUUAU | UAUCAUGGAU |
|  501 | UCUAAAACGG | AUUACCAGGG | AUUUCAGUCG | AUGUACACGU | UCGUCACAUC |
|  551 | UCAUCUACCU | CCCGGUUUUA | AUGAAUACGA | UUUUGUGCCA | GAGUCCUUCG |
|  601 | AUAGGGACAA | GACAAUUGCA | CUGAUCAUGA | ACUCCUCUGG | AUCUACUGGU |
|  651 | CUGCCUAAAG | GUGUCGCUCU | GCCUCAUAGA | ACUGCCUGCG | UGAGAUUCUC |
|  701 | GCAUGCCAGA | GAUCCUAUUU | UUGGCAAUCA | AAUCAUUCCG | GAUACUGCGA |
|  751 | UUUUAAGUGU | UGUUCCAUUC | CAUCACGGUU | UGGAAUGUU  | UACUACACUC |
|  801 | GGAUAUUUGA | UAUGUGGAUU | UCGAGUCGUC | UUAAUGUAUA | GAUUUGAAGA |
|  851 | AGAGCUGUUU | CUGAGGAGCC | UUCAGGAUUA | CAAGAUUCAA | AGUGCGCUGC |
|  901 | UGGUGCCAAC | CCUAUUCUCC | UUCUUCGCCA | AAAGCACUCU | GAUUGACAAA |
|  951 | UACGAUUUAU | CUAAUUUACA | CGAAAUUGCU | UCUGGUGGCG | CUCCCCUCUC |
| 1001 | UAAGGAAGUC | GGGGAAGCGG | UUGCCAAGAG | GUUCCAUCUG | CCAGGUAUCA |
| 1051 | GGCAAGGAUA | UGGGCUCACU | GAGACUACAU | CAGCUAUUCU | GAUUACACCC |
| 1101 | GAGGGGGAUG | AUAAACCGGG | CGCGGUCGGU | AAAGUUGUUC | CAUUUUUUGA |
| 1151 | AGCGAAGGUU | GUGGAUCUGG | AUACCGGGAA | AACGCUGGGC | GUUAAUCAAA |
| 1201 | GAGGCGAACU | GUGUGUGAGA | GGUCCUAUGA | UUAUGUCCGG | UUAUGUAAAC |
| 1251 | AAUCCGGAAG | CGACCAACGC | CUUGAUUGAC | AAGGAUGGAU | GGCUACAUUC |
| 1301 | UGGAGACAUA | GCUUACUGGG | ACGAAGACGA | ACACUUCUUC | AUCGUUGACC |
| 1351 | GCCUGAAGUC | UCUGAUUAAG | UACAAAGGCU | AUCAGGUGGC | UCCCGCUGAA |
| 1401 | UUGGAAUCCA | UCUUGCUCCA | ACACCCCAAC | AUCUUCGACG | CAGGUGUCGC |
| 1451 | AGGUCUUCCC | GACGAUGACG | CCGGUGAACU | UCCCGCCGCC | GUUGUUGUUU |
| 1501 | UGGAGCACGG | AAAGACGAUG | ACGGAAAAAG | AGAUCGUGGA | UUACGUCGCC |
| 1551 | AGUCAAGUAA | CAACCGCGAA | AAAGUUGCGC | GGAGGAGUUG | UGUUUGUGGA |
| 1601 | CGAAGUACCG | AAAGGUCUUA | CCGGAAAACU | CGACGCAAGA | AAAAUCAGAG |
| 1651 | AGAUCCUCAU | AAAGGCCAAG | AAGGGCGGAA | AGAUCGCCGU | GUAAUUCUAG |
| 1701 | UUAUAAGACU | GACUAGCCCG | AUGGGCCUCC | CAACGGGCCC | UCCUCCCCUC |
| 1751 | CUUGCACCGA | GAUUAAUAAA | AAAAAAAAA  | AAAAAAAAAA | AAAAAAAAAA |
| 1801 | AAAAAAAAAA | AAAAAAAAAA | AAAAAAAAAA | AUAUUCCCCC | CCCCCCCCCC |
| 1851 | CCCCCCCCCC | CCCCCUCUAG | ACAAUUGGAA | UU         |            |

Figure 1

```
   1  GGGAGAAAGC  UUGAGGAUGG  AGGACGCCAA  GAACAUCAAG  AAGGGCCCGG
  51  CGCCCUUCUA  CCCGCUGGAG  GACGGGACCG  CCGGCGAGCA  GCUCCACAAG
 101  GCCAUGAAGC  GGUACGCCCU  GGUGCCGGGC  ACGAUCGCCU  UCACCGACGC
 151  CCACAUCGAG  GUCGACAUCA  CCUACGCGGA  GUACUUCGAG  AUGAGCGUGC
 201  GCCUGGCCGA  GGCCAUGAAG  CGGUACGGCC  UGAACACCAA  CCACCGGAUC
 251  GUGGUGUGCU  CGGAGAACAG  CCUGCAGUUC  UUCAUGCCGG  UGCUGGGCGC
 301  CCUCUUCAUC  GGCGUGGCCG  UCGCCCGGC   GAACGACAUC  UACAACGAGC
 351  GGGAGCUGCU  GAACAGCAUG  GGGAUCAGCC  AGCCGACCGU  GGUGUUCGUG
 401  AGCAAGAAGG  GCCUGCAGAA  GAUCCUGAAC  GUGCAGAAGA  AGCUGCCCAU
 451  CAUCCAGAAG  AUCAUCAUCA  UGGACAGCAA  GACCGACUAC  CAGGGCUUCC
 501  AGUCGAUGUA  CACGUUCGUG  ACCAGCCACC  UCCCGCCGGG  CUUCAACGAG
 551  UACGACUUCG  UCCCGGAGAG  CUUCGACCGG  GACAAGACCA  UCGCCCUGAU
 601  CAUGAACAGC  AGCGGCAGCA  CCGGCCUGCC  GAAGGGGGUG  GCCCUGCCGC
 651  ACCGGACCGC  CUGCGUGCGC  UUCUCGCACG  CCCGGGACCC  CAUCUUCGGC
 701  AACCAGAUCA  UCCCGGACAC  CGCCAUCCUG  AGCGUGGUGC  CGUUCCACCA
 751  CGGCUUCGGC  AUGUUCACGA  CCCUGGGCUA  CCUCAUCUGC  GGCUUCCGGG
 801  UGGUCCUGAU  GUACCGGUUC  GAGGAGGAGC  UGUUCCUGCG  GAGCCUGCAG
 851  GACUACAAGA  UCCAGAGCGC  GCUGCUCGUG  CCGACCCUGU  UCAGCUUCUU
 901  CGCCAAGAGC  ACCCUGAUCG  ACAAGUACGA  CCUGUCGAAC  CUGCACGAGA
 951  UCGCCAGCGG  GGGCGCCCCG  CUGAGCAAGG  AGGUGGGCGA  GGCCGUGGCC
1001  AAGCGGUUCC  ACCUCCCGGG  CAUCCGCCAG  GGCUACGGCC  UGACCGAGAC
1051  CACGAGCGCG  AUCCUGAUCA  CCCCCGAGGG  GGACGACAAG  CCGGGCGCCG
1101  UGGGCAAGGU  GGUCCCGUUC  UUCGAGGCCA  AGGUGGUGGA  CCUGGACACC
1151  GGCAAGACCC  UGGGCGUGAA  CCAGCGGGGC  GAGCUGUGCG  UGCGGGGGCC
1201  GAUGAUCAUG  AGCGGCUACG  UGAACAACCC  GGAGGCCACC  AACGCCCUCA
1251  UCGACAAGGA  CGGCUGGCUG  CACAGCGGCG  ACAUCGCCUA  CUGGGACGAG
1301  GACGAGCACU  UCUUCAUCGU  CGACCGGCUG  AAGUCGCUGA  UCAAGUACAA
1351  GGGCUACCAG  GUGGCGCCGG  CCGAGCUGGA  GAGCAUCCUG  CUCCAGCACC
1401  CCAACAUCUU  CGACGCCGGC  GUGGCCGGGC  UGCCGGACGA  CGACGCCGGC
1451  GAGCUGCCGG  CCGCGGUGGU  GGUGCUGGAG  CACGGCAAGA  CCAUGACGGA
1501  GAAGGAGAUC  GUCGACUACG  UGGCCAGCCA  GGUGACCACC  GCCAAGAAGC
1551  UGCGGGGCGG  CGUGGUGUUC  GUGGACGAGG  UCCCGAAGGG  CCUGACCGGG
1601  AAGCUCGACG  CCCGGAAGAU  CCGCGAGAUC  CUGAUCAAGG  CCAAGAAGGG
1651  CGGCAAGAUC  GCCGUGUAAG  ACUAGUUAUA  AGACUGACUA  GCCCGAUGGG
1701  CCUCCCAACG  GGCCCUCCUC  CCUCCUUGC   ACCGAGAUUA  AUAAAAAAAA
1751  AAAAAAAAAA  AAAAAAAAAA  AAAAAAAAAA  AAAAAAAAAA  AAAAAAAAAA
1801  AAAAAAUAUU  CCCCCCCCCC  CCCCCCCCCC  CCCCCCCCCC  UCUAGACAAU
1851  UGGAAUU
```

Figure 2

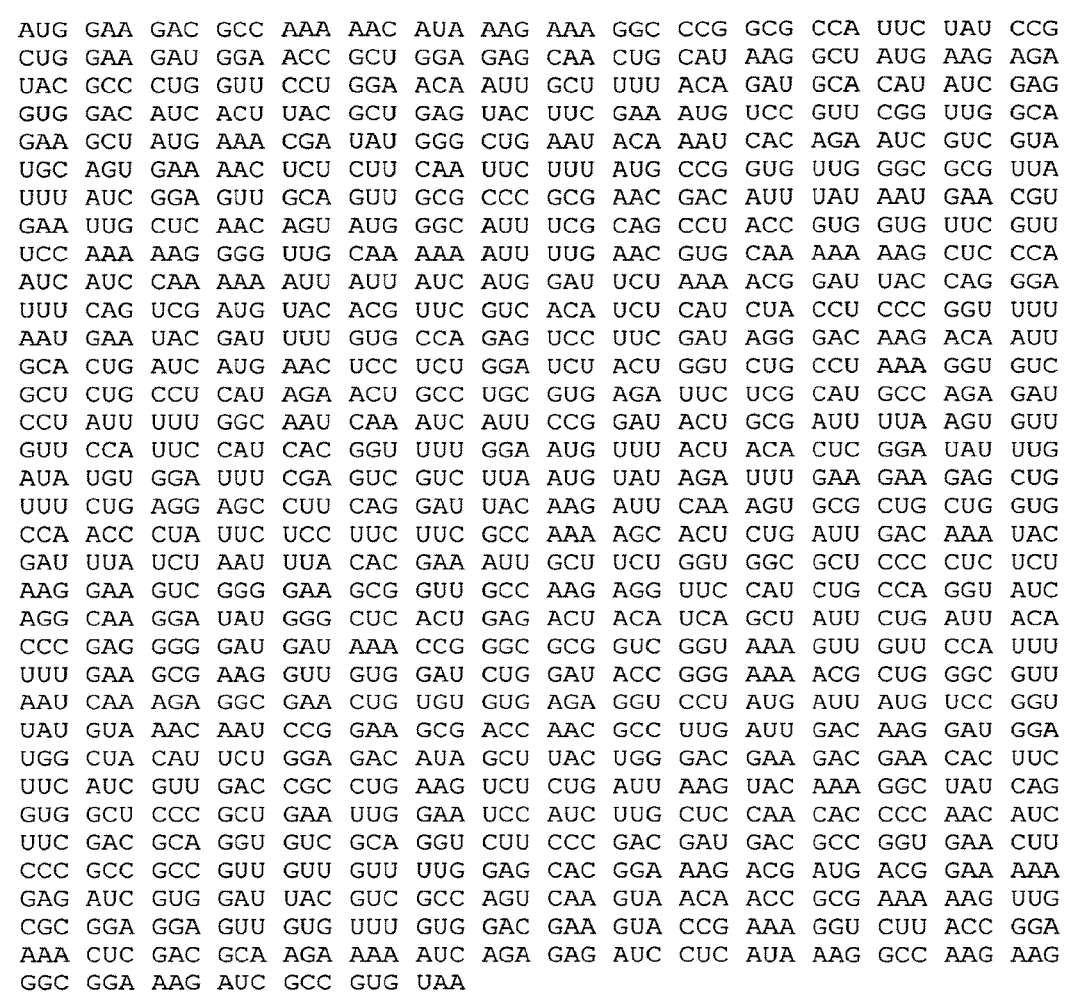

```
AUG GAA GAC GCC AAA AAC AUA AAG AAA GGC CCG GCG CCA UUC UAU CCG
CUG GAA GAU GGA ACC GCU GGA GAG CAA CUG CAU AAG GCU A

```
AUG GAG GAC GCC AAG AAC AUC AAG AAG GGC CCG GCG CCC UUC UAC CCG
CUG GAG GAC GGG ACC GCC GGC GAG CAG CUC CAC AAG GCC AUG AAG CGG
UAC GCC CUG GUG CCG GGC ACG AUC GCC UUC ACC GAC GCC CAC AUC GAG
GUC GAC AUC ACC UAC GCG GAG UAC UUC GAG AUG AGC GUG CGC CUG GCC
GAG GCC AUG AAG CGG UAC GGC CUG AAC ACC AAC CAC CGG AUC GUG GUG
UGC UCG GAG AAC AGC CUG CAG UUC UUC AUG CCG GUG CUG GGC GCC CUC
UUC AUC GGC GUG GCC GUC GCC CCG GCG AAC GAC AUC UAC AAC GAG CGG
GAG CUG CUG AAC AGC AUG GGG AUC AGC CAG CCG ACC GUG GUG UUC GUG
AGC AAG AAG GGC CUG CAG AAG AUC CUG AAC GUG CAG AAG AAG CUG CCC
AUC AUC CAG AAG AUC AUC AUC AUG GAC AGC AAG ACC GAC UAC CAG GGC
UUC CAG UCG AUG UAC ACG UUC GUG ACC AGC CAC CUC CCG CCG GGC UUC
AAC GAG UAC GAC UUC GUC CCG GAG AGC UUC GAC CGG GAC AAG ACC AUC
GCC CUG AUC AUG AAC AGC AGC GGC AGC ACC GGC CUG CCG AAG GGG GUG
GCC CUG CCG CAC CGG ACC GCC UGC GUG CGC UUC UCG CAC GCC CGG GAC
CCC AUC UUC GGC AAC CAG AUC AUC CCG GAC ACC GCC AUC CUG AGC GUG
GUG CCG UUC CAC CAC GGC UUC GGC AUG UUC ACG ACC CUG GGC UAC CUC
AUC UGC GGC UUC CGG GUG GUC CUG AUG UAC CGG UUC GAG GAG GAG CUG
UUC CUG CGG AGC CUG CAG GAC UAC AAG AUC CAG AGC GC

COMPLEXES OF RNA AND CATIONIC PEPTIDES FOR TRANSFECTION AND FOR IMMUNOSTIMULATION

This application is a continuation of U.S. application Ser. No. 12/676,015, now abandoned, which was filed as a national phase application under 35 U.S.C. § 371 of International Application No. PCT/EP2008/007244, filed Sep. 4, 2008, which claims priority to International Application No. PCT/EP2007/007702, filed Sep. 4, 2007. The entire text of each of the above referenced disclosures is specifically incorporated herein by reference.

The present invention relates to a complexed RNA, comprising at least one RNA (molecule) complexed with one or more oligopeptides, wherein the oligopeptide has a length of 8 to 15 amino acids and has the formula $(Arg)_l(Lys)_m(His)_n(Orn)_o(Xaa)_x$. The invention further relates to a method for transfecting a cell or an organism, thereby applying the inventive complexed RNA. Additionally, pharmaceutical compositions and kits comprising the inventive complexed RNA, as well as the use of the inventive complexed RNA for transfecting a cell, tissue or an organism and/or for modulating, preferably inducing or enhancing, an immune response are disclosed herein.

Transfection of nucleic acids into cells or tissues of patients by methods of gene transfer is a central method of molecular medicine, and plays a critical role in therapy and prevention of numerous diseases. Methods for transfection of nucleic acids may lead to immune stimulation of the tissue or organism. Alternatively or additionally, transfection of nucleic acids may be followed by processing of the information coded by the nucleic acids introduced, i.e. translation of desired polypeptides or proteins. DNA or RNA as nucleic acids form alternative approaches to gene therapy. Transfection of nucleic acids may also lead to modulation, e.g. suppression or enhancement of gene expression, dependent on the type of nucleic acid transfected. Transfection of these nucleic acids is typically carried out by using methods of gene transfer.

Methods of gene transfer into cells or tissues have been intensively studied in the last decades, however in part with limited success. Well known methods include physical or physico-chemical methods such as (direct) injection of (naked) nucleic acids or biolistic gene transfer. Biolistic gene transfer (also known as biolistic particle bombardment) is a method developed at Cornell University, that allows introducing genetic material into tissues or culture cells. Biolistic gene transfer is typically accomplished by surface coating metal particles, such as gold or silver particles, and shooting these metal particles, comprising the adsorbed DNA, into cells by using a gene gun. However, biolistic gene transfer methods have not yet been shown to work with RNA, probably due to its fast degradation. Furthermore, these methods are not suitable for in vivo applications, a matter which represents a severe practical limitation.

An alternative physical or physico-chemical method includes the method of in vitro electroporation. In vitro electroporation is based on the use of high-voltage current to make cell membranes permeable to allow the introduction of new DNA or RNA into the cell. Therefore, cell walls are typically weakened prior to transfection either by using chemicals or by a careful process of freezing to make them "electrocompetent". If electrocompetent bacteria or cells (e.g. eukaryotic cells) and DNA (or RNA) are mixed together, the plasmid can be transferred into the cell by using an electric discharge to carry the DNA (or RNA) into cells in the path of the spark crossing the reaction chamber.

Another alternative physical or physico-chemical method includes use of nanoplexes (nanoparticular systems), lipoplexes (liposomal systems), or the use of polyplexes or cationic polymers. Such nanoplexes (nanoparticular systems) involve use of polyacrylates, polyamides, polystyrene, cyanoacrylates, polylactat (PLA), poly(lactic-co-glycolic acid) (PLGA), polyethyl, etc., as carrier systems for the transport of nucleic acids into cells or tissues. Lipoplexes or liposomal systems typically involve use of cationic lipids, which are capable to mimic a cell membrane. Thereby, the positively charged moiety of the lipids interacts with the negatively charged moiety of the nucleic acids and thus enables fusion with the cell membrane. Lipoplexes or liposomal systems include e.g. DOTMA, DOPE, DOSPA, DOTAP, DC-Chol, EDMPC, etc. Polyplexes (cationic polymers) typically form a complex with negatively charged nucleic acids leading to a condensation of nucleic acids and protecting these nucleic acids against degradation. Transport into cells using polyplexes (cationic polymers) typically occurs via receptor mediated endocytosis. Thereby, the DNA is coupled to a distinct molecule, such as Transferrin, via e.g. the polyplex poly-L-lysine (PLL), which binds to a surface receptor and triggers endocytosis. Polyplexes (cationic polymers) include e.g. poly-L-lysine (PLL), chitosan, polyethylenimine (PEI), polydimethylaminoethylmethacrylate (PD-MAEMA), polyamidoamine (PAMAM). Other well known physical or physico-chemical methods of gene transfer into cells or organisms include methods such as virus based transfection methods. As a particular example, DNA viruses may be used as DNA vehicles. Because of their infection properties, such viruses have a very high transfection rate. The viruses typically used are genetically modified in a way, that no functional infectious particles are formed in the transfected cell. In spite of this safety precaution, however, a risk of uncontrolled propagation of the therapeutically active genes introduced and the viral genes cannot be ruled out e.g. because of possible recombination events.

More advantageous in this context is the use of so called translocatory proteins or of protein transduction domains (PTDs) for the transport of macromolecules into cells or tissues. Translocatory proteins are considered as a group of peptides capable of effecting transport of macromolecules between cells (translocatory proteins), such as HIV tat (HIV), antennapedia (*Drosophila antennapedia*), HSV VP22 (*Herpes simplex*), FGF or lactoferrin, etc. In contrast, protein transduction domains (PTDs) are considered as a group of peptides capable of directing proteins and peptides covalently bound to these sequences into a cell via the cell membrane (Leifert and Whitton: Translocatory proteins and protein transduction domains: a critical analysis of their biological effects and the underlying mechanisms. Molecular Therapy Vol. 8 No. 1 2003). Common to translocatory proteins as well as to PTDs is a basic region, which is regarded as mainly responsible for transport of the fusion peptides since it is capable of binding polyanions such as nucleic acids. Without being bound thereto, PTDs may act similar to cationic transfection reagents using receptor dependent non-saturable adsorptive endocytosis. PTDs are typically coupled to proteins or peptides in order to effect or enhance a CTL response when administering a peptide based vaccine (see review: Melikov and Chernomordik, Arginine-rich cell penetrating peptides: from endosomal uptake to nuclear delivery, Cell. Mol. Life Sci. 2005).

Protein transduction domains (PTDs) are sometimes also termed "cell penetrating peptides" (CPPs) due to their capability of penetrating the cell membrane and thus to effect the transport of (macro-) molecules into cells. CPPs are small peptides and typically comprise a high content of basic amino acids and exhibit a length of 7 to 30 amino acids. Macromolecules, which have been shown to be transported into cells via CPPs, include peptides as well as DNA, siRNA or PNAs (peptide nucleic acids), wherein the CPPs are typically bonded to these macromolecules via a covalent bond and transfected into the cells. Although cell penetrating peptides (CPPs) have been successfully used to mediate intracellular delivery of a wide variety of molecules of pharmacological interest both in vitro and in vivo, the mechanisms by which cellular uptake occurs still remains unclear. The group of CPPs is highly diverse and consists of amphipathic, helical peptides such as transportan, penetratin, hydrophobic peptides such as MTS, VP22, MAP, KALA, PpTG20, prolin-rich peptides, MPG-peptides, Pep-1, L-oligomers, calcitonin-peptides, or cationic, hydrophilic arginine-rich peptides, including arginine-rich CPPs, which mediate cellular uptake of (covalently) conjugated molecules via binding to proteoglycanes of the cell, such as the transduction domain of the HIV-1 Tat protein (Review: Deshayes et al. Cell-penetrating peptides: tools for intracellular delivery of therapeutics. Cell. Mol. Life Sci. 2005). Particularly, arginine-rich CPPs are described as vehicles for proteins or DNA, e.g. plasmid DNA, etc. into cells. Poly-arginines may also be used for the transport of (macro-)molecules into cells, which typically comprises a length of at least 60 to 80 amino acids (in particular arginines), more typically from 1000 to 15000 amino acids, and thus represents a high molecular mass compound. Even though the cellular uptake mechanism for CPPs in general remains unclear, endocytosis is suggested as an uptake mechanism for poly-arginine. Endocytosis is a cellular process by which macromolecules may enter a cell without passing through the cell membrane, wherein three different endocytotic mechanisms have been suggested (chlathrin-dependent endocytosis, caveolin-dependent endocytosis and/or F actin-dependent endocytosis, see e.g. review: Melikov and Chernomordik, Arginine-rich cell penetrating peptides: from endosomal uptake to nuclear delivery, Cell. Mol. Life Sci. 2005). Without being bound to any theory, during endocytosis the CPP-complexed macromolecule first binds to the negatively charged cell surface glycosaminoglycans (GAGs), including heparans (HS). Then, the CPP-bound macromolecule enters cell by chlathrin-dependent endocytosis, caveolin-dependent endocytosis and/or F actin-dependent endocytosis, e.g. by folding of the membrane around the CPP-bound macromolecule outside the cell. This results in the formation of a saclike vesicle into which the CPP-bound macromolecule is incorporated. Trafficking of the CPP-bound macromolecule through late endosomes and/or Golgi and/or endoplasmic reticulum (ER) delivers the CPP-bound macromolecule into the cytoplasm, wherein this stage may involve CPP-induced opening of the transient pores in the lipid bilayer. Alternatively, the CPP-complexed macromolecule may be transported to other locations in the cell, e.g. into the endosom, dependent on the mode of action required for the specific purpose. As an example, TLR-7 and TLR-8 receptors are located in the endosome. Thus, transfection of cells with immunostimulatory RNA, which may e.g. be ligands of Toll-like receptors (TLRs) selected from ligands of TLR1-TLR13 (Toll-like receptors: TLR1, TLR2, TLR3, TLR4, TLR5, TLR6, TLR7, TLR8, TLR9, TLR10, TLR11, TLR12 or TLR13) may lead to transport to the endosomes and (depending on the specific interaction and the interaction partners) to e.g. immunostimulation by the RNA ligand.

Cell penetrating peptides (CPPs) as defined above are well known in the art and widely discussed. However, the use of these CPPs (as carriers) is established for the transport of peptides, proteins and DNA as cargo, wherein the CPPs are typically linked to cargo molecules in a covalent manner. In contrast, cellular transport of RNAs using CPPs was only shown for a very limited number of cases, particularly for short RNA sequences, e.g. double stranded siRNA sequences.

By way of example, Futaki et al. (The Journal of Biological Chemistry, Vol 276, No. 8, pp. 5836-5840, 2001) disclose the use of carrier oligopeptides $(Arg)_n$ having a length of 4-16 amino acids for in vitro transfer of cargo peptides, wherein the carrier peptides are covalently linked to the cargo peptides. A translocation optimum was demonstrated for $(Arg)_n$ having a length of 6 or 8 arginines, respectively.

Trans-membrane transport peptides or peptidomimetics by CPPs was also shown by Deshayes et al. (2005, supra). Deshayes et al. (2005, supra) disclose the use of oligopeptides $Arg_7$ and $Arg_9$ for in vitro transfer of cargo peptides and in vivo transfer of cargo proteins such as cyclosporin or catalase.

For transfection of cells with macromolecules, such as DNA, peptides or proteins, high molecular weight polypeptides such as poly-L-arginines (e.g. typically having a MW of about 5000 Da to 15 kDa) or poly-L-lysines (e.g. typically having a MW of about 54 kDa) as well as high molecular weight PEI (polyethyleneimin) (e.g. typically having a MW of about 25 kDa) were used according to the art (see also Bettinger et al., Nucleic Acids Research, Vol. 29 No. 18 (2001)). However, high molecular weight poly-L-lysine and PEI appeared to be ineffective as carrier molecules. Further, when using high molecular weight poly-L-arginines at high concentrations, toxic effects were observed which lead to activation of the complement system. Thus, efforts were undertaken to develop low molecular weight transfection agents, such as, e.g., low molecular weight poly-arginines. However, such low molecular weight poly-arginines typically exhibit a low stability of the carrier-cargo-complex, i.e. the complex formed of, e.g., a poly-arginine as carrier and a DNA molecule as a cargo. Thus, McKenzie et al. (McKenzie et al. A potent new class of reductively activated peptide gene delivery agents; The Journal of Biological Chemistry Vol. 274 No. 14, 2000) tried to increase stability of peptide-DNA-complexes by crosslinking these peptides via glutaraldehyde to the DNA, thereby forming a Schiff's base. However, such crosslinking results in extremely slow dissociation of the complex in the cell and, consequently, expression of the encoded protein is extremely low over time. In order to circumvent this problem, McKenzie et al. (2000, supra) introduced cysteine residues into the CPP carrier, which stabilize the complex by forming disulfide bonds between CPP and DNA. Upon transfection, these disulfide bonds are cleaved in the cell due to the reducing conditions inside the cell, resulting in increased expression of the encoded peptides. However, such crosslinking is elaborative and may cause further undesired modifications of the DNA.

Furthermore, low-molecular weight PEI (e.g. typically having a MW of about 2000 Da) and low-molecular weight poly-L-lysines (e.g. typically having a MW of about 3400 Da) may be used for transfection of such macromolecules as mentioned above. However, even though an improved transfection was observed for low-molecular weight PEI or poly-L-lysines in these experiments, expression was not detectable due to formation of extremely stable complexes of these carrier molecules with the DNA. As a result, these carrier molecules do not appear to exhibit dissociation of their complexed DNA, a necessary step for translation and expression of the encoded protein (see Bettinger et al., (2001), supra).

Transport of DNA by CPPs was further shown by Niidome et al. (The Journal of Biological Chemistry, Vol 272., No. 24, pp. 15307-15312, 1997). Niidome et al. (1997, supra) disclose the use of CPPs, particularly of cationic alpha-helical peptides with a defined arginine content of 25% and a length of 12 or 24 amino acids, respectively, for the transport of plasmid DNA as cargo moiety. As a result, it was found that long and/or hydrophobic peptides can strongly bind to the DNA and effect transport of DNA into cells. Moreover, Niidome et al. (Bioconjugate Chem. 1999, 10, 773-780) showed that peptides having a length of 16 to 17 amino acids were most efficient for the transport of plasmid DNA. However, when using small peptides (e.g. of about 12 amino acids) as CPPs, transfection efficiency of DNA into cells turned out to decrease significantly.

In order to enhance cellular transfection efficiency of short arginine molecules, Futaki et al. (Bioconjugate Chem. 2001, 12, 1005-1011) used stearylated oligopeptides $(Arg)_n$ having a length of 4-16 amino acids. These oligopeptides were used in transfection experiments in comparison to non-stearylated oligopeptides $(Arg)_n$ having a length of 4-16 amino acids and poly-arginine (MW 5000-15000) for in vitro transfer of plasmid DNA coding for luciferase. Accordingly, carrier peptides used for transfection were mixed with plasmid DNA and formed a carrier/cargo complex. A translocation optimum was demonstrated for stearylated $(Arg)_n$ having a length of 8 arginines, whereas arginines having a length of 6-7 and 9-15 arginines showed a significantly reduced cellular transport activity. Furthermore, transport activity of non-stearylated arginines and poly-arginine exhibited poor results, indicating loss of transport activity when using these carrier peptides. The observed difference of transfection efficiency shown by Futaki et al. (2001, supra) for stearylated and non-stearylated carrier peptides is thus due to the presence of lipid moieties, which significantly change the chemical properties of the CPPs used in these experiments.

According to Kim et al., (Kim et al., Basic peptide system for efficient delivery of foreign genes, Biochimica et Biophysica Acta 1640 (2003) 129-136), short arginine carrier peptides such as $(Arg)_9$ to $(Arg)_{15}$ may be used for complexation and cellular transfection of DNA, encoding green fluorescent protein PEGFP-N3. When using arginines $(Arg)_9$ to $(Arg)_{15}$, optimum results were obtained with $(Arg)_{15}$ showing increasing cellular transfection efficiency from $(Arg)_9$ to $(Arg)_{15}$. These results indicate that optimum transport properties for transfecting cells with DNA may be achieved with an $(Arg)_n$ carrier peptide, wherein n is far beyond 15. However, applicability of short arginine peptides for transfection purposes was exclusively documented for DNA molecules as cargo moiety by Kim et al., (2003, supra).

Cells may also be transfected by using CPPs in combination with RNA. However, only a small number of working examples were carried out for the cellular transport of RNA, probably due to its fast degradation and low stability in complexes. Thus, transfection of RNA using CPPs appears to be restricted to more stable double stranded RNAs, such as siRNA. By way of example, Tönges et al., (RNA (2006), 12:1431-1438) used stearylated octa-arginine $(Arg)_8$ for the in vitro transfer of double stranded short siRNA into neuronal hippocampus cells, wherein the stearylated octa-arginine $(Arg)_8$ forms a complex with siRNA. Based on the results of Tönges et al. (2006, supra) the stearyl component of the carrier peptides seems to be indispensible for the transport of siRNA or the transport of other RNA molecules.

Veldhoen et al. (2006) also published the use of specific CPPs in a non-covalent complex for cellular transfection of double stranded short siRNA sequences (Veldhoen et al., Cellular delivery of small interfering RNA by a non-covalently attached cell penetrating peptide: quantitative analysis of uptake and biological effect. Nucleic Acids Research 2006). Peptides used by Veldhoen et al. (2006) were MPGalpha (Ac-GALFLAFLAAALSLMGLWSQPKKKRKV-Cya) and MPGalpha-mNLS (Ac-GALFLAFLAAALSLMGL-WSQPKSKRKV-Cya). These specific peptides were additionally modified with an acetyl moiety (Ac) at the N-terminus and a cysteamide moiety at the C-terminus. Veldhoen et al. (2006) were able to show transfer of double-stranded siRNA, having a length of about 18 to 40 nucleotides, into cells by using the afore-mentioned carrier peptides.

Summarizing the above, use of CPPs or other carrier peptides for the cellular transport of macromolecules was basically shown for peptides and for DNA molecules. Few very specific publications disclose cell penetrating properties of double stranded siRNA.

RNA transfer represents an important tool in modern molecular medicine and exhibits superior properties over DNA cell transfection, since DNA molecules may lead to serious problems. E.g. application of DNA molecules bears the risk that the DNA integrates into the host genome. Integration of foreign DNA into the host genome can have an influence on expression of the host genes and possibly triggers expression of an oncogene or destruction of a tumor suppressor gene. A gene—and therefore the gene product—which is essential to the host may also be inactivated by integration of the foreign DNA into the coding region of this gene. There is a particular danger if integration of the DNA takes place into a gene which is involved in regulation of cell growth. In this case, the host cell may enter into a degenerated state and lead to cancer or tumor formation. Such undesired integration into the DNA may be even more problematic, if the DNA transfected into the cell comprises a potent promoter, such as the viral CMV promoter. Integration of such promoters into the genome of the treated cell can lead to undesirable changes in the regulation of gene expression in the cell. A further disadvantage is that the DNA molecules remain in the cell nucleus for a long time, either as an episome or, as mentioned, integrated into the host genome. This phenomenon leads both to production of transgenic protein which is not limited or cannot be limited in time and to danger of associated tolerance towards this transgenic protein. The development of anti-DNA antibodies (Gilkeson et al., *J Clin Invest* 95, 1398-1402 (1995)) and the induction of autoimmune diseases can furthermore be triggered by injection of DNA. All these risks listed are associated with application of DNA. In contrast, they do not occur if RNA, particularly mRNA, is used instead of DNA. For example, mRNA does not integrate into the host genome, no viral sequences, such as promoters etc., are required for effective transcription etc. A disadvantage resulting from the use of RNA may be due to its instability as compared to DNA (RNA-degrading enzymes, so-called RNases (ribonucleases), in particular, but also numerous other processes which destabilize RNA are responsible for the instability of RNA). However, methods for stabilizing RNA have meanwhile been disclosed in the art, such as, for example, in WO 03/051401, WO 02/098443, WO 99/14346, EP-A-1083232, U.S. Pat. No. 5,580,859 and U.S. Pat. No.

6,214,804. Methods have also been developed for protecting RNA against degradation by ribonucleases, either using liposomes (Martinon et al., *Eur J Immunol* 23, 1719-1722 (1993)) or an intra-cytosolic in vivo administration of the nucleic acid with a ballistic device (gene gun) (Vassilev et al., *Vaccine* 19, 2012-2019 (2001)).

Since RNA molecules as such provide advantageous properties over DNA as discussed above, it is the object of the present invention to provide a suitable and efficient carrier for the transport of RNA into cells. Accordingly, the present invention provides a solution which allows RNA to transfect cells in an efficient manner.

This object of the present invention is achieved by the embodiments of the present invention as characterized by the claims. Particularly, the above object is solved by a complexed RNA (molecule), comprising at least one RNA (molecule), preferably an mRNA, complexed with one or more oligopeptides, wherein the at least one oligopeptide has a length of 8 to 15 amino acids, and wherein the at least one oligopeptide contains l Arg residues, m Lys residues, n His residues, o Orn residues and x Xaa residues positioned in any order within the at least one oligopeptide having the following empirical formula:

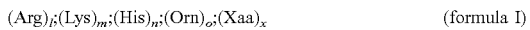  (formula I)

wherein
l+m+n+o+x=8-15, and
l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50%, e.g. at least 60% or 70%, of all amino acids of the oligopeptide; and
Xaa may be any amino acid selected from native (=naturally occurring) or non-native amino acids except of Arg, Lys, His or Orn; and
x may be any number selected from 0, 1, 2, 3, 4, 5, 6, 7 or 8, provided, that the overall content of Xaa does not exceed 50%, e.g. not more than 40% or 30%, of all amino acids of the oligopeptide.

In the context of the present invention, a complexed RNA is to be understood as an RNA (molecule) as defined herein, preferably an mRNA, which is complexed to the one or more oligopeptides according to empirical formula $(Arg)_l;(Lys)_m;(His)_n;(Orn)_o;(Xaa)_x$ by forming a non-covalent complex between RNA and oligopeptide(s). Herein, "non-covalent" means that a reversible association of RNA and oligopeptide is formed by non-covalent interactions of these molecules, wherein the molecules are associated together by any type of interaction of electrons, other than a covalent bond, e.g. by van der Waals-bonds, i.e. a weak electrostatic attraction arising from a nonspecific attractive force of the complexed molecules. Association of an RNA and at least one oligopeptide is in equilibrium with dissociation of that complex. Intracellularly, without being bound to theory, the equilibrium appears to be shifted towards dissociated RNA and oligopeptide(s).

The at least one oligopeptide of the complexed RNA according to the present invention has a length of 8 to 15 amino acids, preferably a length of 8 to 14, 8 to 13, 8 to 12, or 9 to 12 or 9 to 11 amino acids, and more preferably a length of 8 to 10, 9 to 11, 10 to 12, 11 to 13, 12 to 14 or 13 to 15 amino acids, or even more preferably may be selected from a peptide of the above formula having a length of 8, 9, 10, 11, 12, 13, 14 or 15 amino acids.

The oligopeptide of the complexed RNA according to the present invention has the empirical formula $(Arg)_l;(Lys)_m;(His)_n;(Orn)_o;(Xaa)_x$ as defined above wherein l+m+n+o+x=8-15, and l, m, n or o independently of each other may be any number selected from 0, 1, 2, 3, 4, 5, 6, 7, 8, 9, 10, 11, 12, 13, 14 or 15, or any range formed by two of these values, provided that the overall content of (the basic amino acids) Arg, Lys, His and/or Orn represents at least 50% (e.g. at least 51, 52, 53, 54, 55, 56, 57, 58, or 59%) at least 60% (e.g. at least 61, 62, 63, 64, 65, 66, 67, 68, or 69%), at least 70% (e.g. at least 71, 72, 73, 74, 75, 76, 77, 78, or 79%), at least 80% (e.g. at least 81, 82, 83, 84, 85, 86, 87, 88, or 89%) at least 90% (e.g. at least 91, 92, 93, 94, 95, 96, 97, 98, or 99%), or even 100% of all amino acids of the oligopeptide of the complexed RNA according to the present invention. The amino acids Arg, Lys, His and Orn (three letter code) are to be understood as the amino acids arginine, lysine, histidine and ornithine, respectively. In this context, ornithine is an amino acid whose structure is $NH_2$—$CH_2$—$CH_2$—$CH_2$—$CHNH_2$—COOH. Ornithine was artificially incorporated as the $21^{st}$ amino acid and does not belong to the "natively occurring" 20 amino acids in the sense that ornithine is not an amino acid coded for by DNA, and, accordingly, is not involved in primary protein synthesis. However, ornithine is provided by enzymatic reaction starting from L-arginine. It is believed not to be a part of the genetic code because polypeptides containing unprotected ornithines undergo spontaneous lactamization. Ornithine is to be regarded as a basic amino acid since it is one of the products of the reaction of the enzyme Arginase on L-arginine, creating urea.

According to a further preferred embodiment the (single) amino acids of the oligopeptide of the complexed RNA of the present invention, having the empirical formula $(Arg)_l;(Lys)_m;(His)_n;(Orn)_o;(Xaa)_x$ (formula I) as shown above, may occur in any frequency as defined above for the empirical formula, i.e. each basic amino acid (as well as Xaa) may occur in the above defined empirical formula within the above defined values or ranges, wherein any range may be formed from by two of the values as defined above. However, it is particularly preferred, if the content of the basic amino acid Arg in the above empricial formula is at least 10%, more preferably at least 20%, even more preferably at least 30%, 40% or even 50%, even more preferably at least 60%, 70%, 80% 90% or even 100% with respect to the entire empirical formula. According to another particularly preferred embodiment the content of the basic amino acid Lys in the above empricial formula is at least 10%, more preferably at least 20%, even more preferably at least 30%, 40% or even 50%, even more preferably at least 60%, 70%, 80% 90% or even 100% with respect to the entire empirical formula. According to a further particularly preferred embodiment the content of the basic amino acid His in the above empricial formula is at least 10%, more preferably at least 20%, even more preferably at least 30%, 40% or even 50%, even more preferably at least 60%, 70%, 80% 90% or even 100% with respect to the entire empirical formula. According to one other particularly preferred embodiment the content of the basic amino acid Orn in the above empricial formula is at least 10%, more preferably at least 20%, even more preferably at least 30%, 40% or even 50%, even more preferably at least 60%, 70%, 80% 90% or even 100% with respect to the entire empirical formula. Any of the above defined contents, values or ranges of basic amino acids Arg, Lys, His and/or Orn as defined above may also be combined with each other, preferably leading to an overall content of all basic amino acids of the oligopeptide of the complexed RNA of the present invention of at least 50% (at least 51, 52, 53, 54, 55, 56, 57, 58, or 59%) at least 60% (at least 61, 62, 63, 64, 65, 66, 67, 68, or 69%), at least 70% (at least 71, 72, 73, 74, 75, 76, 77, 78, or 79%), at least 80% (at least 81, 82, 83, 84, 85, 86, 87, 88, or 89%) at least 90% (at least 91, 92, 93, 94, 95, 96, 97, 98, or 99%), or even 100%, as defined initially.

The amino acids in the above formula $(Arg)_l;(Lys)_m;(His)_n;(Orn)_o;(Xaa)_x$, i.e. Arg, Lys, His and/or Orn may be furthermore be selected from the native (=naturally occurring) amino acids Arg, Lys, His and Orn or from non-native (=not naturally occurring) amino acids derived from these amino acids. As a non-native (=not naturally occurring) amino acid derived from the amino acids Arg, Lys, His and Orn, any known derivative of these amino acids may be used, which has been chemically modified, provided these derivatives are not toxic for cells or organisms, when provided with the above oligopeptide. (Such derivatives of amino acids are distributed by different companies; see e.g. Sigma Aldrich (see sigmaaldrich.com).

Furthermore, the oligopeptide of the complexed RNA according to the present invention may contain an amino acid Xaa in the above empirical formula $(Arg)_l;(Lys)_m;(His)_n;(Orn)_o; (Xaa)_x$, which may be any amino acid selected from native (=naturally occurring) or non-native (=not naturally occurring) amino acids except of Arg, Lys, His or Orn. Preferably, Xaa may be selected, without being limited thereto, from naturally occurring neutral (and hydrophobic) amino acids, i.e. amino acids, which have neutral (and hydrophobic) side chains, such as alanine (Ala), valine (Val), leucine (Leu), isoleucine (Ile), proline (Pro), tryptophane (Trp), phenylalanine (Phe), or methionine (Met), and/or from naturally occurring neutral (and polar) amino acids, i.e. amino acids, which have neutral (and polar) side chains, such as glycine (Gly), serine (ser), threonine (Thr), tyrosine (Tyr), cysteine (Cys), asparagine (Asn), or glutamine (Glu), and/or from naturally occurring acidic amino acids, i.e. amino acids, which have acidic side chains, such as aspartic acid (Asp) or glutamic acid (Glu). Preferably the oligopeptide of the complexed RNA according to the present invention may contain an amino acid Xaa in the above empirical formula $(Arg)_l;(Lys)_m;(His)_n;(Orn)_o;(Xaa)_x$ which is selected from amino acids having no acidic side chain. Even more preferably, Xaa in empirical formula $(Arg)_l;(Lys)_m; (His)_n;(Orn)_o; (Xaa)_x$ is selected from amino acids having a neutral side chain, i.e. from amino acids, which have a neutral (and hydrophobic) side chain and/or from amino acids, which have a neutral (and polar) side chain, as defined above. Additionally, any known derivative of amino acids may be used for Xaa in the above empirical formula $(Arg)_l;(Lys)_m;(His)_n;(Orn)_o; (Xaa)_x$, i.e. amino acids, which have been chemically modified, provided these derivatives are not toxic for cells or organisms, when provided with the above oligopeptide. (Such derivatives of amino acids are distributed by different companies, see e.g. Sigma Aldrich (see sigmaaldrich.com). Xaa is typically present in the above formula in a content of 0-30%, 0-40% or 0-50% of all amino acids of the entire oligopeptide sequence, i.e. the overall content of Xaa may not exceed 30%, 40% or 50% of all amino acids of the entire oligopeptide sequence, preferably it may not exceed 20%, even more preferably not 10%, and most preferably not 5% of all amino acids of the entire oligopeptide sequence. Thus, x in the empirical formula $(Arg)_l;(Lys)_m; (His)_n;(Orn)_o; (Xaa)_x$ as shown above may be any number selected from 0, 1, 2, 3, 4, 5, 6, 7 or 8, provided, that the content of Xaa does not exceed the above indicated value of 30% (or less), 40% or 50% of all entire amino acids of the oligopeptide of the complexed RNA.

Typically, the amino acids Arg, Lys, His, Orn and Xaa of the oligopeptide of the complexed RNA according to the present invention, having the empirical formula $(Arg)_l;(Lys)_m;(His)_n;(Orn)_o;(Xaa)_x$ as indicated above, may be positioned at any position of the oligopeptide sequence. Accordingly, empirical formula (I) does not determine any specific order of amino acids, but is rather intended to reflect the type of amino acids and their frequency of occurrence in the peptide, indicating that the peptide chain contains a number of l Arg residues, m Lys residues, n His residues, o Orn residues and x Xaa residues, without specifying any order of these residues within the peptide chain.

However, it is preferred, that the above oligopeptide comprises amino acids at one or, preferably, both terminal ends, which do not comprise an acidic side chain. More preferably, the above oligopeptide sequence comprises neutral or basic amino acids at one or, preferably, both terminal ends, even more preferably basic amino acids at one or both terminal ends. In a further preferred embodiment, the oligopeptide according to the general formula given above contains at least two, more preferably at least three, at least four or even at least five terminal basic residues, in particular Arg, Orn or Lys, at either terminus. According to just another preferred embodiment, the oligopeptide according to the general formula given above preferably comprises no cationic amino acids (i.e. no Arg, Orn or Lys) at one or, preferably, at both terminal ends, even more preferably no cationic amino acids (i.e. no Arg, Orn or Lys) at both terminal ends. In other words, one, or more preferably both, terminal ends of the oligopeptide according to the general formula given above may comprise any non-cationic amino acid as defined herein, provided that such non-cationic amino acid is selected from an amino acid except Arg, Orn or Lys or any variant or derivative of these cationic amino acids. The terminal ends may comprise e.g. one, at least two, at least three, at least four, at least five or even more basic non-cationic residues as defined above starting from the N- and/or C-terminal end of the particular sequence.

According to a further preferred embodiment, one or both terminal ends of the oligopeptide of the complexed RNA according to the present invention may comprise at least one histidine residues at one or both of its terminal ends, e.g. the oligopeptide of the complexed RNA according to the present invention may comprise one, two, three or more histidine residues in consecutive order at one or both terminal ends, provided that the overall length of the oligopeptide is limited to 8 to 15 amino acids as defined above.

Additionally, Xaa residues of the oligopeptide of the complexed RNA according to the present invention are typically separated from each other by at least one Arg, Lys, His or Orn. Such a separation of Xaa residues preferably avoids clusters of non-basic amino acids in the oligopeptide, as such non-basic clusters may reduce the advantageous properties of the oligopeptide as a carrier peptide for the complexed RNA according to the present invention.

However, basic amino acid residues of the oligopeptide of the complexed RNA according to the formula given above are selected from Arg, Lys, His or Orn as defined above and typically occur in a cluster of at least 2, preferably at least 3, 4, 5, or even 6 or more basic amino acids as defined herein. According to a particularly preferred embodiment, such clusters may also comprise 6, 7, 8, 9, 10, 11, 12, 13, 14 or even 15 amino acids. Such a cluster of basic amino acids, preferably a cluster of at least 3, 4, 5, or even 6 or more basic amino acids preferably creates a basic surface or binding region within the oligopeptide, which provides advantageous properties to the oligopeptide as a carrier peptide for the complexed RNA according to the present invention.

According to a further preferred embodiment the oligopeptide of the complexed RNA of the present invention, having the empirical formula $(Arg)_l;(Lys)_m;(His)_n;(Orn)_o;(Xaa)_x$ (formula I) as shown above, may be, without being restricted thereto, selected from the following subgroup of formulae:

$Arg_8,Arg_9,Arg_{10},Arg_{11},Arg_{12},Arg_{13},Arg_{14},Arg_{15}$, (SEQ ID NOs: 1-8);

$Lys_8,Lys_9,Lys_{10},Lys_{11},Lys_{12},Lys_{13},Lys_{14},Lys_{15}$, (SEQ ID NOs: 9-16);

$His_8,His_9,His_{10},His_{11},His_{12},His_{13},His_{15},His_{15}$, (SEQ ID NOs: 17-24);

$Orn_8,Orn_9,Orn_{10},Orn_{11},Orn_{12},Orn_{13},Orn_{14},Orn_{15}$, (SEQ ID NOs: 25-32);

According to a further preferred embodiment the oligopeptide of the complexed RNA of the present invention, having the empirical formula $(Arg)_l;(Lys)_m;(His)_n;(Orn)_o;(Xaa)_x$ (formula I) as shown above, may be, without being restricted thereto, selected from following subgroup. This subgroup exemplarily defines specific inventive oligopeptides, which fall under empirical formula I as defined above, wherein the following formulae (as with empirical formula (I)) do not specify any amino acid order, but are intended to reflect empirical formulae by exclusively specifying the (number of) amino acids as components of the respective peptide. Accordingly, empirical formula $Arg_{(7-14)}Lys_1$ is intended to mean that peptides falling under this formula contain 7 to 14 Arg residues and 1 Lys residue of whatsoever order. If the peptides contain 7 Arg residues and 1 Lys residue, all variants having 7 Arg residues and 1 Lys residue are encompassed. The Lys residue may therefore be positioned anywhere in the e.g. 8 amino acid long sequence composed of 7 Arg and 1 Lys residues. The subgroup preferably comprises:

$Arg_{(7-14)}Lys_1$ (SEQ ID NO: 45), $Arg_{(7-14)}His_1$ (SEQ ID NO: 46), $Arg_{(7-14)}Orn_1$ (SEQ ID NO: 47), $Lys_{(7-14)}His_1$ (SEQ ID NO: 48), $Lys_{(7-14)}Orn_1$ (SEQ ID NO: 49), $His_{(7-14)}Orn_1$ (SEQ ID NO: 50);

$Arg_{(6-13)}Lys_2$ (SEQ ID NO: 51), $Arg_{(6-13)}His_2$ (SEQ ID NO: 52), $Arg_{(6-13)}Orn_2$ (SEQ ID NO: 53), $Lys_{(6-13)}His_2$ (SEQ ID NO: 54), $Lys_{(6-13)}Orn_2$ (SEQ ID NO: 55), $His_{(6-13)}Orn_2$ (SEQ ID NO: 56);

$Arg_{(5-12)}Lys_3$ (SEQ ID NO: 57), $Arg_{(5-12)}His_3$ (SEQ ID NO: 58), $Arg_{(5-12)}Orn_3$ (SEQ ID NO: 59), $Lys_{(5-12)}His_3$ (SEQ ID NO: 60), $Lys_{(5-12)}Orn_3$ (SEQ ID NO: 61), $His_{(5-12)}Orn_3$ (SEQ ID NO: 62);

$Arg_{(4-11)}Lys_4$ (SEQ ID NO: 63), $Arg_{(4-11)}His_4$ (SEQ ID NO: 64), $Arg_{(4-11)}Orn_4$ (SEQ ID NO: 65), $Lys_{(4-11)}His_4$ (SEQ ID NO: 66), $Lys_{(4-11)}Orn_4$ (SEQ ID NO: 67), $His_{(4-11)}Orn_4$ (SEQ ID NO: 68);

$Arg_{(3-10)}Lys_5$ (SEQ ID NO: 69), $Arg_{(3-10)}His_5$ (SEQ ID NO: 70), $Arg_{(3-10)}Orn_5$ (SEQ ID NO: 71), $Lys_{(3-10)}His_5$ (SEQ ID NO: 72), $Lys_{(3-10)}Orn_5$ (SEQ ID NO: 73), $His_{(3-10)}Orn_5$ (SEQ ID NO: 74);

$Arg_{(2-9)}Lys_6$ (SEQ ID NO: 75), $Arg_{(2-9)}His_6$ (SEQ ID NO: 76), $Arg_{(2-9)}Orn_6$ (SEQ ID NO: 77), $Lys_{(2-9)}His_6$ (SEQ ID NO: 78), $Lys_{(2-9)}Orn_6$ (SEQ ID NO: 79), $His_{(2-9)}Orn_6$ (SEQ ID NO: 80);

$Arg_{(1-8)}Lys_7$ (SEQ ID NO: 81), $Arg_{(1-8)}His_7$ (SEQ ID NO: 82), $Arg_{(1-8)}Orn_7$ (SEQ ID NO: 83), $Lys_{(1-8)}His_7$ (SEQ ID NO: 84), $Lys_{(1-8)}Orn_7$ (SEQ ID NO: 85), $His_{(1-8)}Orn_7$ (SEQ ID NO: 86);

$Arg_{(6-13)}Lys_1His_1$ (SEQ ID NO: 87), $Arg_{(6-13)}Lys_1Orn_1$ (SEQ ID NO: 88), $Arg_{(6-13)}His_1Orn_1$ (SEQ ID NO: 89) $Arg_1Lys_{(6-13)}His_1$ (SEQ ID NO: 90), $Arg_1Lys_{(6-13)}Orn_1$ (SEQ ID NO: 91), $Lys_{(6-13)}His_1Orn_1$ (SEQ ID NO: 92), $Arg_1Lys_1His_{(6-13)}$ (SEQ ID NO: 93), $Arg_1His_{(6-13)}Orn_1$ (SEQ ID NO: 94), $Lys_1His_{(6-13)}Orn_1$ (SEQ ID NO: 95);

$Arg_{(5-12)}Lys_2His_1$ (SEQ ID NO: 96), $Arg_{(5-12)}Lys_1His_2$ (SEQ ID NO: 97) $Arg_{(5-12)}Lys_2Orn_1$ (SEQ ID NO: 98), $Arg_{(5-12)}Lys_1Orn_2$ (SEQ ID NO: 99), $Arg_{(5-12)}His_2Orn_1$ (SEQ ID NO: 100), $Arg_{(5-12)}His_1Orn_2$ (SEQ ID NO: 101), $Arg_2Lys_{(5-12)}His_1$ (SEQ ID NO: 102), $Arg_1Lys_{(5-12)}His_2$ (SEQ ID NO: 103), $Arg_2Lys_{(5-12)}His_1$ (SEQ ID NO: 104), $Arg_1Lys_{(5-12)}Orn_2$ (SEQ ID NO: 105), $Lys_{(5-12)}His_2Orn_1$ (SEQ ID NO: 106), $Lys_{(5-12)}His_1Orn_2$ (SEQ ID NO: 107), $Arg_2Lys_1His_{(5-12)}$ (SEQ ID NO: 108), $Arg_1Lys_2His_{(5-12)}$ (SEQ ID NO: 109), $Arg_2His_{(5-12)}Orn_1$ (SEQ ID NO: 110), $Arg_1His_{(5-12)}Orn_2$ (SEQ ID NO: 111), $Lys_2His_{(5-12)}Orn_1$(SEQ ID NO: 112), $Lys_1His_{(5-12)}Orn_2$ (SEQ ID NO: 113);

$Arg_{(4-11)}Lys_3His_1$(SEQ ID NO: 114), $Arg_{(4-11)}Lys_2His_2$ (SEQ ID NO: 115), $Arg_{(4-11)}Lys_1His_3$ (SEQ ID NO: 116), $Arg_{(4-11)}Lys_3Orn_1$ (SEQ ID NO: 117), $Arg_{(4-11)}Lys_2Orn_2$ (SEQ ID NO: 118), $Arg_{(4-11)}Lys_1Orn_3$ (SEQ ID NO: 119), $Arg_{(4-11)}His_3Orn_1$ (SEQ ID NO: 120), $Arg_{(4-11)}His_2Orn_2$ (SEQ ID NO: 121), $Arg_{(4-11)}His_1Orn_3$ (SEQ ID NO: 122), $Arg_3Lys_{(4-11)}His_1$ (SEQ ID NO: 123), $Arg_2Lys_{(4-11)}His_2$ (SEQ ID NO: 124), $Arg_1Lys_{(4-11)}His_3$ (SEQ ID NO: 125), $Arg_3Lys_{(4-11)}Orn_1$ (SEQ ID NO: 126), $Arg_2Lys_{(4-11)}Orn_2$ (SEQ ID NO: 127), $Arg_1Lys_{(4-11)}Orn_3$(SEQ ID NO: 128), $Lys_{(4-11)}His_3Orn_1$ (SEQ ID NO: 129), $Lys_{(4-11)}His_2Orn_2$ (SEQ ID NO: 130), $Lys_{(4-11)}His_1Orn_3$ (SEQ ID NO: 131), $Arg_3Lys_1His_{(4-11)}$ (SEQ ID NO: 132), $Arg_2Lys_2His_{(4-11)}$ (SEQ ID NO: 133), $Arg_1Lys_3His_{(4-11)}$ (SEQ ID NO: 134), $Arg_3His_{(4-11)}Orn_1$ (SEQ ID NO: 135), $Arg_2His_{(4-11)}Orn_2$ (SEQ ID NO: 136), $Arg_1His_{(4-11)}Orn_3$ (SEQ ID NO: 137), $Lys_3His_{(4-11)}Orn_1$ (SEQ ID NO: 138), $Lys_2His_{(4-11)}Orn_2$ (SEQ ID NO: 139), $Lys_1His_{(4-11)}Orn_3$ (SEQ ID NO: 140);

$Arg_{(3-10)}Lys_4His_1$ (SEQ ID NO: 141), $Arg_{(3-10)}Lys_3His_2$ (SEQ ID NO: 142), $Arg_{(3-10)}Lys_2His_3$ (SEQ ID NO: 143), $Arg_{(3-10)}Lys_1His_4$ (SEQ ID NO: 144) $Arg_{(3-10)}Lys_4Orn_1$ (SEQ ID NO: 145), $Arg_{(3-10)}Lys_3Orn_2$ (SEQ ID NO: 146), $Arg_{(3-10)}Lys_2Orn_3$ (SEQ ID NO: 147), $Arg_{(3-10)}Lys_1Orn_4$ (SEQ ID NO: 148), $Arg_{(3-10)}His_4Orn_1$ (SEQ ID NO: 149), $Arg_{(3-10)}His_3Orn_2$ (SEQ ID NO: 150), $Arg_{(3-10)}His_2Orn_3$ (SEQ ID NO: 151), $Arg_{(3-10)}His_1Orn_4$ (SEQ ID NO: 152), $Arg_4Lys_{(3-10)}His_1$ (SEQ ID NO: 153), $Arg_3Lys_{(3-10)}His_2$ (SEQ ID NO: 154), $Arg_2Lys_{(3-10)}His_3$ (SEQ ID NO: 155), $Arg_1Lys_{(3-10)}His_4$ (SEQ ID NO: 156), $Arg_4Lys_{(3-10)}Orn_1$ (SEQ ID NO: 157), $Arg_3Lys_{(3-10)}Orn_2$ (SEQ ID NO: 158), $Arg_2Lys_{(3-10)}Orn_3$ (SEQ ID NO: 159), $Arg_1Lys_{(3-10)}Orn_4$ (SEQ ID NO: 160), $Lys_{(3-10)}His_4Orn_1$ (SEQ ID NO: 161), $Lys_{(3-10)}His_3Orn_2$ (SEQ ID NO: 162), $Lys_{(3-10)}His_2Orn_3$ (SEQ ID NO: 163), $Lys_{(3-10)}His_1Orn_4$ (SEQ ID NO: 164), $Arg_4Lys_1His_{(3-10)}$ (SEQ ID NO: 165), $Arg_3Lys_2His_{(3-10)}$ (SEQ ID NO: 166), $Arg_2Lys_3His_{(3-10)}$ (SEQ ID NO: 167), $Arg_1Lys_4His_{(3-10)}$ (SEQ ID NO: 168), $Arg_4His_{(3-10)}Orn_1$ (SEQ ID NO: 169), $Arg_3His_{(3-10)}Orn_2$ (SEQ ID NO: 170), $Arg_2His_{(3-10)}Orn_3$ (SEQ ID NO: 171), $Arg_1His_{(3-10)}Orn_4$ (SEQ ID NO: 172), $Lys_4His_{(3-10)}Orn_1$ (SEQ ID NO: 173), $Lys_3His_{(3-10)}Orn_2$ (SEQ ID NO: 174), $Lys_2His_{(3-10)}Orn_3$ (SEQ ID NO: 175), $Lys_1His_{(3-10)}Orn_4$ (SEQ ID NO: 176);

$Arg_{(2-9)}Lys_5His_1$ (SEQ ID NO: 177), $Arg_{(2-9)}Lys_4His_2$ (SEQ ID NO: 178), $Arg_{(2-9)}Lys_3His_3$ (SEQ ID NO: 179), $Arg_{(2-9)}Lys_2His_4$ (SEQ ID NO: 180) $Arg_{(2-9)}Lys_1His_5$ (SEQ ID NO: 181), $Arg_{(2-9)}Lys_5Orn_1$ (SEQ ID NO: 182), $Arg_{(2-9)}Lys_4Orn_2$ (SEQ ID NO: 183), $Arg_{(2-9)}Lys_3Orn_3$ (SEQ ID NO: 184), $Arg_{(2-9)}Lys_2Orn_4$ (SEQ ID NO: 185), $Arg_{(2-9)}Lys_1Orn_5$ (SEQ ID NO: 186), $Arg_{(2-9)}His_5Orn_1$ (SEQ ID NO: 187), $Arg_{(2-9)}His_4Orn_2$ (SEQ ID NO: 188), $Arg_{(2-9)}His_3Orn_3$ (SEQ ID NO: 189), $Arg_{(2-9)}His_2Orn_4$ (SEQ ID NO: 190), $Arg_{(2-9)}His_1Orn_5$ (SEQ ID NO: 191), $Arg_5Lys_{(2-9)}His_1$ (SEQ ID NO: 192), $Arg_4Lys_{(2-9)}His_2$ (SEQ ID NO: 193), $Arg_3Lys_{(2-9)}His_3$ (SEQ ID NO: 194), $Arg_2Lys_{(2-9)}His_4$ (SEQ ID NO: 195), $Arg_1Lys_{(2-9)}His_5$ (SEQ ID NO: 196), $Arg_5Lys_{(2-9)}Orn_1$ (SEQ ID NO: 197), $Arg_4Lys_{(2-9)}Orn_2$ (SEQ ID NO: 198), $Arg_3Lys_{(2-9)}Orn_3$ (SEQ ID NO: 199), $Arg_2Lys_{(2-9)}Orn_4$ (SEQ ID NO: 200), $Arg_1Lys_{(2-9)}Orn_5$ (SEQ ID NO: 201), $Lys_{(2-9)}His_5Orn_1$ (SEQ ID NO: 202), $Lys_{(2-9)}His_4Orn_2$ (SEQ ID NO: 203), $Lys_{(2-9)}His_3Orn_3$ (SEQ ID NO: 204), $Lys_{(2-9)}His_2Orn_4$ (SEQ ID NO: 205), $Lys_{(2-9)}His_1Orn_5$ (SEQ ID NO: 206), $Arg_5Lys_1His_{(2-9)}$ (SEQ ID NO: 207), $Arg_4Lys_2His_{(2-9)}$ (SEQ ID NO: 208), $Arg_3Lys_3His_{(2-9)}$ (SEQ ID NO: 209), $Arg_2Lys_4His_{(2-9)}$ (SEQ ID NO: 210), $Arg_1Lys_5His_{(2-9)}$ (SEQ ID NO: 211), $Arg_5His_{(2-9)}Orn_1$ (SEQ ID NO: 212), $Arg_4His_{(2-9)}Orn_2$ (SEQ ID NO: 213), $Arg_3His_{(2-9)}Orn_3$ (SEQ ID NO: 214), $Arg_2His_{(2-9)}Orn_4$ (SEQ ID NO: 215), $Arg_1His_{(2-9)}Orn_5$ (SEQ ID NO: 216), $Lys_5His_{(2-9)}Orn_1$ (SEQ ID NO: 217), $Lys_4His_{(2-9)}Orn_2$ (SEQ ID NO: 218), $Lys_3His_{(2-9)}Orn_3$ (SEQ ID NO: 219), $Lys_2His_{(2-9)}Orn_4$ (SEQ ID NO: 220), $Lys_1His_{(2-9)}Orn_5$ (SEQ ID NO: 221);

$Arg_{(1-8)}Lys_6His_1$ (SEQ ID NO: 222), $Arg_{(1-8)}Lys_5His_2$ (SEQ ID NO: 223), $Arg_{(1-8)}Lys_4His_3$ (SEQ ID NO: 224), $Arg_{(1-8)}Lys_3His_4$ (SEQ ID NO: 225), $Arg_{(1-8)}Lys_2His_5$ (SEQ ID NO: 226), $Arg_{(1-8)}Lys_1His_6$ (SEQ ID NO: 227), $Arg_{(1-8)}Lys_6Orn_1$ (SEQ ID NO: 228), $Arg_{(1-8)}Lys_5Orn_2$ (SEQ ID NO: 229), $Arg_{(1-8)}Lys_4Orn_3$ (SEQ ID NO: 230), $Arg_{(1-8)}Lys_3Orn_4$ (SEQ ID NO: 231), $Arg_{(1-8)}Lys_2Orn_5$ (SEQ ID NO: 232), $Arg_{(1-8)}Lys_1Orn_6$ (SEQ ID NO: 233), $Arg_{(1-8)}His_6Orn_1$ (SEQ ID NO: 234), $Arg_{(1-8)}His_5Orn_2$ (SEQ ID NO: 235), $Arg_{(1-8)}His_4Orn_3$ (SEQ ID NO: 236), $Arg_{(1-8)}His_3Orn_4$ (SEQ ID NO: 237), $Arg_{(1-8)}His_2Orn_5$ (SEQ ID NO: 238), $Arg_{(1-8)}His_1Orn_6$ (SEQ ID NO: 239), $Arg_6Lys_{(1-8)}His_1$ (SEQ ID NO: 240), $Arg_5Lys_{(1-8)}His_2$ (SEQ ID NO: 241), $Arg_4Lys_{(1-8)}His_3$ (SEQ ID NO: 242), $Arg_3Lys_{(1-8)}His_4$ (SEQ ID NO: 243), $Arg_2Lys_{(1-8)}His_5$ (SEQ ID NO: 244), $Arg_1Lys_{(1-8)}His_6$ (SEQ ID NO: 245), $Arg_6Lys_{(1-8)}Orn_1$ (SEQ ID NO: 246), $Arg_5Lys_{(1-8)}Orn_2$ (SEQ ID NO: 247), $Arg_4Lys_{(1-8)}Orn_3$ (SEQ ID NO: 248), $Arg_3Lys_{(1-8)}Orn_4$ (SEQ ID NO: 249), $Arg_2Lys_{(1-8)}Orn_5$ (SEQ ID NO: 250), $Arg_1Lys_{(1-8)}Orn_6$ (SEQ ID NO: 251), $Lys_{(1-8)}His_6Orn_1$ (SEQ ID NO: 252), $Lys_{(1-8)}His_5Orn_2$ (SEQ ID NO: 253), $Lys_{(1-8)}His_4Orn_3$ (SEQ ID NO: 254), $Lys_{(1-8)}His_3Orn_4$ (SEQ ID NO: 255), $Lys_{(1-8)}His_2Orn_5$ (SEQ ID NO: 256), $Lys_{(1-8)}His_1Orn_6$ (SEQ ID NO: 257), $Arg_6Lys_1His_{(1-8)}$ (SEQ ID NO: 258), $Arg_5Lys_2His_{(1-8)}$ (SEQ ID NO: 259), $Arg_4Lys_3His_{(1-8)}$ (SEQ ID NO: 260), $Arg_3Lys_4His_{(1-8)}$ (SEQ ID NO: 261), $Arg_2Lys_5His_{(1-8)}$ (SEQ ID NO: 262), $Arg_1Lys_6His_{(1-8)}$ (SEQ ID NO: 263), $Arg_6His_{(1-8)}Orn_1$ (SEQ ID NO: 264), $Arg_5His_{(1-8)}Orn_2$ (SEQ ID NO: 265), $Arg_4His_{(1-8)}Orn_3$ (SEQ ID NO: 266), $Arg_3His_{(1-8)}Orn_4$ (SEQ ID NO: 267), $Arg_2His_{(1-8)}Orn_5$ (SEQ ID NO: 268), $Arg_1His_{(1-8)}Orn_6$ (SEQ ID NO: 269), $Lys_6His_{(1-8)}Orn_1$ (SEQ ID NO: 270), $Lys_5His_{(1-8)}Orn_2$ (SEQ ID NO: 271), $Lys_4His_{(1-8)}Orn_3$ (SEQ ID NO: 272), $Lys_3His_{(1-8)}Orn_4$ (SEQ ID NO: 273), $Lys_2His_{(1-8)}Orn_5$ (SEQ ID NO: 274) $Lys_1His_{(1-8)}Orn_6$ (SEQ ID NO: 275);

$Arg_{(5-12)}Lys_1His_1Orn_1$ (SEQ ID NO: 276), $Arg_1Lys_{(5-12)}His_1Orn_1$ (SEQ ID NO: 277), $Arg_1Lys_1His_{(5-12)}Orn_1$ (SEQ ID NO: 278), $Arg_1Lys_1His_1Orn_{(5-12)}$ (SEQ ID NO: 279);

$Arg_{(4-11)}Lys_2His_1Orn_1$ (SEQ ID NO: 280), $Arg_{(4-11)}Lys_1His_2Orn_1$ (SEQ ID NO: 281), $Arg_{(4-11)}Lys_1His_1Orn_2$ (SEQ ID NO: 282), $Arg_2Lys_{(4-11)}His_1Orn_1$ (SEQ ID NO: 283), $Arg_1Lys_{(4-11)}His_2Orn_1$ (SEQ ID NO: 284), $Arg_1Lys_{(4-11)}His_1Orn_2$ (SEQ ID NO: 285), $Arg_2Lys_1His_{(4-11)}Orn_1$ (SEQ ID NO: 286), $Arg_1LysHis_{(4-11)}Orn_1$ (SEQ ID NO: 287), $Arg_1Lys_1His_{(4-11)}Orn_2$ (SEQ ID NO: 288), $Arg_2Lys_1His_1Orn_{(4-11)}$ (SEQ ID NO: 289), $Arg_1Lys_2His_1Orn_{(4-11)}$ (SEQ ID NO: 290), $Arg_1Lys_1His_2Orn_{(4-11)}$ (SEQ ID NO: 291);

$Arg_{(3-10)}Lys_3His_1Orn_1$ (SEQ ID NO: 292), $Arg_{(3-10)}Lys_2His_2Orn_1$ (SEQ ID NO: 293), $Arg_{(3-10)}Lys_2His_1Orn_2$ (SEQ ID NO: 294), $Arg_{(3-10)}Lys_1His_2Orn_2$ (SEQ ID NO: 295), $Arg_{(3-10)}Lys_1His_1Orn_3$ (SEQ ID NO: 296), $Arg_3Lys_{(3-10)}His_1Orn_1$ (SEQ ID NO: 297), $Arg_2Lys_{(3-10)}His_2Orn_1$ (SEQ ID NO: 298), $Arg_2Lys_{(3-10)}His_1Orn_2$ (SEQ ID NO: 299), $Arg_1Lys_{(3-10)}His_2Orn_2$ (SEQ ID NO: 300), $Arg_1Lys_{(3-10)}His_1Orn_3$ (SEQ ID NO: 301), $Arg_3Lys_1His_{(3-10)}Orn_1$ (SEQ ID NO: 302), $Arg_2Lys_2His_{(3-10)}Orn_1$ (SEQ ID NO: 303), $Arg_2Lys_1His_{(3-10)}Orn_2$ (SEQ ID NO: 304), $Arg_1Lys_2His_{(3-10)}Orn_2$ (SEQ ID NO: 305), $Arg_1Lys_1His_{(3-10)}Orn_3$ (SEQ ID NO: 306), $Arg_3Lys_1His_1Orn_{(3-10)}$ (SEQ ID NO: 307), $Arg_2Lys_2His_1Orn_{(3-10)}$ (SEQ ID NO: 308), $Arg_2Lys_1His_2Orn_{(3-10)}$ (SEQ ID NO: 309), $Arg_1Lys_2His_2Orn_{(3-10)}$ (SEQ ID NO: 310), $Arg_1Lys_1His_3Orn_{(3-10)}$ (SEQ ID NO: 311);

$Arg_{(2-9)}Lys_4His_1Orn_1$ (SEQ ID NO: 312), $Arg_{(2-9)}Lys_1His_4Orn_1$ (SEQ ID NO: 313), $Arg_{(2-9)}Lys_1His_1Orn_4$ (SEQ ID NO: 314), $Arg_{(2-9)}Lys_3His_2Orn_1$ (SEQ ID NO: 315), $Arg_{(2-9)}Lys_3His_1Orn_2$ (SEQ ID NO: 316), $Arg_{(2-9)}Lys_2His_3Orn_1$ (SEQ ID NO: 317), $Arg_{(2-9)}Lys_2His_1Orn_3$ (SEQ ID NO: 318), $Arg_{(2-9)}Lys_1His_3Orn_2$ (SEQ ID NO: 319), $Arg_{(2-9)}Lys_1His_3Orn_2$ (SEQ ID NO: 320), $Arg_{(2-9)}Lys_2His_2Orn_2$ (SEQ ID NO: 321), $Arg_4Lys_{(2-9)}His_1Orn_1$ (SEQ ID NO: 322), $Arg_1Lys_{(2-9)}His_4Orn_1$ (SEQ ID NO: 323), $Arg_1Lys_{(2-9)}His_1Orn_4$ (SEQ ID NO: 324), $Arg_3Lys_{(2-9)}His_2Orn_1$ (SEQ ID NO: 325), $Arg_3Lys_{(2-9)}His_1Orn_2$ (SEQ ID NO: 326), $Arg_2Lys_{(2-9)}His_3Orn_1$ (SEQ ID NO: 327), $Arg_2Lys_{(2-9)}His_1Orn_3$ (SEQ ID NO: 328), $Arg_1Lys_{(2-9)}His_2Orn_3$ (SEQ ID NO: 329), $Arg_1Lys_{(2-9)}His_3Orn_2$ (SEQ ID NO: 330), $Arg_2Lys_{(2-9)}His_2Orn_2$ (SEQ ID NO: 331), $Arg_4Lys_1His_{(2-9)}Orn_1$ (SEQ ID NO: 332), $Arg_1Lys_4His_{(2-9)}Orn_1$ (SEQ ID NO: 333), $Arg_1Lys_1His_{(2-9)}Orn_4$ (SEQ ID NO: 334), $Arg_3Lys_2His_{(2-9)}Orn_1$ (SEQ ID NO: 335), $Arg_3Lys_1His_{(2-9)}Orn_2$ (SEQ ID NO: 336), $Arg_3Lys_2His_{(2-9)}Orn_1$ (SEQ ID NO: 337), $Arg_2Lys_3His_{(2-9)}Orn_1$ (SEQ ID NO: 338), $Arg_2Lys_1His_{(2-9)}Orn_3$ (SEQ ID NO: 339), $Arg_1Lys_2His_{(2-9)}Orn_3$ (SEQ ID NO: 340), $Arg_1Lys_3His_{(2-9)}Orn_2$ (SEQ ID NO: 341), $Arg_2Lys_2His_{(2-9)}Orn_2$ (SEQ ID NO: 342), $Arg_4Lys_1His_1Orn_{(2-9)}$ (SEQ ID NO: 343), $Arg_1Lys_4His_1Orn_{(2-9)}$ (SEQ ID NO: 344), $Arg_1Lys_1His_4Orn_{(2-9)}$ (SEQ ID NO: 345), $Arg_3Lys_2His_1Orn_{(2-9)}$ (SEQ ID NO: 346), $Arg_3Lys_1His_2Orn_{(2-9)}$ (SEQ ID NO: 347), $Arg_3Lys_3His_1Orn_{(2-9)}$ (SEQ ID NO: 348), $Arg_2Lys_1His_3Orn_{(2-9)}$ (SEQ ID NO: 349), $Arg_1Lys_2His_3Orn_{(2-9)}$ (SEQ ID NO: 350), $Arg_1Lys_3His_2Orn_{(2-9)}$ (SEQ ID NO: 351), $Arg_2Lys_2His_2Orn_{(2-9)}$ (SEQ ID NO: 352);

$Arg_{(1-8)}Lys_5His_1Orn_1$ (SEQ ID NO: 353), $Arg_{(1-8)}Lys_1His_5Orn_1$ (SEQ ID NO: 354), $Arg_{(1-8)}Lys_1His_1Orn_5$ (SEQ ID NO: 355), $Arg_{(1-8)}Lys_4His_2Orn_1$ (SEQ ID NO: 356), $Arg_{(1-8)}Lys_2His_2Orn_1$ (SEQ ID NO: 357), $Arg_{(1-8)}Lys_2His_1Orn_4$ (SEQ ID NO: 358), $Arg_{(1-8)}Lys_1His_2Orn_4$ (SEQ ID NO: 359), $Arg_{(1-8)}Lys_1His_4Orn_2$ (SEQ ID NO: 360), $Arg_{(1-8)}Lys_4His_2Orn_2$ (SEQ ID NO: 361) $Arg_{(1-8)}Lys_3His_3Orn_1$ (SEQ ID NO: 362), $Arg_{(1-8)}Lys_3His_1Orn_3$ (SEQ ID NO: 363), $Arg_{(1-8)}Lys_1His_3Orn_3$ (SEQ ID NO: 364), $Arg_5Lys_{(1-8)}His_1Orn_1$ (SEQ ID NO: 365), $Arg_1Lys_{(1-8)}His_5Orn_1$ (SEQ ID NO: 366), $Arg_1Lys_{(1-8)}His_1Orn_5$ (SEQ ID NO: 367), $Arg_4Lys_{(1-8)}His_2Orn_1$ (SEQ ID NO: 368), $Arg_2Lys_{(1-8)}His_4Orn_1$ (SEQ ID NO: 369),

Arg$_2$Lys$_{(1-8)}$His$_1$Orn$_4$ (SEQ ID NO: 370), Arg$_1$Lys$_{(1-8)}$His$_2$Orn$_4$ (SEQ ID NO: 371), Arg$_1$Lys$_{(1-8)}$His$_1$Orn$_4$ (SEQ ID NO: 372), Arg$_4$Lys$_{(1-8)}$His$_1$Orn$_2$(SEQ ID NO: 373), Arg$_3$Lys$_{(1-8)}$His$_3$Orn$_1$ (SEQ ID NO: 374), Arg$_3$Lys$_{(1-8)}$His$_1$Orn$_3$ (SEQ ID NO: 375), Arg$_1$Lys$_{(1-8)}$His$_3$Orn$_3$ (SEQ ID NO: 376), Arg$_5$Lys$_1$His$_{(1-8)}$Orn$_1$ (SEQ ID NO: 377), Arg$_1$Lys$_5$His$_{(1-8)}$Orn$_1$ (SEQ ID NO: 378), Arg$_1$Lys$_1$His$_{(1-8)}$Orn$_5$ (SEQ ID NO: 379), Arg$_4$Lys$_2$His$_{(1-8)}$Orn$_1$ (SEQ ID NO: 380), Arg$_2$Lys$_4$His$_{(1-8)}$Orn$_1$ (SEQ ID NO: 381), Arg$_2$Lys$_1$His$_{(1-8)}$Orn$_4$ (SEQ ID NO: 382), Arg$_1$Lys$_2$His$_{(1-8)}$Orn$_4$ (SEQ ID NO: 383), Arg$_1$Lys$_4$His$_{(1-8)}$Orn$_2$ (SEQ ID NO: 384), Arg$_4$Lys$_1$His$_{(1-8)}$Orn$_2$ (SEQ ID NO: 385), Arg$_3$Lys$_3$His$_{(1-8)}$Orn$_1$ (SEQ ID NO: 386), Arg$_3$Lys$_1$His$_{(1-8)}$Orn$_3$ (SEQ ID NO: 387), Arg$_1$Lys$_3$His$_{(1-8)}$Orn$_3$ (SEQ ID NO: 388), Arg$_5$Lys$_1$His$_1$Orn$_{(1-8)}$ (SEQ ID NO: 389), Arg$_1$Lys$_5$His$_1$Orn$_{(1-8)}$ (SEQ ID NO: 390), Arg$_1$Lys$_1$His$_5$Orn$_{(1-8)}$ (SEQ ID NO: 391), Arg$_4$Lys$_2$His$_1$Orn$_{(1-8)}$ (SEQ ID NO: 392), Arg$_2$Lys$_4$His$_1$Orn$_{(1-8)}$ (SEQ ID NO: 393), Arg$_2$Lys$_1$His$_4$Orn$_{(1-8)}$ (SEQ ID NO: 394), Arg$_1$Lys$_2$His$_4$Orn$_{(1-8)}$ (SEQ ID NO: 395), Arg$_1$Lys$_4$His$_2$Orn$_{(1-8)}$ (SEQ ID NO: 396), Arg$_4$Lys$_1$His$_2$Orn$_{(1-8)}$ (SEQ ID NO: 397), Arg$_3$Lys$_3$His$_1$Orn$_{(1-8)}$ (SEQ ID NO: 398), Arg$_3$Lys$_1$His$_3$Orn$_{(1-8)}$ (SEQ ID NO: 399), Arg$_1$Lys$_3$His$_3$Orn$_{(1-8)}$ (SEQ ID NO: 400);

According to one preferred embodiment, the oligopeptide of the complexed RNA of the present invention, having the empirical formula (Arg)$_i$;(Lys)$_m$;(His)$_n$;(Orn)$_o$;(Xaa)$_x$ as shown above, is selected from the subgroup consisting of: Arg$_8$, Arg$_9$, Arg$_{10}$, Arg$_{11}$, Arg$_{12}$, Arg$_{13}$, Arg$_{14}$, Arg$_{15}$, (SEQ ID NOs: 1-8); Lys$_8$, Lys$_9$, Lys$_{10}$, Lys$_{11}$, Lys$_{12}$, Lys$_{13}$, Lys$_{14}$, Lys$_{15}$, (SEQ ID NOs: 9-16); His$_8$, His$_9$, His$_{10}$, His$_{11}$, His$_{12}$, His$_{13}$, His$_{14}$, His$_{15}$, (SEQ ID NOs: 17-24); or Orn$_8$, Orn$_9$, Orn$_{10}$, Orn$_{11}$, Orn$_{12}$, Orn$_{13}$, Orn$_{14}$, Orn$_{15}$, (SEQ ID NOs: 25-32).

According to another preferred embodiment, the oligopeptide of the complexed RNA of the present invention, having the empirical formula (Arg)$_i$;(Lys)$_m$;(His)$_n$;(Orn)$_o$;(Xaa)$_x$ as shown above, is selected from the subgroup consisting of general formulas Arg$_9$ (also termed R9), Arg$_9$His$_3$ (also termed R9H3), His$_3$Arg$_9$His$_3$ (also termed H3R9H3), TyrSerSerArg$_9$SerSerTyr (also termed YSSR9SSY), His$_3$Arg$_9$SerSerTyr (also termed H3R9SSY), (ArgLysHis)$_4$ (also termed (RKH)4), Tyr(ArgLysHis)$_2$Arg (also termed Y(RKH)2R). Even more preferably, these general formulas are defined as follows:

Arg$_9$:
(SEQ ID NO: 2)
Arg-Arg-Arg-Arg-Arg-Arg-Arg-Arg-Arg

Arg$_9$His$_3$:
(SEQ ID NO: 39)
Arg-Arg-Arg-Arg-Arg-Arg-Arg-Arg-Arg-His-His-His

His$_3$Arg$_9$His$_3$:
(SEQ ID NO: 40)
His-His-His-Arg-Arg-Arg-Arg-Arg-Arg-Arg-Arg-Arg-His-His-His

TyrSerSerArg$_9$SerSerTyr:
(SEQ ID NO: 41)
Tyr-Ser-Ser-Arg-Arg-Arg-Arg-Arg-Arg-Arg-Arg-Arg-Ser-Ser-Tyr

His$_3$Arg$_9$SerSerTyr:
(SEQ ID NO: 42)
His-His-His-Arg-Arg-Arg-Arg-Arg-Arg-Arg-Arg-Arg-Ser-Ser-Tyr (ArgLysHis)$_4$:
(SEQ ID NO: 43)
Arg-Lys-His-Arg-Lys-His-Arg-Lys-His-Arg-Lys-His

Tyr(ArgLysHis)$_2$Arg:
(SEQ ID NO: 44)
Tyr-Arg-Lys-His-Arg-Lys-His-Arg

The at least one oligopeptide of the complexed RNA (molecule) of the present invention, having the empirical formula (Arg)$_i$;(Lys)$_m$;(His)$_n$;(Orn)$_o$;(Xaa)$_x$ as shown above, may be additionally modified. Modifications in the context of the present invention typically comprise any modification suitable for peptides, provided that these modifications do not interfere with the transfection capabilities of the resulting complexed RNA.

Typical modifications may thus include e.g. the use of modified amino acids as defined above. Furthermore, the terminal amino acid residues of the oligopeptide, having the empirical formula (Arg)$_i$;(Lys)$_m$;(His)$_n$;(Orn)$_o$;(Xaa)$_x$ as shown above, with their carboxy (C-terminus) and their amino (N-terminus) groups (as well as carboxy or amide amino acid side chain groups, see above) may be present in their protected (e.g. the C terminus protected by an amide group) and/or unprotected form, using appropriate amino or carboxyl protecting groups. Also, acid-addition salts of the oligopeptide, having the empirical formula (Arg)$_i$;(Lys)$_m$;(His)$_n$;(Orn)$_o$;(Xaa)$_x$ as shown above, may be used. Common acid addition salts are hydrohalic acid salts, i.e., HBr, HI, or more preferably, HCl.

PEGylation of terminal or side chain carboxyl groups or the epsilon-amino group of lysine occurring in the oligopeptide, having the empirical formula (Arg)$_i$;(Lys)$_m$;(His)$_n$;(Orn)$_o$;(Xaa)$_x$ as shown above, confers resistance to agglomeration and serum degradation and is also within the scope of the present invention.

The at least one oligopeptide of the complexed RNA (molecule) of the present invention, having the empirical formula (Arg)$_i$;(Lys)$_m$;(His)$_n$;(Orn)$_o$;(Xaa)$_x$ as shown above, may furthermore be modified to bind to or be coupled to at least one specific ligand, wherein the at least one specific ligand may be bound to or coupled to one or both terminal ends of the at least one oligopeptide. The at least one specific ligand bound to or coupled to one or both terminal ends of the oligopeptide may be identical or different and may be selected from any compound capable to bind to or interact with a receptor or a protein or a protein/receptor complex, e.g. at the cell surface, e, e.g., without being limited thereto, RGD-peptide, transferrin or mannose, etc.

Other preferred modifications resulting in derivatives of the oligopeptide, having the empirical formula (Arg)$_i$;(Lys)$_m$;(His)$_n$;(Orn)$_o$;(Xaa)$_x$ as shown above, are based on carbohydrates and/or lipids which may be covalently coupled to the oligopeptide. It is preferred to couple carbohydrates and/or lipids to serine, threonine, asparagine, glutamine or tyrosine or glutamate or aspartate via their reactive side chain moieties. Alternatively, carbohydrates and/or lipids may also be linked to the terminal moieties of the oligopeptide as defined herein. Furthermore, the oligopeptide may be coupled to a functionally different peptide or protein moiety, which may also stabilize the oligopeptide and/or may serve to improve the transport properties of oligopeptide in body fluids, in particular blood. Suitable peptides or proteins may e.g. be selected from albumin, transferrin etc., which may be directly coupled to the oligopeptide, having the empirical formula (Arg)$_i$;(Lys)$_m$;(His)$_n$;(Orn)$_o$;(Xaa)$_x$ as shown above, or via a peptide or organic linker sequence. Preferably, these peptides or proteins are linked to one of the termini of the oligopeptide.

In this context, it is to be noted that a modification of the oligopeptide with lipids, having the empirical formula $(Arg)_i;(Lys)_m;(His)_n;(Orn)_o;(Xaa)_x$ as shown above, does typically not include the use of (saturated or non-saturated) fatty acids, particularly not the use of long chain (saturated or non-saturated) fatty acids (in particular with a chain length of $>C_{12}$, $>C_{14}$ or $>C_{16}$). Thus, in the context of the present invention, modification of the oligopeptide with fatty acids, having the empirical formula $(Arg)_i;(Lys)_m;(His)_n;(Orn)_o;(Xaa)_x$ as shown above, does not form an integral part of the present invention. However, if fatty acids are used at all to modify the carrier peptide, the x may be selected, without being limited thereto, from the group comprising e.g. butanoic fatty acid (butyric fatty acid), pentanoic fatty acid (valeric fatty acid), hexanoic fatty acid (caproic fatty acid), octanoic fatty acid (caprylic fatty acid), nonanoic fatty acid (pelargonic fatty acid), decanoic fatty acid (capric fatty acid), dodecanoic fatty acid (lauric fatty acid), tetradecanoic fatty acid (myristic fatty acid), hexadecanoic fatty acid (palmitic fatty acid), heptadecanoic fatty acid (margaric (daturic) fatty acid), octadecanoic fatty acid (stearic fatty acid), eicosanoic fatty acid (arachidic fatty acid), docosanoic fatty acid (behenic fatty acid), tetracosanoic fatty acid (lignoceric fatty acid), hexacosanoic fatty acid (cerotic fatty acid), heptacosanoic fatty acid (carboceric fatty acid), octacosanoic fatty acid (montanic fatty acid), triacontanoic fatty acid (melissic fatty acid), dotriacontanoic fatty acid (lacceroic fatty acid), tritriacontanoic fatty acid (ceromelissic (psyllic) fatty acid), tetratriacontanoic fatty acid (geddic fatty acid), pentatriacontanoic fatty acid (ceroplastic fatty acid), etc., or their non-saturated analogs. As a particular example, the present invention does typically not include the use of octadecanoic fatty acid (stearic fatty acid) or its non-saturated analogs for modification of the carrier peptides of formula I, i.e. typically no stearylated oligopeptides of formula I may be used herein for complexation of the RNA component of the inventive complex.

In order to circumvent the problem of degradation of the oligopeptide, having the empirical formula $(Arg)_i;(Lys)_m;(His)_n;(Orn)_o;(Xaa)_x$ as shown above, according to another embodiment of the present invention a retro-inverso isomer of the above oligopeptide composed of D amino acids or at least partially composed of D amino acids may be used. The term "retro-inverso isomer" refers to an isomer of a linear peptide in which the direction of the sequence is reversed and the chirality of each amino acid residue is inverted (see, e.g., Jameson et al., Nature, 368, 744-746 (1994); Brady et al., Nature, 368, 692-693 (1994)). With respect to the parent peptide, the retro-inverso peptide is assembled in reverse order of amino acids, typically with F-moc amino acid derivatives. Typically, the crude peptides may be purified by reversed phase HPLC.

Other modifications, which may be introduced into the oligopeptide, having the empirical formula $(Arg)_i;(Lys)_m;(His)_n;(Orn)_o;(Xaa)_x$ as shown above, relate to modifications of the peptide backbone. Preferably, the modified oligopeptides are scaffold mimetics. Their backbone is different from the natural occurring backbone, while their side-chain structures are identical with the oligopeptides or their fragments, variants or derivatives. In general, scaffold mimetics exhibit a modification of one or more of the backbone chain members (NH, CH, CO), either as substitution (preferably) or as an insertion. Substituents are e.g. (I) —O—, —S—, or —CH$_2$— instead of —NH—; (II) —N—, C-Alkyl-, or —BH— instead of —CHR— and (III) —CS—, —CH$_2$—, —SO$_n$—, —P=O(OH)—, or —B(OH)— instead of —CO—. A peptide mimetic of an oligopeptide, having the empirical formula $(Arg)_i;(Lys)_m;(His)_n;(Orn)_o;(Xaa)_x$ as defined herein, may be a combination of each of these modifications. In particular, modifications of each the groups I, II and III may be combined. In a peptide mimetic each backbone chain member may be modified or, alternatively, only a certain number of chain members may be exchanged for a non-naturally occurring moiety. Preferably, all backbone chain members of an oligopeptide, having the empirical formula $(Arg)_i;(Lys)_m;(His)_n;(Orn)_o;(Xaa)_x$ as defined herein, of either —NH—, —CHR— or CO are exchanged for another non-naturally occurring group. In case the amide bond (—NH—CO—) of the oligopeptide backbone is substituted (in the entire molecule or at least in one single position), preferable substitution moieties are bioisosteric, e.g. retro-inverse amide bonds (—CO—NH—), hydroxyl ethylene (—CH(OH)—CH$_2$—), alkene (CH$_2$=CH—), carba (CH$_2$—CH$_2$—) and/or —P=O (OH)—CH$_2$—). Alternatively, backbone chain elongation by insertions may occur in a scaffold mimetic of the oligopeptide, having the empirical formula $(Arg)_i;(Lys)_m;(His)_n;(Orn)_o;(Xaa)_x$ as defined herein, e.g. by moieties flanking the C-alpha atom. On either side of the C-alpha atom e.g. —O—, —S—, —CH—, —NH— may be inserted.

Particularly preferred are oligocarbamate peptide backbone structure of the oligopeptide, having the empirical formula $(Arg)_i;(Lys)_m;(His)_n;(Orn)_o;(Xaa)_x$, as defined herein. Thereby amide bond may be replaced by a carbamate moiety. The monomeric N-protected amino alkyl carbonates are accessible via the corresponding amino acids or amino alcohols. They are converted into active esters, e.g. p-nitro phenyl ester by using the F-moc moiety or a photo sensitive nitroatryloxycarbonyl group by solid phase synthesis.

The complexed RNA of the present invention further comprises at least one RNA (molecule) suitable for transfection purposes, wherein this at least one RNA (molecule) is complexed with one or more oligopeptides, as disclosed above with empirical formula I $((Arg)_i;(Lys)_m;(His)_n;(Orn)_o;(Xaa)_x)$.

The at least one RNA (molecule) of the complexed RNA of the present invention may have any length (preferably dependent on the type of RNA to be applied as a complexed RNA according to the present invention). Without being restricted thereto, the at least one RNA (molecule) may have a length of 5 to 20000 nucleotides, more preferably a length of 5 to 10000 or of 300 to 10000 nucleotides, even more preferably a length of 5 to 5000 nucleotides, and most preferably a length of 20 to 5000, of 50 to 5000, of 100 to 5000 or of 300 to 10000 nucleotides depending on the type of RNA to be transfected (see disclosure below).

The at least one RNA (molecule) of the complexed RNA of the present invention may be any RNA, preferably, without being limited thereto, a short RNA oligonucleotide (preferable length 5 to 80 or, more preferably 20 to 80 nucleotides), a coding RNA, an immunostimulatory RNA, a siRNA, an antisense RNA, or riboswitches, ribozymes or aptamers. Furthermore, the at least one RNA (molecule) of the complexed RNA of the present invention may be a single- or a double-stranded RNA (which may also be regarded as an RNA (molecule) due to non-covalent association of two single-stranded RNA (molecules)) or a partially double-stranded RNA (which is typically formed by a longer and a shorter single-stranded RNA molecule or by two single stranded RNA-molecules, which are about equal in length, wherein one single-stranded RNA molecule is partially complementary to the other single-stranded RNA molecule and both thus form a double-stranded RNA molecule in this region). Preferably, the at least one RNA (molecule) of the complexed RNA of the present invention may be a single-stranded RNA. The at least one RNA (molecule) of the complexed RNA of the present invention may also be a circular or linear RNA, preferably a linear RNA. More preferably, the at least one RNA (molecule) of the complexed RNA of the present invention may be a (linear) single-stranded RNA. The at least one RNA (molecule) of the complexed RNA of the present invention may be a ribosomal RNA (rRNA), a transfer RNA (tRNA), a messenger RNA (mRNA), or a viral RNA (vRNA), preferably a mRNA. The present invention allows all of these RNAs to be transfected into the cell. In this context, an mRNA is typically an RNA, which is composed of several structural elements, e.g. an optional 5'-UTR region, an upstream positioned ribosomal binding site followed by a coding region, an optional 3'-UTR region, which may be followed by a poly-A tail (and/or a poly-C-tail). An mRNA may occur as a mono-, di-, or even multicistronic RNA, i.e. an RNA which carries the coding sequences of one, two or more proteins. Such coding sequences in di-, or even multicistronic mRNA may be separated by at least one IRES sequence, e.g. as defined herein.

Short RNA Oligonucleotides

In a first embodiment, the at least one RNA (molecule) of the complexed RNA of the present invention may be a short RNA oligonucleotide. Short RNA oligonucleotides in the context of the present invention may comprise any RNA as defined above. Preferably, the short RNA oligonucleotide may be a single- or a double-stranded RNA oligonucleotide, more preferably a single-stranded RNA oligonucleotide. Even more preferably, the short RNA oligonucleotide may be a linear single-stranded RNA oligonucleotide.

Preferably, the short RNA oligonucleotides as used herein comprise a length as defined above in general for RNA molecules, more preferably a length of 5 to 100, of 5 to 50, or of 5 of 30, or, alternatively, a length of 20 to 100, of 20 to 80, or, even more preferably, of 20 of 60 nucleotides. Short RNA oligonucleotides may be used for various purposes, e.g. for (unspecific) immune stimulation, or reducing/suppressing transcription/translation of genes.

Coding RNA

In a second embodiment, the at least one RNA (molecule) of the complexed RNA of the present invention may be a coding RNA. The coding RNA of the complexed RNA of the present invention may be any RNA as defined above. Preferably, the coding RNA may be a single- or a double-stranded RNA, more preferably a single-stranded RNA, and/or a circular or linear RNA, more preferably a linear RNA. Even more preferably, the coding RNA may be a (linear) single-stranded RNA. Most preferably, the coding RNA may be a ((linear) single-stranded) messenger RNA (mRNA).

The coding RNA may further encode a protein or a peptide, which may be selected, without being restricted thereto, e.g. from therapeutically active proteins or peptides, tumor antigens, antibodies, immunostimulating proteins or peptides, etc., or from any other protein or peptide suitable for a specific (therapeutic) application, wherein the at least one RNA (molecule) encoding the protein is to be transported into a cell, a tissue or an organism and the protein is expressed subsequently in this cell, tissue or organism.

In this context, therapeutically active proteins may be selected from any recombinant or isolated proteins known to a skilled person from the prior art. Without being restricted thereto therapeutically active proteins as encoded by the at least one RNA (molecule) of the complexed RNA as defined herein may be selected from apoptotic factors or apoptosis related proteins including AIF, Apaf e.g. Apaf-1, Apaf-2, Apaf-3, oder APO-2 (L), APO-3 (L), Apopain, Bad, Bak, Bax, Bcl-2, Bcl-x$_L$, Bcl-x$_5$, bik, CAD, Calpain, Caspase e.g. Caspase-1, Caspase-2, Caspase-3, Caspase-4, Caspase-5, Caspase-6, Caspase-7, Caspase-8, Caspase-9, Caspase-10, Caspase-11, ced-3, ced-9, c-Jun, c-Myc, crm A, cytochrom C, CdR1, DcR1, DD, DED, DISC, DNA-PK$_{C5}$, DR3, DR4, DR5, FADD/MORT-1, FAK, Fas (Fas-ligand CD95/fas (receptor)), FLICE/MACH, FLIP, fodrin, fos, G-Actin, Gas-2, gelsolin, granzyme A/B, ICAD, ICE, JNK, lamin A/B, MAP, MCL-1, Mdm-2, MEKK-1, MORT-1, NEDD, NF-$_{kappa}$B, NuMa, p53, PAK-2, PARP, perforin, PITSLRE, PKCdelta, pRb, presenilin, prICE, RAIDD, Ras, RIP, sphingomyelinase, thymidinkinase from herpes simplex, TRADD, TRAF2, TRAIL-R1, TRAIL-R2, TRAIL-R3, transglutaminase, etc.

Therapeutically active proteins as encoded by the at least one RNA (molecule) of the complexed RNA as defined herein may also be selected from recombinant proteins, including proteins selected from the group consisting of 0ATL3, 0FC3, 0PA3, 0PD2, 4-1BBL, 5T4, 6Ckine, 707-AP, 9D7, A2M, AA, AAAS, AACT, AASS, ABAT, ABCA1, ABCA4, ABCB1, ABCB11, ABCB2, ABCB4, ABCB7, ABCC2, ABCC6, ABCC8, ABCD1, ABCD3, ABCG5, ABCC8, ABL1, ABO, ABR ACAA1, ACACA, ACADL, ACADM, ACADS, ACADVL, ACAT1, ACCPN, ACE, ACHE, ACHM3, ACHM1, ACLS, ACPI, ACTA1, ACTC, ACTN4, ACVRL1, AD2, ADA, ADAMTS13, ADAMTS2, ADFN, ADH1B, ADH1C, ADLDH3A2, ADRB2, ADRB3, ADSL, AEZ, AFA, AFD1, AFP, AGA, AGL, AGMX2, AGPS, AGS1, ACT, AGTR1, AGXT, AH02, AHCY, AHDS, AHHR, AHSG, AIC, AIED, AIH2, AIH3, AIM-2, AIPL1, AIRE, AK1, ALAD, ALAS2, ALB, HPG1, ALDH2, ALDH3A2, ALDH4A1, ALDH5A1, ALDH1A1, ALDOA, ALDOB, ALMS1, ALPL, ALPP, ALS2, ALX4, AMACR, AMBP, AMCD, AMCD1, AMCN, AMELX, AMELY, AMGL, AMH, AMHR2, AMPD3, AMPD1, AMT, ANC, ANCR, ANK1, ANOP1, AOM, AP0A4, AP0C2, AP0C3, AP3B1, APC, aPKC, APOA2, APOA1, APOB, APOC3, APOC2, APOE, APOH, APP, APRT, APS1, AQP2, AR, ARAF1, ARG1, ARHGEF12, ARMET, ARSA, ARSB, ARSC2, ARSE, ART-4, ARTC1/m, ARTS, ARVD1, ARX, AS, ASAH, ASAT, ASD1, ASL, ASMD, ASMT, ASNS, ASPA, ASS, ASSP2, ASSP5, ASSP6, AT3, ATD, ATHS, ATM, ATP2A1, ATP2A2, ATP2C1, ATP6B1, ATP7A, ATP7B, ATP8B1, ATPSK2, ATRX, ATXN1, ATXN2, ATXN3, AUTS1, AVMD, AVP, AVPR2, AVSD1, AXIN1, AXIN2, AZF2, B2M, B4GALT7, B7H4, BAGE, BAGE-1, BAX, BBS2, BBS3, BBS4, BCA225, BCAA, BCH, BCHE, BCKDHA, BCKDHB, BCL10, BCL2, BCL3, BCL5, BCL6, BCPM, BCR, BCR/ABL, BDC, BDE, BDMF, BDMR, BEST1, beta-Catenin/m, BF, BFHD, BFIC, BFLS, BFSP2, BGLAP, BGN, BHD, BHR1, BING-4, BIRC5, BJS, BLM, BLMH, BLNK, BMPR2, BPGM, BRAF, BRCA1, BRCA1/m, BRCA2, BRCA2/m, BRCD2, BRCD1, BRDT, BSCL, BSCL2, BTAA, BTD, BTK, BUB1, BWS, BZX, C0L2A1, C0L6A1, C1 NH, C1QA, C1QB, C1QG, C1S, C2, C3, C4A, C4B, C5, C6, C7, C7orf2, C8A, C8B, C9, CA125, CA15-3/CA27-29, CA195, CA19-9, CA72-4, CA2, CA242, CA50, CABYR, CACD, CACNA2D1, CACNA1A, CACNA1F, CACNA1S, CACNB2, CACNB4, CAGE, CA1, CALB3, CALCA, CALCR, CALM, CALR, CAM43, CAMEL, CAP-1, CAPN3, CARD15, CASP-5/m, CASP-8, CASP-8/m, CASR, CAT, CATM, CAV3, C131, CBBM, CBS, CCA1, CCAL2, CCAL1, CCAT, CCL-1, CCL-11, CCL-12, CCL-13, CCL-14, CCL-15, CCL-16, CCL-17, CCL-18, CCL-19, CCL-2, CCL-20, CCL-21, CCL-22, CCL-23, CCL-24, CCL-25, CCL-27, CCL-3, CCL-4, CCL-5, CCL-7, CCL-8, CCM1, CCNB1, CCND1, CCO, CCR2, CCR5, CCT, CCV, CCZS, CD1, CD19, CD20, CD22, CD25, CD27, CD27L, cD3, CD30, CD30, CD30L, CD33, CD36, CD3E, CD3G, CD3Z, CD4, CD40, CD40L, CD44, CD44v, CD44v6, CD52, CD55, CD56, CD59, CD80, CD86, CDAN1, CDAN2, CDAN3, CDC27, CDC27/m, CDC2L1, CDH1, CDK4, CDK4/m, CDKN1C, CDKN2A, CDKN2A/m, CDKN1A, CDKN1C, CDL1, CDPD1, CDR1, CEA, CEACAM1, CEACAM5, CECR, CECR9, CEPA, CETP, CFNS, CFTR, CGF1, CHAC, CHED2, CHED1, CHEK2, CHM, CHML, CHR39c, CHRNA4, CHRNA1, CHRNB1, CHRNE, CHS, CHS1, CHST6, CHX10, CIAS1, CIDX, CKN1, CLA2, CLA3, CLA1, CLCA2, CLCN1, CLCN5, CLCNKB, CLDN16, CLP, CLN2, CLN3, CLN4, CLN5, CLN6, CLN8, C1 QA, C1 QB, C1QG, C1R, CLS, CMCWTD, CMDJ, CMD1A, CMD1B, CMH2, MH3, CMH6, CMKBR2, CMKBR5, CML28, CML66, CMM, CMT2B, CMT2D, CMT4A, CMT1A, CMTX2, CMTX3, C-MYC, CNA1, CND, CNGA3, CNGA1, CNGB3, CNSN, CNTF, COA-1/m, COCH, COD2, COD1, COH1, COL10A, COL2A2, COL11A2, COL17A1, COL1A1, COL1A2, COL2A1, COL3A1, COL4A3, COL4A4, COL4A5, COL4A6, COL5A1, COL5A2, COL6A1, COL6A2, COL6A3, COL7A1, COL8A2, COL9A2, COL9A3, COL11A1, COL1A2, COL23A1, COL1A1, COLQ, COMP, COMT, CORD5, CORD1, COX10, COX-2, CP, CPB2, CPO, CPP, CPS1, CPT2, CPT1A, CPX, CRAT, CRB1, CRBM, CREBBP, CRH, CRHBP, CRS, CRV, CRX, CRYAB, CRYBA1, CRYBB2, CRYGA, CRYGC, CRYGD, CSA, CSE, CSF1R, CSF2RA, CSF2RB, CSF3R, CSF1R, CST3, CSTB, CT, CT7, CT-9/BRD6, CTAA1, CTACK, CTEN, CTH, CTHM, CTLA4, CTM, CTNNB1, CTNS, CTPA, CTSB, CTSC, CTSK, CTSL, CTS1, CUBN, CVD1, CX3CL1, CXCL1, CXCL10, CXCL11, CXCL12, CXCL13, CXCL16, CXCL2, CXCL3, CXCL4, CXCL5, CXCL6, CXCL7, CXCL8, CXCL9, CYB5, CYBA, CYBB, CYBB5, CYFRA 21-1, CYLD, CYLD1, CYMD, CYP11B1, CYP11B2, CYP17, CYP17A1, CYP19, CYP19A1, CYP1A2, CYP1B1, CYP21A2, CYP27A1, CYP27B1, CYP2A6, CYP2C, CYP2C19, CYP2C9, CYP2D, CYP2D6, CYP2D7P1, CYP3A4, CYP7B1, CYPB1, CYP11B1, CYP1A1, CYP1B1, CYRAA, D40, DADI, DAM, DAM-10/MAGE-B1, DAM-6/MAGE-B2, DAX1, DAZ, DBA, DBH, DBI, DBT, DCC, DC-CK1, DCK, DCR, DCX, DDB 1, DDB2, DDIT3, DDU, DECR1, DEK-CAN, DEM, DES, DF, DFN2, DFN4, DFN6, DFNA4, DFNA5, DFNB5, DGCR, DHCR7, DHFR, DHOF, DHS, DIA1, DIAPH2, DIAPH1, DIH1, DIO1, DISCI, DKC1, DLAT, DLD, DLL3, DLX3, DMBT1, DMD, DM1, DMPK, DMWD, DNAI1, DNASE1, DNMT3B, DPEP1, DPYD, DPYS, DRD2, DRD4, DRPLA, DSCR1, DSG1, DSP, DSPP, DSS, DTDP2, DTR, DURS1, DWS, DYS, DYSF, DYT2, DYT3, DYT4, DYT2, DYT1, DYX1, EBAF, EBM, EBNA, EBP, EBR3, EBS1, ECA1, ECB2, ECE1, ECGF1, ECT, ED2, ED4, EDA, EDAR, ECA1, EDN3, EDNRB, EEC1, EEF1A1L14, EEGV1, EFEMP1, EFTUD2/m, EGFR, EGFR/Her1, EGI, EGR2, EIF2AK3, elF4G, EKV, EI IS, ELA2, ELF2, ELF2M, ELK1, ELN, ELONG, EMD, EML1, EMMPRIN, EMX2, ENA-78, ENAM, END3, ENG, ENO1, ENPP1, ENUR2, ENUR1, EOS, EP300, EPB41, EPB42, EPCAM, EPD, EphA1, EphA2, EphA3, EphrinA2, EphrinA3, EPHX1, EPM2A, EPO, EPOR, EPX, ERBB2, ERCC2 ERCC3, ERCC4, ERCC5, ERCC6, ERVR, ESR1, ETFA, ETFB, ETFDH, ETM1, ETV6-AML1, ETV1, EVC, EVR2, EVR1, EWSR1, EXT2, EXT3, EXT1, EYA1, EYCL2, EYCL3, EYCL1, EZH2, F10, F11, F12, F13A1, F13B, F2, F5, F5F8D, F7, F8, F8C, F9, FABP2, FACL6, FAH, FANCA, FANCB, FANCC, FANCD2, FANCF, FasL, FBN2, FBN1, FBP1, FCG3RA, FCGR2A, FCGR2B, FCGR3A, FCHL, FCMD, FCP1, FDPSL5, FECH, FEO, FEOM1, FES, FGA, FGB, FGD1, FGF2, FGF23, FGF5, FGFR2, FGFR3, FGFR1, FGG, FGS1, FH, FIC1, FIH, F2, FKBP6, FLNA, FLT4, FMO3, FMO4, FMR2, FMR1, FN, FN1/m, FOXC1, FOXE1, FOXL2, FOXO1A, FPDMM, FPF, Fra-1, FRAXF, FRDA, FSHB, FSHMD1A, FSHR, FTH1, FTHL17, FTL, FTZF1, FUCA1, FUT2, FUT6, FUT1, FY, G250, G250/CAIX, G6PC, G6PD, G6PT1, G6PT2, GAA, GABRA3, GAGE-1, GAGE-2, GAGE-3, GAGE-4, GAGE-5, GAGE-6, GAGE-7b, GAGE-8, GALC, GALE, GALK1, GALNS, GALT, GAMT, GAN, GAST, GASTRIN17, GATA3, GATA, GBA, GBE, GC, GCDH, GCGR, GCH1, GCK, GCP-2, GCS1, G-CSF, GCSH, GCSL, GCY, GDEP, GDF5, GDI1, GDNF, GDXY, GFAP, GFND, GGCX, GGT1, GH2, GH1, GHR, GHRHR, GHS, GIF, GINGF, GIP, GJA3, GJA8, GJB2, GJB3, GJB6, GJB1, GK, GLA, GLB, GLB1, GLC3B, GLC1B, GLC1C, GLDC, GLI3, GLP1, GLRA1, GLUD1, GM1 (fuc-GM1), GM2, GM-CSF, GMPR, GNAI2, GNAS, GNAT1, GNB3, GNE, GNPTA, GNRH, GNRH1, GNRHR, GNS, GnT-V, gp100, GP1BA, GP1BB, GP9, GPC3, GPD2, GPDS1, GP1, GP1BA, GPN1LW, GPNMB/m, GPSC, GPX1, GRHPR, GRK1, GRO, GRO, GRO, GRPR, GSE, GSM1, GSN, GSR, GSS, GTD, GTS, GUCAIA, GUCY2D, GULOP, GUSB, GUSM, GUST, GYPA, GYPC, GYS1, GYS2, HOKPP2, HOMG2, HADHA, HADHB, HAGE, HAGH, HAL, HAST-2, HB 1, HBA2, HBA1, HBB, HBBP1, HBD, HBE1, HBG2, HBG1, HBHR, HBP1, HBQ1, HBZ, HBZP, HCA, HCC-1, HCC-4, HCF2, HCG, HCL2, HCL1, HCR, HCVS, HD, HPN, HER2, HER2/NEU, HER3, HERV-K-MEL, HESX1, HEXA, HEXB, HF1, HFE, HF1, HGD, HHC2, HHC3, HHG, HK1 HLA-A, HLA-A*0201-R1701, HLA-A11/m, HLA-A2/m, HLA-DPB1 HLA-DRA, HLCS, HLXB9, HMBS, HMGA2, HMGCL, HMI, HMN2, HMOX1, HMS1 HMW-MAA, HND, HNE, HNF4A, HOAC, HOMEOBOX NKX 3.1, HOM-TES-14/SCP-1, HOM-TES-85, HOXA1 HOXD13, HP, HPC1, HPD, HPE2, HPE1, HPFH, HPFH2, HPRT1, HPS1, HPT, HPV-E6, HPV-E7, HR, HRAS, HRD, HRG, HRPT2, HRPT1, HRX, HSD11B2, HSD17B3, HSD17B4, HSD3B2, HSD3B3, HSN1, HSP70-2M, HSPG2, HST-2, HTC2, HTC1, hTERT, HTN3, HTR2C, HVBS6, HVBS1, HVEC, HV1S, HYAL1, HYR, 1-309, IAB, IBGC1, IBM2, ICAM1, ICAM3, iCE, ICHQ, ICR5, ICR1, ICS1, IDDM2, IDDM1, IDS, IDUA, IF, IFNa/b, IFNGR1, IGAD1, IGER, IGF-1R, IGF2R, IGF1, IGH, IGHC, IGHG2, IGHG1, IGHM, IGHR, IGKC, IHG1, 1HH, IKBKG, IL1, IL-1 RA, IL10, IL-11, IL12, IL12RB1, IL13, IL-13Rα2, IL-15, IL-16, IL-17, IL18, IL-1a, IL-1α, IL-1b, IL-1β, IL1RAPL1, IL2, IL24, IL-2R, IL2RA, IL2RG, IL3, IL3RA, IL4, IL4R, IL4R, IL-5, IL6, IL-7, IL7R, IL-8, IL-9, Immature laminin receptor, IMMP2L, INDX, INFGR1, INFGR2, INFα, IFNβINFγ, INS, INSR, INVS, IP-10, IP2, IPF1, IP1, IRF6, IRS1, ISCW, ITGA2, ITGA2B, ITGA6, ITGA7, ITGB2, ITGB3, ITGB4, ITIH1, ITM2B, IV, IVD, JAG1, JAK3, JBS, JBTS1, JMS, JPD, KAL1, KAL2, KALI, KLK2, KLK4, KCNA1, KCNE2, KCNE1, KCNH2, KCNJ1, KCNJ2, KCNJ1, KCNQ2, KCNQ3, KCNQ4, KCNQ1, KCS, KERA, KFM, KFS, KFSD, KHK, ki-67, KIAA0020, KIAA0205, KIAA0205/m, KIF1B, KIT, KK-LC-1, KLK3, KLKB1, KM-HN-1, KMS, KNG, KNO, K-RAS/m, KRAS2, KREV1, KRT1, KRT10, KRT12, KRT13, KRT14, KRT14L1, KRT14L2, KRT14L3, KRT16, KRT16L1, KRT16L2, KRT17, KRT18, KRT2A, KRT3, KRT4, KRT5, KRT6 A, KRT6B, KRT9, KRTHB1, KRTHB6, KRT1, KSA, KSS, KWE, KYNU, LOH19CR1, L1CAM, LAGE, LAGE-1, LALL, LAMA2, LAMA3, LAMB3, LAMB1, LAMC2, LAMP2, LAP, LCA5, LCAT, LCCS, LCCS 1, LCFS2, LCS1, LCT, LDHA, LDHB, LDHC, LDLR, LDLR/FUT, LEP, LEWISY, LGCR, LGGF-PBP, LGI1, LGMD2H, LGMD1A, LGMD1B, LHB, LHCGR, LHON, LHRH, LHX3, LIF, LIG1, LIMM, LIMP2, LIPA, LIPA, LIPB, LIPC, LIVIN, L1CAM, LMAN1, LMNA, LMX1B, LOLR, LOR, LOX, LPA, LPL, LPP, LQT4, LRP5, LRS 1, LSFC, LT-β, LTBP2, LTC4S, LYL1, XCL1, LYZ, M344, MA50, MAA, MADH4, MAFD2, MAFD1, MAGE, MAGE-A1, MAGE-A10, MAGE-A12, MAGE-A2, MAGE-A3, MAGE-A4, MAGE-A6, MAGE-A9, MAGEB1, MAGE-B10, MAGE-B16, MAGE-B17, MAGE-B2, MAGE-B3, MAGE-B4, MAGE-B5, MAGE-B6, MAGE-C1, MAGE-C2, MAGE-C3, MAGE-D1, MAGE-D2, MAGE-D4, MAGE-E1, MAGE-E2, MAGE-F1, MAGE-H1, MAGEL2, MGB1, MGB2, MAN2A1, MAN2B1, MANBA, MANBB, MAOA, MAOB, MAPK8IP1, MAPT, MART-1, MART-2, MART2/m, MAT1A, MBL2, MBP, MBS1, MC1R, MC2R, MC4R, MCC, MCCC2, MCCC1, MCDR1, MCF2, MCKD, MCL1, MC1R, MCOLN1, MCOP, MCOR, MCP-1, MCP-2, MCP-3, MCP-4, MCPH2, MCPH1, MCS, M-CSF, MDB, MDCR, MDM2, MDRV, MDS1, ME1, ME1/m, ME2, ME20, ME3, MEAX, MEB, MEC CCL-28, MECP2, MEFV, MELANA, MELAS, MEN1 MSLN, MET, MF4, MG50, MG50/PXDN, MGAT2, MGAT5, MGC1 MGCR, MGCT, MGI, MGP, MHC2TA, MHS2, MHS4, MIC2, MIC5, MIDI, MIF, MIP, MIP-5/HCC-2, MITF, MJD, MK167, MKKS, MKS1, MLH1, MLL, MLLT2, MLLT3, MLLT7, MLLT1, MLS, MLYCD, MMA1a, MMP 11, MMVP1, MN/CA IX-Antigen, MNG1, MN1, MOC31, MOCS2, MOCS1, MOG, MORC, MOS, MOV18, MPD1, MPE, MPFD, MPI, MPIF-1, MPL, MPO, MPS3C, MPZ, MRE11A, MROS, MRP1, MRP2, MRP3, MRSD, MRX14, MRX2, MRX20, MRX3, MRX40, MRXA, MRX1, MS, MS4A2, MSD, MSH2, MSH3, MSH6, MSS, MSSE, MSX2, MSX1, MTATP6, MTC03, MTCO1, MTCYB, MTHFR, MTM1, MTMR2, MTND2, MTND4, MTND5, MTND6, MTND1, MTP, MTR, MTRNR2, MTRNR1, MTRR, MTTE, MTTG, MTTI, MTTK, MTTL2, MTTL1, MTTN, MTTP, MTTS1, MUC1, MUC2, MUC4, MUC5AC, MUM-1, MUM-1/m, MUM-2, MUM-2/m, MUM-3, MUM-3/m, MUT, mutant p21 ras, MUTYH, MVK, MX2, MXI1, MY05A, MYB, MYBPC3, MYC, MYCL2, MYH6, MYH7, MYL2, MYL3, MYMY, MYO15A, MYO1G, MYO5A, MYO7A, MYOC, Myosin/m, MYP2, MYP1, NA88-A, N-acetylglucosaminyl-transferase-V, NAGA, NAGLU, NAMSD, NAPB, NAT2, NAT, NBIA1, NBS1, NCAM, NCF2, NCF1, NDN, NDP, NDUFS4, NDUFS7, NDUFS8, NDUFV1, NDUFV2, NEB, NEFH, NEM1, Neo-PAP, neo-PAP/m, NEU1, NEUROD1, NF2, NF1, NFYC/m, NGEP, NHS, NKS1, NKX2E, NM, NME1, NMP22, NMTC, NODAL, NOG, NOS3, NOTCH3, NOTCH1, NP, NPC2, NPC1, NPHL2, NPHP1, NPHS2, NPHS1, NPM/ALK, NPPA, NQO1, NR2E3, NR3C1, NR3C2, NRAS, NRAS/m, NRL, NROB1, NRTN, NSE, NSX, NTRK1, NUMA1, NXF2, NY-CO1, NY-ESO1, NY-ESO-B, NY-LU-12, ALDOA, NYS2, NYS4, NY-SAR-35, NYS1, NYX, OA3, OA1, OAP, OASD, OAT, OCA1, OCA2, OCD1, OCRL, OCRL1, OCT, ODDD, ODT1, OFC1, OFD1, OGDH, OGT, OGT/m, OPA2, OPA1, OPD1, OPEM, OPG, OPN, OPN1 LW, OPN1MW, OPN1SW, OPPG, OPTB1, TTD, ORM1, ORP1, OS-9, OS-9/m, OSM LIF, OTC, OTOF, OTSC1, OXCT1, OYTES1, P15, P190 MINOR BCR-ABL, P2RY12, P3, P16, P40, P4HB, P-501, P53, P53/m, P97, PABPN1, PAFAH1B1, PAFAH1P1, PAGE-4, PAGE-5, PAH, PAI-1, PAI-2, PAK3, PAP, PAPPA, PARK2, PART-1, PATE, PAX2, PAX3, PAX6, PAX7, PAX8, PAX9, PBCA, PBCRA1, PBT, PBX1, PBXP1, PC, PCBD, PCCA, PCCB, PCK2, PCK1, PCLD, PCOS1, PCSK1, PDB1, PDCN, PDE6A, PDE6B, PDEF, PDGFB, PDGFR, PDGFRL, PDHA1, PDR, PDX1, PECAM1, PEE1, PEO1, PEPD, PEX10, PEX12, PEX13, PEX3, PEX5, PEX6, PEX7, PEX1, PF4, PFBI, PFC, PFKFB1, PFKM, PGAM2, PGD, PGK1, PGK1P1, PGL2, PGR, PGS, PHA2A, PHB, PHEX, PHGDH, PHKA2, PHKA1, PHKB, PHKG2, PHP, PHYH, P1, P13, PIGA, PIM1-KINASE, PIN1, PIP5K1B, PITX2, PITX3, PKD2, PKD3, PKD1, PKDTS, PKHD1, PKLR, PKP1, PKU1, PLA2G2A, PLA2G7, PLAT, PLEC1, PLG, PLI, PLOD, PLP1, PMEL17, PML, PML/RARα, PMM2, PMP22, PMS2, PMS1, PNKD, PNLIP, POF1, POLA, POLH, POMC, PON2, PON1, PORC, POTE, POU1F1, POU3F4, POU4F3, POU1F1, PPAC, PPARG, PPCD, PPGB, PPH1, PPKB, PPMX, PPOX, PPP1R3A, PPP2R2B, PPT1, PRAME, PRB, PRB3, PRCA1, PRCC, PRD, PRDX5/m, PRF1, PRG4, PRKAR1A, PRKCA, PRKDC, PRKWNK4, PRNP, PROC, PRODH, PROM1, PROP1, PRO51, PRST, PRP8, PRPF31, PRPF8, PRPH2, PRPS2, PRPS1, PRS, PRSS7, PRSS1, PRTN3, PRX, PSA, PSAP, PSCA, PSEN2, PSEN1, PSG1, PSGR, PSM, PSMA, PSORS1, PTC, PTCH, PTCH1, PTCH2, PTEN, PTGS1, PTH, PTHR1, PTLAH, PTOS1, PTPN12, PTPNI I, PTPRK, PTPRK/m, PTS, PUJO, PVR, PVRL1, PWCR, PXE, PXMP3, PXR1, PYGL, PYGM, QDPR, RAB27A, RAD54B, RAD54L, RAG2, RAGE, RAGE-1, RAG1, RAP1, RARA, RASA1, RBAF600/m, RB1, RBP4, RBP4, RBS, RCA1, RCAS1, RCCP2, RCD1, RCV1, RDH5, RDPA, RDS, RECQL2, RECQL3, RECQL4, REG1A, REHOBE, REN, RENBP, RENS1, RET, RFX5, RFXANK, RFXAP, RGR, RHAG, RHAMM/CD168, RHD, RHO, Rip-1, RLBP1, RLN2, RLN1, RLS, RMD1, RMRP, ROM1, ROR2, RP, RP1, RP14, RP17, RP2, RP6, RP9, RPD1, RPE65, RPGR, RPGRIP1, RP1, RP10, RPS19, RPS2, RPS4X, RPS4Y, RPS6KA3, RRAS2, RS1, RSN, RSS, RU1, RU2, RUNX2, RUNXI, RWS, RY R1, S-100, SAA1, SACS, SAG, SAGE, SALL1, SARDH, SART1, SART2, SART3, SAS, SAX1, SCA2, SCA4, SCA5, SCA7, SCA8, SCA1, SCC, SCCD, SCF, SCLC1, SCN1A, SCN1B, SCN4A, SCN5A, SCNN1A, SCNN1B, SCNN1G, SCO2, SCP1, SCZD2, SCZD3, SCZD4, SCZD6, SCZD1, SDF-1α/β SDHA, SDHD, SDYS, SEDL, SERPENA7, SERPINA3, SERPINA6, SERPINA1, SERPINC1, SERPIND1, SERPINE1, SERPINF2, SERPING1, SERPINI1, SFTPA1, SFTPB, SFTPC, SFTPD, SGCA, SGCB, SGCD, SGCE, SGM1, SGSH, SGY-1, SH2D1A, SHBG, SHFM2, SHFM3, SHFM1, SHH, SHOX, SI, SIAL, SIALYL LEWISX, SIASD, S11, SIM1, SIRT2/m, SIX3, SJS1, SKP2, SLC10A2, SLC12A1, SLC12A3, SLC17A5, SLC19A2, SLC22A1L, SLC22A5, SLC25A13, SLC25A15, SLC25A20, SLC25A4, SLC25A5, SLC25A6, SLC26A2, SLC26A3, SLC26A4, SLC2A1, SLC2A2, SLC2A4, SLC3A1, SLC4A1, SLC4A4, SLC5A1, SLC5A5, SLC6A2, SLC6A3, SLC6A4, SLC7A7, SLC7A9, SLC11A1, SLOS, SMA, SMAD1, SMAL, SMARCB1, SMAX2, SMCR, SMCY, SM1, SMN2, SMN1, SMPD1, SNCA, SNRPN, SOD2, SOD3, SOD1, SOS1, SOST, SOX9, SOX10, Sp17, SPANXC, SPG23, SPG3A, SPG4, SPG5A, SPG5B, SPG6, SPG7, SPINK1, SPINK5, SPPK, SPPM, SPSMA, SPTA1, SPTB, SPTLC1, SRC, SRD5A2, SRPX, SRS, SRY, βhCG, SSTR2, SSX1, SSX2 (HOM-MEL-40/SSX2), SSX4, ST8, STAMP-1, STAR, STARP1, STATH, STEAP, STK2, STK11, STn/KLH, STO, STOM, STS, SUOX, SURF1, SURVIVIN-2B, SYCP1, SYM1, SYN1, SYNS1, SYP, SYT/SSX, SYT-SSX-1, SYT-SSX-2, TA-90, TAAL6, TACSTD1, TACSTD2, TAG72, TAF7L, TAF1, TAGE, TAG-72, TALI, TAM, TAP2, TAP1, TAPVR1, TARC, TARP, TAT, TAZ, TBP, TBX22, TBX3, TBX5, TBXA2R, TBXAS1, TCAP, TCF2, TCF1, TCIRG1, TCL2, TCL4, TCL1A, TCN2, TCOF1, TCR, TCRA, TDD, TDFA, TDRD1, TECK, TECTA, TEK, TEL/AML1, TELAB1, TEX15, TF, TFAP2B, TFE3, TFR2, TG, TGFα, TGFβ, TGFβI, TGFβ1, TGFβR2, TGFβRE, TGFγ, TGFβRII, TGIF, TGM-4, TGM1, TH, THAS, THBD, THC, THC2, THM, THPO, THRA, THRB, TIMM8A, TIMP2, TIMP3, TIMP1, TITF1, TKCR, TKT, TLP, TLR1, TLR10, TLR2, TLR3, TLR4, TLR4, TLR5, TLR6, TLR7, TLR8, TLR9, TLX1, TM4SF1, TM4SF2, TMC1, TMD, TMIP, TNDM, TNF, TNFRSF11A, TNFRSF1A, TNFRSF6, TNFSF5, TNFSF6, TNFα, TNFβ, TNNI3, TNNT2, TOC, TOP2A, TOP1, TP53, TP63, TPA, TPBG, TPI, TPI/m, TPI1, TPM3, TPM1, TPMT, TPO, TPS, TPTA, TRA, TRAG3, TRAPPC2, TRC8, TREH, TRG, TRH, TRIM32, TRIM37, TRP1, TRP2, TRP-2/6b, TRP-2/INT2, Trp-p8, TRPS1, TS, TSC2, TSC3, TSC1, TSG101, TSHB, TSHR, TSP-180, TST, TTGA2B, TTN, TTPA, TTR, TU M2-PK, TULP1, TWIST, TYH, TYR, TYROBP, TYROBP, TYRP1, TYS, UBE2A, UBE3A, UBE1, UCHL1, UFS, UGT1A, ULR, UMPK, UMPS, UOX, UPA, UQCRC1, URO5, UROD, UPK1B, UROS, USH2A, USH3A, USH1A, USH1C, USP9Y, UV24, VBCH, VCF, VDI, VDR, VEGF, VEGFR-2, VEGFR-1, VEGFR-2/FLK-1, VHL, VIM, VMD2, VMD1, VMGLOM, VNEZ, VNF, VP, VRNI, VWF, VWS, WAS, WBS2, WFS2, WFS1, WHCR, WHN, WISP3, WMS, WRN, WS2A, WS2B, WSN, WSS, WT2, WT3, WT1, WTS, WWS, XAGE, XDH, XIC, XIST, XK, XM, XPA, XPC, XRCC9, XS, ZAP70, ZFHX1B, ZFX, ZFY, ZIC2, ZIC3, ZNF145, ZNF261, ZNF35, ZNF41, ZNF6, ZNF198, and ZWS1.

Additionally, therapeutically active proteins as encoded by the at least one RNA (molecule) of the complexed RNA as defined herein may also be selected from growth hormones or growth factors, for example for promoting growth in a (transgenic) living being, such as, for example, TGFα and the IGFs (insulin-like growth factors), proteins that influence the metabolism and/or haematopoiesis, such as, for example, α-anti-trypsin, LDL receptor, erythropoietin (EPO), insulin, GATA-1, etc., or proteins such as, for example, factors VIII and XI of the blood coagulation system, etc. Such proteins further include enzymes, such as, for example, β-galactosidase (lacZ), DNA restriction enzymes (e.g. EcoRI, HindIII, etc.), lysozymes, etc., or proteases, such as, for example, papain, bromelain, keratinases, trypsin, chymotrypsin, pepsin, renin (chymosin), suizyme, nortase, etc. These proteins may be encoded by the at least one RNA (molecule) of the complexed RNA as defined herein. Accordingly, the invention provides a technology which allows to substitute proteins which are defective in the organism to be treated (e.g. either due to mutations, due to defective or missing expression) and thereby effective and increased expression of proteins, which are not functional in the organism to be treated, as e.g. occurring in monogenetic disorders, preferably without leading to an innate immune response.

Alternatively, therapeutically active proteins as encoded by the at least one RNA (molecule) of the complexed RNA as defined herein may also be selected from proteases etc. which allow to cure a specific disease due to e.g. (over) expression of a dysfunctional or exogenous proteins causing disorders or diseases. Accordingly, the invention may be used to therapeutically introduce the complexed RNA into the organism, which attacks a pathogenic organism (virus, bacteria etc). E.g. RNA encoding therapeutic proteases may be used to cleave viral proteins which are essential to the viral assembly or other essential steps of virus production.

Therapeutically active proteins as encoded by the at least one RNA (molecule) of the complexed RNA as defined herein may also be selected from proteins which modulate various intracellular pathways by e.g. signal transmission modulation (inhibition or stimulation) which may influence pivotal intracellular processes like apoptosis, cell growth etc, in particular with respect to the organism's immune system. Accordingly, immune modulators, e.g. cytokines, lymphokines, monokines, interferones etc. may be expressed efficiently by the complexed RNA as defined herein. Preferably, these proteins therefore also include, for example, cytokines of class I of the cytokine family that contain 4 position-specific conserved cysteine residues (CCCC) and a conserved sequence motif Trp-Ser-X-Trp-Ser (WSXWS), wherein X represents an unconserved amino acid. Cytokines of class I of the cytokine family include the GM-CSF sub-family, for example IL-3, IL-5, GM-CSF, the IL-6 sub-family, for example IL-6, IL-11, IL-12, or the IL-2 sub-family, for example IL-2, IL-4, IL-7, IL-9, IL-15, etc., or the cytokines IL-1α, IL-1β, IL-10 etc. By analogy, such proteins can also include cytokines of class II of the cytokine family (interferon receptor family), which likewise contain 4 position-specific conserved cysteine residues (CCCC) but no conserved sequence motif Trp-Ser-X-Trp-Ser (WSXWS). Cytokines of class II of the cytokine family include, for example, IFN-α, IFN-β, IFN-γ, etc. Proteins coded for by the at least one modified (m)RNA (of the inventive immunosuppressive composition) used according to the invention can further include also cytokines of the tumour necrosis family, for example TNF-α, TNF-β, TNF-RI, TNF-RII, CD40, Fas, etc., or cytokines of the chemokine family, which contain 7 transmembrane helices and interact with G-protein, for example IL-8, MIP-1, RANTES, CCR5, CXR4, etc. Such proteins can also be selected from apoptosis factors or apoptosis-related or -linked proteins, including AIF, Apaf, for example Apaf-1, Apaf-2, Apaf-3, or APO-2 (L), APO-3 (L), apopain, Bad, Bak, Bax, Bcl-2, Bcl-$x_L$, Bcl-$x_S$, bik, CAD, calpain, caspases, for example caspase-1, caspase-2, caspase-3, caspase-4, caspase-5, caspase-6, caspase-7, caspase-8, caspase-9, caspase-10, caspase-11, ced-3, ced-9, c-Jun, c-Myc, crm A, cytochrome C, CdR1, DcR1, DD, DED, DISC, DNA-PK$_{CS}$, DR3, DR4, DR5, FADD/MORT-1, FAK, Fas (Fas ligand CD95/fas (receptor)), FLICE/MACH, FLIP, fodrin, fos, G-actin, Gas-2, gelsolin, granzymes A/B, ICAD, ICE, JNK, lamin A/B, MAP, MCL-1, Mdm-2, MEKK-1, MORT-1, NEDD, NF-$_K$B, NuMa, p53, PAK-2, PARP, perforin, PITSLRE, PKCδ, pRb, presenilin, prICE, RAIDD, Ras, RIP, sphingomyelinase, thymidine kinase from Herpes simplex, TRADD, TRAF2, TRAIL, TRAIL-R1, TRAIL-R2, TRAIL-R3, transglutaminase, etc. Additionally, therapeutically active proteins as encoded by the at least one RNA (molecule) of the complexed RNA as defined herein may also code for antigen specific T cell receptors. The T cell receptor or TCR is a molecule found on the surface of T lymphocytes (or T cells) that is generally responsible for recognizing antigens bound to major histocompatibility complex (MHC) molecules. It is a heterodimer consisting of an alpha and beta chain in 95% of T cells, while 5% of T cells have TCRs consisting of gamma and delta chains. Engagement of the TCR with antigen and MHC results in activation of its T lymphocyte through a series of biochemical events mediated by associated enzymes, co-receptors and specialized accessory molecules. Hence, these proteins allow to specifically target specific antigen and may support the functionality of the immune system due to their targeting properties. Accordingly, transfection of cells in vivo by administering the at least one RNA (molecule) of the complexed RNA as defined herein coding for these receptors or, preferably, an ex vivo cell transfection approach (e.g. by transfecting specifically certain immune cells), may be pursued. The T cell receptor molecules introduced recognize specific antigens on MHC molecule and may thereby support the immune system's awareness of antigens to be attacked.

The therapeutically active proteins, which may be encoded by the at least one RNA (molecule) of the complexed RNA as defined herein, may furthermore comprise an adjuvant protein. In this context, an adjuvant protein is preferably to be understood as any protein, which is capable to elicit an innate immune response as defined herein. Preferably, such an innate immune response comprises an activation of a pattern recognition receptor, such as e.g. a receptor selected from the Toll-like receptor (TLR) family, including e.g. a Toll like receptor selected from human TLR1 to TLR10 or from murine Toll like receptors TLR1 to TLR13. Preferably, an innate immune response is elicited in a mammal, more preferably in a human. Preferably, the adjuvant protein is selected from human adjuvant proteins or from pathogenic adjuvant proteins, in particular from bacterial adjuvant proteins. In addition, mRNA encoding human proteins involved in adjuvant effects may be used as well.

Human adjuvant proteins, which may be encoded by the at least one RNA (molecule) of the complexed RNA as defined herein, typically comprise any human protein, which is capable of eliciting an innate immune response (in a mammal), e.g. as a reaction of the binding of an exogenous TLR ligand to a TLR. More preferably, human adjuvant proteins which may be encoded by the complexed RNA of the present invention are selected from the group consisting of, without being limited thereto, cytokines which induce or enhance an innate immune response, including IL-2, IL-12, IL-15, IL-18, IL-21CCL21, GM-CSF and TNF-alpha; cytokines which are released from macrophages, including IL-1, IL-6, IL-8, IL-12 and TNF-alpha; from components of the complement system including C1q, MBL, C1r, C1s, C2b, Bb, D, MASP-1, MASP-2, C4b, C3b, C5a, C3a, C4a, C5b, C6, C7, C8, C9, CR1, CR2, CR3, CR4, C1qR, C1INH, C4bp, MCP, DAF, H, I, P and CD59; from proteins which are components of the signalling networks of the pattern recognition receptors including TLR and IL-1R1, whereas the components are ligands of the pattern recognition receptors including IL-1alpha, IL-1 beta, Beta-defensin, heat shock proteins, such as HSP10, HSP60, HSP65, HSP70, HSP75 and HSP90, gp96, Fibrinogen, TypIII repeat extra domain A of fibronectin; the receptors, including IL-1R1, TLR1, TLR2, TLR3, TLR4, TLR5, TLR6, TLR7, TLR8, TLR9, TLR10, TLR11; the signal transducers including components of the Small-GTPases signalling (RhoA, Ras, Rac1, Cdc42 etc.), components of the PIP signalling (PI3K, Src-Kinases, etc.), components of the MyD88-dependent signalling (MyD88, IRAK1, IRAK2, etc.), components of the MyD88-independent signalling (TICAM1, TICAM2 etc.); activated transcription factors including e.g. NF-κB, c-Fos, c-Jun, c-Myc; and induced target genes including e.g. IL-1 alpha, IL-1 beta, Beta-Defensin, IL-6, IFN gamma, IFN alpha and IFN beta; from costimulatory molecules, including CD28 or CD40-ligand or PD1; protein domains, including LAMP; cell surface proteins; or human adjuvant proteins including CD80, CD81, CD86, trif, fit-3 ligand, thymopentin, Gp96 or fibronectin, etc., or any species homolog of any of the above human adjuvant proteins.

Pathogenic adjuvant proteins, which may be encoded by the at least one RNA (molecule) of the complexed RNA as defined herein, typically comprise any pathogenic (adjuvant) protein, which is capable of eliciting an innate immune response (in a mammal), more preferably selected from pathogenic (adjuvant) proteins derived from bacteria, protozoa, viruses, or fungi, animals, etc., and even more preferably from pathogenic adjuvant proteins selected from the group consisting of, without being limited thereto, bacterial proteins, protozoan proteins (e.g. profilin—like protein of *Toxoplasma gondii*), viral proteins, or fungal proteins, animal proteins, etc.

In this context, bacterial (adjuvant) proteins which may be encoded by the at least one RNA (molecule) of the complexed RNA as defined herein, may comprise any bacterial protein, which is capable of eliciting an innate immune response (preferably in a mammal). More preferably, bacterial (adjuvant) proteins, which may be encoded by the complexed RNA, may comprise bacterial adjuvant proteins selected from the group consisting of, without being limited thereto, bacterial flagellins, including flagellins from organisms including *Agrobacterium, Aquifex, Azospirillum, Bacillus, Bartonella, Bordetella, Borrelia, Burkholderia, Campylobacter, Caulobacte, Clostridium, Escherichia, Helicobacter, Lachnospiraceae, Legionellla, Listeria, Proteus, Pseudomonas, Rhizobium, Rhodobacter, Roseburia, Salmonella, Serpulina, Serratia, Shigella, Treponema, Vibrio, Wolinella, Yersinia*, more preferably flagellins from the species, without being limited thereto, *Agrobacterium tumefaciens, Aquifex pyrophilus, Azospirillum brasilense, Bacillus subtilis, Bacillus thuringiensis, Bartonella bacilliformis, Bordetella bronchiseptica, Borrelia burgdorferi, Burkholderia cepacia, Campylobacter jejuni, Caulobacter crescentus, Clostridium botulinum* strain Bennett clone 1, *Escherichia coli, Helicobacter pylori Lachnospiraceae bacterium, Legionella pneumophila, Listeria monocytogenes, Proteus mirabilis, Pseudomonas aeroguinosa, Pseudomonas syringae, Rhizobium meliloti, Rhodobacter sphaeroides, Roseburia cecicola, Roseburis hominis, Salmonella typhimurium, Salmonella bongori Salmonella typhi, Salmonella enteritidis, Serpulina hyodysenteriae, Serratia marcescens, Shigella boydii, Treponema phagedenis, Vibrio alginolyticus, Vibrio cholerae, Vibrio parahaemolyticus, Wolinella succinogenes* and *Yersinia enterocolitica*.

Bacterial flagellins, which may be encoded by the at least one RNA (molecule) of the complexed RNA as defined herein, are particularly preferred and may be selected from any bacterial flagellin showing adjuvant character, more preferably from bacterial flagellins selected from the group consisting of bacterial heat shock proteins or chaperons, including Hsp60, Hsp70, Hsp90, Hsp100; OmpA (Outer membrane protein) from gram-negative bacteria; bacterial porins, including OmpF; bacterial toxins, including pertussis toxin (PT) from *Bordetella pertussis*, pertussis adenylate cyclase toxin CyaA and CyaC from *Bordetella pertussis*, PT-9K/129G mutant from *pertussis* toxin, pertussis adenylate cyclase toxin CyaA and CyaC from *Bordetella pertussis*, tetanus toxin, cholera toxin (CT), cholera toxin B-subunit, CTK63 mutant from cholera toxin, CTE112K mutant from CT, *Escherichia coli* heat-labile enterotoxin (LT), B subunit from heat-labile enterotoxin (LTB) *Escherichia coli* heat-labile enterotoxin mutants with reduced toxicity, including LTK63, LTR72; phenol-soluble modulin; neutrophil-activating protein (HP-NAP) from *Helicobacter pylori* Surfactant protein D; Outer surface protein A lipoprotein from *Borrelia burgdorferi*, Ag38 (38 kDa antigen) from *Mycobacterium tuberculosis*, proteins from bacterial fimbriae; Enterotoxin CT of *Vibrio cholerae*, Pilin from pili from gram negative bacteria, and Surfactant protein A; etc., or any species homolog of any of the above bacterial (adjuvant) proteins.

Bacterial flagellins, which may be encoded by the at least one RNA (molecule) of the complexed RNA as defined herein, even more preferably comprise a sequence selected from the group comprising any of the following sequences as referred to their accession numbers:

| organism | species | gene name | accession No | GI No |
|---|---|---|---|---|
| *Agrobacterium* | *Agrobacterium tumefaciens* | FlaD (flaD) FlhB (flhB) FliG (fliG) FliN (fliN) FliM (fliM) MotA (motA) FlgF (flgF) FliI (fliI) FlgB (flgB) FlgC (flgC) FliE (fliE) FlgG (flgG) FlgA (flgA) FlgI (flgI) FlgH (flgH) FliL (fliL) FliP (fliP) FlaA (flaA) FlaB (flaB) FlaC (flaC) | U95165 | GI: 14278870 |
| *Aquifex* | *Aquifex pyrophilus* | | U17575 | GI: 596244 |
| *Azospirillum* | *Azospirillum brasilense* | Lafl | U26679 | GI: 1173509 |
| *Bacillus* | *Bacillus subtilis* | hag | AB033501 | GI: 14278870 |
| *Bacillus* | *Bacillus thuringiensis* | flab | X67138 | GI: 46019718 |
| *Bartonella* | *Bartonella bacilliformis* | | L20677 | GI: 304184 |
| *Bordetella* | *Bordetella bronchiseptica* | flaA | L13034 | GI: 289453 |
| *Borrelia* | *Borrelia burgdorferi* | | X16833 | GI: 39356 |
| *Burkholderia* | *Burkholderia cepacia* | fliC | AF011370 | GI: 2935154 |
| *Campylobacter* | *Campylobacter jejuni* | flaA flaB | J05635 | GI: 144197 |
| *Caulobacter* | *Caulobacter crescentus* | | J01556 | GI: 144239 |
| *Clostridium* | *Clostridium botulinum* strain Bennett clone 1 | FlaA | DQ845000 | GI: 114054886 |
| *Escherichia* | *Escherichia coli* | hag | M14358 AJ 884569 (EMBL-SVA) | GI: 146311 |
| *Helicobacter* | *Helicobacter pylori* | flaA | X60746 | GI: 43631 |
| *Lachnospiraceae* | *Lachnospiraceae bacterium* | | DQ789131 | GI: 113911615 |
| *Legionella* | *Legionella pneumophila* | flaA | X83232 | GI: 602877 |
| *Listeria* | *Listeria monocytogenes* | flaA | X65624 | GI: 44097 |
| *Proteus* | *Proteus mirabilis* | FlaD (flaD) FlaA (flaA) FlaB (flaB) FliA (fliA) FliZ (fliZ) | AF221596 | GI: 6959881 |
| *Pseudomonas* | *Pseudomonas aeroguinosa* | flaA | M57501 | GI: 151225 |
| *Pseudomonas* | *Pseudomonas syringae* | fliC | EF544882 | GI: 146335619 |
| *Rhizobium* | *Rhizobium meliloti* | flaA flaB | M24526 | GI: 152220 |
| *Rhodobacter* | *Rhodobacter sphaeroides* | fliC | AF274346 | GI: 10716972 |
| *Roseburia* | *Roseburia cecicola* | | M20983 | GI: 152535 |

-continued

| organism | species | gene name | accession No | GI No |
|---|---|---|---|---|
| Roseburia | Roseburis hominis | Fla2 | DQ789141 | GI: 113911632 |
| Salmonella | Salmonella typhimurium | | D13689 (NCBI ID) | GI: 217062 |
| Salmonella | Salmonella bongori | fliC | AY603412 | GI: 51342390 |
| Salmonella | Salmonella typhi | flag | L21912 | GI: 397810 |
| Salmonella | Salmonella enteritidis | fliC | M84980 | GI: 154015 |
| Serpulina | Serpulina hyodysenteriae | flaB2 | X63513 | GI: 450669 |
| Serratia | Serratia marcescens | hag | M27219 | GI: 152826 |
| Shigella | Shigella boydii | fliC-SB | D26165 | GI: 442485 |
| Treponema | Treponema phagedenis | flaB2 | M94015 | GI: 155060 |
| Vibrio | Vibrio alginolyticus | flaA | EF125175 | GI: 119434395 |
| Vibrio s | Vibrio parahaemolyticus | | AF069392 | GI: 7327274 |
| Wolinella | Wolinella succinogenes | flag | M82917 | GI: 155337 |
| Yersinia | Yersinia enterocolitica | | L33467 | GI: 496295 |

Protozoan proteins, which may be encoded by the at least one RNA (molecule) of the complexed RNA as defined herein, may be selected from any protozoan protein showing adjuvant character, more preferably, from the group consisting of, without being limited thereto, Tc52 from *Trypanosoma cruzi*, PFTG from *Trypanosoma gondii*, Protozoan heat shock proteins, LeIF from *Leishmania* spp., profilin-like protein from *Toxoplasma gondii*, etc.

Viral proteins, which may be encoded by the at least one RNA (molecule) of the complexed RNA as defined herein, may be selected from any viral protein showing adjuvant character, more preferably, from the group consisting of, without being limited thereto, Respiratory Syncytial Virus fusion glycoprotein (F-protein), envelope protein from MMT virus, mouse leukemia virus protein, Hemagglutinin protein of wild-type measles virus, etc.

Fungal proteins, which may be encoded by the at least one RNA (molecule) of the complexed RNA as defined herein, may be selected from any fungal protein showing adjuvant character, more preferably, from the group consisting of, without being limited thereto, fungal immunomodulatory protein (FIP; LZ-8), etc.

Finally, pathogenic adjuvant proteins, which may be encoded by the at least one RNA (molecule) of the complexed RNA as defined herein, may finally be selected from any further pathogenic protein showing adjuvant character, more preferably, from the group consisting of, without being limited thereto, Keyhole limpet hemocyanin (KLH), OspA, etc. The at least one RNA (molecule) of the complexed RNA of the present invention may alternatively encode an antigen. According to the present invention, the term "antigen" refers to a substance which is recognized by the immune system and is capable of triggering an antigen-specific immune response, e.g. by formation of antibodies. Antigens can be classified according to their origin. Accordingly, there are two major classes of antigens: exogenous and endogenous antigens. Exogenous antigens are antigens that enter the cell or the body from outside (the cell or the body), for example by inhalation, ingestion or injection, etc. These antigens are internalized by antigen-presenting cells ("APCs", such as dendritic cells or macrophages) and processed into fragments. APCs then present the fragments to T helper cells (e.g. CD4$^+$) by the use of MHC II molecules on their surface. Recognition of these antigen fragments by T cells leads to activation of the T cells and secretion of cytokines. Cytokines are substances that can activate proliferation of immune cells such as cytotoxic T cells, B cells or macrophages. In contrast, endogenous antigens are antigens which have been generated within the cell, e.g. as a result of normal cell metabolism. Fragments of these antigens are presented on MHC I molecules on the surface of APCs. These antigens are recognized by activated antigen-specific cytotoxic CD8$^+$ T cells. After recognition, those T cells react in secretion of different toxins that cause lysis or apoptosis of the antigen-presenting cell. Endogenous antigens comprise antigens, e.g. proteins or peptides encoded by a foreign nucleic acid inside the cell as well as proteins or peptides encoded by the genetic information of the cell itself, or antigens from intracellularly occurring viruses. One class of endogenous antigens is the class of tumor antigens. Those antigens are presented by the MHC I molecules on the surface of tumor cells. This class can be divided further in tumor-specific antigens (TSAs) and tumor-associated-antigens (TAAs). TSAs can only be presented by tumor cells and never by normal "healthy" cells. They typically result from a tumor specific mutation. TAAs, which are more common, are usually presented by both tumor and healthy cells. These antigens are recognized and the antigen-presenting cell can be destroyed by cytotoxic T cells. Additionally, tumor antigens can also occur on the surface of the tumor in the form of e.g. a mutated receptor. In this case, they can be recognized by antibodies.

Antigens, which may be encoded by the at least one RNA (molecule) of the complexed RNA of the present invention, may include e.g. proteins, peptides or fragments thereof. Preferably, antigens are proteins and peptides or fragments thereof, such as epitopes of those proteins or peptides. Epitopes (also called "antigen determinants"), typically, are fragments located on the outer surface of such antigenic protein or peptide structures having 5 to 15, preferably 9 to 15, amino acids (B-cell epitopes and T-cell epitopes are typically presented on MHC molecules, wherein e.g. MHC-I typically presents epitopes with a length of about 9 aa and MHC-II typically presents epitopes with a length of about 12-15 aa). Furthermore, antigens encoded by the at least one RNA (molecule) of the complex according to the invention may also comprise any other biomolecule, e.g., lipids, carbohydrates, etc., which may be covalently or non-covalently attached to the RNA (molecule).

In accordance with the invention, antigens, which may be encoded by the at least one RNA (molecule) of the complexed RNA of the present invention, may be exogenous or endogenous antigens. Endogenous antigens comprise antigens generated in the cell, especially in degenerate cells such as tumor cells. These antigens are referred to as "tumor antigens". Preferably, without being restricted thereto, they are located on the surface of the cell. Furthermore, "tumor antigens" means also antigens expressed in cells which are (were) not by themselves (or originally not by themselves) degenerate but are associated with the supposed tumor. Antigens which are connected with tumor-supplying vessels or (re)formation thereof, in particular those antigens which are associated with neovascularization, e.g. growth factors, such as VEGF, bFGF etc., are also included herein. Antigens connected with a tumor furthermore include antigens from cells or tissues, typically embedding the tumor. Further, some substances (usually proteins or peptides) are expressed in patients suffering (knowingly or not-knowingly) from a cancer disease and they occur in increased concentrations in the body fluids of said patients, e.g. proteins, which are associated with tumor cell invasion and migration. These substances are also referred to as "tumor antigens", however they are not antigens in the stringent meaning of an immune response inducing substance. Use thereof is also encompassed by the scope of the present invention.

Antigens, which may be encoded by the at least one RNA (molecule) of the complexed RNA of the present invention, may be exemplarily selected, without being restricted thereto, e.g. from any antigen suitable for the specific purpose, e.g. from antigens, which are relevant (or causal) for specific infection diseases, such as defined herein, from cancer antigens such as tumor specific surface antigens, from antigens expressed in cancer diseases, from mutant antigens expressed in cancer diseases, or from protein antigens involved in the etiology of further diseases, e.g. autoimmune diseases, allergies, etc. E.g. these antigens may be used to desensitize a patient by administering an antigen causing the patient's allergic or autoimmune status.

Preferred exemplary antigenic (poly)peptides encoded by the at least one RNA (molecule) of the complexed RNA as defined herein include all known antigenic peptides, for example tumour antigens, etc. Specific examples of tumour antigens are inter alia tumour-specific surface antigens (TSSAs), for example 5T4, alpha5beta1-integrin, 707-AP, AFP, ART-4, B7H4, BAGE, Bcr-abl, MN/C IX antigen, CA125, CAMEL, CAP-1, CASP-8, beta-catenin/m, CD4, CD19, CD2O, CD22, CD25, CDC27/m, CD 30, CD33, CD52, CD56, CD80, CDK4/m, CEA, CT, Cyp-B, DAM, EGFR, ErbB3, ELF2M, EMMPRIN, EpCam, ETV6-AML1, G250, GAGE, GnT-V, Gp100, HAGE, HER-2/new, HLA-A*0201-R170I, HPV-E7, HSP70-2M, HAST-2, hTERT (or hTRT), iCE, IGF-1R, IL-2R, IL-5, KIAA0205, LAGE, LDLR/FUT, MAGE, MART-1/melan-A, MART-2/Ski, MC1R, myosin/m, MUC1, MUM-1, -2, -3, NA88-A, PAP, proteinase-3, p190 minor bcr-abl, Pml/RARalpha, PRAME, PSA, PSM, PSMA, RAGE, RU1 or RU2, SAGE, SART-1 or SART-3, survivin, TEL/AML1, TGFbeta, TPI/m, TRP-1, TRP-2, TRP-2/INT2, VEGF and WT1, or from sequences such as, for example, NY-Eso-1 or NY-Eso-B. Any class of tumor antigens is suitable for the purpose of the present invention, e.g. tumor antigens known to be involved in neovascularization, influencing the extracellular matrix structure etc. Fragments and analogues of the above antigens are also encompassed.

Examples of tumor antigens which may be encoded by the at least one RNA (molecule) of the complexed RNA of the present invention are shown in Tables 1 and 2 below. These tables illustrate specific (protein) antigens (i.e. "tumor antigens") with respect to the cancer disease, they are associated with. According to the invention, the terms "cancer diseases" and "tumor diseases" are used synonymously herein.

TABLE 1

Antigens expressed in cancer diseases

| Tumor antigen | Name | Expression site |
|---|---|---|
| 5T4 | | colorectal cancer, gastric cancer, ovarian cancer |
| 707-AP | 707 alanine proline | melanoma |
| 9D7 | | renal cell carcinoma |
| AFP | alpha-fetoprotein | hepatocellular carcinoma, gallbladder cancer, testicular cancer, ovarian cancer, bladder cancer |
| AlbZIP HPG1 | | prostate cancer |
| alpha5beta1-Integrin | | |
| alpha5beta6-Integrin | | colon cancer |
| alpha-methylacyl-coenzyme A racemase | | prostate cancer |
| ART-4 | adenocarcinoma antigen recognized by T cells 4 | lung cancer, head and neck cancer, leukemia, esophageal cancer, gastric cancer, cervical cancer, ovarian cancer, breast cancer, squamous cell carcinoma |
| B7H4 | | ovarian cancer |
| BAGE-1 | B antigen | bladder cancer, head and neck cancer, lung cancer, melanoma, squamous cell carcinoma |
| BCL-2 | | leukemia |
| BING-4 | | melanoma |

TABLE 1-continued

Antigens expressed in cancer diseases

| Tumor antigen | Name | Expression site |
|---|---|---|
| CA 15-3/CA 27-29 | | breast cancer, ovary cancer, lung cancer, prostate cancer |
| CA 19-9 | | gastric cancer, pancreatic cancer, liver cancer, breast cancer, gallbladder cancer, colon cancer, ovary cancer, lung cancer |
| CA 72-4 | | ovarian cancer |
| CA125 | | ovarian cancer, colorectal cancer, gastric cancer, liver cancer, pancreatic cancer, uterus cancer, cervix carcinoma, colon cancer, breast cancer, lung cancer |
| calreticulin | | bladder cancer |
| CAMEL | CTL-recognized antigen on melanoma | melanoma |
| CASP-8 | caspase-8 | head and neck cancer |
| cathepsin B | | breast cancer |
| cathepsin L | | breast cancer |
| CD19 | | B-cell malignancies |
| CD20 | | |
| CD22 | | |
| CD25 | | |
| CD30 | | |
| CD33 | | |
| CD4 | | |
| CD52 | | |
| CD55 | | |
| CD56 | | |
| CD80 | | |
| CEA | carcinoembryonic antigen | gut carcinoma, colorectal cancer, colon cancer, hepatocellular cancer, lung cancer, breast cancer, thyroid cancer, pancreatic cancer, liver cancer cervix cancer, bladder cancer, melanoma |
| CLCA2 | calcium-activated chloride channel-2 | lung cancer |
| CML28 | | leukemia |
| Coactosin-like protein | | pancreatic cancer |
| Collagen XXIII | | prostate cancer |
| COX-2 | | ovarian cancer, breast cancer, colorectal cancer |
| CT-9/BRD6 | bromodomain testis-specific protein | |
| Cten | C-terminal tensin-like protein | prostate cancer |
| cyclin B1 | | |
| cyclin D1 | | ovarian cancer |
| cyp-B | cyclophilin B | bladder cancer, lung cancer, T-cell leukemia, squamous cell carcinoma, |
| CYPB1 | cytochrom P450 1B1 | leukemia |
| DAM-10/MAGE-B1 | differentiation antigen melanoma 10 | melanoma, skin tumors, ovarian cancer, lung cancer |
| DAM-6/MAGE-B2 | differentiation antigen melanoma 6 | melanoma, skin tumors, ovarian cancer, lung cancer |
| EGFR/Her1 | | lung cancer, ovarian cancer, head and neck cancer, colon cancer, pancreatic cancer, breast cancer |
| EMMPRIN | tumor cell-associated extracellular matrix metalloproteinase inducer/ | lung cancer, breast cancer, bladder cancer, ovarian cancer, brain cancer, lymphoma |
| EpCam | epithelial cell adhesion molecule | ovarian cancer, breast cancer, colon cancer, lung cancer |
| EphA2 | ephrin type-A receptor 2 | glioma |
| EphA3 | ephrin type-A receptor 2 | melanoma, sarcoma, lung cancer |
| ErbB3 | | breast cancer |
| EZH2 | (enhancer of Zeste homolog 2) | endometrium cancer, melanoma, prostate cancer, breast cancer |
| FGF-5 | fibroblast growth factor-5 | renal cell carcinoma, breast cancer, prostate cancer |
| FN | fibronectin | melanoma |
| Fra-1 | Fos-related antigen-1 | breast cancer, esophageal cancer, renal cell carcinoma, thyroid cancer |
| G250/CAIX | glycoprotein 250 | leukemia, renal cell carcinoma, head and neck cancer, colon cancer, ovarian cancer, cervical cancer |
| GAGE-1 | G antigen 1 | bladder cancer, lung cancer, sarcoma, melanoma, head and neck cancer |

TABLE 1-continued

Antigens expressed in cancer diseases

| Tumor antigen | Name | Expression site |
| --- | --- | --- |
| GAGE-2 | G antigen 2 | bladder cancer, lung cancer, sarcoma, melanoma, head and neck cancer |
| GAGE-3 | G antigen 3 | bladder cancer, lung cancer, sarcoma, melanoma, head and neck cancer |
| GAGE-4 | G antigen 4 | bladder cancer, lung cancer, sarcoma, melanoma, head and neck cancer |
| GAGE-5 | G antigen 5 | bladder cancer, lung cancer, sarcoma, melanoma, head and neck cancer |
| GAGE-6 | G antigen 6 | bladder cancer, lung cancer, sarcoma, melanoma, head and neck cancer |
| GAGE-7b | G antigen 7b | bladder cancer, lung cancer, sarcoma, melanoma, head and neck cancer |
| GAGE-8 | G antigen 8 | bladder cancer, lung cancer, sarcoma, melanoma, head and neck cancer |
| GDEP | gene differentially expressed in prostate | prostate cancer |
| GnT-V | N-acetylglucosaminyltransferase V | glioma, melanoma |
| gp100 | glycoprotein 100 kDa | melanoma |
| GPC3 | glypican 3 | hepatocellular carcinoma, melanoma |
| HAGE | helicase antigen | bladder cancer |
| HAST-2 | human signet ring tumor-2 | |
| hepsin | | prostate |
| Her2/neu/ErbB2 | human epidermal receptor-2/neurological | breast cancer, bladder cancer, melanoma, ovarian cancer, pancreas cancer, gastric cancer |
| HERV-K-MEL | | melanoma |
| HNE | human neutrophil elastase | leukemia |
| homeobox NKX 3.1 | | prostate cancer |
| HOM-TES-14/SCP-1 | | ovarian cancer |
| HOM-TES-85 | | |
| HPV-E6 | | cervical cancer |
| HPV-E7 | | cervical cancer |
| HST-2 | | gastric cancer |
| hTERT | human telomerase reverse transcriptase | breast cancer, melanoma, lung cancer, ovarian cancer, sarcoma, Non-Hodgkin-lymphoma, acute leukemia |
| iCE | intestinal carboxyl esterase | renal cell carcinoma |
| IGF-1R | | colorectal cancer |
| IL-13Ra2 | interleukin 13 receptor alpha 2 chain | glioblastoma |
| IL-2R | | colorectal cancer |
| IL-5 | | |
| immature laminin receptor | | renal cell carcinoma |
| kallikrein 2 | | prostate cancer |
| kallikrein 4 | | prostate cancer |
| Ki67 | | prostate cancer, breast cancer, Non-Hodgkin-lymphoma, melanoma |
| KIAA0205 | | bladder cancer |
| KK-LC-1 | Kita-kyushu lung cancer antigen 1 | lung cancer |
| KM-HN-1 | | tongue cancer, hepatocellular carcinomas, melanoma, gastric cancer, esophageal, colon cancer, pancreatic cancer |
| LAGE-1 | L antigen | bladder cancer, head and neck cancer, melanoma |
| livin | | bladder cancer, melanoma |
| MAGE-A1 | melanoma antigen-A1 | bladder cancer, head and neck cancer, melanoma, colon cancer, lung cancer, sarcoma, leukemia |
| MAGE-A10 | melanoma antigen-A10 | bladder cancer, head and neck cancer, melanoma, colon cancer, lung cancer, sarcoma, leukemia |
| MAGE-A12 | melanoma antigen-A12 | bladder cancer, head and neck cancer, melanoma, colon cancer, lung cancer, sarcoma, leukemia, prostate cancer, myeloma, brain tumors |
| MAGE-A2 | melanoma antigen-A2 | bladder cancer, head and neck cancer, melanoma, colon cancer, lung cancer, sarcoma, leukemia |
| MAGE-A3 | melanoma antigen-A3 | bladder cancer, head and neck cancer, melanoma, colon cancer, lung cancer, sarcoma, leukemia |

TABLE 1-continued

Antigens expressed in cancer diseases

| Tumor antigen | Name | Expression site |
| --- | --- | --- |
| MAGE-A4 | melanoma antigen-A4 | bladder cancer, head and neck cancer, melanoma, colon cancer, lung cancer, sarcoma, leukemia |
| MAGE-A6 | melanoma antigen-A6 | bladder cancer, head and neck cancer, melanoma, colon cancer, lung cancer, sarcoma, leukemia |
| MAGE-A9 | melanoma-antigen-A9 | bladder cancer, head and neck cancer, melanoma, colon cancer, lung cancer, sarcoma, leukemia |
| MAGE-B1 | melanoma-antigen-B1 | melanoma |
| MAGE-B10 | melanoma-antigen-B10 | melanoma |
| MAGE-B16 | melanoma-antigen-B16 | melanoma |
| MAGE-B17 | melanoma-antigen-B17 | melanoma |
| MAGE-B2 | melanoma-antigen-B2 | melanoma |
| MAGE-B3 | melanoma-antigen-B3 | melanoma |
| MAGE-B4 | melanoma-antigen-B4 | melanoma |
| MAGE-B5 | melanoma-antigen-B5 | melanoma |
| MAGE-B6 | melanoma-antigen-B6 | melanoma |
| MAGE-C1 | melanoma-antigen-C1 | bladder cancer, melanoma |
| MAGE-C2 | melanoma-antigen-C2 | melanoma |
| MAGE-C3 | melanoma-antigen-C3 | melanoma |
| MAGE-D1 | melanoma-antigen-D1 | melanoma |
| MAGE-D2 | melanoma-antigen-D2 | melanoma |
| MAGE-D4 | melanoma-antigen-D4 | melanoma |
| MAGE-E1 | melanoma-antigen-E1 | bladder cancer, melanoma |
| MAGE-E2 | melanoma-antigen-E2 | melanoma |
| MAGE-F1 | melanoma-antigen-F1 | melanoma |
| MAGE-H1 | melanoma-antigen-H1 | melanoma |
| MAGEL2 | MAGE-like 2 | melanoma |
| mammaglobin A | | breast cancer |
| MART-1/Melan-A | melanoma antigen recognized by T cells-1/melanoma antigen A | melanoma |
| MART-2 | melanoma antigen recognized by T cells-2 | melanoma |
| matrix protein 22 | | bladder cancer |
| MC1R | melanocortin 1 receptor | melanoma |
| M-CSF | macrophage colony-stimulating factor gene | ovarian cancer |
| mesothelin | | ovarian cancer |
| MG50/PXDN | | breast cancer, glioblastoma, melanoma |
| MMP 11 | M-phase phosphoprotein 11 | leukemia |
| MN/CA IX-antigen | | renal cell carcinoma |
| MRP-3 | multidrug resistance-associated protein 3 | lung cancer |
| MUC1 | mucin 1 | breast cancer |
| MUC2 | mucin 2 | breast cancer, ovarian cancer, pancreatic cancer |
| NA88-A | NA cDNA clone of patient M88 | melanoma |
| N-acetylglucosaminyltransferase-V | | |
| Neo-PAP | Neo-poly(A) polymerase | |
| NGEP | | prostate cancer |
| NMP22 | | bladder cancer |
| NPM/ALK | nucleophosmin/anaplastic lymphoma kinase fusion protein | |
| NSE | neuron-specific enolase | small cell cancer of lung, neuroblastoma, Wilm' tumor, melanoma, thyroid cancer, kidney cancer, testicle cancer, pancreas cancer |
| NY-ESO-1 | New York esophageous 1 | bladder cancer, head and neck cancer, melanoma, sarcoma, B-lymphoma, hepatoma, pancreatic cancer, ovarian cancer, breast cancer |
| NY-ESO-B | | |
| OA1 | ocular albinism type 1 protein | melanoma |
| OFA-iLRP | oncofetal antigen-immature laminin receptor | leukemia |
| OGT | O-linked N-acetylglucosamine transferase gene | |
| OS-9 | | |
| osteocalcin | | prostate cancer |
| osteopontin | | prostate cancer, breast cancer, ovarian cancer |

TABLE 1-continued

Antigens expressed in cancer diseases

| Tumor antigen | Name | Expression site |
|---|---|---|
| p15 | protein 15 | |
| p15 | | melanoma |
| p190 minor bcr-abl | | |
| p53 | | |
| PAGE-4 | prostate GAGE-like protein-4 | prostate cancer |
| PAI-1 | plasminogen acitvator inhibitor 1 | breast cancer |
| PAI-2 | plasminogen acitvator inhibitor 2 | breast cancer |
| PAP | prostate acic phosphatase | prostate cancer |
| PART-1 | | prostate cancer |
| PATE | | prostate cancer |
| PDEF | | prostate cancer |
| Pim-1-Kinase | | |
| Pin1 | Propyl isomerase | prostate cancer |
| POTE | | prostate cancer |
| PRAME | preferentially expressed antigen of melanoma | melanoma, lung cancer, leukemia, head and neck cancer, renal cell carcinoma, sarcoma |
| prostein | | prostate cancer |
| proteinase-3 | | |
| PSA | prostate-specific antigen | prostate cancer |
| PSCA | | prostate cancer |
| PSGR | | prostate cancer |
| PSM | | |
| PSMA | prostate-specific membrane antigen | prostate cancer |
| RAGE-1 | renal antigen | bladder cancer, renal cancer, sarcoma, colon cancer |
| RHAMM/CD168 | receptor for hyaluronic acid mediated motility | leukemia |
| RU1 | renal ubiquitous 1 | bladder cancer, melanoma, renal cancer |
| RU2 | renal ubiquitous 1 | bladder cancer, melanoma, sarcoma, brain tumour, esophagel cancer, renal cancer, colon cancer, breast cancer |
| S-100 | | melanoma |
| SAGE | sarcoma antigen | |
| SART-1 | squamous antigen rejecting tumor 1 | esophageal cancer, head and neck cancer, lung cancer, uterine cancer |
| SART-2 | squamous antigen rejecting tumor 1 | head and neck cancer, lung cancer, renal cell carcinoma, melanoma, brain tumour |
| SART-3 | squamous antigen rejecting tumor 1 | head and neck cancer, lung cancer, leukemia, melanoma, esophageal cancer |
| SCC | squamous cell carcinoma antigen | lung cancer |
| Sp17 | sperm protein 17 | multiple myeloma |
| SSX-1 | synovial sarcoma X breakpoint 1 | hepatocellular cell carcinom, breast cancer |
| SSX-2/HOM-MEL-40 | synovial sarcoma X breakpoint 2 | breast cancer |
| SSX-4 | synovial sarcoma X breakpoint 4 | bladder cancer, hepatocellular cell carcinoma, breast cancer |
| STAMP-1 | | prostate cancer |
| STEAP | six transmembrane epithelial antigen prostate | prostate cancer |
| survivin | | bladder cancer |
| survivin-2B | intron 2-retaining survivin | bladder cancer |
| TA-90 | | melanoma |
| TAG-72 | | prostate carcinoma |
| TARP | | prostate cancer |
| TGFb | TGFbeta | |
| TGFbRII | TGFbeta receptor II | |
| TGM-4 | prostate-specific transglutaminase | prostate cancer |
| TRAG-3 | taxol resistant associated protein 3 | breast cancer, leukemia, and melanoma |
| TRG | testin-related gene | |
| TRP-1 | tyrosine related protein 1 | melanoma |
| TRP-2/6b | TRP-2/novel exon 6b | melanoma, glioblastoma |
| TRP-2/INT2 | TRP-2/intron 2 | melanoma, glioblastoma |
| Trp-p8 | | prostate cancer |
| Tyrosinase | | melanoma |
| UPA | urokinase-type plasminogen activator | breast cancer |
| VEGF | vascular endothelial growth factor | |
| VEGFR-2/FLK-1 | vascular endothelial growth factor receptor-2 | |

TABLE 1-continued

Antigens expressed in cancer diseases

| Tumor antigen | Name | Expression site |
|---|---|---|
| WT1 | Wilm' tumor gene | gastric cancer, colon cancer, lung cancer, breast cancer, ovarian cancer, leukemia |

TABLE 2

Mutant antigens expressed in cancer diseases

| Mutant antigen | Name | Expression site |
|---|---|---|
| alpha-actinin-4/m | | lung carcinoma |
| ARTC1/m | | melanoma |
| bcr/abl | breakpoint cluster region-Abelson fusion protein | CML |
| beta-Catenin/m | beta-Catenin | melanoma |
| BRCA1/m | | breast cancer |
| BRCA2/m | | breast cancer |
| CASP-5/m | | colorectal cancer, gastric cancer, endometrial carcinoma |
| CASP-8/m | | head and neck cancer, squamous cell carcinoma |
| CDC27/m | cell-division-cycle 27 | |
| CDK4/m | cyclin-dependent kinase 4 | melanoma |
| CDKN2A/m | | melanoma |
| CML66 | | CML |
| COA-1/m | | colorectal cancer |
| DEK-CAN | fusion protein | AML |
| EFTUD2/m | | melanoma |
| ELF2/m | Elongation factor 2 | lung squamous cell carcinoma |
| ETV6-AML1 | Ets variant gene6/acute myeloid leukemia 1 gene fusion protein | ALL |
| FN1/m | fibronectin 1 | melanoma |
| GPNMB/m | | melanoma |
| HLA-A*0201-R170I | arginine to isoleucine exchange at residue 170 of the alpha-helix of the alpha2-domain in the HLA-A2 gene | renal cell carcinoma |
| HLA-A11/m | | melanoma |
| HLA-A2/m | | renal cell carcinoma |
| HSP70-2M | heat shock protein 70-2 mutated | renal cell carcinoma, melanoma, neuroblastoma |
| KIAA0205/m | | bladder tumor |
| K-Ras/m | | pancreatic carcinoma, colorectal carcinoma |
| LDLR-FUT | LDR-Fucosyltransferase fusion protein | melanoma |
| MART2/m | | melanoma |
| ME1/m | | non-small cell lung carcinoma |
| MUM-1/m | melanoma ubiquitous mutated 1 | melanoma |
| MUM-2/m | melanoma ubiquitous mutated 2 | melanoma |
| MUM-3/m | melanoma ubiquitous mutated 3 | melanoma |
| Myosin class I/m | | melanoma |
| neo-PAP/m | | melanoma |
| NFYC/m | | lung squamous cell carcinoma |
| N-Ras/m | | melanoma |
| OGT/m | | colorectal carcinoma |
| OS-9/m | | melanoma |
| p53/m | | |
| Pml/RARa | promyelocytic leukemia/retinoic acid receptor alpha | APL, PML |
| PRDX5/m | | melanoma |
| PTPRK/m | receptor-type protein-tyrosine phosphatase kappa | melanoma |
| RBAF600/m | | melanoma |
| SIRT2/m | | melanoma |
| SYT-SSX-1 | synaptotagmin I/synovial sarcoma X fusion protein | sarcoma |
| SYT-SSX-2 | synaptotagmin I/synovial sarcoma X fusion protein | sarcoma |
| TEL-AML1 | translocation Ets-family leukemia/acute myeloid leukemia 1 fusion protein | AML |

TABLE 2-continued

Mutant antigens expressed in cancer diseases

| Mutant antigen | Name | Expression site |
| --- | --- | --- |
| TGFbRII | TGFbeta receptor II | colorectal carcinoma |
| TPI/m | triosephosphate isomerase | melanoma |

In a preferred embodiment according to the invention, examples of tumor antigens which may be encoded by the at least one RNA (molecule) of the complexed RNA of the present invention are selected from the group consisting of 5T4, 707-AP, 9D7, AFP, AlbZIP HPG1, 5 1-integrin, 5 6-integrin, -actinin-4/m, methylacyl-coenzyme A racemase, ART-4, ARTC1/m, B7H4, BAGE-1, BCL-2, bcr/abl, catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD2O, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R17I, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PART-1, PATE, PDEF, Pim-1-Kinase, Pin-1, Pml/PARα, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP, survivin, survivin-2B, SYT-SSX-1, SYT-SSX-2, TA-90, TAG-72, TARP, TEL-AML1, TGFβ, TGFβRII, TGM-4, TPI/m, TRAG-3, TRG, TRP-1, TRP-2/6b, TRP/INT2, TRP-p8, tyrosinase, UPA, VEGF, VEGFR-2/FLK-1, and WT1.

In a preferred embodiment according to the invention, examples of tumor antigens which may be encoded by the at least one RNA (molecule) of the complexed RNA of the present invention are selected from the group consisting of MAGE-A1 [accession number M77481], MAGE-A6 [accession number NM_005363], melan-A [accession number NM_005511], GP100 [accession number M77348], tyrosinase [accession number NM_000372], survivin [accession number AF077350], CEA [accession number NM_004363], Her-2/neu [accession number M11730], WT1 [accession number NM_000378], PRAME [accession number NM_006115], EGFR1 (epidermal growth factor receptor 1) [accession number AF288738], mucin-1 [accession number NM_002456] and SEC61G [accession number NM_014302].

As a further alternative, the at least one RNA (molecule) of the complexed RNA of the present invention may encode an antibody. According to the present invention, such an antibody may be selected from any antibody, e.g. any recombinantly produced or naturally occurring antibodies, known in the art, in particular antibodies suitable for therapeutic, diagnostic or scientific purposes, or antibodies which have been identified in relation to specific cancer diseases. Herein, the term "antibody" is used in its broadest sense and specifically covers monoclonal and polyclonal antibodies (including agonist, antagonist, and blocking or neutralizing antibodies) and antibody species with polyepitopic specificity. According to the invention, "antibody" typically comprises any antibody known in the art (e.g. IgM, IgD, IgG, IgA and IgE antibodies), such as naturally occurring antibodies, antibodies generated by immunization in a host organism, antibodies which were isolated and identified from naturally occurring antibodies or antibodies generated by immunization in a host organism and recombinantly produced by biomolecular methods known in the art, as well as chimeric antibodies, human antibodies, humanized antibodies, bispecific antibodies, intrabodies, i.e. antibodies expressed in cells and optionally localized in specific cell compartments, and fragments and variants of the aforementioned antibodies. In general, an antibody consists of a light chain and a heavy chain both having variable and constant domains. The light chain consists of an N-terminal variable domain, $V_L$, and a C-terminal constant domain, $C_L$. In contrast, the heavy chain of the IgG antibody, for example, is comprised of an N-terminal variable domain, $V_H$, and three constant domains, $C_H1$, $C_H2$ und $C_H3$. Single chain antibodies may be encoded by the at least one RNA (molecule) of the complexed RNA as defined herein as well, preferably by a single-stranded RNA, more preferably by an mRNA.

According to a first alternative, the at least one RNA (molecule) of the complexed RNA of the present invention may encode a polyclonal antibody. In this context, the term, "polyclonal antibody" typically means mixtures of antibodies directed to specific antigens or immunogens or epitopes of a protein which were generated by immunization of a host organism, such as a mammal, e.g. including goat, cattle, swine, dog, cat, donkey, monkey, ape, a rodent such as a mouse, hamster and rabbit. Polyclonal antibodies are generally not identical, and thus usually recognize different epitopes or regions from the same antigen. Thus, in such a case, typically a mixture (a composition) of different RNA molecules complexed as claimed by the present invention will be applied, each encoding a specific (monoclonal) antibody being directed to specific antigens or immunogens or epitopes of a protein.

According to a further alternative, the at least one RNA (molecule) of the complexed RNA of the present invention may encode a monoclonal antibody. The term "monoclonal antibody" herein typically refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed to a single antigenic site. Furthermore, in contrast to conventional (polyclonal) antibody preparations which typically include different antibodies directed to different determinants (epitopes), each monoclonal antibody is directed to a single determinant on the antigen. For example, monoclonal antibodies as defined above may be made by the hybridoma method first described by Kohler and Milstein, Nature, 256:495 (1975), or may be made by recombinant DNA methods, e.g. as described in U.S. Pat. No. 4,816,567. "Monoclonal antibodies" may also be isolated from phage libraries generated using the techniques described in McCafferty et al., Nature, 348:552-554 (1990), for example. According to Kohler and Milstein, an immunogen (antigen) of interest is injected into a host such as a mouse and B-cell lymphocytes produced in response to the immunogen are harvested after a period of time. The B-cells are combined with myeloma cells obtained from mouse and introduced into a medium which permits the B-cells to fuse with the myeloma cells, producing hybridomas. These fused cells (hybridomas) are then placed in separate wells in microtiter plates and grown to produce monoclonal antibodies. The monoclonal antibodies are tested to determine which of them are suitable for detecting the antigen of interest. After being selected, the monoclonal antibodies can be grown in cell cultures or by injecting the hybridomas into mice. However, for the purposes of the present invention, the peptide sequences of these monoclonal antibodies have to be sequenced and RNA sequences encoding these antibodies may be prepared according to procedures well known in the art.

For therapeutical purposes in humans, non-human monoclonal or polyclonal antibodies, such as murine antibodies may also be encoded by the at least one RNA (molecule) of the complexed RNA of the present invention. However, such antibodies are typically only of limited use, since they generally induce an immune response by production of human antibodies directed to the said non-human antibodies, in the human body. Therefore, a particular non-human antibody can only be administered once to the human. To solve this problem, chimeric, humanized non-human and human antibodies can be encoded by the at least one RNA (molecule) of the complexed RNA of the present invention. "Chimeric" antibodies, which may be encoded by the at least one RNA (molecule) of the complexed RNA of the present invention, are preferably antibodies in which the constant domains of an antibody described above are replaced by sequences of antibodies from other organisms, preferably human sequences. "Humanized" (non-human) antibodies, which may be also encoded by the at least one RNA (molecule) of the complexed RNA of the present invention, are antibodies in which the constant and variable domains (except for the hypervariable domains) described above of an antibody are replaced by human sequences. According to another alternative, the at least one RNA (molecule) of the complexed RNA of the present invention may encode human antibodies, i.e. antibodies having only human sequences. Such human antibodies can be isolated from human tissues or from immunized non-human host organisms which are transgene for the human IgG gene locus, sequenced RNA sequences may be prepared according to procedures well known in the art. Additionally, human antibodies can be provided by the use of a phage display.

In addition, the at least one RNA (molecule) of the complexed RNA of the present invention may encode bispecific antibodies. "Bispecific" antibodies in context of the invention are preferably antibodies which act as an adaptor between an effector and a respective target, e.g. for the purposes of recruiting effector molecules such as toxins, drugs, cytokines etc., targeting effector cells such as CTL, NK cells, makrophages, granulocytes, etc. (see for review: Kontermann R. E., Acta Pharmacol. Sin, 2005, 26(1): 1-9). Bispecific antibodies as described herein are, in general, configured to recognize, e.g. two different antigens, immunogens, epitopes, drugs, cells (or receptors on cells), or other molecules (or structures) as described above. Bispecificity means herewith that the antigen-binding regions of the antibodies are specific for two different epitopes. Thus, different antigens, immunogens or epitopes, etc. can be brought close together, what, optionally, allows a direct interaction of the two components. For example, different cells such as effector cells and target cells can be connected via a bispecific antibody. Encompassed, but not limited, by the present invention are antibodies or fragments thereof which bind, on the one hand, a soluble antigen as described herein, and, on the other hand, an antigen or receptor on the surface of a tumor cell.

In summary, according to the invention, the at least one RNA (molecule) of the complexed RNA of the present invention may also encode antibodies as defined above. Since these antibodies are intracellularly expressed antibodies, i.e. antibodies which are encoded by nucleic acids localized in specific compartments of the cell and also expressed there, such antibodies may also be termed intrabodies.

Antibodies as encoded by the at least one RNA (molecule) of the complexed RNA of the present invention may preferably comprise full-length antibodies, i.e. antibodies composed of the full heavy and full light chains, as described above. However, derivatives of antibodies such as antibody fragments, variants or adducts may be encoded by the above at least one RNA of the complexed RNA in accordance with the present invention.

The at least one RNA (molecule) of the complexed RNA of the present invention may also encode antibody fragments selected from Fab, Fab', F(ab')$_2$, Fc, Facb, pFc', Fd and Fv fragments of the aforementioned antibodies. In general, antibody fragments are known in the art. For example, a Fab ("fragment, antigen binding") fragment is composed of one constant and one variable domain of each of the heavy and the light chain. The two variable domains bind the epitope on specific antigens. The two chains are connected via a disulfide linkage. A scFv ("single chain variable fragment") fragment, for example, typically consists of the variable domains of the light and heavy chains. The domains are linked by an artificial linkage, in general a polypeptide linkage such as a peptide composed of 15-25 glycine, proline and/or serine residues.

According to the invention, the at least one RNA (molecule) of the complexed RNA of the present invention may encode fragments and/or variants of the aforementioned therapeutically active proteins, antigens or antibodies, wherein the fragments and/or variants may have a sequence identity to one of the aforementioned therapeutically active proteins, antigens or antibodies of at least 70%, 80% or 85%, preferably at least 90%, more preferably at least 95% and most preferably at least 99% over the whole length of the coding nucleic acid or amino acid sequences encoding these therapeutically active proteins, antigens or antibodies. Preferably, the fragments and/or variants have the same biological function or specific activity compared to the full-length native therapeutically active proteins, antigens or antibodies, e.g. specific binding capacity (e.g. of particular antigens), catalytic activity (e.g. of therapeutically active proteins), etc. In this context, "biological function" of antibodies described herein also comprises neutralization of antigens, complement activation or opsonization. Thereby, antibodies typically recognize either native epitopes on the cell surface or free antigens. Antibodies as defined above can interact with the cell-presenting antigens and initiate different defense mechanisms. On the one hand, the antibody can initiate signaling mechanisms in the targeted cell that leads to the cell's self-destruction (apoptosis). On the other hand, it can mark the cell in such a way that other components or effector cells of the body's immune system can recognize and attack. The attack mechanisms are referred to as antibody-dependent complement-mediated cytotoxicity (CMC) and antibody-dependent cellular cytotoxicity (ADCC). ADCC involves a recognition of the antibody by immune cells that engage the antibody-marked cells and either through their direct action, or through the recruitment of other cell types, lead to the tagged-cell's death. CMC is a process where a cascade of different complement proteins becomes activated, usually when several antibodies are in close proximity to each other, either resulting in cell lysis or attracting other immune cells to this location for effector cell function. In the neutralization of an antigen, the antibody can bind an antigen and neutralize the same. Such neutralization reaction, in turn, leads in general to blocking of the antibody. Thus, the antibody can bind only one antigen, or, in case of a bispecific antibody, two antigens. In particular, scFv antibody fragments are useful for neutralization reactions because they don't contain the functionalities of the constant domain of an antibody. In the complement activation, the complex system of complement proteins can be activated via binding of an antibody which is independent of the Fc part of an antibody. End products of the complement cascade result in lysis of the cell and generation of an inflammatory milieu. In the opsonization, pathogens or other non-cellular particles are made accessible to phagocytes via binding the constant domain of an antibody. Alternatively, cells recognized as foreign can be lysed via antibody-dependent cell-mediated cytotoxicity (ADCC). In particular, NK-cells can display lysis functions by activating Fc receptors.

In order to determine the percentage to which two RNA sequences (nucleic or amino acid) are identical, the sequences can be aligned in order to be subsequently compared to one another. Therefore, e.g. gaps can be inserted into the sequence of the first sequence and the component at the corresponding position of the second sequence can be compared. If a position in the first sequence is occupied by the same component as is the case at a position in the second sequence, the two sequences are identical at this position. The percentage to which two sequences are identical is a function of the number of identical positions divided by the total number of positions.

The percentage to which two sequences are identical can be determined using a mathematical algorithm. A preferred, but not limiting, example of a mathematical algorithm which can be used is the algorithm of Karlin et al., (1993), PNAS USA, 90:5873-5877 or Altschul et al. (1997), Nucleic Acids Res, 25:3389-3402. Such an algorithm is integrated in the BLAST program. Sequences which are identical to the sequences of the RNA of the complexed RNA of the present invention to a certain extent can be identified by this program.

Those at least one RNA molecules (of the complexed RNA of the present invention) encoding amino acid sequences which have (a) conservative substitution(s) compared to the physiological sequence in particular fall under the term variants. Substitutions in which encoded amino acids which originate from the same class are exchanged for one another are called conservative substitutions. In particular, these are encoded amino acids encoded aliphatic side chains, positively or negatively charged side chains, aromatic groups in the side chains or encoded amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

Immunostimulatory RNA

According to a third embodiment, the at least one RNA (molecule) of the complexed RNA of the present invention may be an immunostimulatory RNA. Thereby, the immunostimulatory RNA may exhibit an immunostimulatory effect already prior to complexation of the RNA with the inventive oligopeptide according to formula (I) as defined above, or, more preferably, an immunostimulatory effect of the RNA as used herein can be enhanced or even induced by complexation of the RNA with the inventive oligopeptide according to formula (I) as defined above. The immunostimulatory RNA of the complexed RNA of the present invention may be any RNA, e.g. a coding RNA, as defined above. Preferably, the immunostimulatory RNA may be a single-stranded, a double-stranded or a partially double-stranded RNA, more preferably a single-stranded RNA, and/or a circular or linear RNA, more preferably a linear RNA. More preferably, the immunostimulatory RNA may be a (linear) single-stranded RNA. Even more preferably, the immunostimulatory RNA may be a ((linear) single-stranded) messenger RNA (mRNA). An immunostimulatory RNA may also occur as a short RNA oligonucleotide as defined above.

An immunostimulatory RNA as used herein may furthermore be selected from any class of RNA molecules, found in nature or being prepared synthetically, and which can induce an immune response. In this context, an immune response may occur in various ways. A substantial factor for a suitable immune response is the stimulation of different T-cell sub-populations. T-lymphocytes are typically divided into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of the effector proteins (cytokines)

produced by them. Thus, Th1 cells assist the cellular immune response by activation of macrophages and cytotoxic T-cells. Th2 cells, on the other hand, promote the humoral immune response by stimulation of the B-cells for conversion into plasma cells and by formation of antibodies (e.g. against antigens). The Th1/Th2 ratio is therefore of great importance in the immune response. In connection with the present invention, the Th1/Th2 ratio of the immune response is preferably shifted in the direction towards the cellular response (Th1 response) and a cellular immune response is thereby induced. According to one example, the immune system may be activated by ligands of Toll-like receptors (TLRs). TLRs are a family of highly conserved pattern recognition receptor (PRR) polypeptides that recognize pathogen-associated molecular patterns (PAMPs) and play a critical role in innate immunity in mammals. Currently at least thirteen family members, designated TLR1-TLR13 (Toll-like receptors: TLR1, TLR2, TLR3, TLR4, TLR5, TLR6, TLR7, TLR8, TLR9, TLR10, TLR11, TLR12 or TLR13), have been identified. Furthermore, a number of specific TLR ligands have been identified. It was e.g. found that unmethylated bacterial DNA and synthetic analogs thereof (CpG DNA) are ligands for TLR9 (Hemmi H et al., (2000) Nature 408:740-5; Bauer S et al. (2001) Proc Nat-lAcadSci USA 98, 9237-42). Furthermore, it has been reported that ligands for certain TLRs include certain nucleic acid molecules and that certain types of RNA are immunostimulatory in a sequence-independent or sequence-dependent manner, wherein these various immunostimulatory RNAs may e.g. stimulate TLR3, TLR7, or TLR8, or intracellular receptors such as RIG-1, MDA-5, etc. E.g. Lipford et al., determined certain G, U-containing oligoribonucleotides as immunostimulatory by acting via TLR7 and TLR8 (see WO 03/086280). The immunostimulatory G, U-containing oligoribonucleotides described by Lipford et al. were believed to be derivable from RNA sources including ribosomal RNA, transfer RNA, messenger RNA, and viral RNA.

According to the present invention, it was found that any RNA (molecule) as e.g. defined above (irrespective of its specific length, strandedness, modification and/or nucleotide sequence) complexed with a carrier peptide according to empirical formula $(Arg)_l;(Lys)_m;(His)_n;(Orn)_o;(Xaa)_x$ (formula I) may have immunostimulatory properties, i.e. enhance the immune response. RNA as defined above complexed with a carrier peptide according to empirical formula $(Arg)_l;(Lys)_m;(His)_n;(Orn)_o;(Xaa)_x$ (formula I) may thus be used to enhance (unspecific) immunostimulation, if suitable and desired for a specific treatment. Accordingly, it can be an intrinsic property of the complexed RNA of the invention to provide immunestimulatory effects by complexation of any RNA with a peptide according to formula (I).

The at least one (immunostimulatory) RNA (molecule) of the complexed RNA of the present invention may thus comprise any RNA sequence known to be immunostimulatory, including, without being limited thereto, RNA sequences representing and/or encoding ligands of TLRs, preferably selected from family members TLR1-TLR13, more preferably from TLR7 and TLR8, ligands for intracellular receptors for RNA (such as RIG-I or MAD-5, etc.) (see e.g. Meylan, E., Tschopp, J. (2006). Toll-like receptors and RNA helicases: two parallel ways to trigger antiviral responses. Mol. Cell. 22, 561-569), or any other immunostimulatory RNA sequence. Furthermore, (classes of) RNA molecules, which may be used as immunostimulatory RNA may include any other RNA capable of eliciting an immune response. Without being limited thereto, such immunostimulatory RNA may include ribosomal RNA (rRNA), transfer RNA (tRNA), messenger RNA (mRNA), and viral RNA (vRNA).

Such further (classes of) RNA molecules, which may be used as the at least one (immunostimulatory) RNA (molecule) of the complexed RNA of the present invention, may comprise, without being limited thereto, e.g. an RNA molecule of formula (IIa):

$$G_l X_m G_n,$$

wherein:
G is guanosine, uracil or an analogue of guanosine or uracil;
X is guanosine, uracil, adenosine, thymidine, cytosine or an analogue of the above-mentioned nucleotides;
l is an integer from 1 to 40,
wherein when l=1 G is guanosine or an analogue thereof,
when l>1 at least 50% of the nucleotides are guanosine or an analogue thereof;
m is an integer and is at least 3;
wherein when m=3 X is uracil or an analogue thereof,
when m>3 at least 3 successive uracils or analogues of uracil occur;
n is an integer from 1 to 40,
wherein when n=1 G is guanosine or an analogue thereof,
when n>1 at least 50% of the nucleotides are guanosine or an analogue thereof.

In addition, such further (classes of) RNA molecules, which may be used as the at least one (immunostimulatory) RNA (molecule) of the complexed RNA of the present invention may comprise, without being limited thereto, e.g. an RNA molecule of formula (IIb):

$$C_l X_m C_n,$$

wherein:
C is cytosine, uracil or an analogue of cytosine or uracil;
X is guanosine, uracil, adenosine, thymidine, cytosine or an analogue of the above-mentioned nucleotides;
l is an integer from 1 to 40,
wherein when l=1 C is cytosine or an analogue thereof,
when l>1 at least 50% of the nucleotides are cytosine or an analogue thereof;
m is an integer and is at least 3;
wherein when m=3 X is uracil or an analogue thereof,
when m>3 at least 3 successive uracils or analogues of uracil occur;
n is an integer from 1 to 40,
wherein when n=1 C is cytosine or an analogue thereof,
when n>1 at least 50% of the nucleotides are cytosine or an analogue thereof.

Preferably, the immunostimulatory RNA molecules as used herein as the at least one RNA (molecule) of the complexed RNA of the present invention comprise a length as defined above in general for RNA molecules of the complexed RNA of the present invention, more preferably a length of 5 to 5000, of 500 to 5000 or, more preferably, of 1000 to 5000 or, alternatively, of 5 to 1000, 5 to 500, 5 to 250, of 5 to 100, of 5 to 50 or, more preferably, of 5 to 30 nucleotides.

The at least one immunostimulatory RNA as used herein as the at least one RNA (molecule) of the complexed RNA of the present invention may be furthermore modified, preferably "chemically modified" in order to enhance the immunostimulatory properties of said DNA. The term "chemical modification" means that the RNA used as immuostimulatory RNA according to the invention is modified by replacement, insertion or removal of individual or several atoms or atomic groups compared with naturally occurring RNA species.

Preferably, the chemical modification of the RNA comprises at least one analogue of naturally occurring nucleotides. In a list which is in no way conclusive, examples which may be mentioned for nucleotide analogues which can be used according to the invention are analogues of guanosine, uracil, adenosine, thymidine, cytosine. The modifications may refer to modifications of the base, the ribose moiety and/or the phosphate backbone moiety. In this context, analogues of guanosine, uracil, adenosine, and cytosine include, without implying any limitation, any naturally occurring or non-naturally occurring guanosine, uracil, adenosine, thymidine or cytosine that has been altered chemically, for example by acetylation, methylation, hydroxylation, etc., including 1-methyl-adenosine, 1-methyl-guanosine, 1-methyl-inosine, 2,2-dimethyl-guanosine, 2,6-diaminopurine, 2'-Amino-2'-deoxyadenosine, 2'-Amino-2'-deoxycytidine, 2'-Amino-2'-deoxyguanosine, 2'-Amino-2'-deoxyuridine, 2-Amino-6-chloropurineriboside, 2-Aminopurine-riboside, 2'-Araadenosine, 2'-Aracytidine, 2'-Arauridine, 2'-Azido-2'-deoxyadenosine, 2'-Azido-2'-deoxycytidine, 2'-Azido-2'-deoxyguanosine, 2'-Azido-2'-deoxyuridine, 2-Chloroadenosine, 2'-Fluoro-2'-deoxyadenosine, 2'-Fluoro-2'-deoxycytidine, 2'-Fluoro-2'-deoxyguanosine, 2'-Fluoro-2'-deoxyuridine, 2'-Fluorothymidine, 2-methyl-adenosine, 2-methyl-guanosine, 2-methyl-thio-N6-isopenenyl-adenosine, 2'-O-Methyl-2-aminoadenosine, 2'-O-Methyl-2'-deoxyadenosine, 2'-O-Methyl-2'-deoxycytidine, 2'-O-Methyl-2'-deoxyguanosine, 2'-O-Methyl-2'-deoxyuridine, 2'-O-Methyl-5-methyluridine, 2'-O-Methylinosine, 2'-O-Methylpseudouridine, 2-Thiocytidine, 2-thio-cytosine, 3-methyl-cytosine, 4-acetyl-cytosine, 4-Thiouridine, 5-(carboxyhydroxymethyl)-uracil, 5,6-Dihydrouridine, 5-Aminoallylcytidine, 5-Aminoallyl-deoxy-uridine, 5-Bromouridine, 5-carboxymethylaminomethyl-2-thio-uracil, 5-carboxymethylamonomethyl-uracil, 5-Chloro-Ara-cytosine, 5-Fluorouridine, 5-Iodouridine, 5-methoxycarbonylmethyl-uridine, 5-methoxy-uridine, 5-methyl-2-thio-uridine, 6-Azacytidine, 6-Azauridine, 6-Chloro-7-deaza-guanosine, 6-Chloropurineriboside, 6-Mercapto-guanosine, 6-Methyl-mercaptopurine-riboside, 7-Deaza-2'-deoxy-guanosine, 7-Deazaadenosine, 7-methyl-guanosine, 8-Azaadenosine, 8-Bromoadenosine, 8-Bromo-guanosine, 8-Mercapto-guanosine, 8-Oxoguanosine, Benzimidazole-riboside, Beta-D-mannosyl-queosine, Dihydro-uracil, Inosine, N1-Methyladenosine, N6-([6-Aminohexyl]carbamoyl methyl)-adenosine, N6-isopentenyl-adenosine, N6-methyl-adenosine, N7-Methyl-xanthosine, N-uracil-5-oxyacetic acid methyl ester, Puromycin, Queosine, Uracil-5-oxyacetic acid, Uracil-5-oxyacetic acid methyl ester, Wybutoxosine, Xanthosine, and Xylo-adenosine. The preparation of such analogues is known to a person skilled in the art, for example from U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642. In the case of an analogue as described above, particular preference is given according to the invention to those analogues that increase the immunogenicity of the immunostimulatory RNA sequence as used herein as the at least one RNA (molecule) of the complexed RNA of the present invention and/or do not interfere with a further modification that has been introduced into said immunostimulatory RNA.

siRNA

In a forth embodiment, the at least one RNA (molecule) of the complexed RNA of the present invention may be in the form of siRNA. A siRNA is of interest particularly in connection with the phenomenon of RNA interference. Attention was drawn to the phenomenon of RNA interference in the course of immunological research. In recent years, a RNA-based defense mechanism has been discovered, which occurs both in the kingdom of the fungi and in the plant and animal kingdom and acts as an "immune system of the genome". The system was originally described in various species independently of one another, first in *C. elegans*, before it was possible to identify the underlying mechanisms of the processes as being identical: RNA-mediated virus resistance in plants, PTGS (posttranscriptional gene silencing) in plants, and RNA interference in eukaryotes are accordingly based on a common procedure. The in vitro technique of RNA interference (RNAi) is based on double-stranded RNA molecules (dsRNA), which trigger the sequence-specific suppression of gene expression (Zamore (2001) Nat. Struct. Biol. 9: 746-750; Sharp (2001) Genes Dev. 5:485-490: Hannon (2002) Nature 41: 244-251). In the transfection of mammalian cells with long dsRNA, the activation of protein kinase R and RnaseL brings about unspecific effects, such as, for example, an interferon response (Stark et al., (1998) Annu. Rev. Biochem. 67: 227-264; He and Katze (2002) Viral Immunol. 15: 95-119). These unspecific effects are avoided when shorter, for example 21- to 23-mer, so-called siRNA (small interfering RNA), is used, because unspecific effects are not triggered by siRNA that is shorter than 30 bp (Elbashir et al. (2001) Nature 411: 494-498). Recently, dsRNA molecules have also been used in vivo (McCaffrey et al., (2002), Nature 418: 38-39; Xia et al., (2002), Nature Biotech. 20: 1006-1010; Brummelkamp et al., (2002), Cancer Cell 2: 243-247). Thus, a siRNA as used for the complexed RNA according to the present invention typically comprises a (single- or) double stranded, preferably a double-stranded, RNA sequence with about 8 to 30 nucleotides, preferably 17 to 25 nucleotides, even more preferably from 20 to 25 and most preferably from 21 to 23 nucleotides. In principle, all the sections having a length of from 17 to 29, preferably from 19 to 25, most preferably from 21 to 23 base pairs that occur in the coding region of a RNA sequence as mentioned above, e.g. of an (m)RNA sequence, can serve as target sequence for a siRNA. Equally, siRNAs can also be directed against nucleotide sequences of a (therapeutically relevant) protein or antigen described hereinbefore that do not lie in the coding region, in particular in the 5' non-coding region of the RNA, for example, therefore, against non-coding regions of the RNA having a regulatory function. The target sequence of the siRNA can therefore lie in the translated and/or untranslated region of the RNA and/or in the region of the control elements. The target sequence of a siRNA can also lie in the overlapping region of untranslated and translated sequence; in particular, the target sequence can comprise at least one nucleotide upstream of the start triplet of the coding region of the RNA.

Antisense RNA

According to a fifth embodiment, the at least one RNA (molecule) of the complexed RNA of the present invention may be an antisense RNA. In the context of the present invention, an antisense RNA is preferably a (single-stranded) RNA molecule transcribed on the basis of the coding, rather than the template, strand of DNA, so that it is complementary to the sense (messenger) RNA. An antisense RNA as used herein as the at least one RNA (molecule) of the complexed RNA of the present invention typically forms a duplex between the sense and antisense RNA molecules and is thus capable to block translation of the mRNA. An antisense RNA as used herein as the at least one RNA (molecule) of the complexed RNA of the present invention can be directed against (may be complementary to) any portion of the mRNA sequence, which may encode a (therapeutically relevant) protein or antigen (e.g. as described hereinbefore), if thereby translation of the encoded protein is reduced/suppressed. Accordingly, the target sequence of the antisense RNA on the targeted mRNA may be located in the translated and/or untranslated region of the mRNA, e.g. in the region of the mRNA control elements, in particular in the 5' non-coding region of the RNA exerting a regulatory function. The target sequence of an antisense RNA on the targeted mRNA may also be constructed such that the antisense RNA binds to the mRNA by covering with its sequence a region which is partially complementary to the untranslated and to translated (coding) sequence of the targeted mRNA; in particular, the antisense RNA may be complementary to the target mRNA sequence by at least one nucleotide upstream of the start triplet of the coding region of the targeted mRNA. Preferably, the antisense RNA as used herein as the at least one RNA (molecule) of the complexed RNA of the present invention comprises a length as generally defined above for RNA molecules (of the complexed RNA of the present invention). Typically the antisense RNA as used herein as the at least one RNA (molecule) of the complexed RNA of the present invention will be a fragment of the targeted mRNA. In more detail, the antisense RNA may have more preferably a length of 5 to 5000, of 500 to 5000, and, more preferably, of 1000 to 5000 or, alternatively, of 5 to 1000, 5 to 500, 5 to 250, of 5 to 100, of 5 to 50 or of 5 to 30 nucleotides, or, alternatively, and even more preferably a length of 20 to 100, of 20 to 80, or of 20 to 60 nucleotides.

Modifications of the RNA

According to one embodiment, the RNA as used herein as the at least one RNA (molecule) of the complexed RNA of the present invention (irrespective of its e.g. specific therapeutic potential, length, and/or sequence), particularly the short RNA oligonucleotide, the coding RNA, the immunostimulatory RNA, the siRNA, the antisense RNA, the riboswitches, ribozymes or aptamers, may provided as a modified RNA, wherein any modification, in particular a modification disclosed in the following) may be introduced (in any combination or as such) into the RNA (molecules) as defined above. Certain types of modifications may, however, be more suitable for specific RNA types (e.g. more suitable for coding RNA), while other modifications may be applied for any RNA molecule, e.g. as defined herein without being restricted to specific RNA types. Accordingly, modifications of the RNA may be introduced in order to achieve specific or complex effects which may desired for the use of the subject-matter of the invention. Accordingly, modifications may be designed to e.g. stabilize the RNA against degradation, to enhance their transfection efficacy, to improve its translation efficacy, to increase their immunogenic potential and/or to enhance their therapeutic potential (e.g. enhance their silencing or antisense properties). It is particularly preferred, if the modified RNA as component of the inventive complexed RNA allows to combine improvement of at least one, more preferably of at least two functional properties, e.g. to stabilized the RNA and to improve the therapeutic or immunogenic potential.

Generally, it is a primary object to stabilize the RNA as used herein as the at least one RNA (molecule) of the complexed RNA of the present invention, which allows to extend their half-life time in vivo. Preferably, the half-life time of a modified RNA under in vivo conditions is extended (as compared to the unmodified RNA) by at least 20, more preferably at least 40, more preferably at least 50 and even more preferably at least 70, 80, 90, 100, 150 or 200%. The stabilization achieved by the modification may extend the half-life time of the modified mRNA by at least 5, 10, 15, 30 or more preferably at least 60 min as compared to the unmodified RNA.

According to one embodiment the at least one RNA (molecule) of the complexed RNA of the present invention, preferably a coding RNA, e.g. mRNA, may be stabilized by modifying the G/C content of e.g. the coding region of the RNA. In a particularly preferred embodiment of the present invention, the G/C content of the coding region of the RNA (of the complexed RNA of the present invention) is altered, particularly increased, compared to the G/C content of the coding region of its corresponding wild-type RNA, i.e. the unmodified RNA. The encoded amino acid sequence of the modified RNA is preferably not altered as compared to the amino acid sequence encoded by the corresponding wild-type RNA.

This modification of the RNA as used herein as the at least one RNA (molecule) of the complexed RNA of the present invention is based on the fact that the coding sequence of any RNA to be translated is important for efficient translation of that RNA. In particular, sequences having an increased G (guanosine)/C (cytosine) content are more stable than sequences having an increased A (adenosine)/U (uracil) content. According to the invention, the codons of the RNA are therefore altered compared to the wild-type RNA, while retaining the translated amino acid sequence, such that they include an increased amount of G/C nucleotides. In respect to the fact that several codons code for one and the same amino acid (so-called degeneration of the genetic code), the most favorable codons for the stability can be determined (so-called alternative codon usage).

Depending on the amino acid to be encoded by the RNA as used herein as the at least one RNA (molecule) of the complexed RNA of the present invention, there are various possibilities for modification of the RNA sequence, compared to its wild-type sequence. In the case of amino acids which are encoded by codons which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present.

In contrast, codons which contain A and/or U nucleotides can be modified by substitution of other codons which code for the same amino acids but contain no A and/or U. Examples of these are:

the codons for Pro can be modified from CCU or CCA to CCC or CCG;
the codons for Arg can be modified from CGU or CGA or AGA or AGG to CGC or CGG;
the codons for Ala can be modified from GCU or GCA to GCC or GCG;
the codons for Gly can be modified from GGU or GGA to GGC or GGG.

In other cases, although A or U nucleotides cannot be eliminated from the codons, it is however possible to decrease the A and U content by using codons which contain a lower content of A and/or U nucleotides. Examples of these are:

the codons for Phe can be modified from UUU to UUC;
the codons for Leu can be modified from UUA, UUG, CUU or CUA to CUC or CUG;
the codons for Ser can be modified from UCU or UCA or AGU to UCC, UCG or AGC;
the codon for Tyr can be modified from UAU to UAC;
the codon for Cys can be modified from UGU to UGC;
the codon for His can be modified from CAU to CAC;
the codon for Gln can be modified from CAA to CAG;
the codons for Ile can be modified from AUU or AUA to AUC;
the codons for Thr can be modified from ACU or ACA to ACC or ACG;
the codon for Asn can be modified from AAU to AAC;
the codon for Lys can be modified from AAA to AAG;
the codons for Val can be modified from GUU or GUA to GUC or GUG;
the codon for Asp can be modified from GAU to GAC;
the codon for Glu can be modified from GAA to GAG;
the stop codon UAA can be modified to UAG or UGA.

In the case of the codons for Met (AUG) and Trp (UGG), on the other hand, there is no possibility of sequence modification.

The substitutions listed above can be used either individually or in all possible combinations to increase the G/C content of the RNA as used herein as the at least one RNA (molecule) of the complexed RNA of the present invention compared to its particular wild-type RNA (i.e. the original sequence). Thus, for example, all codons for Thr occurring in the wild-type sequence can be modified to ACC (or ACG). Preferably, however, for example, combinations of the above substitution possibilities are used:
substitution of all codons coding for Thr in the original sequence (wild-type RNA) to ACC (or ACG) and
substitution of all codons originally coding for Ser to UCC (or UCG or AGC);
substitution of all codons coding for Ile in the original sequence to AUC and
substitution of all codons originally coding for Lys to AAG and
substitution of all codons originally coding for Tyr to UAC;
substitution of all codons coding for Val in the original sequence to GUC (or GUG) and
substitution of all codons originally coding for Glu to GAG and
substitution of all codons originally coding for Ala to GCC (or GCG) and
substitution of all codons originally coding for Arg to CGC (or CGG);
substitution of all codons coding for Val in the original sequence to GUC (or GUG) and
substitution of all codons originally coding for Glu to GAG and
substitution of all codons originally coding for Ala to GCC (or GCG) and
substitution of all codons originally coding for Gly to GGC (or GGG) and
substitution of all codons originally coding for Asn to AAC;
substitution of all codons coding for Val in the original sequence to GUC (or GUG) and
substitution of all codons originally coding for Phe to UUC and
substitution of all codons originally coding for Cys to UGC and
substitution of all codons originally coding for Leu to CUG (or CUC) and
substitution of all codons originally coding for Gln to CAG and
substitution of all codons originally coding for Pro to CCC (or CCG); etc.

Preferably, the G/C content of the coding region of the RNA as used herein as the at least one RNA (molecule) of the complexed RNA of the present invention is increased by at least 7%, more preferably by at least 15%, particularly preferably by at least 20%, compared to the G/C content of the coded region of the wild-type RNA which codes for a protein. According to a specific embodiment at least 60%, more preferably at least 70%, even more preferably at least 80% and most preferably at least 90%, 95% or even 100% of the substitutable codons in the region coding for a protein or the whole sequence of the wild type RNA sequence are substituted, thereby increasing or even maximizing the GC/content of said sequence.

In this context, it is particularly preferable to increase the G/C content of the RNA as used herein as the at least one RNA (molecule) of the complexed RNA of the present invention to the maximum (i.e. 100% of the substitutable codons), in particular in the region coding for a protein, compared to the wild-type sequence.

According to the invention, a further preferred modification of the RNA as used herein as the at least one RNA (molecule) of the complexed RNA of the present invention is based on the finding that the translation efficiency is also determined by a different frequency in the occurrence of tRNAs in cells. Thus, if so-called "rare codons" are present in an RNA sequence to an increased extent, the corresponding modified RNA sequence is translated to a significantly poorer degree than in the case where codons coding for relatively "frequent" tRNAs are present.

According to the invention, in the RNA as used herein as the at least one RNA (molecule) of the complexed RNA of the present invention, the region which codes for the protein is modified compared to the corresponding region of the wild-type RNA such that at least one codon of the wild-type sequence which codes for a tRNA which is relatively rare in the cell is exchanged for a codon which codes for a tRNA which is relatively frequent in the cell and carries the same amino acid as the relatively rare tRNA. By this modification, the RNA sequences are modified such that codons for which frequently occurring tRNAs are available are inserted. In other words, according to the invention, by this modification all codons of the wild-type sequence which code for a tRNA which is relatively rare in the cell can in each case be exchanged for a codon which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content which is increased, in particular maximized, in the RNA as used herein as the at least one RNA (molecule) of the complexed RNA of the present invention, with the "frequent" codons without modifying the amino acid sequence of the protein encoded by the coding region of the RNA. This preferred embodiment allows provision of a particularly efficiently translated and stabilized (modified) RNA of the complexed RNA according to the present invention.

The determination of the G/C content of an RNA as used herein as the at least one RNA (molecule) of the complexed RNA of the present invention (increased G/C content; exchange of tRNAs) can be carried out using the computer program explained in WO 02/098443—the disclosure content of which is included in its full scope in the present invention. Using this computer program, the nucleotide sequence of any desired RNA can be modified with the aid of the genetic code or the degenerative nature thereof such that a maximum G/C content results, in combination with the use of codons which code for tRNAs occurring as frequently as possible in the cell, the amino acid sequence coded by the RNA (molecule) preferably not being modified compared to the non-modified sequence. Alternatively, it is also possible to modify only the G/C content or only the codon usage compared to the original sequence. The source code in Visual Basic 6.0 (development environment used: Microsoft Visual Studio Enterprise 6.0 with Servicepack 3) is also described in WO 02/098443.

In a further preferred embodiment of the present invention, the A/U content in the environment of the ribosome binding site of the at least one RNA (molecule) of the complexed RNA of the present invention is increased compared to the A/U content in the environment of the ribosome binding site of its particular wild-type RNA. This modification (an increased A/U content around the ribosome binding site) increases the efficiency of ribosome binding to the modified RNA. An effective binding of the ribosomes to the ribosome binding site (Kozak sequence: GCCGCCAC-CAUGG (SEQ ID NO: 33), the AUG forms the start codon) in turn has the effect of an efficient translation of the modified RNA.

According to a further embodiment of the present invention the at least one RNA (molecule) of the complexed RNA of the present invention may be modified with respect to potentially destabilizing sequence elements. Particularly, the coding region and/or the 5' and/or 3' untranslated region of this RNA may be modified compared to the particular wild-type RNA such that is contains no destabilizing sequence elements, the coded amino acid sequence of the RNA (molecule) preferably not being modified compared to its particular wild-type RNA. It is known that, for example, in sequences of eukaryotic RNAs destabilizing sequence elements (DSE) occur, to which signal proteins bind and regulate enzymatic degradation of RNA in vivo. For further stabilization of the RNA (molecule), optionally in the region which encodes for a protein, one or more such modifications compared to the corresponding region of the wild-type RNA can therefore be carried out, so that no or substantially no destabilizing sequence elements are contained there. According to the invention, DSE present in the untranslated regions (3'- and/or 5'-UTR) can also be eliminated from the at least one RNA (molecule) of the complexed RNA of the present invention by such modifications.

Such destabilizing sequences are e.g. AU-rich sequences (AURES), which occur in 3'-UTR sections of numerous unstable RNAs (Caput et al., Proc. Natl. Acad. Sci. USA 1986, 83: 1670 to 1674). The RNA of the complexed RNA according to the present invention is therefore preferably modified compared to the wild-type RNA such that the RNA contains no such destabilizing sequences. This also applies to those sequence motifs which are recognized by possible endonucleases, e.g. the sequence GAACAAG, which is contained in the 3'-UTR segment of the gene which codes for the transferrin receptor (Binder et al., EMBO J. 1994, 13: 1969 to 1980). These sequence motifs are also preferably removed according to the invention in the at least one RNA (molecule) of the complexed RNA of the present invention.

According to the present invention, the at least one RNA (molecule) of the complexed RNA of the present invention can have a 5' cap structure. Examples of cap structures which can be used according to the invention are m7G(5') ppp, (5'(A,G(5')ppp(5')A and G(5')ppp(5')G.

Another modification enhancing the stability of the at least one RNA (molecule) of the complexed RNA of the present invention is based on 5'- or 3' elongations of the RNA, typically homonucleotide elongations of a length of 10 to 200 nucleotides. These elongations may contain, particularly if the RNA is provided as mRNA, a poly-A tail at the 3' terminus of typically about 10 to 200 adenosine nucleotides, preferably about 10 to 100 adenosine nucleotides, more preferably about 20 to 70 adenosine nucleotides or even more preferably about 20 to 60 adenosine nucleotides. Alternatively or additionally, the at least one RNA (molecule) of the complexed RNA of the present invention may contain, particularly if the RNA is provided as mRNA, a poly-C tail at the 3' terminus of typically about 10 to 200 cytosine nucleotides, preferably about 10 to 100 cytosine nucleotides, more preferably about 20 to 70 cytosine nucleotides or even more preferably about 20 to 60 or even 10 to 40 cytosine nucleotides.

Another modification, which may occur in the at least one RNA (molecule) of the complexed RNA of the present invention, particularly if the RNA is provided as mRNA, refers preferably to at least one IRES and/or at least one 5' and/or 3' stabilizing sequence. According to the invention, one or more so-called IRES (internal ribosomal entry site) may be inserted into the RNA. An IRES can thus function as the sole ribosome binding site, but it can also serve to provide a RNA which codes several proteins which are to be translated by the ribosomes independently of one another (multicistronic RNA). Examples of IRES sequences which can be used according to the invention are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukoma virus (MLV), simian immunodeficiency viruses (SIV) or cricket paralysis viruses (CrPV).

According to the invention, the at least one RNA (molecule) of the complexed RNA of the present invention may exhibit at least one 5' and/or 3' stabilizing sequence as known from the art. These stabilizing sequences in the 5' and/or 3' untranslated regions have the effect of increasing the half-life of the RNA in the cytosol. These stabilizing sequences can have 100% sequence homology to naturally occurring sequences which occur in viruses, bacteria and eukaryotes, but can also be partly or completely synthetic. The untranslated sequences (UTR) of the globin gene, e.g. from *Homo sapiens* or *Xenopus laevis* may be mentioned as an example of stabilizing sequences which can be used in the present invention for a stabilized RNA. Another example of a stabilizing sequence has the general formula (C/U) CCAN$_x$CCC(U/A)Py$_x$UC(C/U)CC (SEQ ID NO: 34), which is contained in the 3'UTR of the very stable RNA which codes for globin, (I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art. The at least one RNA (molecule) of the complexed RNA of the present invention is therefore preferably present as globin UTR (untranslated regions)-stabilized RNA, in particular as globin UTR-stabilized RNA.

If desired, the at least one RNA (molecule) of the complexed RNA of the present invention may contain backbone modifications. A backbone modification in connection with the present invention is a modification in which phosphates of the backbone of the nucleotides contained in the RNA are chemically modified. Such backbone modifications typically include, without implying any limitation, modifications from the group consisting of methylphosphonates, phosphoramidates and phosphorothioates (e.g. cytidine-5'-O-(1-thiophosphate)).

The at least one RNA (molecule) of the complexed RNA of the present invention may additionally or alternatively also contain sugar modifications. A sugar modification in connection with the present invention is a chemical modification of the sugar of the nucleotides present and typically includes, without implying any limitation, sugar modifications selected from the group consisting of 2'-deoxy-2'-fluoro-oligoribonucleotide (2'-fluoro-2'-deoxycytidine-5'-triphosphate, 2'-fluoro-2'-deoxyuridine-5'-triphosphate), 2'-deoxy-2'-deamine oligoribonucleotide (2'-amino-2'-deoxycytidine-5'-triphosphate, 2'-amino-2'-deoxyuridine-5'-triphosphate), 2'-O-alkyl oligoribonucleotide, 2'-deoxy-2'-C-alkyl oligoribonucleotide (2'-O-methylcytidine-5'-triphosphate, 2'-methyluridine-5'-triphosphate), 2'-C-alkyl oligoribonucleotide, and isomers thereof (2'-aracytidine-5'-triphosphate, 2'-arauridine-5'-triphosphate), or azidotriphosphate (2'-azido-2'-deoxycytidine-5'-triphosphate, 2'-azido-2'-deoxyuridine-5'-triphosphate).

The at least one RNA (molecule) of the complexed RNA of the present invention may additionally or alternatively also contain at least one base modification, which is preferably suitable for increasing the expression of the protein coded for by the at least one RNA (molecule) significantly as compared with the unaltered, i.e. natural (=native), RNA sequence. Significant in this case means an increase in the expression of the protein compared with the expression of the native RNA sequence by at least 20%, preferably at least 30%, 40%, 50% or 60%, more preferably by at least 70%, 80%, 90% or even 100% and most preferably by at least 150%, 200% or even 300%. In connection with the present invention, a nucleotide having a base modification is preferably selected from the group of the base-modified nucleotides consisting of 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-tri phosphate, 8-azaadenosine-5'-triphosphate, 8-azidoadenosine-5'-tri phosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

The at least one RNA (molecule) of the complexed RNA of the present invention may additionally or alternatively also contain at least one modification of a nucleoside of a nucleotide as contained in the at least one RNA (molecule), which acts immunosuppressive, i.e. is preferably suitable for preventing or decreasing an immune response, when administered to a patient in need thereof. Such at least one modification is preferably selected from nucleoside modifications selected from:
 a) a chemical modification at the 4-, 5- or 6-position of the pyrimidine base of the nucleosides of cytidine and/or uridine;
 b) a chemical modification at the 2-, 6-, 7- or 8-position of the purine base of the nucleosides of adenosine, inosine and/or guanosine; and/or
 c) a chemical modification at the 2'-position of the sugar of the nucleosides of adenosine, inosine, guanosine, cytidine and/or uridine.

In this context, an (m)RNA is a nucleic acid chain formed by a number of nucleotides typically selected from adenosine-5'-monophosphate, guanosine-5'-monophosphate, inosine-5'-monophosphate, cytidine-5'-monophosphate and/or uridine-5'-monophosphate. Those nucleotides are linked to each other via their monophosphate. Nucleotides comprise nucleosides and a 5'-monophosphate as a structural component, wherein the nucleosides are typically formed by a nucleobase, i.e. a pyrimidine (uracil or cytosine) or a purine (adenine or guanine) base, and a sugar. Accordingly, a modification of a nucleoside of at least one RNA (molecule) of the complexed RNA of the present invention is always intended to mean a modification in the nucleoside structure of the respective nucleotide of said at least one RNA (molecule).

According to a first modification a), at least one nucleoside of the at least one RNA (molecule) of the complexed RNA of the present invention, may be modified with a chemical modification at the 5- or 6-position of the pyrimidine base of the nucleosides cytidine and/or uridine. Without being limited thereto, such chemical modifications at the 4-, 5- or 6-position of the base pyrimidine of the nucleosides cytidine and/or uridine may be selected from the group consisting of: 4-thio, 5-iodo-/(5-1-), 5-bromo-/(5-Br—), 5-aminoallyl-, 5-fluoro-/(5-F—), 5-hydroxy-, 5-hydro-/(5-H—), 5-nitro-, 5-propynyl-/(5-(C≡C—$CH_3$)—), 5-methyl-, 5-methyl-2-thio-, 5-formyl-, 5-hydroxymethyl-, 5-methoxy-, 5-oxyacetic acid methyl ester-, 5-oxyacetic acid-, 5-carboxyhydroxymethyl-, 5-(carboxyhydroxymethyl)pyrimidine methyl ester-, 5-methoxycarbonylmethyl-, 5-methoxycarbonylmethyl-2-thio, 5-aminomethyl-, 5-aminomethyl-2-thio-, 5-aminomethyl-2-seleno-, 5-methylaminomethyl-, 5-carbamoylmethyl-, 5-carboxymethylaminomethyl-, 5-carboxymethylaminomethyl-2-thio-, 5-carboxymethyl-, 5-methyldihydro-, 5-taurinomethyl-, 5-taurinomethyl-2-thiouridine, 5-isopentenylaminomethyl-, 5-isopentenylaminomethyl-2-thio-, 5-aminopropyl-/(5-($C_3H_6NH_3$)—), 5-methoxy-ethoxy-methyl-/(5-($CH_2$—O—$C_2H_4$—O—$CH_3$)—), or 6-aza-.

According to second modification b), at least one nucleoside of the at least one RNA (molecule) of the complexed RNA of the present invention, suitable for suppressing and/or avoiding an (innate) immunostimulatory response in a mammal typically exhibited when administering the corresponding unmodified at least one RNA (molecule), may be alternatively modified with a chemical modification at the 2-, 6-, 7- or 8-position of the purine base of the nucleosides adenosine, inosine and/or guanosine. Without being limited thereto, such chemical modifications at the 2-, 6-, 7- or 8-position of the purine base of the nucleosides adenosine, inosine and/or guanosine may be selected from the group consisting of 2-Amino-, 7-Deaza-, 8-Aza-, or 8-Azido-.

According to a third modification c), at least one nucleoside of the at least one RNA (molecule) of the complexed RNA of the present invention, suitable for suppressing and/or avoiding an (innate) immunostimulatory response in a mammal typically exhibited when administering the corresponding unmodified at least one RNA (molecule), may be modified with at least one chemical modification at the 2'-position of the sugar of the nucleosides adenosine, inosine, guanosine, cytidine and/or uridine, when incorporated in the RNA sequence. Without being limited thereto, such chemical modifications at the 2'-position of the sugar of the nucleosides adenosine, inosine, guanosine, cytidine and/or uridine may be selected from the group consisting of: 2'-deoxy-, 2'-amino-2'-deoxy-, 2'-amino-, 2'-fluoro-2'-deoxy-, 2'-fluoro-, 2'-O-methyl-2'-deoxy- or 2'-O-methyl-.

According to a particularly preferred embodiment, at least one nucleoside of the at least one RNA (molecule) of the complexed RNA of the present invention has been modified at the 4,-5- or 6-position of the base pyrimidine of the nucleosides cytidine and/or uridine and at the 2'-position of the ribose sugar according to modifications a) and c) as defined above.

According to another particularly preferred embodiment, at least one nucleoside of the at least one RNA (molecule) of the complexed RNA of the present invention has been modified at the 2-, 6-, 7- or 8-position of the purine base of the nucleosides adenosine, inosine and/or guanosine and at the 2'-position of the ribose sugar according to modifications b) and c) as defined above, more preferably as defined above.

According to an even more particularly preferred embodiment, at least one nucleoside of the at least one RNA (molecule) of the complexed RNA of the present invention has been modified leading to chemically modified nucleotides (of the (m)RNA) selected from the following group: 4-thio-uridine-5'-(mono)phosphate, 2-Aminopurine-riboside-5'-(mono)phosphate, 5-Aminoallylcytidine-5'-(mono)phosphate, 5-Aminoallyluridine-5'-(mono)phosphate, 5-Bromocytidine-5'-(mono)phosphate, 5-Bromo-2'-deoxycytidine-5'-(mono)phosphate, 5-Bromouridine-5'-(mono)phosphate, 5-Bromo-2'-deoxyuridine-5'-(mono)phosphate, 5-Iodocytidine-5'-(mono)phosphate, 5-Iodo-2'-deoxycytidine-5'-(mono)phosphate, 5-Iodouridine-5'-(mono)phosphate, 5-Iodo-2'-deoxyuridine-5'-(mono)phosphate, 5-Propynyl-2'-deoxycytidine-5'-(mono)phosphate, 5-Propynyl-2'-deoxyuridine-5'-(mono)phosphate, 5-formylcytidine-5'-(mono)phosphate, 5,2'-O-dimethylcytidine-5'-(mono)phosphate, 5-hydroxymethylcytidine-5'-(mono)phosphate, 5-formyl-2'-O-methylcytidine-5'-(mono)phosphate, 5,2'-O-dimethyluridine-5'-(mono)phosphate, 5-methyl-2-thiouridine-5'-(mono)phosphate, 5-hydroxyuridine-5'-(mono)phosphate, 5-methoxyuridine-5'-(mono)phosphate, uridine 5-oxyacetic acid-5'-(mono)phosphate, uridine 5-oxyacetic acid methyl ester-5'-(mono)phosphate, 5-(carboxyhydroxymethyl)uridine-5'-(mono)phosphate, 5-(carboxyhydroxymethyl)uridine methyl ester-5'-(mono)phosphate, 5-methoxycarbonylmethyluridine-5'-(mono)phosphate, 5-methoxycarbonylmethyl-2'-O-methyluridine-5'-(mono)phosphate, 5-methoxycarbonylmethyl-2-thiouridine-5'-(mono)phosphate, 5-aminomethyl-2-thiouridine-5'-(mono)phosphate, 5-methylaminomethyluridine-5'-(mono)phosphate, 5-methylaminomethyl-2-thiouridine-5'-(mono)phosphate, 5-methylaminomethyl-2-selenouridine-5'-(mono)phosphate, 5-carbamoylmethyluridine-5'-(mono)phosphate, 5-carbamoylmethyl-2'-O-methyluridine-5'-(mono)phosphate, 5-carboxymethylaminomethyluridine-5'-(mono)phosphate, 5-carboxymethylaminomethyl-2'-O-methyluridine-5'-(mono)phosphate, 5-carboxymethylaminomethyl-2-thiouridine-5'-(mono)phosphate, 5-carboxymethyluridine-5'-(mono)phosphate, 5-methyldihydrouridine-5'-(mono)phosphate, 5-taurinomethyluridine-5'-(mono)phosphate, 5-taurinomethyl-2-thiouridine-5'-(mono)phosphate, 5-(isopentenylaminomethyl)uridine-5'-(mono)phosphate, 5-(isopentenylaminomethyl)-2-thiouridine-5'-(mono)phosphate, 5-(isopentenylaminomethyl)-2'-O-methyluridine-5'-(mono)phosphate, 6-Azacytidine-5'-(mono)phosphate, 7-Deazaadenosine-5'-(mono)phosphate, 7-Deazaguanosine-5'-(mono)phosphate, 8-Azaadenosine-5'-(mono)phosphate, 8-Azidoadenosine-5'-(mono)phosphate, Pseudouridine-5'-(mono)phosphate, 2'-Amino-2'-deoxycytidine-(mono)phosphate, 2'-Fluorothymidine-5'-(mono)phosphate, inosine-5'-(mono)phosphate, 2'-O-Methyl-inosine-5'-(mono)phosphate.

If desired, the at least one RNA (molecule) of the complexed RNA of the present invention may contain substitutions, additions or deletions of nucleotides, which are preferably introduced to achieve functional effects. These various types of nucleotide modifications may be introduced, if the RNA, e.g. the mRNA, is derived from a WT sequence. Hereby, a DNA matrix is used for preparation of the RNA of the complexed RNA according to the present invention by techniques of the well known site directed mutagenesis (see e.g. Maniatis et al., Molecular Cloning: A Laboratory Manual, Cold Spring Harbor Laboratory Press, 3rd ed., Cold Spring Harbor, N.Y., 2001). In such a process, for preparation of the RNA, a corresponding DNA molecule may be transcribed in vitro. This DNA matrix has a suitable promoter, e.g. a T7 or SP6 promoter, for in vitro transcription, which is followed by the desired nucleotide sequence for the RNA to be prepared and a termination signal for in vitro transcription. According to the invention, the DNA molecule which forms the matrix of a RNA of interest may be prepared by fermentative proliferation and subsequent isolation as part of a plasmid which can be replicated in bacteria. Plasmids which may be mentioned as suitable for the present invention are e.g. the plasmids pT7Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, Fla., 2001.

The mass or molar ratio of the components of the RNA complex according to the present invention, which means the mass or molar ratio of the RNA (be it single- or double-stranded) to the one or more oligopeptides typically is by no way restricted and is chosen as suitable for the particular application. However, the mass or molar ratio of the one or more oligopeptides and the RNA may be less than 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, or less than 1:20. Alternatively, the mass or molar ratio of the one or more oligopeptides and the RNA may higher than 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1. Preferably, the mass or molar ratio of the one or more oligopeptides and the RNA may not be less than 1:5 with respect to the content of the one or more oligopeptides. More preferably, the (molar or) mass ratio of the one or more oligopeptides and the RNA is from 1:5 to 20:1, more preferably from 1:3 to 15:1.

According to a particular preferred embodiment, the mass ratio of the components of the RNA complex according to the present invention, particularly the mass ratio of the at least one RNA (molecule) of the complexed RNA to the one or more oligopeptides is preferably in a range of about 1:100 to about 1:0.5, more preferably has a value of about 1:50 to about 1:1, or even more preferably about 1:100, about 1:90, about 1:80, about 1:70, about 1:60, about 1:50, about 1:45, about 1:40, about 1:35, about 1:30, about 1:25, about 1:20, about 1:15, about 1:10, about 1:5, about 1:4, about 1:3, about 1:2, about 1:1 or even about 1:0.5 regarding the ratio of RNA:peptide in the complex, wherein any range may be formed by combining two of the above specifically indicated values. Most preferably, the mass ratio of the at least one RNA (molecule) of the complexed RNA to the one or more oligopeptides may be in a range of about 1:50 to about 1:1.

Likewise, the molar ratio of the components of the RNA complex according to the present invention, particularly the molar ratio of the at least one RNA (molecule) of the complexed RNA to the one or more oligopeptides is preferably, according to a particular preferred embodiment, in a range of about 1:20000 to about 1:500 or even 1:250, more preferably in a range of about 1:10000 to about 1:1000, or even more preferably has a value of about 1:9500, about 1:9000, about 1:8500, about 1:8000, about 1:7500, about 1:7000, about 1:6500, about 1:6000, about 1:5500, about 1:5000, about 1:4500, about 1:4000, about 1:3500, about 1:3000, about 1:2500, about 1:2000, about 1:1500, about 1:1000, about 1:500, about 1:450, about 1:400, about 1:350, about 1:300, or about 1:250 regarding the ratio of RNA:peptide in the complex, wherein any range may be formed by combining two of the above specifically indicated values. Most preferably, the molar ratio of the at least one RNA (molecule) of the complexed RNA to the one or more oligopeptides may be in a range of about 1:10000 to about 1:1000. For immunostimulation purposes, the molar ratio of the components of the RNA complex according to the present invention may be in a range of about 1:10000 to about 1:100 or even in a range of about 1:10000 to about 1:500.

In the context of the present invention, the molar ratio and the mass ratio are typically dependent on each other, wherein each of these ratios may be influenced by factors such as RNA length or peptide length. However, for purposes of determination, the mass ratio and the molar ratio may be calculated for an average complex size, wherein a mass ratio of about 1:50-1:1 approximately corresponds to a molar ratio of about 1:10000-1:1000. An exemplary schedule of molar and mass ratios is given in the Examples, which may be used for calculation additionally.

Furthermore, the ratio of the RNA complex components according to the present invention, particularly the ratio of the at least one RNA (molecule) of the complexed RNA to the one or more oligopeptides, may also be calculated on the basis of the nitrogen/phosphate ratio (N/P-ratio) of the entire RNA complex. For example, 1 µg RNA typically contains about 3 nmol phosphate residues, provided the RNA exhibits a statistical distribution of bases. Additionally, 1 µg peptide typically contains about x nmol nitrogen residues, dependent on the molecular weight and the number of basic amino acids. When exemplarily calculated for $(Arg)_9$ (molecular weight 1424 g/mol, 9 nitrogen atoms), 1 µg $(Arg)_9$ contains about 700 pmol $(Arg)_9$ and thus 700×9=6300 pmol basic amino acids=6.3 nmol nitrogen atoms. For a mass ratio of about 1:1 RNA/$(Arg)_9$ an N/P ratio of about 2 can be calculated. When exemplarily calculated for protamine (molecular weight about 4250 g/mol, 21 nitrogen atoms, when protamine from salmon is used) with a mass ratio of about 2:1 with 2 µg RNA, 6 nmol phosphate are to be calculated for the RNA; 1 µg protamine contains about 235 pmol protamine molecules and thus 235×21=4935 pmol basic nitrogen atoms=4.9 nmol nitrogen atoms. For a mass ratio of about 2:1 RNA/protamine an N/P ratio of about 0.81 can be calculated. For a mass ratio of about 8:1 RNA/protamine an N/P ratio of about 0.2 can be calculated. In the context of the present invention, an N/P-ratio is preferably in the range of about 0.2-50, preferably in a range of about 0.5-50 and most preferably in a range of about 0.75-25 or 1-25 regarding the ratio of RNA:peptide in the complex, even more preferably in the range of about 10-50 and most preferably in the range of about 25-50).

Another embodiment of the present invention relates to a composition, preferably a pharmaceutical composition, comprising a complexed RNA according to the present invention and optionally a (pharmaceutically) suitable carrier and/or further auxiliary substances and additives. The (pharmaceutical) composition employed according to the present invention typically comprises a safe and effective amount of a complexed RNA according to the present invention. As used herein, a "safe and effective amount" means an amount of a complexed RNA according to the present invention such as to provide an effect in cells or tissues in vitro or in vivo, e.g. to induce significantly an expression (in vitro or in vivo) of an encoded protein as described above, such as a therapeutically active protein, an antibody or an antigene, or any other protein or peptide as described above, to induce a positive change of a state to be treated (in vivo) in a cell, a tissue or an organism, e.g. a tumour disease or cancer disease, a cardiovascular disease, an infectious disease, an autoimmune disease, (mono-)genetic diseases, etc. as described herein, and/or to induce or enhance an immune response. At the same time, however, a "safe and effective amount" is low enough to avoid serious side effects, particularly in the therapy of diseases as mentioned herein, that is to say to render possible a reasonable ratio of advantage and risk. Determination of these limits typically lies within the range of reasonable medical judgement. The concentration of the complexed RNA according to the invention in such (pharmaceutical) compositions can therefore vary, for example, without being limited thereto, within a wide range of from e.g. 0.1 ng to 1,000 mg/ml or even more. Such a "safe and effective amount" of a complexed RNA according to the invention can vary in connection with the particular state to be treated and the age and the physical state of the patient to be treated, the severity of the state, the duration of the treatment, the nature of the concomitant therapy, of the particular (pharmaceutically) suitable carrier used and similar factors within the knowledge and experience of the treating doctor. The (pharmaceutical) composition described here can be employed for human and also for veterinary medicine purposes.

The (pharmaceutical) composition according to the invention described here can optionally comprise a suitable carrier, preferably a pharmaceutically suitable carrier. The term "suitable carrier" used here preferably includes one or more compatible solid or liquid fillers, or diluents or encapsulating compounds which are suitable for administration to a person. The term "compatible" as used here means that the constituents of the composition are capable of being mixed together with the complexed RNA according to the invention and the auxiliary substance optionally contained in the composition, as such and with one another in a manner such that no interaction which would substantially reduce the (pharmaceutical) effectiveness of the composition under usual condition of use occurs, such as e.g. would reduce the (pharmaceutical) activity of the encoded proteins or even suppress or impair expression of the coded proteins or e.g. would inhibit the immunogenic potential of the complexed RNA. Suitable carrier must of course have a sufficiently high purity and a sufficiently low toxicity to render them suitable for administration to a person to be treated.

Carriers are chosen dependent on the way of administration, be it in solid or liquid form. Accordingly, the choice of a (pharmaceutically) suitable carrier as described above is determined in particular by the mode in which the (pharmaceutical) composition according to the invention is administered. The (pharmaceutical) composition according to the invention can be administered, for example, systemically. Administration routes include e.g. intra- or transdermal, oral, parenteral, including subcutaneous, intramuscular, i.a. or intravenous injections, topical and/or intranasal routes. The suitable amount of the (pharmaceutical) composition according to the invention which is to be used can be determined by routine experiments using animal models. Such models include, but without being limited thereto, models of the rabbit, sheep, mouse, rat, dog and non-human primate models.

If administered in liquid form, e.g. by injection, the carrier may be selected from pyrogen-free water; isotonic saline solution and buffered solutions, e.g. phosphate buffered solutions. Preferred unit dose forms for injection include sterile solutions of water, physiological saline solution or mixtures thereof, e.g. Ringer-Lactat solution. The pH of such solutions should be adjusted to about 7.0 to about 7.6, preferably about 7.4.

Preferably, the (pharmaceutical) composition contains the inventive complexed RNA in water. Alternatively, the (pharmaceutical) composition according to the invention may contain an injection buffer as carrier for liquid preparation, which preferably improves transfection and, if the RNA of the complexed RNA of the present invention codes for a protein, also the translation of the encoded protein, in cells, tissues or an organism. The (pharmaceutical) composition according to the invention can comprise, for example, an aqueous injection buffer or water which contains, with respect to the total (pharmaceutical) composition, if this is in liquid form, a sodium salt, preferably at least 50 mM sodium salt, a calcium salt, preferably at least 0.01 mM calcium and/or magnesium salt, and optionally a potassium salt, preferably at least 3 mM potassium salt. According to a preferred embodiment, the sodium salts, calcium and/or magnesium salts and optionally potassium salts contained in such an injection buffer are in the form of halides, e.g. chlorides, iodides or bromides, or in the form of their hydroxides, carbonates, bicarbonates or sulfates. Examples which are to be mentioned here are, for the sodium salt NaCl, NaI, NaBr, $Na_2CO_3$, $NaHCO_3$, and/or $Na_2SO_4$, for the potassium salt optionally present KCl, KI, KBr, $K_2CO_3$, $KHCO_3$, and/or $K_2SO_4$, and for the calcium and/or magnesium salt $CaCl_2$, $CaI_2$, $CaBr_2$, $CaCO_3$, $CaSO_4$, $Ca(OH)_2$, $MgCl_2$, $MgI_2$, $MgBr_2$, $MgCO_3$, $MgSO_4$, and/or $Mg(OH)_2$. The injection buffer can also contain organic anions of the abovementioned cations. In a particularly preferred embodiment, such an injection buffer contains as salts sodium chloride (NaCl), calcium chloride ($CaCl_2$) and optionally potassium chloride (KCl), it also being possible for other anions to be present in addition to the chlorides.

These salts are typically present in the injection buffer optionally used in the (pharmaceutical) composition according to the invention, with respect to the total (pharmaceutical) composition (if this is in liquid form), in a concentration of at least 50 mM sodium chloride (NaCl), at least 3 mM potassium chloride (KCl) and at least 0.01 mM calcium and/or magnesium chloride ($CaCl_2$). The injection buffer can be in the form of both hypertonic and isotonic or hypotonic injection buffers. In connection with the present invention, in this context the injection buffer is hypertonic, isotonic or hypotonic in each case with respect to the particular reference medium, i.e. the injection buffer has either a higher, the same or a lower salt content compared with the particular reference medium, such concentrations of the abovementioned salts which do not lead to damage to the cells caused by osmosis or other concentration effects preferably being employed. Reference media here are, for example, liquids which occur in "in vivo" methods, such as, for example, blood, lymph fluid, cytosol fluids or other fluids which occur in the body, or liquids or buffers conventionally employed in "in vitro" methods. Such liquids and buffers are known to a person skilled in the art.

The injection buffer optionally contained in the (pharmaceutical) composition according to the invention can also contain further components, for example sugars (mono-, di-, tri- or polysaccharides), in particular glucose or mannitol. In a preferred embodiment, however, no sugars are present in the injection buffer used. It is also preferable for the injection buffer precisely to contain no non-charged components, such as, for example, sugars. The injection buffer typically contains exclusively metal cations, in particular from the group consisting of the alkali or alkaline earth metals, and anions, in particular the anions described above. The pH of the injection buffer used, with respect to the total (pharmaceutical) composition, if this is in liquid form, is preferably between 1 and 8.5, preferably between 3 and 5, more preferably between 5.5 and 7.5, in particular between 5.5 and 6.5. If appropriate, the injection buffer can also contain a buffer system which fixes the injection buffer at a buffered pH. This can be, for example, a phosphate buffer system, HEPES or $Na_2HPO_4/NaH_2PO_4$. However, the injection buffer used very particularly preferably contains none of the abovementioned buffer systems or contains no buffer system at all.

The injection buffer optionally contained in the (pharmaceutical) composition according to the invention can contain, in addition to or as an alternative to the monovalent and divalent cations described, divalent cations, in particular from the group consisting of alkaline earth metals, such as, for example, magnesium ($Mg^{2+}$), or also iron ($Fe^{2+}$), and monovalent cations, in particular from the groups consisting of alkali metals, such as, for example, lithium ($Li^+$). These monovalent cations are preferably in the form of their salts, e.g. in the form of halides, e.g. chlorides, iodides or bromides, or in the form of their hydroxides, carbonates, bicarbonates or sulfates. Examples which are to be mentioned here are, for the lithium salt LiCl, LiI, LiBr, $Li_2CO_3$, $LiHCO_3$, $Li_2SO_4$, for the magnesium salt $MgCl_2$, $MgI_2$, $MgBr_2$, $MgCO_3$, $MgSO_4$, and $Mg(OH)_2$, and for the iron salt $FeCl_2$, $FeBr_2$, $FeI_2$, $FeF_2$, $Fe_2O_3$, $FeCO_3$, $FeSO_4$, $Fe(OH)_2$. All the combinations of di- and/or monovalent cations, as described above, are likewise included. Such injection buffers which contain only divalent, only monovalent or di- and monovalent cations can thus be used in the (pharmaceutical) composition according to the invention. Such injection buffers which contain only one type of di- or monovalent cations, particularly preferably e.g. only $Ca^{2+}$ cations, or a salt thereof, e.g. $CaCl_2$, can likewise be used. The molarities given above for $Ca^{2+}$ (as a divalent cation) and $Na^{1+}$ (as a monovalent cation) (that is to say typically concentrations of at least 50 mM $Na^+$, at least 0.01 mM $Ca^{2+}$ and optionally at least 3 mM $K^+$) in the injection buffer can also be taken into consideration if another di- or monovalent cation, in particular other cations from the group consisting of the alkaline earth metals and alkali metals, are employed instead of some or all the $Ca^{2+}$ or, respectively, $Na^{1+}$ in the injection buffer used according to the invention for the preparation of the injection solution. All the $Ca^{2+}$ or $Na^{1+}$, as mentioned above, can indeed be replaced by in each case other di- or, respectively, monovalent cations in the injection buffer used, for example also by a combination of other divalent cations (instead of $Ca^{2+}$) and/or a combination of other monovalent cations (instead of $Na^{1+}$) (in particular a combination of other divalent cations from the group consisting of the alkaline earth metals or, respectively, of other monovalent cations from the group consisting of the alkali metals), but it is preferable to replace at most some of the $Ca^{2+}$ or $Na^{1+}$, i.e. for at least 20%, preferably at least 40%, even more preferably at least 60% and still more preferably at least 80% of the particular total molarities of the mono- and divalent cations in the injection to be occupied by $Ca^{2+}$ and, respectively, $Na^{1+}$. However, it is very particularly preferable if the injection buffer optionally contained in the pharmaceutical composition according to the invention contains exclusively $Ca^{2+}$ as a divalent cation and $Na^{1+}$ as a monovalent cation, that is to say, with respect to the total pharmaceutical composition, $Ca^{2+}$ represents 100% of the total molarity of divalent cations, just as $Na^{1+}$ represents 100% of the total molarity of monovalent cations. The aqueous solution of the injection buffer can contain, with respect to the total pharmaceutical composition, up to 30 mol % of the salts contained in the solution, preferably up to 25 mol %, preferably up to 20 mol %, furthermore preferably up to 15 mol %, more preferably up to 10 mol %, even more preferably up to 5 mol %, likewise more preferably up to 2 mol % of insoluble or sparingly soluble salts. Salts which are sparingly soluble in the context of the present invention are those of which the solubility product is $<10^{-4}$. Salts which are readily soluble are those of which the solubility product is $>10^{-4}$. Preferably, the injection buffer optionally contained in the pharmaceutical composition according to the invention is from 50 mM to 800 mM, preferably from 60 mM to 500 mM, more preferably from 70 mM to 250 mM, particularly preferably 60 mM to 110 mM in sodium chloride (NaCl), from 0.01 mM to 100 mM, preferably from 0.5 mM to 80 mM, more preferably from 1.5 mM to 40 mM in calcium chloride ($CaCl_2$) and optionally from 3 mM to 500 mM, preferably from 4 mM to 300 mM, more preferably from 5 mM to 200 mM in potassium chloride (KCl). Organic anions can also occur as further anions in addition to the abovementioned inorganic anions, for example halides, sulfates or carbonates. Among these there may be mentioned succinate, lactobionate, lactate, malate, maleate etc., which can also be present in combination.

An injection buffer optionally contained in the (pharmaceutical) composition according to the invention preferably contains lactate. If it contains an organic anion, such an injection buffer particularly preferably contains exclusively lactate as the organic anion. Lactate in the context of the invention can be any desired lactate, for example L-lactate and D-lactate. Lactate salts which occur in connection with the present invention are typically sodium lactate and/or calcium lactate, especially if the injection buffer contains only $Na^+$ as a monovalent cation and $Ca^{2+}$ as a divalent cation. An injection buffer optionally used in the (pharmaceutical) composition according to the invention and as described above preferably contains, with respect to the total pharmaceutical composition, from 15 mM to 500 mM, more preferably from 15 mM to 200 mM, and even more most preferably from 15 mM to 100 mM lactate.

If formulated in non-liquid form (e.g. in solid or semi-solid form), the pharmaceutical composition of the invention may be contain compounds which can serve as suitable carriers or constituents thereof, e.g. sugars, such as, for example, lactose, glucose and sucrose; starches, such as, for example, corn starch or potato starch; cellulose and its derivatives, such as, for example, sodium carboxymethylcellulose, ethylcellulose, cellulose acetate; pulverized tragacanth; malt; gelatine; tallow; solid lubricants, such as, for example, stearic acid, magnesium stearate; calcium sulfate; plant oils, such as, for example, groundnut oil, cottonseed oil, sesame oil, olive oil, corn oil and oil from *Theobroma*; polyols, such as, for example, polypropylene glycol, glycerol, sorbitol, mannitol and polyethylene glycol; alginic acid. However, the above compounds may also be used for the provision of liquid compositions.

Other components which may be included in a pharmaceutical composition of the invention are e.g. emulsifiers, such as, for example, Tween®; wetting agents, such as, for example, sodium lauryl sulfate; colouring agents; flavouring agents; medicament carriers; tablet-forming agents; stabilizers; antioxidants; preservatives.

Other suitable carriers for injection include hydrogels, devices for controlled or delayed release, polylactic acid and collagen matrices. Suitable carriers which can be used here include those which are suitable for use in lotions, creams, gels and the like. If the compound is to be administered perorally, tablets, capsules and the like are the preferred unit dose form. The suitable carriers for the preparation of unit dose forms which can be used for oral administration are well-known in the prior art. Their choice will depend on secondary considerations, such as flavour, cost and storage stability, which are not critical for the purposes of the present invention and can be implemented without difficulties by a person skilled in the art.

The present invention also provides an (in vitro or in vivo) transfection method for transfecting cells or a tissue with the complexed RNA of the present invention as described above. The inventive (in vitro or in vivo) transfection method preferably comprises the following steps:
  a) Optionally preparing and/or providing a complexed RNA according to the present invention, comprising at least one RNA complexed with one or more oligopeptides having the empirical formula $(Arg)_l;(Lys)_m;(His)_n;(Orn)_o;(Xaa)_x$;
  b) Transfecting a cell, a (living) tissue or an organism (in vitro or in vivo) using the complexed RNA prepared and/or provided according to step a).

Preparing and/or providing a complexed RNA as defined above according to step a) of the inventive in vitro or in vivo transfection method for transfecting cells or a tissue with the complexed RNA of the present invention, may be carried out by any method known in the art. A complexed RNA as used herein comprises at least one RNA complexed with one or more oligopeptides having the empirical formula $(Arg)_l;(Lys)_m;(His)_n;(Orn)_o;(Xaa)_x$. Preparing and/or providing a complexed RNA as defined above according to step a) may thus comprise the preparation and/or provision of the least one RNA and the one or more oligopeptides having the empirical formula $(Arg)_l;(Lys)_m;(His)_n;(Orn)_o;(Xaa)_x$.

Methods for preparation of short peptide sequences such as $(Arg)_l;(Lys)_m;(His)_n;(Orn)_o;(Xaa)_x$ are widely known in the art and may employ e.g. solid phase synthesis such as Fmoc solid phase synthesis or other suitable methods (see e.g. R. Martin, Ed., *Protein Synthesis: Methods and Protocols. Methods in Molecular Biology*, Vol. 77Humana Press (1998)).

Preparing and/or providing the at least one RNA (molecule) as component of the inventive complex as defined above may comprise according to step a) a first sub-step a1), namely provision and/or preparation of a nucleic acid template, which typically comprises a sequence corresponding to the desired RNA. The sequence of the nucleic acid template may be any nucleic acid, e.g. a single- or double-stranded DNA, cDNA, genomic DNA or fragments thereof, etc., which may code for a therapeutically active protein, an antibody or an antigene, or any other protein or peptide as described above. Typically, DNA sequences, e.g. DNA plasmids, preferably in linearized form, may be employed for this purpose. Preferably, the sequence of the nucleic acid template may be an (expression) vector, more preferably an (expression)vector having an RNA polymerase binding site. Any (expression) vectors known in the prior art, e.g. commercially available (expression) vectors (see above), can be used for this. Preferred (expression) vectors are, for example, those which have an SP6 or a T7 or T3 binding site upstream and/or downstream of the cloning site. The vector may comprise a nucleic acid sequence encoding a therapeutically active protein, an antibody or an antigen, or any other protein or peptide as described above, which is typically cloned into the (expression) vector, e.g. via a multiple cloning site of the vector used.

Prior to transcription the (expression) vector is typically cleaved with restriction enzymes at the site at which the future 3' end of the RNA is to be found, using a suitable restriction enzyme, and the fragment is purified. This prevents the transcribed RNA from containing vector sequences, and an RNA transcript of defined length may be obtained. In this context, preferably no restriction enzymes which generate overhanging ends (such as, e.g., AatII, ApaI, BanII, BglI, Bsp1286, BstXI, CfoI, HaeII, HgiAI, HhaI, KpnI, PstI, PvuI, SacI, SacII, SfiI, SphI, etc.) are used. Should such restriction enzymes nevertheless be used, the overhanging 3' end preferably may be filled up, e.g. with Klenow or T4 DNA polymerase.

As an alternative to the above, the nucleic acid template used for preparing and/or providing the at least one RNA (molecule) of the complexed RNA of the invention, may be prepared by employing a polymerase chain reaction (PCR). The nucleic acid template preferably and one of the primers used therefore, typically contains the sequence of an RNA polymerase binding site. Furthermore, the 5' end of the primer used preferably contains an extension of about 10-50 further nucleotides, more preferably of from 15 to 30 further nucleotides and most preferably of about 20 nucleotides.

Prior to in vitro transcription, the nucleic acid, e.g. the DNA or cDNA template, used as transcription template, is typically purified and free from RNase in order to ensure a high yield. In this context, purification of such template can be carried out with the aid of any method known in the prior art, for example using a caesium chloride gradient, ion exchange methods or by purification via agarose gel electrophoresis.

Subsequent to preparing and/or providing the nucleic acid template, an in vitro transcription reaction according to a second sub-step a2) may be carried out for preparing the desired the at least one RNA (molecule) of the complexed RNA of the invention using the nucleic acid template prepared according to first sub-step a1) as defined above.

The in vitro transcription reaction according to a second sub-step a2) is typically carried out in an in vitro transcription reaction. A suitable in vitro transcription medium initially comprises the nucleic acid template as described above, for example about 0.1-10 µg, preferably about 1-5 µg, more preferably 2.5 µg and most preferably about 1 µg of such a nucleic acid. A suitable in vitro transcription medium furthermore optionally comprises a reducing agent, e.g. DTT, more preferably about 1-20 µl 50 mM DTT, even more preferably about 5 µl 50 mM DTT. The in vitro transcription medium typically comprises nucleotides, e.g. a nucleotide mix, in the case of the present invention comprising a mixture of nucleotides of A, G, C or U, typically about 0.1-10 mM per nucleotide, preferably 0.1 to 1 mM per nucleotide, preferably about 4 mM in total. A suitable in vitro transcription medium likewise comprises an RNA polymerase, e.g. T7 RNA polymerase (for example T7-Opti mRNA Kit, CureVac, Tübingen, Germany), T3 RNA polymerase or SP6, typically about 10 to 500 U, preferably about 25 to 250 U, more preferably about 50 to 150 U, and most preferably about 100 U of RNA polymerase. The in vitro transcription medium is furthermore preferably kept free from RNase in order to avoid degradation of the transcribed the at least one RNA (molecule) of the complexed RNA of the invention. A suitable in vitro transcription medium therefore optionally additionally comprises an RNase inhibitor.

The nucleic acid template may be then incubated in the in vitro transcription medium and is transcribed to the at least one RNA (molecule) of the complexed RNA of the invention, which may encode for a therapeutically active protein, an antibody or an antigene, or any other protein or peptide as described above. The incubation times are typically about 30 to 240 minutes, preferably about 40 to 120 minutes and most preferably about 90 minutes. The incubation temperatures are typically about 30-45° C., preferably 37-42° C. The incubation temperature depends on the RNA polymerase used, e.g. for T7 RNA polymerase it is about 37° C. The at least one RNA (molecule) of the complexed RNA of the invention obtained by the transcription is preferably an mRNA. The yields obtained in the in vitro transcription are, for the stated starting amounts employed above, typically in the region of about 30 µg of RNA per pg of template DNA used. In the context of the present invention, the yields obtained in the in vitro transcription can be increased by linear up scaling. For this, the stated starting amounts employed above are preferably increased according to the yields required, e.g. by a multiplication factor of 5, 10, 50, 100, 500, 1,000, 5,000, 10,000, 50,000, 100,000 etc.

After incubation, a purification of the transcribed at least one RNA (molecule) of the complexed RNA of the invention can optionally take place. Any suitable method known in the prior art, e.g. chromatographic purification methods, e.g. affinity chromatography, gel filtration etc., can be used for this. By the purification, non-incorporated, i.e. excess nucleotides and template DNA can be removed from the in vitro transcription medium and a clean RNA can be obtained. For example, after the transcription the reaction mixture with the transcribed RNA can typically be digested with DNase in order to remove the DNA template still contained in the reaction mixture. The transcribed at least one RNA (molecule) of the complexed RNA of the invention can be subsequently or alternatively precipitated with LiCl. Purification of the transcribed RNA can then take place via IP RP-HPLC. This renders in particular effective separation of longer and shorter fragments from one another possible.

Preferably, in this context purification of the RNA may take place via a method for purification of RNA on a preparative scale, which is distinguished in that the RNA is purified by means of HPLC using a porous reverse phase as the stationary phase (PURE Messenger). For example, for the purification a reverse phase can be employed as the stationary phase for the HPLC purification. For the chromatography with reverse phases, a non-polar compound typically serves as stationary phases, and a polar solvent, such as mixtures of water, which is usually employed in the form of buffers, with acetonitrile and/or methanol, serves as the mobile phase for the elution. Preferably, the porous reverse phase has a particle size of 8.0±2 µm, preferably ±1 µm, more preferably +/−0.5 µm. The reverse phase material can be in the form of beads. The purification can be carried out in a particularly favourable manner with a porous reverse phase having this particle size, optionally in the form of beads, particularly good separation results being obtained. The reverse phase employed is preferably porous since with stationary reverse phases which are not porous, such as are described e.g. by Azarani A. and Hecker K. H., pressures which are too high are built up, so that preparative purification of the RNA is possible, if at all, only with great difficulty. The reverse phase preferably has a pore size of from 200 to 5,000, in particular a pore size of from 300 to 4,000. Particularly preferred pore sizes for the reverse phases are 200-400, 800-1,200 and 3,500-4,500. With a reverse phase having these pore sizes, particularly good results are achieved in respect of the purification of the transcribed RNA. The material for the reverse phase is preferably a polystyrene-divinylbenzene, and non-alkylated polystyrene-divinylbenzenes can be employed in particular. Stationary phases with polystyrene-divinylbenzene are known per se. For the purification, the polystyrene-divinylbenzenes which are known per se and already employed for HPLC methods and are commercially obtainable can be used. A non-alkylated porous polystyrene-divinylbenzene which in particular has a particle size of 8.0±0.5 µm and a pore size of 250-300, 900-1,100 or 3,500-4,500 is very particularly preferably used for the purification. The advantages described above can be achieved in a particularly favourable manner with this material for the reverse phases.

The HPLC purification can be carried out by the ion pair method, an ion having a positive charge being added to the mobile phase as a counter-ion to the negatively charged RNA. An ion pair having a lipophilic character, which is slowed down by the non-polar stationary phase of the reverse phase system, is formed in this manner. In practice, the precise conditions for the ion pair method must be worked out empirically for each specific separation problem. The size of the counter-ion, its concentration and the pH of the solution contribute greatly towards the result of the separation. In a favourable manner, alkylammonium salts, such as triethylammonium acetate and/or tetraalkylammonium compounds, such as tetrabutylammonium, are added to the mobile phase. Preferably, 0.1 M triethylammonium acetate is added and the pH is adjusted to about 7. The choice of mobile phase depends on the nature of the desired separation. This means that the mobile phase found for a specific separation, such as can be known, for example, from the prior art, cannot be transferred readily to another separation problem with adequate prospect of success. The ideal elution conditions, in particular the mobile phase used, must be determined for each separation problem by empirical experiments. A mixture of an aqueous solvent and an organic solvent can be employed as the mobile phase for elution of the RNA by the HPLC method. In this context, it is favourable if a buffer which has, in particular, a pH of about 7, for example 6.5-7.5, e.g. 7.0, is used as aqueous solvent; preferably, the buffer triethylammonium acetate is used, particularly preferably a 0.1 M triethylammonium acetate buffer which, as described above, also acts as a counter-ion to the RNA in the ion pair method. The organic solvent employed in the mobile phase can be acetonitrile, methanol or a mixture of these two, very particularly preferably acetonitrile. The purification of the RNA using an HPLC method as described is carried out in a particularly favourable manner with these organic solvents. The mobile phase is particularly preferably a mixture of 0.1 M triethylammonium acetate, pH 7, and acetonitrile. It has emerged to be likewise particularly favourable if the mobile phase contains 5.0 vol. % to 20.0 vol. % of organic solvent, based on the mobile phase, and the remainder to make up 100 vol. % is the aqueous solvent. It is very particularly favourable for the method according to the invention if the mobile phase contains 9.5 vol. % to 14.5 vol. % of organic solvent, based on the mobile phase, and the remainder to make up 100 vol. % is the aqueous solvent. Elution of the RNA can subsequently be carried out isocratically or by means of a gradient separation. In the case of an isocratic separation, elution of the RNA is carried out with a single eluting agent or a mixture of several eluting agents which remains constant, it being possible for the solvents described above in detail to be employed as the eluting agent.

Alternatively, the at least one RNA (molecule) according to step a) of the inventive method of transfection may well be prepared by chemical synthesis. Hereby, various methods known in the art may be used. The phosphoroamidite method is used most widely as a method of chemically synthesizing oligonucleotides, e.g. RNA fragments (Nucleic Acid Research, 17:7059-7071, 1989). In general, this phosphoroamidite method makes use of a condensation reaction between a nucleoside phosphoroamidite and a nucleoside as a key reaction using tetrazole as an accelerator. Because this reaction usually occurs competitively on both the hydroxyl group in a sugar moiety and the amino group in a nucleoside base moiety, the selective reaction on only the hydroxyl group in a sugar moiety is required to synthesize a desired nucleotide. Accordingly, the side reaction on the amino group is usually prevented by protecting the amino group. The protective group is removed when synthesis is finished. More specific information about how to synthesize RNA molecules may be retrieved from Arnold et al., "Chloridite and Amidite Automated Synthesis of Oligodeoxyribonucleotides Using Amidine Protected Nucleosides," reported in "7th Symposium Chem. Nucleic Acid Components," Nucleic Acids Symposium Series, 18, 181-184 (Aug. 30, 1987); Chemical Abstracts, 108(19), p. 692, Abstr. No. 167875z (May 9, 1988); Hayakawa et al., "Benzimidazolium Triflate as an Efficient Promoter for Nucleotide Synthesis via the Phosphoramidite Method," J. Organic Chemistry, 61(23), 7996-7997 (Nov. 15, 1996); Pirrung et al., "Proofing of Photolithographic DNA Synthesis with 3',5'-Dimethoxybenzoinyloxycarbonyl-Protected Deoxynucleoside Phosphoramidites," J. Organic Chemistry, 63(2), 241-246 (Jan. 23, 1998); Effenberger et al., Trifluoromethanesulfonic Imidazolide—A Convenient Reagent for Introducing the Triflate Group, Tetrahedron Letters, 1980 (45), 3947-3948 (September 1980), al of them incorporated herein by reference.

Preparation of the complexed RNA according to step a) of the present invention typically occurs according to sub-step a3) by adding a specific amount of the at least one RNA (molecule) to a specific amount to the one or more oligopeptides having the empirical formula $(Arg)_l;(Lys)_m;(His)_n;(Orn)_o;(Xaa)_x$. Thereby, molar or mass ratios as indicated above of the at least one RNA (molecule) and the one or more oligopeptides having the herein defined empirical formula $(Arg)_l;(Lys)_m;(His)_n;(Orn)_o;(Xaa)_x$ are typically envisaged. Complex formation typically occurs upon mixing both components. Thereby, the peptidic component is typically added o the RNA component, in some cases, however, vice versa.

Such a preparation step according to method step a), however, is optional and may not take place if the complexed RNA according to the present invention is already available. Accordingly, sub-steps a1), a2) and a3) as defined above are also optional and need not to be carried out, if the RNA used for the complexed RNA is already available. Similarly, the one or more oligopeptides having the empirical formula $(Arg)_l;(Lys)_m;(His)_n;(Orn)_o;(Xaa)_x$ may be used directly and need not to be prepared, if already available, e.g. from a supplier.

According to step b) of the inventive method for transfecting cells or tissues in vitro or in vivo a cell or a tissue may be transfected using the complexed RNA provided and/or prepared according to step a). Transfection of the cells or tissues in vitro or in vivo is in general carried out by adding the complexed RNA provided and/or prepared according to step a) to the cells or tissue. Preferably, the complexed RNA then enters into the cells by using cellular mechanisms, e.g. endocytosis. Addition of the complexed RNA as such to the cells or tissues may occur according to the invention without addition of any further components due to the transfectional potential of the complexed RNA (molecule) of the invention. Alternatively, addition of the complexed RNA provided and/or prepared according to step a) to the cells or tissue may occur in the form of a composition, e.g. as component of an aqueous solution, preferably a pharmaceutical composition as defined above, which may optionally contain additional components for further enhancement of the transfection activity.

Cells (or host cells) in this context for transfection of the complexed RNA (provided and/or prepared according to step a)) in vitro includes any cell, and preferably, with out being restricted thereto, cells, which shall be transfected by any RNA molecule (as defined above) by using the inventive complexed RNA. In particular, RNA transfection may allow for expression of a protein encoded by the RNA of the complexed RNA according to the invention in the cell or may allow RNA (e.g. siRNA, anti-sense RNA) of the inventive complex to attenuate or suppress the expression of a cellular gene. Cells in this context preferably include cultured eukaryotic cells (e.g. yeast cells, plant cells, animal cells and human cells) or prokaryotic cells (e.g. bacteria cells etc.) or induce an immune response. Cells of multicellular organisms are preferably chosen if posttranslational modifications, e.g. glycosylation of the encoded protein, are necessary (N- and/or O-coupled). In contrast to prokaryotic cells, such (higher) eukaryotic cells render posttranslational modifications of the protein synthesized possible. The person skilled in the art knows a large number of such higher eukaryotic cells or cell lines, e.g. 293T (embryonal kidney cell line), HeLa (human cervix carcinoma cells), CHO (cells from the ovaries of the Chinese hamster) and further cell lines, including such cells and cell lines developed for laboratory purposes, such as, for example, hTERT-MSC, HEK293, Sf9 or COS cells. Suitable eukaryotic cells furthermore include cells or cell lines which are impaired by diseases or infections, e.g. cancer cells, in particular cancer cells of any of the types of cancer mentioned here in the description, cells impaired by HIV, and/or cells of the immune system or of the central nervous system (CNS). Suitable cells can likewise be derived from eukaryotic microorganisms, such as yeast, e.g. *Saccharomyces cerevisiae* (Stinchcomb et al., Nature, 282:39, (1997)), *Schizosaccharomyces pombe, Candida, Pichia*, and filamentous fungi of the genera *Aspergillus, Penicillium*, etc. Suitable cells likewise include prokaryotic cells, such as e.g. bacteria cells, e.g. from *Escherichia coli* or from bacteria of the general *Bacillus, Lactococcus, Lactobacillus, Pseudomonas, Streptomyces, Streptococcus, Staphylococcus*, preferably *E. coli*, etc. Human cells or animal cells, e.g. of animals as mentioned herein, are particularly preferred as eukaryotic cells. Furthermore, antigen presenting cells (APCs) may be used for ex vivo transfection of the complexed RNA according to the present invention. Particularly preferred are dendritic cells, which may be used for ex vivo transfection of the complexed RNA according to the present invention.

According to a particularly preferred embodiment, blood cells and/or haemopoietic cells, or partial populations thereof, i.e. any type of cells, which may be isolated from (whole) blood and/or which may be derived from cultivated cell lines derived from those cells, may be transfected with a complexed RNA as defined herein using the above method of transfection, e.g. red blood cells (erythrocytes), granulocytes, mononuclear cells (peripheral blood mononuclear cells, PBMCs) and/or blood platelets (thrombocytes), APSs, DCs, etc. Preferably, blood cells are used, especially partial populations thereof, which are characterized in particular in that they contain a small proportion of well-differentiated professional APCs, such as DCs. The transfected cells may contain preferably less than 5%, particularly preferably no more than 2%, of DCs when used for transfection. In the context of the present invention "blood cells" are preferably understood as a mixture or an enriched to substantially pure population of red blood cells, granulocytes, mononuclear cells (PBMCs) and/or blood platelets from whole blood, blood serum or another source, e.g. from the spleen or lymph nodes, only a small proportion of professional APCs being present. The blood cells as used according to the present invention are preferably fresh blood cells, i.e. the period between collection of the blood cells (especially blood withdrawal) and transfection being only short, e.g. less than 12 h, preferably less than 6 h, particularly preferably less than 2 h and very particularly preferably less than 1 h. Furthermore, the blood cells to be transfected using the above method for transfecting the complexed RNA according to the present invention preferably originate from the actual patient who will be treated with the pharmaceutical composition of the present invention. The use of blood cells, haematopoietic cells or partial populations thereof as defined above is based on the surprising discovery that for vaccination of a patient to be treated against certain antigens encoded by an mRNA as defined herein, it is not necessary to differentiate blood cells, e.g. PBMCs, obtained e.g. from the blood of an individual, especially the actual patient to be treated, by means of laborious, lengthy and expensive cell culture techniques, into a population of cells with a high proportion of professional antigen presenting cells (APCs), especially dendritic cells (DCs), but that it is sufficient, for a successful immune stimulation, to transfect blood cells directly with the mRNA coding for one or more antigens in order to obtain a pharmaceutical composition which effects a suitable immune stimulation e.g. in the actual patient from whom the blood cells, especially the abovementioned partial populations thereof, have been obtained, said immune stimulation preferably being directed against one or more antigens from a tumour or one or more antigens from a pathogenic germ or agent. Transfection of a complexed RNA as defined herein into blood cells or cells derived therefrom (either isolated therefrom or from respective cultivated cell lines) is not limited to antigens and, of course, relates to any RNA as defined herein used for a complexed RNA, e.g. any further immunostimulating RNA as defined herein, any coding RNA, etc.

While there is the need to transfect cultivated cells in vitro (e.g. human or animal cells) or to transfect explanted cells (e.g. human or animal cells) in vitro (before retransplantation into the host organism), direct administration of the complexed RNA of the invention to patients for in vivo transfection is envisaged as well. Accordingly, transfection of the complexed RNA (provided and/or prepared according to step a)) may also occur in vivo according to step b), i.e. may be administered to living tissues and/or organisms. Therefore, the complexed RNA provided according to step a) of the inventive transfection method may be administered to a living tissue or an organism either as such or e.g. as component of a (liquid) composition, in particular an aqueous composition, e.g. a pharmaceutical composition as defined above. In this context, an organism (or a being) typically means mammals, selected from, without being restricted thereto, the group comprising humans, and animals, including e.g. pig, goat, cattle, swine, dog, cat, donkey, monkey, ape or rodents, including mouse, hamster and rabbit. Furthermore, living tissues as mentioned above, are preferably derived from these organisms. Administration of the complexed RNA to those living tissues and/or organisms may occur via any suitable administration route, e.g. systemically, and include e.g. intra- or transdermal, oral, parenteral, including subcutaneous, intramuscular or intravenous injections, topical and/or intranasal routes as defined above.

Moreover, the method for transfection, which may be used in vitro or ex vivo, may also be well suited for use in vivo, e.g. as method of treatment of various diseases as mentioned herein. In a preferred form of a method of treatment according to the invention a further step may be included, which may contain administration of another pharmaceutically effective substance, e.g. an antibody, an antigen (in particular a pathogenic or a tumor antigen as disclosed herein) or the administration of at least one cytokine. Both may be administered separately from the complexed RNA as DNA or RNA coding for e.g. the cytokine or the antigen or the cytokine or antigen may be administered as such. The method of treatment may also comprise the administration of an additional adjuvant (as disclosed herein), which may further activate the immune system.

According to a further embodiment of the present invention, the complexed RNA as defined above, comprising at least one RNA complexed with one or more oligopeptides, wherein the oligopeptide shows a length of 8 to 15 amino acids and has the empirical formula $(Arg)_l;(Lys)_m;(His)_n;(Orn)_o;(Xaa)_x$, may be used for treatment and/or prophylaxis of specific diseases as mentioned herein. Treatment and/or prophylaxis of specific diseases is typically dependent on selection of a suitable protein encoded by the RNA of the complexed RNA of the present invention. Treatment in this context may occur either by administering the complexed RNA according to the present invention (encoding this protein) as such or by administering the (pharmaceutical) composition according to the present invention as defined above.

Without being limited thereto, diseases or states include in this context, for example, cancer or tumour diseases chosen from melanomas, malignant melanomas, colon carcinomas, lymphomas, sarcomas, blastomas, kidney carcinomas, gastrointestinal tumours, gliomas, prostate tumours, bladder cancer, rectal tumours, stomach cancer, oesophageal cancer, pancreatic cancer, liver cancer, mammary carcinomas (=breast cancer), uterine cancer, cervical cancer, acute myeloid leukaemia (AML), acute lymphoid leukaemia (ALL), chronic myeloid leukaemia (CML), chronic lymphocytic leukaemia (CLL), hepatomas, diverse virus-induced tumours, such as e.g. papilloma virus-induced carcinomas (e.g. cervix carcinoma=cervical cancer), adenocarcinomas, herpes virus-induced tumours (e.g. Burkitt's lymphoma, EBV-induced B cell lymphoma), hepatitis B-induced tumours (hepatocell carcinomas), HTLV-1- and HTLV-2-induced lymphomas, acusticus neurinoma, lung carcinomas (=lung cancer=bronchial carcinoma), small cell lung carcinomas, throat cancer, anal carcinoma, glioblastoma, rectum carcinoma, astrocytoma, brain tumours, retinoblastoma, basalioma, brain metastases, medulloblastomas, vaginal cancer, testicular cancer, thyroid carcinoma, Hodgkin's syndrome, meningeomas, Schneeberger's disease, pituitary tumour, mycosis fungoides, carcinoids, neurinoma, spinalioma, Burkitt's lymphoma, laryngeal cancer, kidney cancer, thymoma, corpus carcinoma, bone cancer, non-Hodgkin's lymphomas, urethral cancer, CUP syndrome, head/neck tumours, oligodendroglioma, vulval cancer, intestinal cancer, colon carcinoma, oesophageal carcinoma (=oesophageal cancer), wart conditions, small intestine tumours, craniopharyngeomas, ovarian carcinoma, soft tissue tumours, ovarian cancer (=ovarian carcinoma), pancreatic carcinoma (=pancreatic cancer), endometrium carcinoma, liver metastases, penis cancer, tongue cancer, gallbladder cancer, leukaemia, plasmocytoma, lid tumour, prostate cancer (=prostate tumours) etc.

Diseases or states may also include in this context infectious diseases chosen from, e.g., viral infectious diseases chosen from, without being limited thereto, SARS, yellow fever, Lyme, anthrax, AIDS, condyloma acuminata, molluscum contagiosum, dengue fever, three-day fever, Ebola virus, colds, early summer meningoencephalitis (ESME), influenza, shingles, hepatitis, herpes simplex type I, herpes simplex type II, herpes zoster, influenza, Japanese encephalitis, Lassa fever, Marburg virus, measles, foot and mouth disease, mononucleosis, mumps, Norwalk virus infection, Pfeiffer's glandular fever, smallpox, polio (poliomyelitis), pseuodcroup, infectious erythema, rabies, warts, West Nile fever, chicken-pox, cytomegalovirus (CMV), bacterial infectious diseases, such as abortion (prostate inflammation), anthrax, appendicitis (inflammation of the caecum), borreliosis, botulism, *Campylobacter*, *Chlamydia trachomatis* (inflammation of the urethra, conjunctiva), cholera, diphtheria, donavonosis, epiglottitis, louse-borne typhus, typhoid fever, gas gangrene, gonorrhoea, hare plague, *Helicobacter pylori*, whooping-cough, climatic bubo, osteomyelitis, legionnaires' disease, leprosy, listeriosis, pneumonia, meningitis, bacterial meningitis, anthrax, inflammation of the middle ear, *Mycoplasma* hominis, neonatal sepsis (chorioamnionitis), noma, paratyphoid fever, plague, Reiter's syndrome, Rocky Mountain spotted fever, *Salmonella* paratyphoid fever, *Salmonella* typhoid fever, scarlet fever, syphilis, tetanus, gonorrhoea, tsutsugamushi fever, tuberculosis, typhus, vaginitis (colpitis), soft chancre and infectious diseases caused by parasites, protozoa or fungi, such as amoebic dysentery, bilharziosis, Chagas' disease, *Echinococcus*, fish tapeworm, ichthyotoxism (ciguatera), fox tapeworm, mycosis pedis, dog tapeworm, candiosis, ptyriasis, the itch (scabies), leishmaniasis, cutaneous leishmaniasis, lamblian dysentery (giadiasis), lice, malaria, microscopy, onchocercosis (river blindness), fungal diseases, beef tapeworm, schistosomiasis, sleeping sickness, pork tapeworm, toxoplasmosis, trichomoniasis, trypanosomiasis (sleeping sickness), visceral leishmaniasis, nappy dermatitis or dwarf tapeworm.

Diseases in the context of the present invention likewise include, without being limited thereto, (infectious) virus diseases caused by viruses chosen from, without being limited thereto, HIV, orthopox variola virus, orthopox alastrim virus, parapox ovis virus, molluscum contagiosum virus, herpes simplex virus 1, herpes simplex virus 2, herpes B virus, varicella zoster virus, pseudorabies virus, human cytomegaly virus, human herpes virus 6, human herpes virus 7, Epstein-Barr virus, human herpes virus 8, hepatitis B virus, chikungunya virus, O'nyong'nyong virus, rubivirus, hepatitis C virus, GB virus C, West Nile virus, dengue virus, yellow fever virus, louping ill virus, St. Louis encephalitis virus, Japan B encephalitis virus, Powassan virus, FSME virus, SARS-associated corona virus, human corona virus 229E, human corona virus Oc43, Torovirus, human T cell lymphotropic virus type I, human T cell lymphotropic virus type II, human immunodeficiency virus type 1, human immunodeficiency virus type 2, Lassa virus, lymphocytic choriomeningitis virus, Tacaribe virus, Junin virus, Machupo virus, Borna disease virus, Bunyamwera virus, California encephalitis virus, Rift Valley fever virus, sand fly fever virus, Toscana virus, Crimean-Congo haemorrhagic fever virus, Hazara virus, Khasan virus, Hantaan virus, Seoul virus, Prospect Hill virus, Puumala virus, Dobrava Belgrade virus, Tula virus, sin nombre virus, Lake Victoria Marburg virus, Zaire Ebola virus, Sudan Ebola virus, Ivory Coast Ebola virus, influenza virus A, influenza virus B, influenza viruses C, parainfluenza virus, measles virus, mumps virus, respiratory syncytial virus, human metapneumovirus, vesicular stomatitis Indiana virus, rabies virus, Mokola virus, Duvenhage virus, European bat lyssavirus 1+2, Australian bat lyssavirus, adenoviruses A-F, human papilloma viruses, condyloma virus 6, condyloma virus 11, polyoma viruses, adeno-associated virus 2, rotaviruses, or orbiviruses etc. These diseases may e.g. be treated by a vaccine according to the invention.

Additionally, diseases or states may include cardiovascular diseases chosen from, without being limited thereto, coronary heart disease, arteriosclerosis, apoplexy and hypertension, and neuronal diseases chosen from Alzheimer's disease, amyotrophic lateral sclerosis, dystonia, epilepsy, multiple sclerosis and Parkinson's disease etc.

Diseases or states may also include in this context an allergic disorder or disease. Allergy is a condition that typically involves an abnormal, acquired immunological hypersensitivity to certain foreign antigens or allergens. Allergies normally result in a local or systemic inflammatory response to these antigens or allergens and leading to an immunity in the body against these allergens. Allergens in this context include e.g. grasses, pollens, molds, drugs, or numerous environmental triggers, etc. Without being bound to any theory, several different disease mechanisms are supposed to be involved in the development of allergies. According to a classification scheme by P. Gell and R. Coombs the word "allergy" was restricted to type I hypersensitivities, which are caused by the classical IgE mechanism. Type I hypersensitivity is characterised by excessive activation of mast cells and basophils by IgE, resulting in a systemic inflammatory response that can result in symptoms as benign as a runny nose, to life-threatening anaphylactic shock and death. Well known types of allergies include, without being limited thereto, allergic asthma (leading to swelling of the nasal mucosa), allergic conjunctivitis (leading to redness and itching of the conjunctiva), allergic rhinitis ("hay fever"), anaphylaxis, angiodema, atopic dermatitis (eczema), urticaria (hives), eosinophilia, respiratory, allergies to insect stings, skin allergies (leading to and including various rashes, such as eczema, hives (urticaria) and (contact) dermatitis), food allergies, allergies to medicine, etc. With regard to the present invention, e.g. a pharmaceutical composition is provided, which contains e.g. an RNA coding for an allergen (e.g. from a cat allergen, a dust allergen, a mite antigen, a plant antigen (e.g. a birch antigen) etc.) as a complex of the invention. Hereby, the encoded allergen may desensitize the patient immune response. Alternatively, the pharmaceutical compositions of the present invention may shift the (exceeding) immune response to a stronger TH1 response, thereby suppressing or attenuating the undesired IgE response from the patient suffers.

Furthermore, diseases or states as defined herein may include autoimmune diseases. Autoimmune diseases can be broadly divided into systemic and organ-specific or localised autoimmune disorders, depending on the principal clinicopathologic features of each disease. Autoimmune disease may be divided into the categories of systemic syndromes, including SLE, Sjörgen's syndrome, Scleroderma, rheumatoid arthritis and polyomyositis or local syndromes which may be endocrinologic (DM Type 1, Hashimoto's thyroiditis, Addison's disease, etc.), dermatologic (pemphigus vulgaris), haematologic (autoimmune haemolytic anaemia), neural (multiple sclerosis) or can involve virtually any circumscribed mass of body tissue. The autoimmune diseases to be treated may be selected from the group consisting of type I autoimmune diseases or type II autoimmune diseases or type III autoimmune diseases or type IV autoimmune diseases, such as, for example, multiple sclerosis (MS), rheumatoid arthritis, diabetes, type I diabetes (Diabetes mellitus), systemic lupus erythematosus (SLE), chronic polyarthritis, Basedow's disease, autoimmune forms of chronic hepatitis, colitis ulcerosa, allergy type I diseases, allergy type II diseases, allergy type III diseases, allergy type IV diseases, fibromyalgia, hair loss, Bechterew's disease, Crohn's disease, Myasthenia gravis, neurodermitis, Polymyalgia rheumatica, progressive systemic sclerosis (PSS), psoriasis, Reiter's syndrome, rheumatic arthritis, psoriasis, vasculitis, etc, or type II diabetes.

While the exact mode as to why the immune system induces a immune reaction against autoantigens has not been elucidated so far, there are several findings with regard to the etiology. Accordingly, the autoreaction may be due to a T-Cell Bypass. A normal immune system requires the activation of B-cells by T-cells before the former can produce antibodies in large quantities. This requirement of a T-cell can be by-passed in rare instances, such as infection by organisms producing super-antigens, which are capable of initiating polyclonal activation of B-cells, or even of T-cells, by directly binding to the –subunit of T-cell receptors in a non-specific fashion. Another explanation deduces autoimmune diseases from a molecular mimicry. An exogenous antigen may share structural similarities with certain host antigens; thus, any antibody produced against this antigen (which mimics the self-antigens) can also, in theory, bind to the host antigens and amplify the immune response. The most striking form of molecular mimicry is observed in Group A beta-haemolytic streptococci, which shares antigens with human myocardium, and is responsible for the cardiac manifestations of rheumatic fever. The present invention allows therefore to provide an RNA coding for an autoantigen as component of the complexed RNA of the invention (or a (liquid) composition containing such a complexed RNA of the invention) or to provide a pharmaceutical composition containing an autoantigen (as protein, mRNA or DNA encoding for a autoantigen protein) and a complexed RNA of the invention all of which typically allow the immune system to be desensitized.

Finally, diseases to be treated in the context of the present invention likewise include monogenetic diseases, i.e. (hereditary) diseases, or genetic diseases in general. Such genetic diseases are typically caused by genetic defects, e.g. due to gene mutations resulting in loss of protein activity or regulatory mutations which do not allow transcription or translation of the protein. Frequently, these diseases lead to metabolic disorders or other symptoms, e.g. muscle dystrophy. Accordingly, the present invention allows to treat these diseases by providing the complexed RNA as defined herein. Insofar, the following diseases may be treated: 3-beta-hydroxysteroid dehydrogenase deficiency (type II); 3-keto-thiolase deficiency; 6-mercaptopurine sensitivity; Aarskog-Scott syndrome; Abetalipoproteinemia; Acatalasemia; Achondrogenesis; Achondrogenesis-hypochondrogenesis; Achondroplasia; Achromatopsia; Acromesomelic dysplasia (Hunter-Thompson type); ACTH deficiency; Acyl-CoA dehydrogenase deficiency (short-chain, medium chain, long chain); Adenomatous polyposis coli; Adenosin-deaminase deficiency; Adenylosuccinase deficiency; Adhalinopathy; Adrenal hyperplasia, congenital (due to 11-beta-hydroxylase deficiency; due to 17-alpha-hydroxylase deficiency; due to 21-hydroxylase deficiency); Adrenal hypoplasia, congenital, with hypogonadotropic hypogonadism; Adrenogenital syndrom; Adrenoleukodystrophy; Adrenomyeloneuropathy; Afibrinogenemia; Agammaglobulinemia; Alagille syndrome; Albinism (brown, ocular, oculocutaneous, rufous); Alcohol intolerance, acute; Aldolase A deficiency; Aldosteronism, glucocorticoid-remediable; Alexander disease; Alkaptonuria; Alopecia universalis; Alpha-11-antichymotrypsin deficiency; Alpha-methylacyl-CoA racemase deficiency; Alpha-thalassemia/mental retardation syndrome; Alport syndrome; Alzheimer disease-1 (APP-related); Alzheimer disease-3; Alzheimer disease-4; Amelogenesis imperfecta; Amyloid neuropathy (familial, several allelic types); Amyloidosis (Dutch type; Finnish type; hereditary renal; renal; senile systemic); Amytrophic lateral sclerosis; Analbuminemia; Androgen insensitivity; Anemia (Diamond-Blackfan); Anemia (hemolytic, due to PK deficiency); Anemia (hemolytic, Rh-null, suppressor type); Anemia (neonatal hemolytic, fatal and nearfatal); Anemia (sideroblastic, with ataxia); Anemia (sideroblastic/hypochromic); Anemia due to G6PD deficiency; Aneurysm (familial arterial); Angelman syndrome; Angioedema; Aniridia; Anterior segment anomalies and cataract; Anterior segment mesenchymal dysgenesis; Anterior segment mesenchymal dysgenesis and cataract; Antithrombin III deficiency; Anxiety-related personality traits; Apert syndrome; Apnea (postanesthetic); ApoA-I and apoC-III deficiency (combined); Apolipoprotein A-II deficiency; Apolipoprotein B-100 (ligand-defective); Apparent mineralocorticoid excess (hypertension due to); Argininemia; Argininosuccinicaciduria; Arthropathy (progressive pseudorheumatoid, of childhood); Aspartylglucosaminuria; Ataxia (episodic); Ataxia with isolated vitamin E deficiency; Ataxia-telangiectasia; Atelosteogenesis II; ATP-dependent DNA ligase I deficiency; Atrial septal defect with atrioventricular conduction defects; Atrichia with papular lesions; Autism (succinylpurinemic); Autoimmune polyglandular disease, type I; Autonomic nervous system dysfunction; Axenfeld anomaly; Azoospermia; Bamforth-Lazarus syndrome; Bannayan-Zonana syndrome; Barthsyndrome; Bartter syndrome (type 2 or type 3); Basal cell carcinoma; Basal cell nevus syndrome; BCG infection; Beare-Stevenson cutis gyrata syndrome; Becker muscular dystrophy; Beckwith-Wiedemann syndrome; Bernard-Soulier syndrome (type B; type C); Bethlem myopathy; Bile acid malabsorption, primary; Biotinidase deficiency; Bladder cancer; Bleeding disorder due to defective thromboxane A2 receptor; Bloom syndrome; Brachydactyl (type B1 or type C); Branchiootic syndrome; Branchiootorenal syndrome; Breast cancer (invasive intraductal; lobular; male, with Reifenstein syndrome; sporadic); Breast cancer-1 (early onset); Breast cancer-2 (early onset); Brody myopathy; Brugada syndrome; Brunner syndrome; Burkitt lymphoma; Butterfly dystrophy (retinal); C1q deficiency (type A; type B; type C); C1r/C1s deficiency; C1s deficiency, isolated; C2 deficiency; C3 deficiency; C3b inactivator deficiency; C4 deficiency; C8 deficiency, type II; C9 deficiency; Campomelic dysplasia with autosomal sex reversal; Camptodactyl-arthropathy-coxa varapericarditis syndrome; Canavan disease; Carbamoylphosphate synthetase I deficiency; Carbohydrate-deficient glycoprotein syndrome (type I; type Ib; type II); Carcinoid tumor of lung; Cardioencephalomyopathy (fatal infantile, due to cytochrome c oxidase deficiency); Cardiomyopathy (dilated; X-linked dilated; familial hypertrophic; hypertrophic); Carnitine deficiency (systemic primary); Carnitine-acylcarnitine translocase deficiency; Carpal tunnel syndrome (familial); Cataract (cerulean; congenital; crystalline aculeiform; juvenile-onset; polymorphic and lamellar; punctate; zonular pulverulent); Cataract, Coppock-like; CD59 deficiency; Central core disease; Cerebellar ataxia; Cerebral amyloid angiopathy; Cerebral arteriopathy with subcortical infarcts and leukoencephalopathy; Cerebral cavernous malformations-1; Cerebrooculofacioskeletal syndrome; Cerebrotendinous xanthomatosis; Cerebrovascular disease; Ceroid lipofuscinosis (neuronal, variant juvenile type, with granular osmiophilic deposits); Ceroid lipofuscinosis (neuronal-1, infantile); Ceroid-lipofuscinosis (neuronal-3, juvenile); Char syndrome; Charcot-Marie-Tooth disease; Charcot-Marie-Tooth neuropathy; Charlevoix-Saguenay type; Chediak-Higashi syndrome; Chloride diarrhea (Finnish type); Cholestasis (benign recurrent intrahepatic); Cholestasis (familial intrahepatic); Cholestasis (progressive familial intrahepatic); Cholesteryl ester storage disease; Chondrodysplasia punctata (brachytelephalangic; rhizomelic; X-linked dominant; X-linked recessive; Grebe type); Chondrosarcoma; Choroideremia; Chronic granulomatous disease (autosomal, due to deficiency of CYBA); Chronic granulomatous disease (X-linked); Chronic granulomatous disease due to deficiency of NCF-1; Chronic granulomatous disease due to deficiency of NCF-2; Chylomicronemia syndrome, familial; Citrullinemia; classical Cockayne syndrome-1; Cleft lip, cleft jaw, cleft palate; Cleft lip/palate ectodermal dysplasia syndrome; Cleidocranial dysplasia; CMO II deficiency; Coats disease; Cockayne syndrome-2, type B; Coffin-Lowry syndrome; Colchicine resistance; Colon adenocarcinoma; Colon cancer; Colorblindness (deutan; protan; tritan); Colorectal cancer; Combined factor V and VIII deficiency; Combined hyperlipemia (familial); Combined immunodeficiency (X-linked, moderate); Complex I deficiency; Complex neurologic disorder; Cone dystrophy-3; Cone-rod dystrophy 3; Cone-rod dystrophy 6; Cone-rod retinal dystrophy-2; Congenital bilateral absence of vas deferens; Conjunctivitis, ligneous; Contractural arachnodactyly; Coproporphyria; Cornea plana congenita; Corneal clouding; Corneal dystrophy (Avellino type; gelatinous drop-like; Groenouw type I; lattice type I; Reis-Bucklers type); Cortisol resistance; Coumarin resistance; Cowden disease; CPT deficiency, hepatic (type I; type II); Cramps (familial, potassium-aggravated); Craniofacial-deafness-hand syndrome; Craniosynostosis (type 2); Cretinism; Creutzfeldt-Jakob disease; Crigler-Najjar syndrome; Crouzon syndrome; Currarino syndrome; Cutis laxa; Cyclic hematopoiesis; Cyclic ichthyosis; Cylindromatosis; Cystic fibrosis; Cystinosis (nephropathic); Cystinuria (type II; type III); Daltonism; Darier disease; D-bifunctional protein deficiency; Deafness, autosomal dominant 1; Deafness, autosomal dominant 11; Deafness, autosomal dominant 12; Deafness, autosomal dominant 15; Deafness, autosomal dominant 2; Deafness, autosomal dominant 3; Deafness, autosomal dominant 5; Deafness, autosomal dominant 8; Deafness, autosomal dominant 9; Deafness, autosomal recessive 1; Deafness, autosomal recessive 2; Deafness, autosomal recessive 21; Deafness, autosomal recessive 3; Deafness, autosomal recessive 4; Deafness, autosomal recessive 9; Deafness, nonsyndromic sensorineural 13; Deafness, X-linked 1; Deafness, X-linked 3; Debrisoquine sensitivity; Dejerine-Sottas disease; Dementia (familial Danish); Dementia (frontotemporal, with parkinsonism); Dent disease; Dental anomalies; Dentatorubro-pallidoluysian atrophy; Denys-Drash syndrome; Dermatofibrosarcoma protuberans; Desmoid disease; Diabetes insipidus (nephrogenic); Diabetes insipidus (neurohypophyseal); Diabetes mellitus (insulin-resistant); Diabetes mellitus (rare form); Diabetes mellitus (type II); Diastrophic dysplasia; Dihydropyrimidinuria; Dosage-sensitive sex reversal; Doyne honeycomb degeneration of retina; Dubin-Johnson syndrome; Duchenne muscular dystrophy; Dyserythropoietic anemia with thrombocytopenia; Dysfibrinogenemia (alpha type; beta type; gamma type); Dyskeratosis congenita-1; Dysprothrombinemia; Dystonia (DOPAresponsive); Dystonia (myoclonic); Dystonia-1 (torsion); Ectodermal dysplasia; Ectopia lentis; Ectopia pupillae; Ectrodactyly (ectodermal dysplasia, and cleft lip/palate syndrome 3); Ehlers-Danlos syndrome (progeroid form); Ehlers-Danlos syndrome (type I; type II; type III; type IV; type VI; type VII); Elastin Supravalvar aortic stenosis; Elliptocytosis-1; Elliptocytosis-2; Elliptocytosis-3; Ellis-van Creveld syndrome; Emery-Dreifuss muscular dystrophy; Emphysema; Encephalopathy; Endocardial fibroelastosis-2; Endometrial carcinoma; Endplate acetylcholinesterase deficiency; Enhanced S-cone syndrome; Enlarged vestibular aqueduct; Epidermolysis bullosa; Epidermolysis bullosa dystrophica (dominant or recessive); Epidermolysis bullosa simplex; Epidermolytic hyperkeratosis; Epidermolytic palmoplantar keratoderma; Epilepsy (generalize; juvenile; myoclonic; nocturnal frontal lobe; progressive myoclonic); Epilepsy, benign, neonatal (type1 or type2); Epiphyseal dysplasia (multiple); Episodic ataxia (type 2); Episodic ataxia/myokymia syndrome; Erythremias (alpha-; dysplasia); Erythrocytosis; Erythrokeratoderma; Estrogen resistance; Exertional myoglobinuria due to deficiency of LDH-A; Exostoses, multiple (type 1; type 2); Exudative vitreoretinopathy, X-linked; Fabry disease; Factor H deficiency; Factor VII deficiency; Factor X deficiency; Factor XI deficiency; Factor XII deficiency; Factor XIIIA deficiency; Factor XIIIB deficiency; Familial Mediterranean fever; Fanconi anemia; Fanconi-Bickel syndrome; Farber lipogranulomatosis; Fatty liver (acute); Favism; Fish-eye disease; Foveal hypoplasia; Fragile X syndrome; Frasier syndrome; Friedreich ataxia; fructose-bisphosphatase Fructose intolerance; Fucosidosis; Fumarase deficiency; Fundus albipunctatus; Fundus flavimaculatus; G6PD deficiency; GABA-transaminase deficiency; Galactokinase deficiency with cataracts; Galactose epimerase deficiency; Galactosemia; Galactosialidosis; GAMT deficiency; Gardner syndrome; Gastric cancer; Gaucher disease; Generalized epilepsy with febrile seizures plus; Germ cell tumors; Gerstmann-Straussler disease; Giant cell hepatitis (neonatal); Giant platelet disorder; Giant-cell fibroblastoma; Gitelman syndrome; Glanzmann thrombasthenia (type A; type B); Glaucoma 1A; Glaucoma 3A; Glioblastoma multiforme; Glomerulosclerosis (focal segmental); Glucose transport defect (blood-brain barrier); Glucose/galactose malabsorption; Glucosidase I deficiency; Glutaricaciduria (type I; type IIB; type IIC); Gluthation synthetase deficiency; Glycerol kinase deficiency; Glycine receptor (alpha-1 polypeptide); Glycogen storage disease I; Glycogen storage disease II; Glycogen storage disease III; Glycogen storage disease IV; Glycogen storage disease VI; Glycogen storage disease VII; Glycogenosis (hepatic, autosomal); Glycogenosis (X-linked hepatic); GM1-gangliosidosis; GM2-gangliosidosis; Goiter (adolescent multinodular); Goiter (congenital); Goiter (nonendemic, simple); Gonadal dysgenesis (XY type); Granulomatosis, septic; Graves disease; Greig cephalopolysyndactyly syndrome; Griscelli syndrome; Growth hormone deficient dwarfism; Growth retardation with deafness and mental retardation; Gynecomastia (familial, due to increased aromatase activity); Gyrate atrophy of choroid and retina with ornithinemia (B6 responsive or unresponsive); Hailey-Hailey disease; Haim-Munk syndrome; Hand-foot-uterus syndrome; Harderoporphyrinuria; HDL deficiency (familial); Heart block (nonprogressive or progressive); Heinz body anemia; HELLP syndrome; Hematuria (familial benign); Heme oxygenase-1 deficiency; Hemiplegic migraine; Hemochromotosis; Hemoglobin H disease; Hemolytic anemia due to ADA excess; Hemolytic anemia due to adenylate kinase deficiency; Hemolytic anemia due to band 3 defect; Hemolytic anemia due to glucosephosphate isomerase deficiency; Hemolytic anemia due to glutathione synthetase deficiency; Hemolytic anemia due to hexokinase deficiency; Hemolytic anemia due to PGK deficiency; Hemolytic-uremic syndrome; Hemophagocytic lymphohistiocytosis; Hemophilia A; Hemophilia B; Hemorrhagic diathesis due to factor V deficiency; Hemosiderosis (systemic, due to aceruloplasminemia); Hepatic lipase deficiency; Hepatoblastoma; Hepatocellular carcinoma; Hereditary hemorrhagic telangiectasia-1; Hereditary hemorrhagic telangiectasia-2; Hermansky-Pudlak syndrome; Heterotaxy (X-linked visceral); Heterotopia (periventricular); Hippel-Lindau syndrome; Hirschsprung disease; Histidine-rich glycoprotein Thrombophilia due to HRG deficiency; HMG-CoA lyase deficiency; Holoprosencephaly-2; Holoprosencephaly-3; Holoprosencephaly-4; Holoprosencephaly-5; Holt-Oram syndrome; Homocystinuria; Hoyeraal-Hreidarsson; HPFH (deletion type or nondeletion type); HPRT-related gout; Huntington disease; Hydrocephalus due to aqueductal stenosis; Hydrops fetalis; Hyperbetalipoproteinemia; Hypercholesterolemia, familial; Hyperferritinemia-cataract syndrome; Hyperglycerolemia; Hyperglycinemia; Hyperimmunoglobulinemia D and periodic fever syndrome; Hyperinsulinism; Hyperinsulinism-hyperammonemia syndrome; Hyperkalemic periodic paralysis; Hyperlipoproteinemia; Hyperlysinemia; Hypermethioninemia (persistent, autosomal, dominant, due to methionine, adenosyltransferase I/III deficiency); Hyperornithinemia-hyperammonemiahomocitrullinemia syndrome; Hyperoxaluria; Hyperparathyroidism; Hyperphenylalaninemia due to pterin-4-acarbinolamine dehydratase deficiency; Hyperproinsulinemia; Hyperprolinemia; Hypertension; Hyperthroidism (congenital); Hypertriglyceridemia; Hypoalphalipoproteinemia; Hypobetalipoproteinemia; Hypocalcemia; Hypochondroplasia; Hypochromic microcytic anemia; Hypodontia; Hypofibrinogenemia; Hypoglobulinemia and absent B cells; Hypogonadism (hypergonadotropic); Hypogonadotropic (hypogonadism); Hypokalemic periodic paralysis; Hypomagnesemia; Hypomyelination (congenital); Hypoparathyroidism; Hypophosphatasia (adult; childhood; infantile; hereditary); Hypoprothrombinemia; Hypothyroidism (congenital; hereditary congenital; nongoitrous); Ichthyosiform erythroderma; Ichthyosis; Ichthyosis bullosa of Siemens; IgG2 deficiency; Immotile cilia syndrome-1; Immunodeficiency (T-cell receptor/CD3 complex); Immunodeficiency (X-linked, with hyper-IgM); Immunodeficiency due to defect in CD3-gamma; Immunodeficiency-centromeric instabilityfacial anomalies syndrome; Incontinentia pigmenti; Insensitivity to pain (congenital, with anhidrosis); Insomnia (fatal familial); Interleukin-2 receptor deficiency (alpha chain); Intervertebral disc disease; Iridogoniodysgenesis; Isolated growth hormone deficiency (Illig type with absent GH and Kowarski type with bioinactive GH); Isovalericacidemia; Jackson-Weiss sydnrome; Jensen syndrome; Jervell and Lange-Nielsen syndrome; Joubert syndrome; Juberg-Marsidi syndrome; Kallmann syndrome; Kanzaki disease; Keratitis; Keratoderma (palmoplantar); Keratosis palmoplantaris striata I; Keratosis palmoplantaris striata II; Ketoacidosis due to SCOT deficiency; Keutel syndrome; Klippel-Trenaurnay syndrome; Kniest dysplasia; Kostmann neutropenia; Krabbe disease; Kurzripp-Polydaktylie syndrome; Lacticacidemia due to PDX1 deficiency; Langer mesomelic dysplasia; Laron dwarfism; Laurence-Moon-Biedl-Bardet syndrom; LCHAD deficiency; Leber congenital amaurosis; Left-right axis malformation; Leigh syndrome; Leiomyomatosis (diffuse, with Alport syndrome); Leprechaunism; Leri-Weill dyschondrosteosis; Lesch-Nyhan syndrome; Leukemia (acute myeloid; acute promyelocytic; acute T-cell lymphoblastic; chronic myeloid; juvenile myelomonocytic; Leukemia-1 (T-cell acute lymphocytic); Leukocyte adhesion deficiency; Leydig cell adenoma; Lhermitte-Duclos syndrome; Liddle syndrome; Li-Fraumeni syndrome; Lipoamide dehydrogenase deficiency; Lipodystrophy; Lipoid adrenal hyperplasia; Lipoprotein lipase deficiency; Lissencephaly (X-linked); Lissencephaly-1; liver Glycogen storage disease (type 0); Long QT syndrome-1; Long QT syndrome-2; Long QT syndrome-3; Long QT syndrome-5; Long QT syndrome-6; Lowe syndrome; Lung cancer; Lung cancer (nonsmall cell); Lung cancer (small cell); Lymphedema; Lymphoma (B-cell non-Hodgkin); Lymphoma (diffuse large cell); Lymphoma (follicular); Lymphoma (MALT); Lymphoma (mantel cell); Lymphoproliferative syndrome (X-linked); Lysinuric protein intolerance; Machado-Joseph disease; Macrocytic anemia refractory (of 5q syndrome); Macular dystrophy; Malignant mesothelioma; Malonyl-CoA decarboxylase deficiency; Mannosidosis, (alpha- or beta-); Maple syrup urine disease (type Ia; type Ib; type II); Marfan syndrome; Maroteaux-Lamy syndrome; Marshall syndrome; MASA syndrome; Mast cell leukemia; Mastocytosis with associated hematologic disorder; McArdle disease; McCune-Albright polyostotic fibrous dysplasia; McKusick-Kaufman syndrome; McLeod phenotype; Medullary thyroid carcinoma; Medulloblastoma; Meesmann corneal dystrophy; Megaloblastic anemia-1; Melanoma; Membroproliferative glomerulonephritis; Meniere disease; Meningioma (NF2-related; SIS-related); Menkes disease; Mental retardation (X-linked); Mephenyloin poor metabolizer; Mesothelioma; Metachromatic leukodystrophy; Metaphyseal chondrodysplasia (Murk Jansen type; Schmid type); Methemoglobinemia; Methionine adenosyltransferase deficiency (autosomal recessive); Methylcobalamin deficiency (cbl G type); Methylmalonicaciduria (mutase deficiency type); Mevalonicaciduria; MHC class II deficiency; Microphthalmia (cataracts, and iris abnormalities); Miyoshi myopathy; MODY; Mohr-Tranebjaerg syndrome; Molybdenum cofactor deficiency (type A or type B); Monilethrix; Morbus Fabry; Morbus Gaucher; Mucopolysaccharidosis; Mucoviscidosis; Muencke syndrome; Muir-Torre syndrome; Mulibrey nanism; Multiple carboxylase deficiency (biotinresponsive); Multiple endocrine neoplasia; Muscle glycogenosis; Muscular dystrophy (congenital merosindeficient); Muscular dystrophy (Fukuyama congenital); Muscular dystrophy (limb-girdle); Muscular dystrophy) Duchenne-like); Muscular dystrophy with epidermolysis bullosa simplex; Myasthenic syndrome (slow-channel congenital); Mycobacterial infection (atypical, familial disseminated); Myelodysplastic syndrome; Myelogenous leukemia; Myeloid malignancy; Myeloperoxidase deficiency; Myoadenylate deaminase deficiency; Myoglobinuria/hemolysis due to PGK deficiency; Myoneurogastrointestinal encephalomyopathy syndrome; Myopathy (actin; congenital; desmin-related; cardioskeletal; distal; nemaline); Myopathy due to CPT II deficiency; Myopathy due to phosphoglycerate mutase deficiency; Myotonia congenita; Myotonia levior; Myotonic dystrophy; Myxoid liposarcoma; NAGA deficiency; Nailpatella syndrome; Nemaline myopathy 1 (autosomal dominant); Nemaline myopathy 2 (autosomal recessive); Neonatal hyperparathyroidism; Nephrolithiasis; Nephronophthisis (juvenile); Nephropathy (chronic hypocomplementemic); Nephrosis-1; Nephrotic syndrome; Netherton syndrome; Neuroblastoma; Neurofibromatosis (type 1 or type 2); Neurolemmomatosis; neuronal-5 Ceroid-lipofuscinosis; Neuropathy; Neutropenia (alloimmune neonatal); Niemann-Pick disease (type A; type B; type C1; type D); Night blindness (congenital stationary); Nijmegen breakage syndrome; Noncompaction of left ventricular myocardium; Nonepidermolytic palmoplantar keratoderma; Norrie disease; Norum disease; Nucleoside phosphorylase deficiency; Obesity; Occipital hornsyndrome; Ocular albinism (Nettleship-Falls type); Oculopharyngeal muscular dystorphy; Oguchi disease; Oligodontia; Omenn syndrome; Opitz G syndrome; Optic nerve coloboma with renal disease; Ornithine transcarbamylase deficiency; Oroticaciduria; Orthostatic intolerance; OSMED syndrome; Ossification of posterior longitudinal ligament of spine; Osteoarthrosis; Osteogenesis imperfecta; Osteolysis; Osteopetrosis (recessive or idiopathic); Osteosarcoma; Ovarian carcinoma; Ovarian dysgenesis; Pachyonychia congenita (Jackson-Lawler type or Jadassohn-Lewandowsky type); Paget disease of bone; Pallister-Hall syndrome; Pancreatic agenesis; Pancreatic cancer; Pancreatitis; Papillon-Lefevre syndrome; Paragangliomas; Paramyotonia congenita; Parietal foramina; Parkinson disease (familial or juvenile); Paroxysmal nocturnal hemoglobinuria; Pelizaeus-Merzbacher disease; Pendred syndrome; Perineal hypospadias; Periodic fever; Peroxisomal biogenesis disorder; Persistent hyperinsulinemic hypoglycemia of infancy; Persistent Mullerian duct syndrome (type II); Peters anomaly; Peutz-Jeghers syndrome; Pfeiffer syndrome; Phenylketonuria; Phosphoribosyl pyrophosphate synthetaserelated gout; Phosphorylase kinase deficiency of liver and muscle; Piebaldism; Pilomatricoma; Pinealoma with bilateral retinoblastoma; Pituitary ACTH secreting adenoma; Pituitary hormone deficiency; Pituitary tumor; Placental steroid sulfatase deficiency; Plasmin inhibitor deficiency; Plasminogen deficiency (types I and II); Plasminogen Tochigi disease; Platelet disorder; Platelet glycoprotein IV deficiency; Platelet-activating factor acetylhydrolase deficiency; Polycystic kidney disease; Polycystic lipomembranous osteodysplasia with sclerosing leukenencephalophathy; Polydactyly, postaxial; Polyposis; Popliteal pterygium syndrome; Porphyria (acute hepatic or acute intermittent or congenital erythropoietic); Porphyria cutanea tarda; Porphyria hepatoerythropoietic; Porphyria variegata; Prader-Willi syndrome; Precocious puberty; Premature ovarian failure; Progeria Type I; Progeria Typ II; Progressive external ophthalmoplegia; Progressive intrahepatic cholestasis-2; Prolactinoma (hyperparathyroidism, carcinoid syndrome); Prolidase deficiency; Propionicacidemia; Prostate cancer; Protein S deficiency; Proteinuria; Protoporphyria (erythropoietic); Pseudoachondroplasia; Pseudohermaphroditism; Pseudohypoaldosteronism; Pseudohypoparathyroidism; Pseudovaginal perineoscrotal hypospadias; Pseudovitamin D deficiency rickets; Pseudoxanthoma elasticum (autosomal dominant; autosomal recessive); Pulmonary alveolar proteinosis; Pulmonary hypertension; Purpura fulminans; Pycnodysostosis; Pyropoikilocytosis; Pyruvate carboxylase deficiency; Pyruvate dehydrogenase deficiency; Rabson-Mendenhall syndrome; Refsum disease; Renal cell carcinoma; Renal tubular acidosis; Renal tubular acidosis with deafness; Renal tubular acidosis-osteopetrosis syndrome; Reticulosis (familial histiocytic); Retinal degeneration; Retinal dystrophy; Retinitis pigmentosa; Retinitis punctata albescens; Retinoblastoma; Retinol binding protein deficiency; Retinoschisis; Rett syndrome; Rh(mod) syndrome; Rhabdoid predisposition syndrome; Rhabdoid tumors; Rhabdomyosarcoma; Rhabdomyosarcoma (alveolar); Rhizomelic chondrodysplasia punctata; Ribbing-Syndrom; Rickets (vitamin D-resistant); Rieger anomaly; Robinow syndrome; Rothmund-Thomson syndrome; Rubenstein-Taybi syndrome; Saccharopinuria; Saethre-Chotzen syndrome; Salla disease; Sandhoff disease (infantile, juvenile, and adult forms); Sanfilippo syndrome (type A or type B); Schindler disease; Schizencephaly; Schizophrenia (chronic); Schwannoma (sporadic); SCID (autosomal recessive, T-negative/Bpositive type); Secretory pathway w/TMD; SED congenita; Segawa syndrome; Selective T-cell defect; SEMD (Pakistani type); SEMD (Strudwick type); Septooptic dysplasia; Severe combined immunodeficiency (B cellnegative); Severe combined immunodeficiency (T-cell negative, B-cell/natural killer cell-positive type); Severe combined immunodeficiency (Xlinked); Severe combined immunodeficiency due to ADA deficiency; Sex reversal (XY, with adrenal failure); Sezary syndrome; Shah-Waardenburg syndrome; Short stature; Shprintzen-Goldberg syndrome; Sialic acid storage disorder; Sialidosis (type I or type II); Sialuria; Sickle cell anemia; Simpson-Golabi-Behmel syndrome; Situs ambiguus; Sjogren-Larsson syndrome; Smith-Fineman-Myers syndrome; Smith-Lemli-Opitz syndrome (type I or type II); Somatotrophinoma; Sorsby fundus dystrophy; Spastic paraplegia; Spherocytosis; Spherocytosis-1; Spherocytosis-2; Spinal and bulbar muscular atrophy of Kennedy; Spinal muscular atrophy; Spinocerebellar ataxia; Spondylocostal dysostosis; Spondyloepiphyseal dysplasia tarda; Spondylometaphyseal dysplasia (Japanese type); Stargardt disease-1; Steatocystoma multiplex; Stickler syndrome; Sturge-Weber syndrome; Subcortical laminal heterotia; Subcortical laminar heterotopia; Succinic semialdehyde dehydrogenase deficiency; Sucrose intolerance; Sutherland-Haan syndrome; Sweat chloride elevation without CF; Symphalangism; Synostoses syndrome; Synpolydactyly; Tangier disease; Tay-Sachs disease; T-cell acute lymphoblastic leukemia; T-cell immunodeficiency; T-cell prolymphocytic leukemia; Thalassemia (alpha- or delta-); Thalassemia due to Hb Lepore; Thanatophoric dysplasia (types I or II); Thiamine-responsive megaloblastic anemia syndrome; Thrombocythemia; Thrombophilia (dysplasminogenemic); Thrombophilia due to heparin cofactor II deficiency; Thrombophilia due to protein C deficiency; Thrombophilia due to thrombomodulin defect; Thyroid adenoma; Thyroid hormone resistance; Thyroid iodine peroxidase deficiency; Tietz syndrome; Tolbutamide poor metabolizer; Townes-Brocks syndrome; Transcobalamin II deficiency; Treacher Collins mandibulofacial dysostosis; Trichodontoosseous syndrome; Trichorhi nophalangeal syndrome; Trichothiodystrophy; Trifunctional protein deficiency (type I or type II); Trypsinogen deficiency; Tuberous sclerosis-1; Tuberous sclerosis-2; Turcot syndrome; Tyrosine phosphatase; Tyrosinemia; Ulnar-mammary syndrome; Urolithiasis (2,8-dihydroxyadenine); Usher syndrome (type 1B or type 2A); Venous malformations; Ventricular tachycardia; Virilization; Vitamin K-dependent coagulation defect; VLCAD deficiency; Vohwinkel syndrome; von Hippel-Lindau syndrome; von Willebrand disease; Waardenburg syndrome; Waardenburg syndrome/ocular albinism; Waardenburg-Shah neurologic variant; Waardenburg-Shah syndrome; Wagner syndrome; Warfarin sensitivity; Watson syndrome; Weissenbacher-Zweymuller syndrome; Werner syndrome; Weyers acrodental dysostosis; White sponge nevus; Williams-Beuren syndrome; Wilms tumor (type1); Wilson disease; Wiskott-Aldrich syndrome; Wolcott-Rallison syndrome; Wolfram syndrome; Wolman disease; Xanthinuria (type I); Xeroderma pigmentosum; X-SCID; Yemenite deaf-blind hypopigmentation syndrome; ypocalciuric hypercalcemia (type I); Zellweger syndrome; Zlotogora-Ogur syndrome.

Preferred diseases to be treated which have a genetic inherited background and which are typically caused by a single gene defect and are inherited according to Mendel's laws are preferably selected from the group consisting of autosomal-recessive inherited diseases, such as, for example, adenosine deaminase deficiency, familial hypercholesterolaemia, Canavan's syndrome, Gaucher's disease, Fanconi anaemia, neuronal ceroid lipofuscinoses, mucoviscidosis (cystic fibrosis), sickle cell anaemia, phenylketonuria, alcaptonuria, albinism, hypothyreosis, galactosaemia, alpha-1-anti-trypsin deficiency, Xeroderma pigmentosum, Ribbing's syndrome, mucopolysaccharidoses, cleft lip, jaw, palate, Laurence Moon Biedl Bardet sydrome, short rib polydactylia syndrome, cretinism, Joubert's syndrome, type II progeria, brachydactylia, adrenogenital syndrome, and X-chromosome inherited diseases, such as, for example, colour blindness, e.g. red/green blindness, fragile X syndrome, muscular dystrophy (Duchenne and Becker-Kiener type), haemophilia A and B, G6PD deficiency, Fabry's disease, mucopolysaccharidosis, Norrie's syndrome, Retinitis pigmentosa, septic granulomatosis, X-SCID, ornithine transcarbamylase deficiency, Lesch-Nyhan syndrome, or from autosomal-dominant inherited diseases, such as, for example, hereditary angiooedema, Marfan syndrome, neurofibromatosis, type I progeria, Osteogenesis imperfecta, Klippel-Trenaurnay syndrome, Sturge-Weber syndrome, Hippel-Lindau syndrome and tuberosis sclerosis.

The present invention also allows treatment of diseases, which have not been inherited, or which may not be summarized under the above categories. Such diseases may include e.g. the treatment of patients, which are in need of a specific protein factor, e.g. a specific therapeutically active protein as mentioned above. This may e.g. include dialysis patients, e.g. patients which undergo a (regular) a kidney or renal dialysis, and which may be in need of specific therapeutically active proteins as defined above, e.g. erythropoietin (EPO), etc.

According to another embodiment, the present invention comprises the use of the at least one complexed RNA according to the present invention for transfecting a cell or an organism. Transfection of the cell or the organism may preferably be carried out using the above (in vitro or in vivo) transfection method for transfecting cells or a tissue with the complexed RNA of the present invention.

According to one further embodiment, the present invention comprises the use of at least one complexed RNA according to the present invention (for the preparation of an agent) for the treatment of any of the above mentioned diseases, disorders, conditions or pathological states. An agent in this context may be e.g. a pharmaceutical composition as defined above or an injection buffer as defined herein, additionally containing the inventive complexed RNA, a vaccine, etc. If more than one complexed RNA molecule type is used, the complexed RNAs may be different by their RNA (molecules) thereby forming a mixture of at least two distinct complexed RNA (molecule) types. If more than one complexed RNA is used (for the preparation of an agent) for the treatment of any of the above mentioned diseases the same or (at least two) different RNA (molecule) types may be contained in these complexed RNA mixtures. In this context, any of the above mentioned RNA (molecules) may be used for the inventive complexed RNA, e.g. a short RNA oligonucleotide, a coding RNA, an immunostimulatory RNA, a siRNA, an antisense RNA, or riboswitches, ribozymes or aptamers, etc. More preferably a coding RNA (molecule), even more preferably a linear coding RNA (molecule), and most preferably an mRNA may be used. Preferably, such a coding RNA (molecule), more preferably a linear coding RNA (molecule), and more preferably an mRNA is used for the complexed RNA, the RNA (molecule) typically encodes a protein or peptide suitable for the therapy of the specific disease, e.g. an antibody, which is capable of binding to a specific cancer antigen, or a tumor antigen, when treating a (specific) cancer, etc. The combinations of suitable RNA (molecules) are known to a skilled person from the art and from the disclosure of the present invention.

According to another embodiment of the present invention, it may be preferred to (additionally) elicit, e.g. induce or enhance, an immune response during therapy. In this context, an immune response may occur in various ways. A substantial factor for a suitable immune response is the stimulation of different T-cell sub-populations. T-lymphocytes are typically divided into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of the effector proteins (cytokines) produced by them. Thus, Th1 cells assist the cellular immune response by activation of macrophages and cytotoxic T-cells. Th2 cells, on the other hand, promote the humoral immune response by stimulation of the B-cells for conversion into plasma cells and by formation of antibodies (e.g. against antigens). The Th1/Th2 ratio is therefore of major importance for the immune response. For various diseases to be treated by the present invention, the Th1/Th2 ratio of the immune response is preferably shifted in the direction towards the cellular response (Th1 response) and a cellular immune response is thereby induced. Accordingly, the present invention may also be used to revert this immune response shift. Therefore, the present invention encompasses also the use of at least one complexed RNA according to the present invention (for the preparation of an agent) for the treatment of any of the above mentioned diseases, wherein the agent (and/or the complexed RNA) may be capable to elicit, e.g. induce or enhance, an immune response in a tissue or an organism as defined above. Again, an agent in this context may be e.g. a pharmaceutical composition as defined above, or an injection buffer as defined herein, which contains the inventive complexed RNA, etc. If more than one complexed RNA type is used in this context (for the preparation of an agent) for the treatment of any of the above mentioned diseases, the complexed RNA types may be different with respect to their RNA (molecules) and may form a mixture of distinct RNA types.

However, for the present embodiment, it is preferred that at least one of these complexed RNAs induces or enhances the immune response during therapy, while other complexed RNA(s) need not to induce or enhance the immune response or may be used to prevent an immune response. In this context, any of the above mentioned RNA (molecules) may be used for the inventive complexed RNA, e.g. a short RNA oligonucleotide, a coding RNA, an immunostimulatory RNA, a siRNA, an antisense RNA, or riboswitches, ribozymes or aptamers, etc. More preferably, a coding RNA (molecule), even more preferably a linear coding RNA (molecule), and most preferably an mRNA may be used for the complexed RNA. If the RNA (molecule) is a coding RNA (molecule), more preferably a linear coding RNA (molecule), and more preferably an mRNA, it typically encodes a protein or peptide suitable for the therapy of the specific disease, e.g. an antibody, which is capable of binding to a specific cancer antigen, when treating a (specific) cancer, etc. If more than one complexed RNA is contained in the agent, different combinations of proteins or peptides may be selected. Such combinations of suitable RNA (molecules) (and, if a coding RNA is used, of encoded proteins or peptides) are known to a skilled person from the art or may be combined from RNAs encoding therapeutically effective proteins, etc., as defined in the disclosure of the present invention. Induction or enhancement of the immune response concurrent to the treatment of a specific disease using one pharmaceutical composition or agent as defined above may be particularly advantageous in cases where an induced or enhanced immune response supports the treatment of a specific disease as mentioned above.

Alternatively, treatment of the disease and induction or enhancement of the immune response may be carried out by using different pharmaceutical compositions or agents as defined above in a time staggered manner. E.g. one may induce or enhance the immune response by administering a pharmaceutical composition or an agent as defined herein, containing an inventive complexed (immunostimulatory) RNA, prior to (or concurrent to) administering another pharmaceutical composition or an agent as defined herein which may contain an inventive complexed RNA, e.g. a short RNA oligonucleotide, a coding RNA, an immunostimulatory RNA, a siRNA, an antisense RNA, or riboswitches, ribozymes or aptamers, etc., which is suitable for the therapy of the specific disease.

According to one embodiment, the present invention furthermore comprises the use of at least one complexed RNA according to the present invention (for the preparation of an agent) for modulating, preferably to induce or enhance, an immune response in a tissue or an organism as defined above, more preferably to support a disease or state as mentioned herein. Hereby, the inventive complexed RNA may be used to activate the immune system unspecifically, e.g. to trigger the production of certain cytokines. The complexed RNA may therefore be used to support the specific immune response, which is elicited by e.g. an antigen derived from pathogens or tumors. An agent in this context may be e.g. a pharmaceutical composition as defined above or an injection buffer as defined herein, containing the inventive complexed RNA, a vaccine, etc. The immune response may be modulated either by the at least one complexed RNA due to the one or more oligopeptides having a length of 8 to 15 amino acids and showing the empirical formula $(Arg)_l;(Lys)_m;(His)_n;(Orn)_o;(Xaa)_x$, and/or by the immunostimulatory properties of the protein encoded by the RNA of the complexed RNA.

The present invention may therefore, whenever appropriate, well serve to achieve various objects. A complexed RNA as such or as a component of an inventive composition may by itself improve the transfection properties of the RNA as component of the inventive complex. This underlying property of the inventive complexed RNA is beneficial to a wide variety of applications. Whenever it is intended to introduce an RNA into a cell, improved transfection efficacy is ensured by the present invention. This property as such may allow the present invention to be used for the treatment of a huge variety of diseases, e.g. the treatment of monogenetic or genetic diseases as defined above.

In addition, the present invention may be used whenever treatment of immune disorders, e.g. allergies or autoimmune diseases, is envisaged. Moreover, the present invention may activate the patients's immune system by enhancing its unspecific or specific immune response. Accordingly, it may elicit an unspecific immune response, whenever appropriate, to cure a disease. And, whenever required, it may elicit a specific immune response as such (e.g. by encoding an antigen by the RNA as component of the inventive complex) or by a combination of the inventive complexed RNA with an antigen, e.g. in the same composition. Whenever required, the inventive complexed RNA may be preferably an antigen or an antibody, or any other protein or peptide as defined above, capable of modulating the immune response (preferably of inducing or enhancing same or, in case of allergies or autoimmune diseases by desensitizing the patient's immune system towards a specific allergen or autoantigen). In order to modulate, e.g. induce or enhance, an immune response in a tissue or an organism the complexed RNA may be administered to this tissue or organism as defined above either as such or as an agent as defined above. The administration modes, which may be used, may be the same as described above for pharmaceutical compositions. Administration of the agent may occur prior, concurrent and/or subsequent to a therapy of diseases or states as mentioned herein, e.g. by administration of the agent prior, concurrent and/or subsequent to a therapy or an administration of a therapeutic suitable for these diseases or states.

According to an alternative embodiment, the present invention also encompasses the use of the peptide $(Arg)_7$ in a complex with an RNA (molecule) as defined herein or the peptide $(Arg)_7$ alone (for the preparation of an agent) for modulating, preferably to elicit, e.g. to induce or enhance, an immune response, preferably an unspecific immune response by e.g. triggering the production of cytokines, in a tissue or an organism as defined above, and preferably to support a disease or state as mentioned herein. While determining the ranges of the peptide of the inventive formula (I), the present inventors have surprisingly found that $(Arg)_7$ is capable to significantly induce or enhance an immune response in hPBMCs, even if no transfection of nucleic acids, particularly RNA into hPBMCs, was observed. An RNA (molecule) may be any RNA (molecule) as defined herein, preferably, without being limited thereto, a short RNA oligonucleotide, a coding RNA, an immunostimulatory RNA, a siRNA, an antisense RNA, or riboswitches, ribozymes or aptamers. Again, an agent in this context may be e.g. a pharmaceutical composition as defined above, or an injection buffer as defined herein, which additionally contains the inventive complexed RNA, etc., wherein in the inventive complexed RNA in the agent as defined herein has been replaced by the peptide $(Arg)_7$ in a complex with an RNA (molecule) as defined herein or the peptide $(Arg)_7$ alone.

According to another alternative embodiment, the present invention also encompasses the use of the peptide $(Arg)_7$ in a complex with an RNA (molecule) as defined herein or the peptide $(Arg)_7$ alone (for the preparation of an agent) for the treatment of any of the above mentioned diseases or states.

According to a final embodiment, the present invention also provides kits containing a complexed RNA according to the invention and/or a pharmaceutical composition according to the invention as well as, optionally, technical instructions with information on the administration and dosage of the complexed RNA according to the invention and/or the pharmaceutical composition according to the invention. The kit may separately further comprise one or more of the following group of components: at least one antigen or at least one antibody or a composition containing an antigen or an antibody, an additional adjuvant or a composition containing at least one adjuvant and/or at least one cytokine or a composition containing at least one cytokine. The antigen, antibody and/or the cytokine may be provided as such (proteins) or may be provided as DNA or RNA coding for the antigen, antibody or cytokine.

The present invention also provides kits containing the peptide $(Arg)_7$ in a complex with an RNA (molecule) as defined herein or the peptide $(Arg)_7$ alone as well as, optionally, technical instructions with information on the administration and dosage of the peptide $(Arg)_7$. Such kits may applied e.g. for any of the above mentioned applications or uses, preferably for the use of at least one complexed RNA according to the present invention (for the preparation of an agent) for the treatment of any of the above mentioned diseases. The kits may also be applied for the use of at least one complexed RNA according to the present invention (for the preparation of an agent) for the treatment of any of the above mentioned diseases, wherein the agent (and/or the complexed RNA) may be capable to induce or enhance an immune response in a tissue or an organism as defined above. Such kits may further be applied for the use of at least one complexed RNA according to the present invention (for the preparation of an agent) for modulating, preferably to elicit, e.g. to induce or enhance, an immune response in a tissue or an organism as defined above, and preferably to support a disease or state as mentioned herein.

FIGURES

The following Figures are intended to illustrate the invention further. They are not intended to limit the subject matter of the invention thereto.

FIG. 1: depicts the sequence of a stabilized luciferase mRNA sequence, wherein the native luciferase encoding mRNA is modified with a poly-A/poly-C-tag (A70-C30). This first construct (construct CAP-Ppluc(wt)-muag-A70-C30, SEQ ID NO: 35) contained following sequence elements:
- stabilizing sequences from the alpha-Globin gene,
- 70× Adenosin at the 3'-terminal end (poly-A-tail),
- 30× Cytosin at the 3'-terminal end (poly-C-tail); represented by following symbols:
  - _____ =coding sequence
  - ——— =3'-UTR of the alpha globin gene
  - ········· =poly-A-tail
  - ----- =poly-C-tail FIG. 2: shows the sequence of a stabilized luciferase mRNA sequence, wherein the construct according to SEQ ID NO: 35 (see FIG. 1) is further modified with a GC-optimized sequence for a better codon usage. The final construct (construct CAP-Ppluc(GC)-muag-A70-C30, SEQ ID NO: 36) contained following sequence elements:
- GC-optimized sequence for a better codon usage
- stabilizing sequences from the alpha-Globin gene
- 70× Adenosin at the 3'-terminal end (poly-A-tail),
- 30× Cytosin at the 3'-terminal end (poly-C-tail); represented by following symbols:
  - _____ =coding sequence
  - ——— =modified 3'-UTR of the alpha globin gene
  - ········· =poly-A-tail
  - ----- =poly-C-tail FIG. 3: shows the coding sequence of the sequence according to SEQ ID NO: 35 (SEQ ID NO: 37) (see FIG. 1).

FIG. 4: shows the GC-optimized coding sequence of the sequence according to SEQ ID NO: 36 (SEQ ID NO: 38) (see FIG. 2). The GC-optimized codons are underlined.

FIG. 5: shows the immunostimulatory effect of RNA complexed with nona-arginine $((Arg)_9)$ in hPBMC cells by measuring IL-6 production. As can be seen, hPBMC cells show a significant IL-6 production, i.e. a significant immunostimulatory effect of RNA complexed with nona-arginine $((Arg)_9)$.

Figure 6:
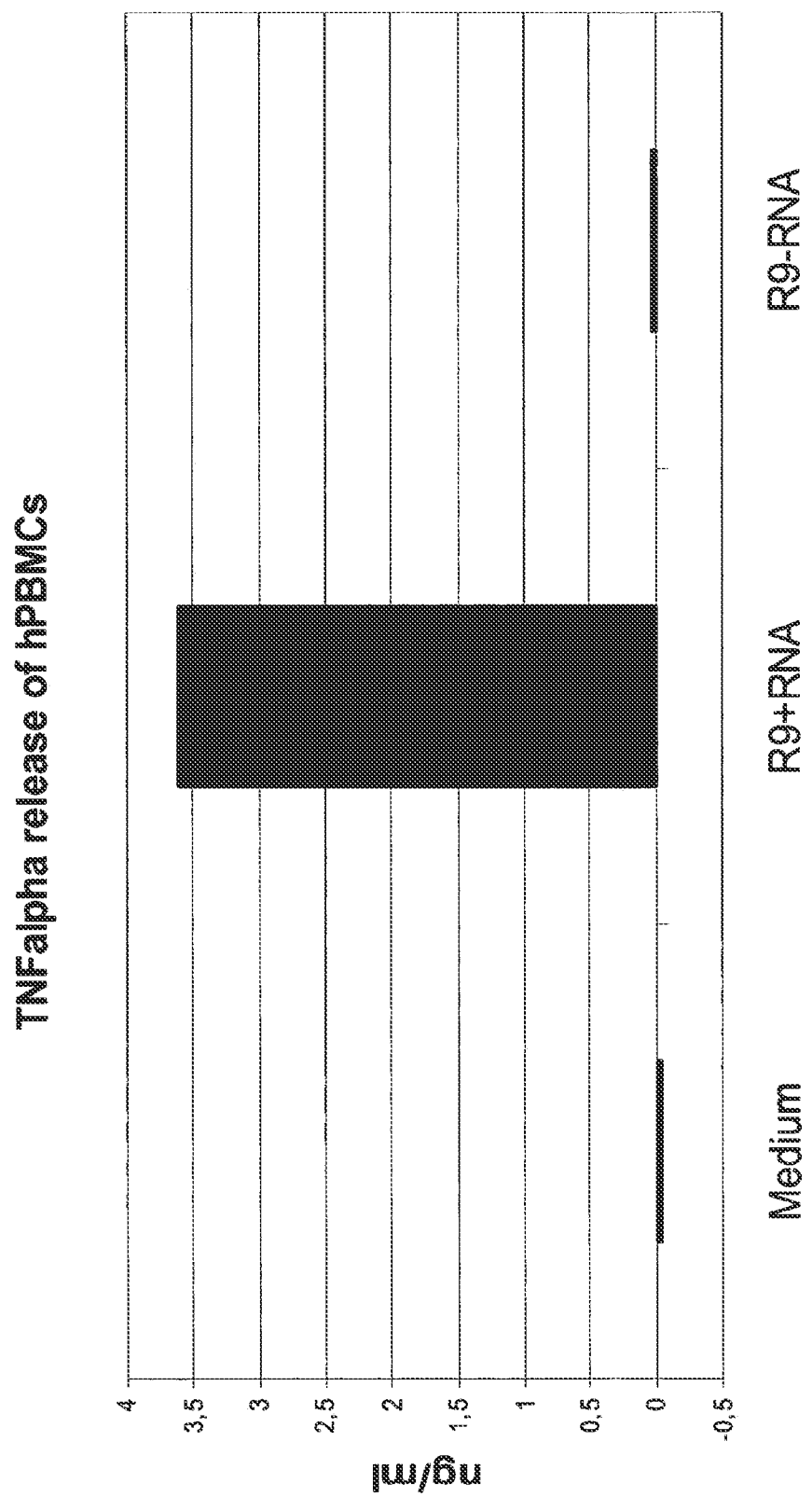

FIG. 6: shows the immunostimulatory effect of RNA complexed with nona-arginine $((Arg)_9)$ in hPBMC cells by measuring TNF-alpha production. As can be seen, hPBMC cells show a significant TNF-alpha production, i.e. a significant immunostimulatory effect of RNA complexed with nona-arginine $((Arg)_9)$.

Figure 7:
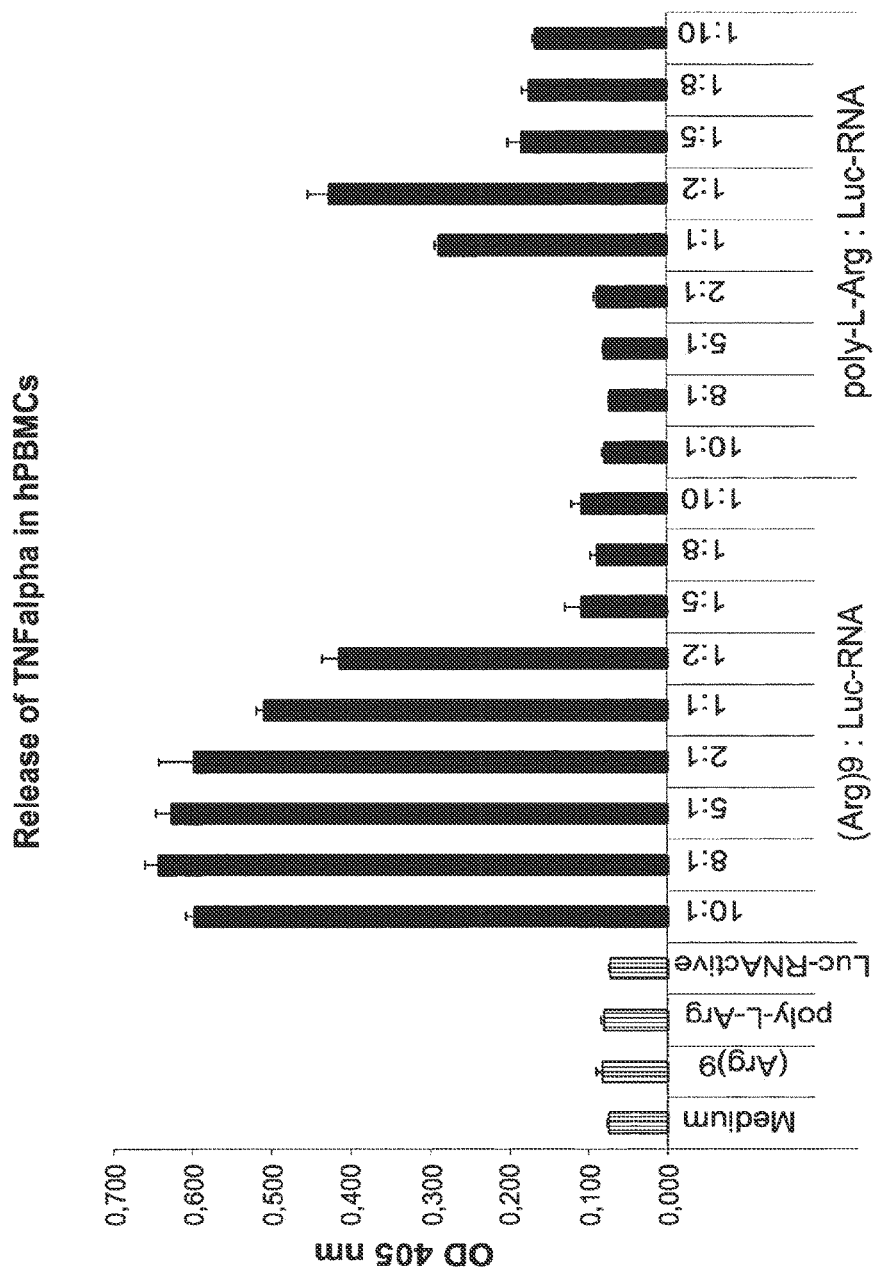

FIG. 7: shows in an comparative example the comparison of immunostimulatory effects of RNA complexed with either nona-arginine $((Arg)_9)$ or poly-L-arginine, respectively, in hPBMCs. Advantageously, a significant immunostimulatory effect can be observed for mass ratios lower than 1:5 (RNA:nona-arginine) (1:10; 1:8; 1:5; 1:2; 1:1; 2:1). However, when using mass ratios of RNA:nona-arginine (5:1) no significant TNFalpha production can be observed. The same applies to stimulation experiments, using nona-arginine $((Arg)_9)$ or mRNA alone. Additionally, it was observed, that complexation of mRNA with poly-L-arginine leads to significantly lower induction of TNF-alpha production in comparison to nona-arginine $((Arg)_9)$. Apparently, higher concentrations of poly-L-arginine appear to be toxic for cells transfected therewith, particularly when using a mass ratio of 1:2 RNA:poly-L-arginine:RNA or higher, since the cells were lysed.

Figure 8:
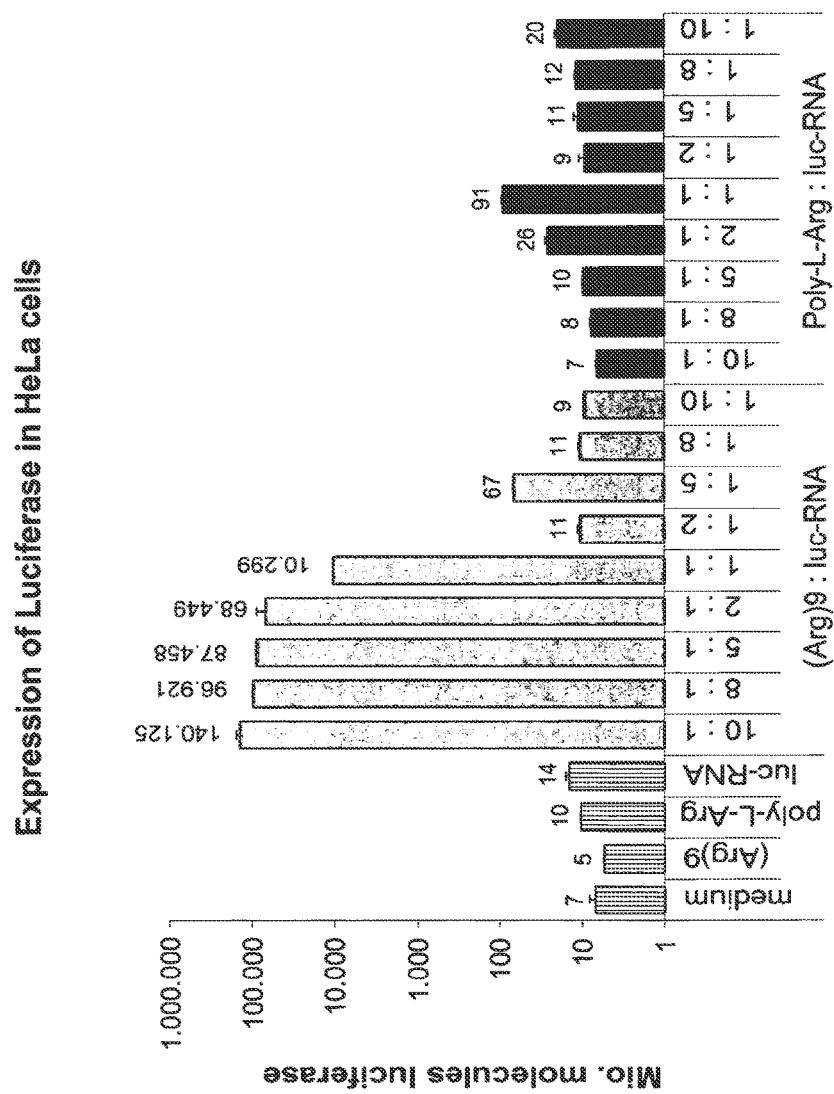

FIG. 8: shows luciferase expression upon transfection of complexes of RNA with nona-arginine $((Arg)_9)$ in HeLa cells. As may be derived from FIG. 8 a mass ratio of less than 2:1 (RNA:nona-arginine) appears to be advantageous. In contrast, complexation with (high molecular mass) poly-L-arginine does not lead to a significant luciferase-activity. Thus, (high molecular mass) poly-L-arginine does not appear to be suitable for transfection of mRNA.

Figure 9:
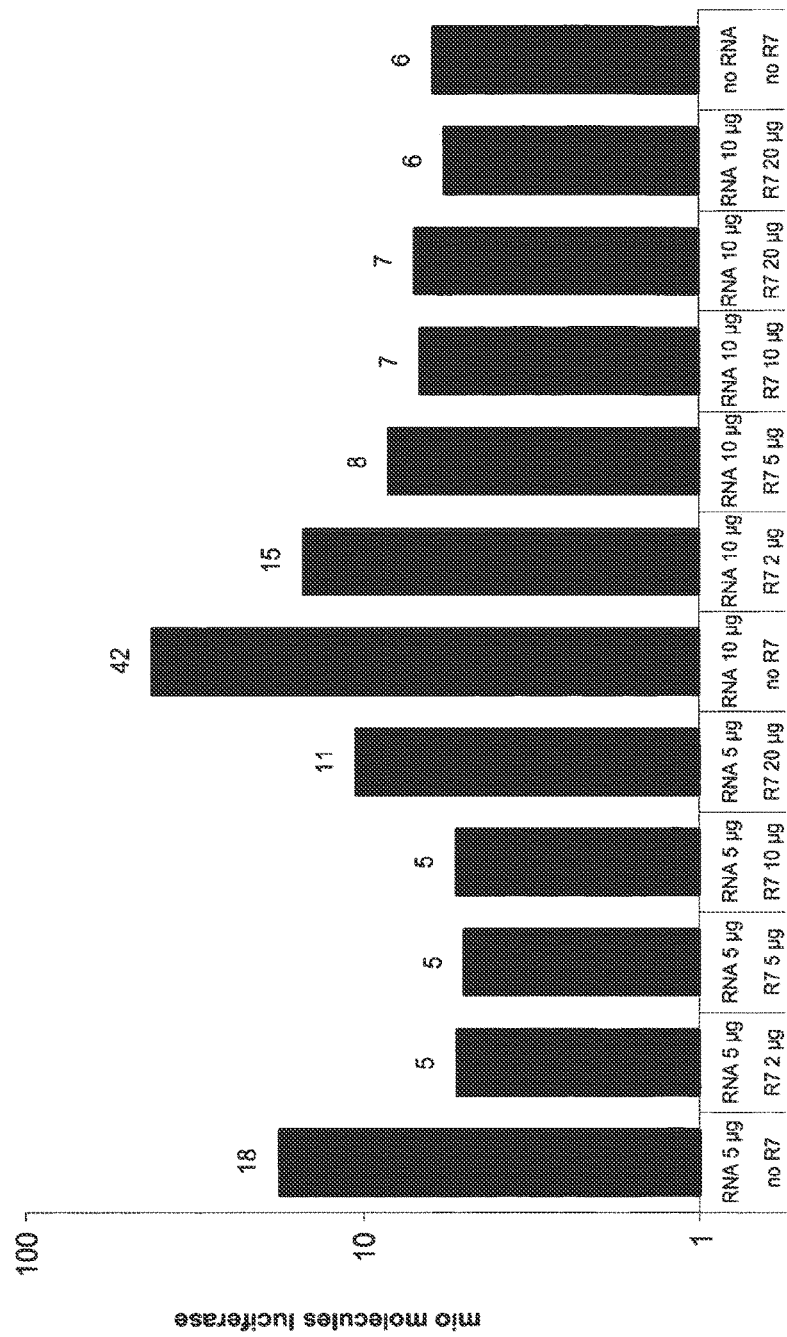

FIG. 9: depicts in a comparative example the luciferase expression upon transfection of complexes of RNA with hepta-arginine $((Arg)_7)$ in HeLa cells. As may be derived from FIG. 9, transfection of complexes of RNA with hepta-arginine $((Arg)_7)$ does not lead to a significant luciferase-activity. Thus, hepta-arginine $((Arg)_7)$ does also not appear to be suitable for transfection of mRNA.

Figure 10:
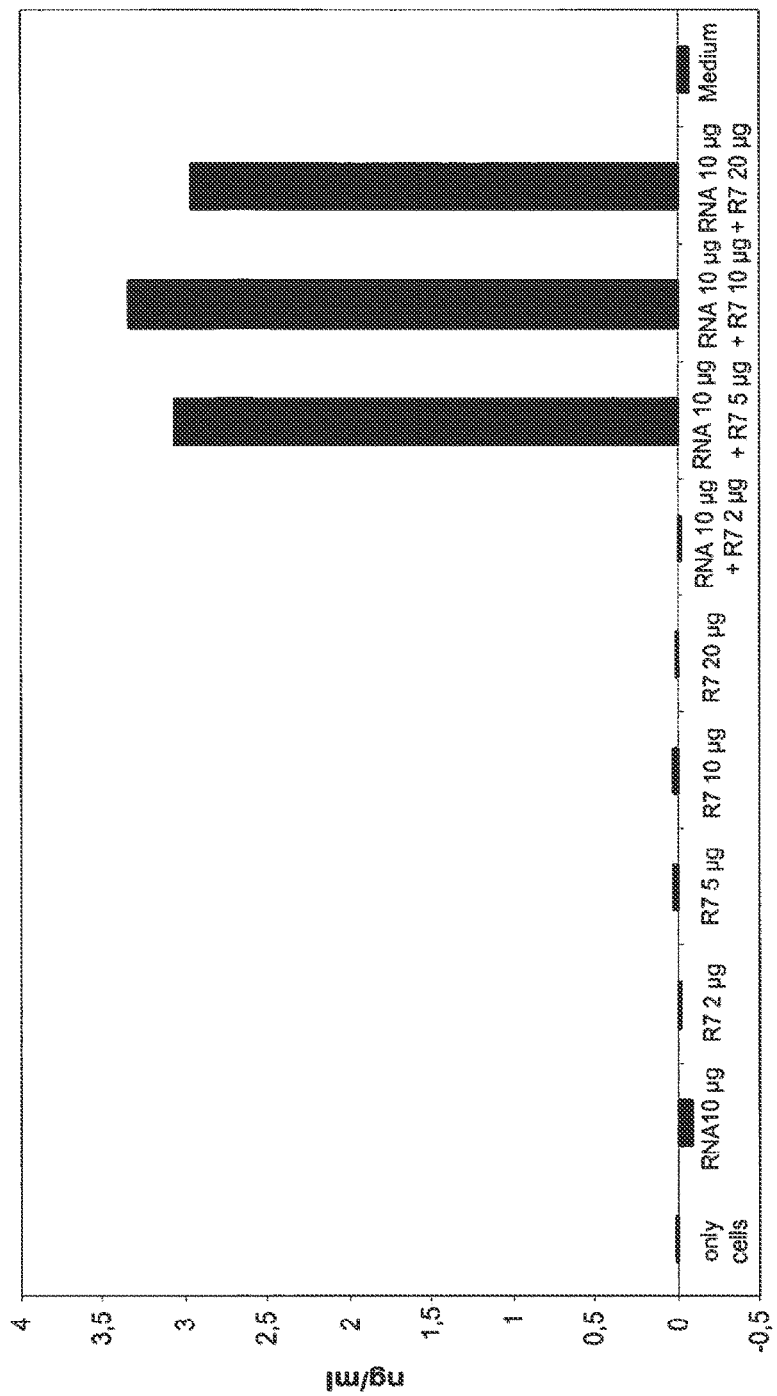

FIG. 10: shows the immunostimulatory effect of RNA complexed with hepta-arginine $((Arg)_7)$ in hPBMC cells by measuring IL-6 production. As can be seen, hPBMC cells show a significant IL-6 production, i.e. a significant immunostimulatory effect of RNA complexed with hepta-arginine $((Arg)_7)$.

Figure 11:
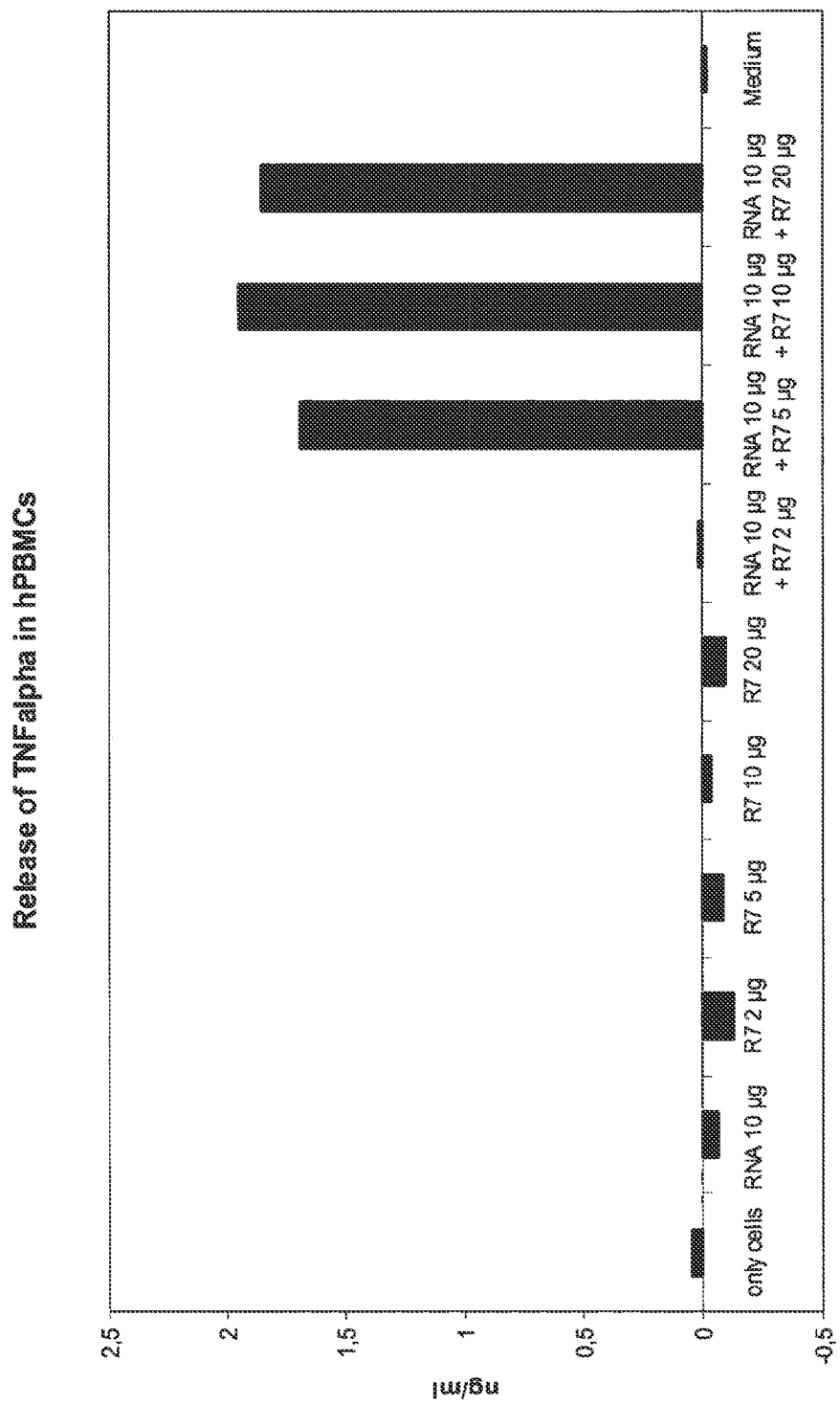

FIG. 11: shows the immunostimulatory effect of RNA complexed with hepta-arginine $((Arg)_7)$ in hPBMC cells by measuring TNF-alpha production. As can be seen, hPBMC cells show a significant TNF-alpha production, i.e. a significant immunostimulatory effect of RNA complexed with hepta-arginine $((Arg)_7)$.

Figure 12:
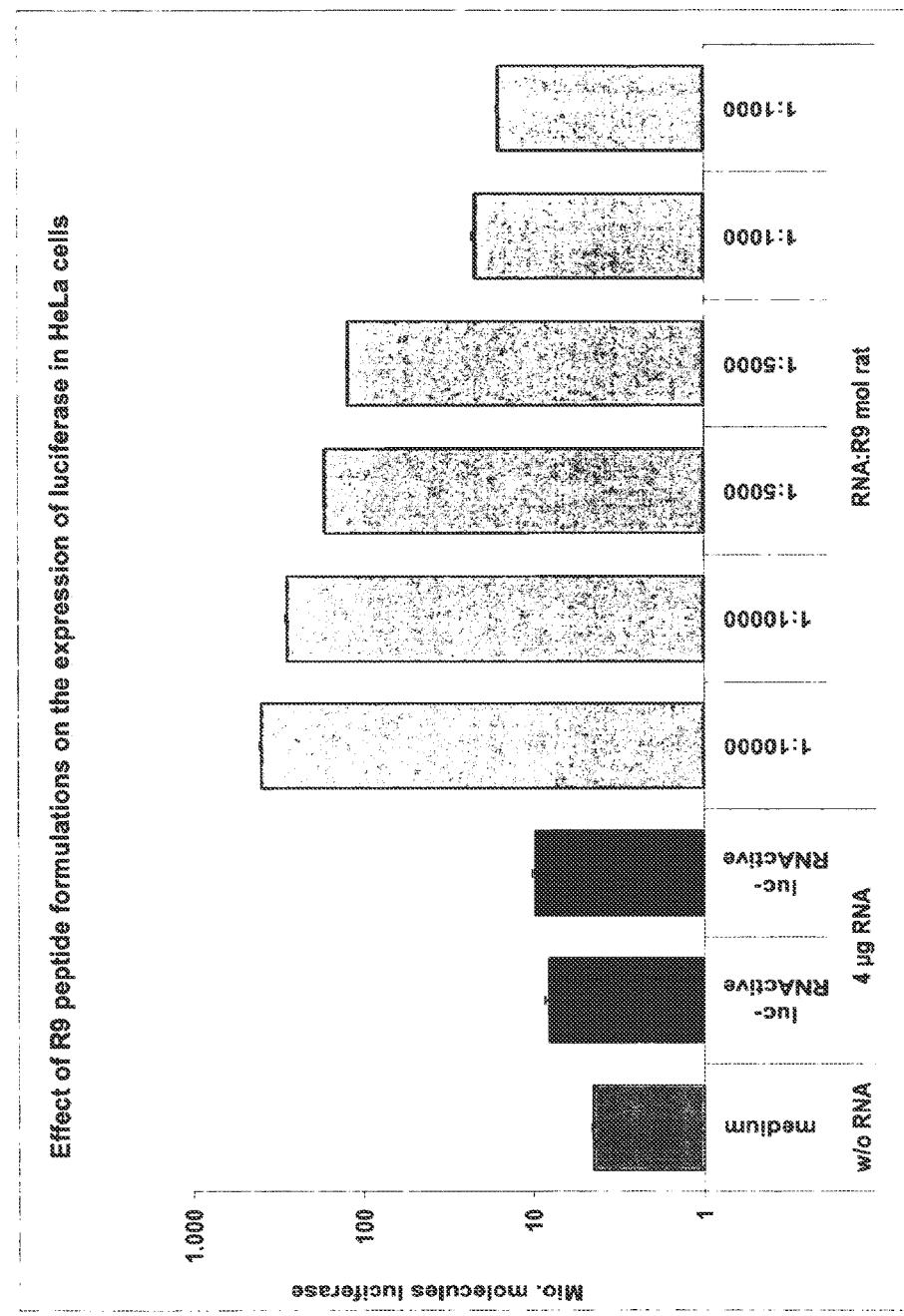

FIG. 12: shows the effect of RNA complexed with R9 peptide on the expression of luciferase in HeLa cells.

Figure 13:
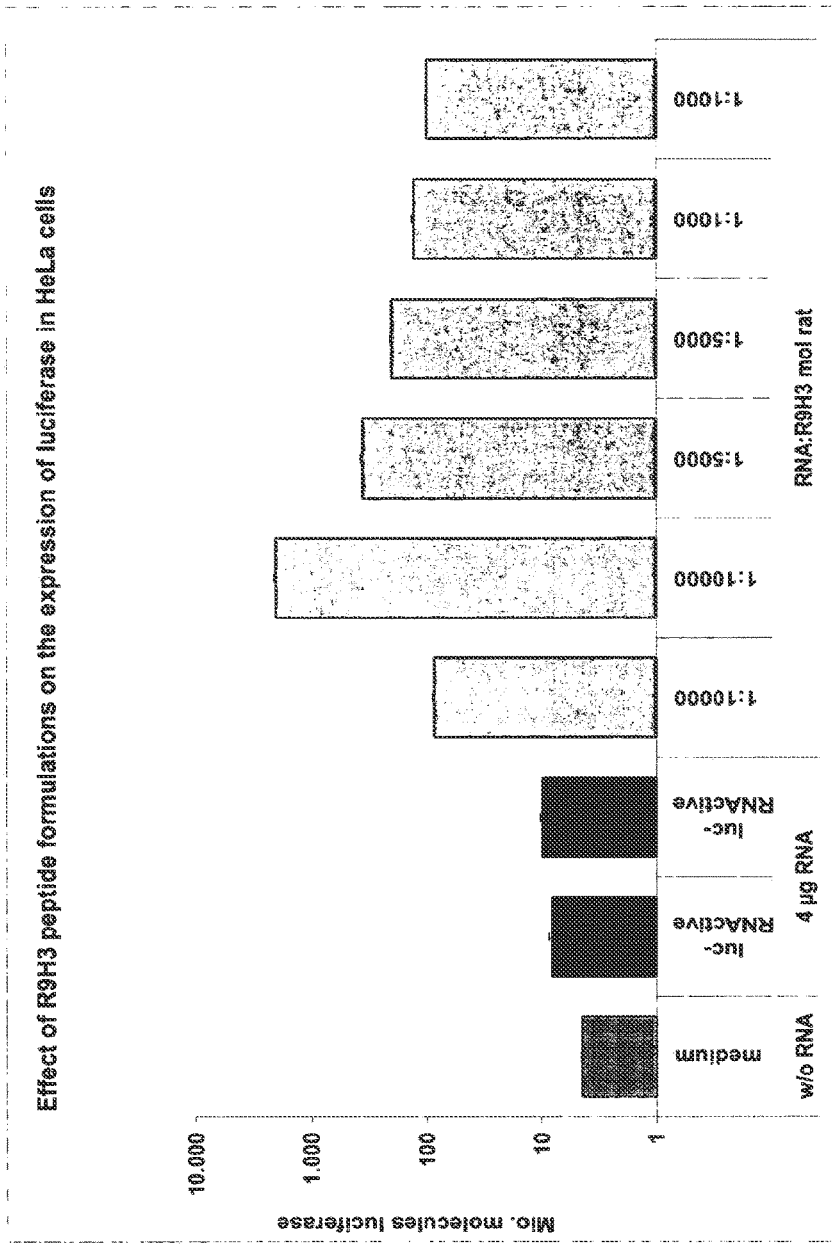

FIG. 13: shows the effect of RNA complexed with R9H3 peptide on the expression of luciferase in HeLa cells.

Figure 14:
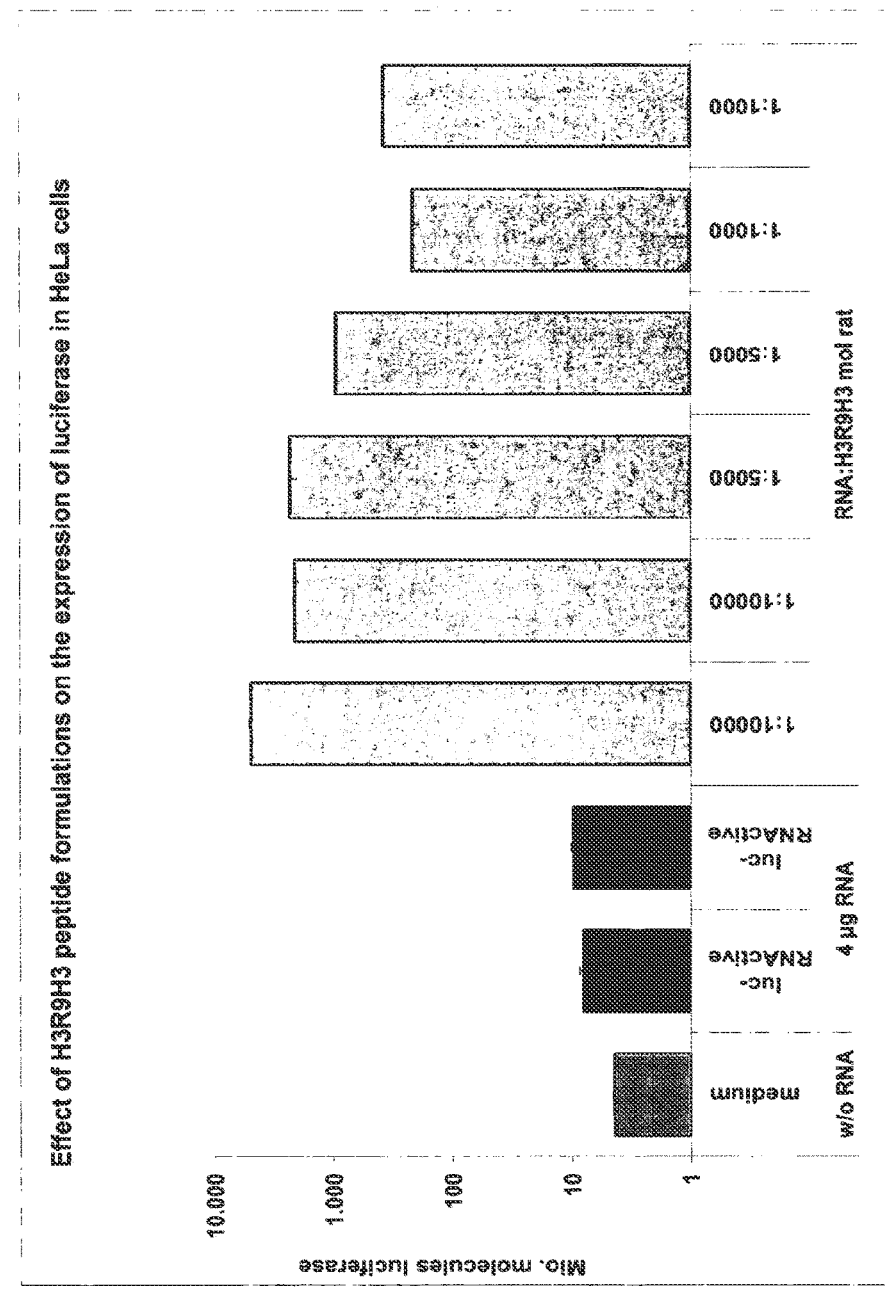

FIG. 14: shows the effect of RNA complexed with H3R9H3 peptide on the expression of luciferase in HeLa cells.

Figure 15:
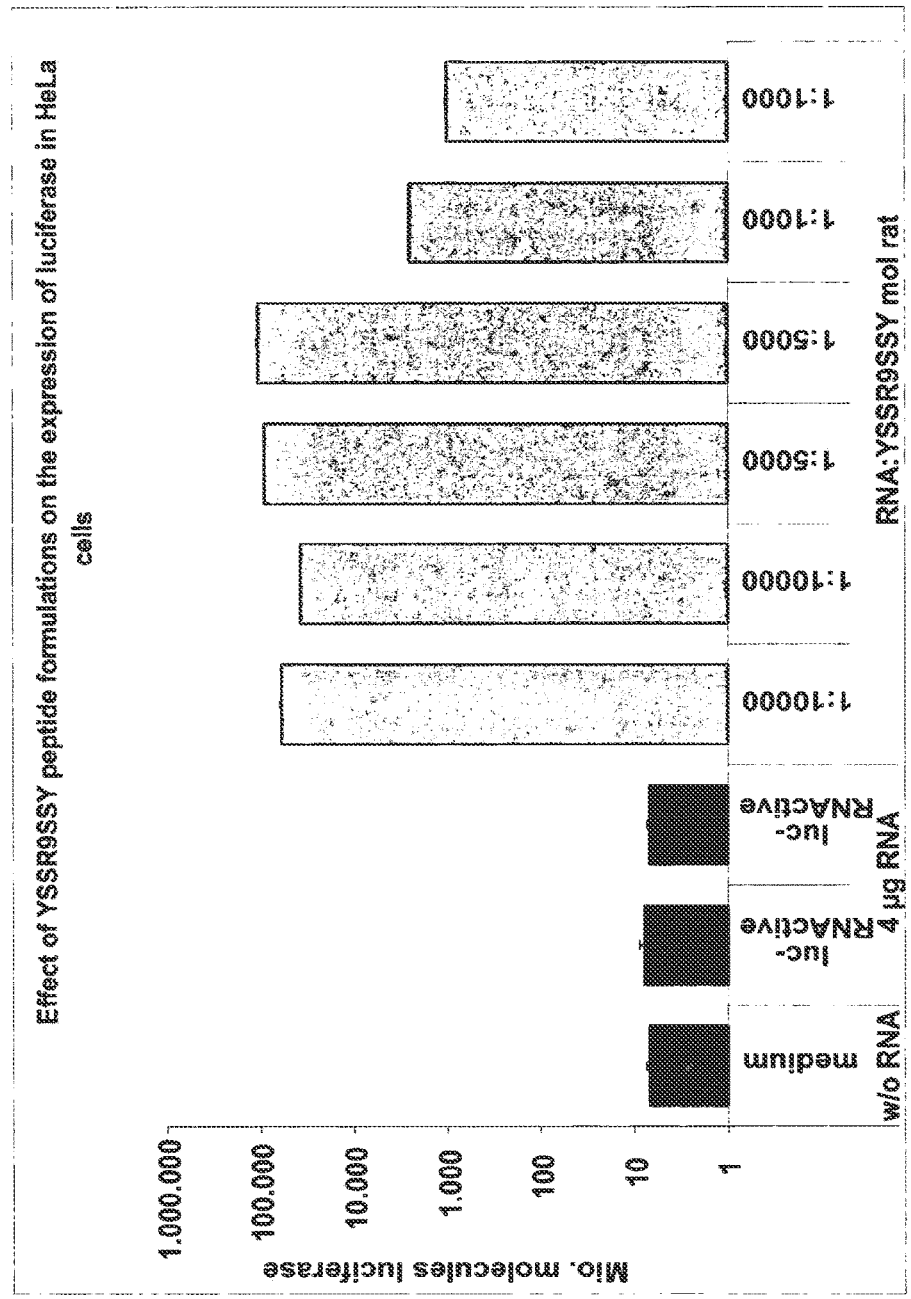

FIG. 15: shows the effect of RNA complexed with YYYR9SSY (SEQ ID NO: 401) peptide on the expression of luciferase in Hela cells.

Figure 16:
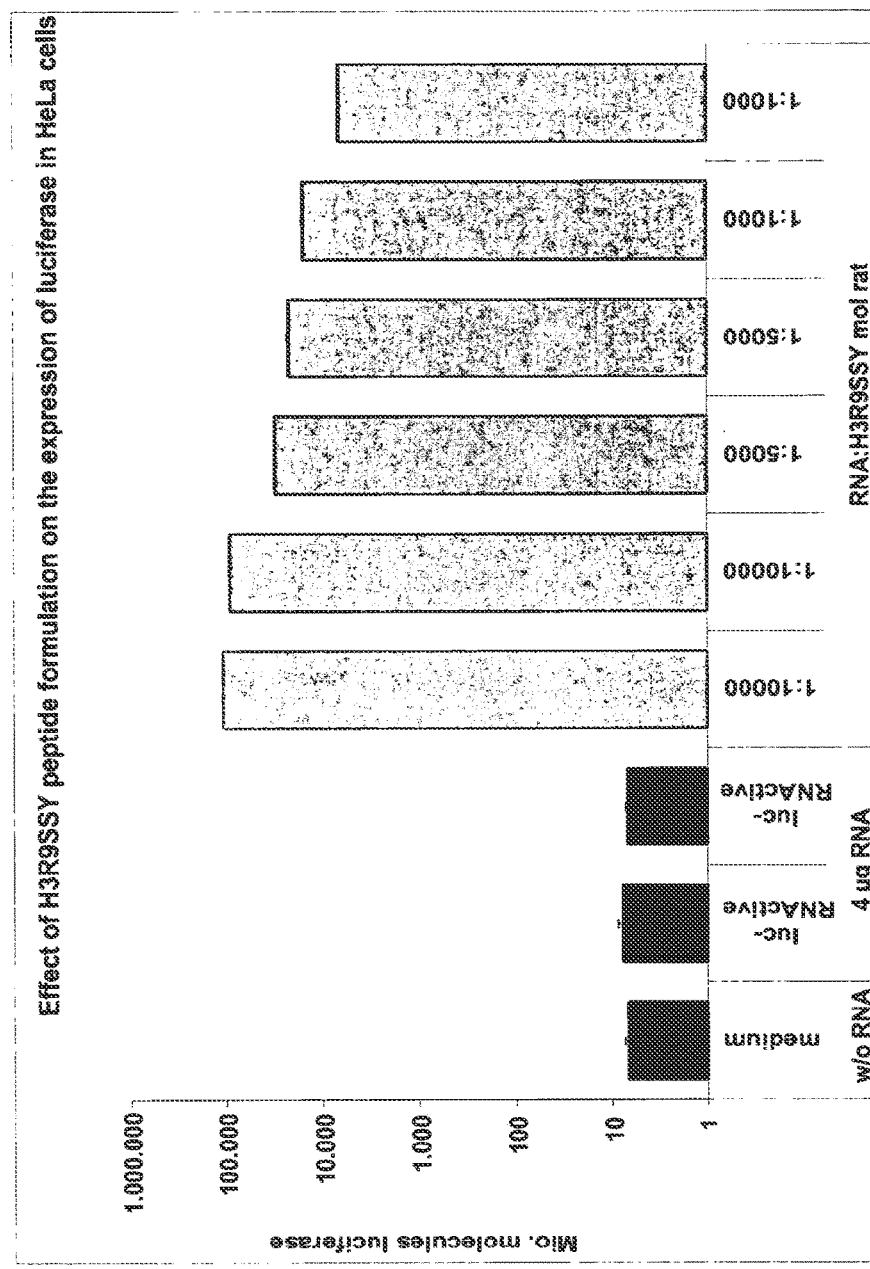

FIG. 16: shows the effect of RNA complexed with H3R9SSY peptide on the expression of luciferase in HeLa cells.

Figure 17:
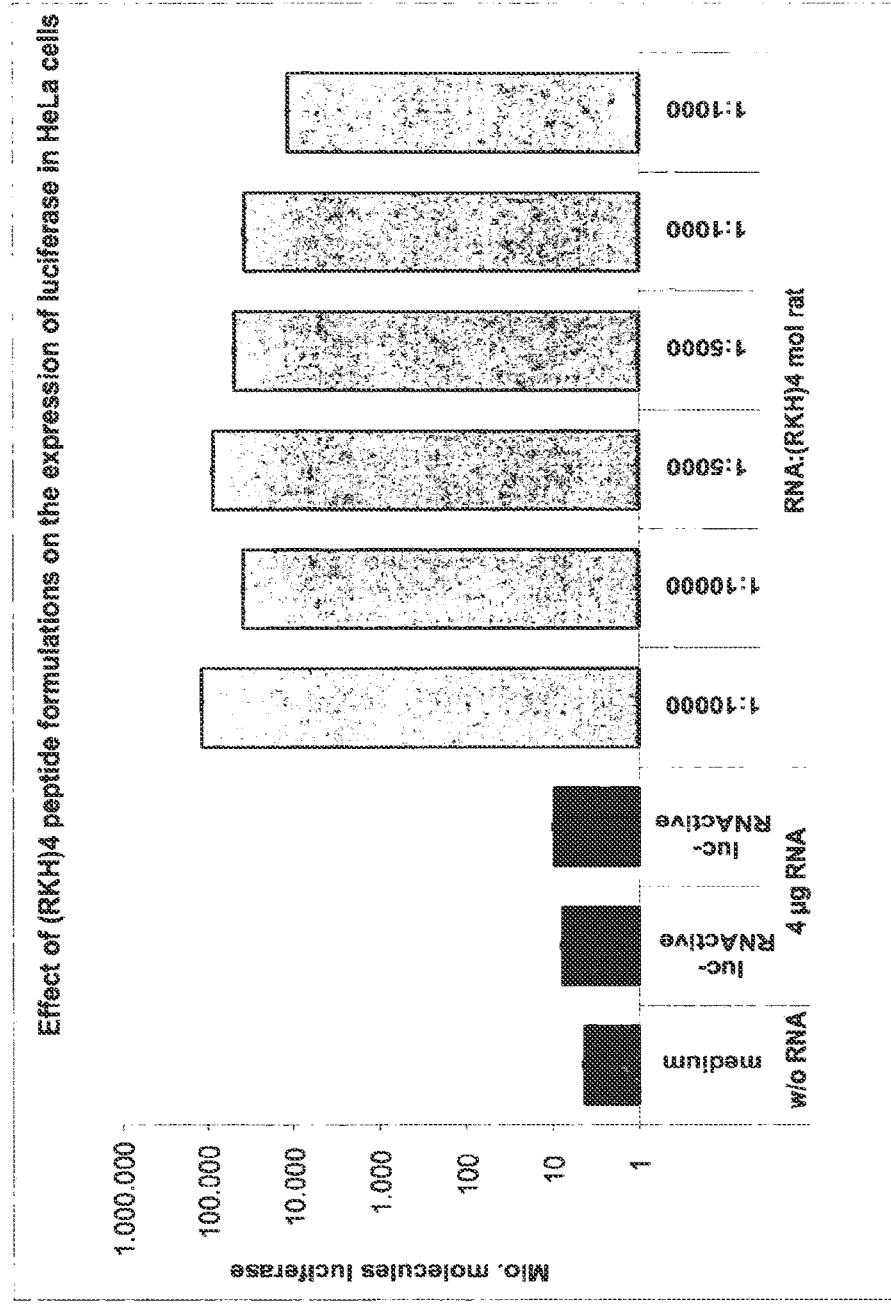

FIG. 17: shows the effect of RNA complexed with $(RKH)_4$ peptide on the expression of luciferase in HeLa cells.

Figure 18:
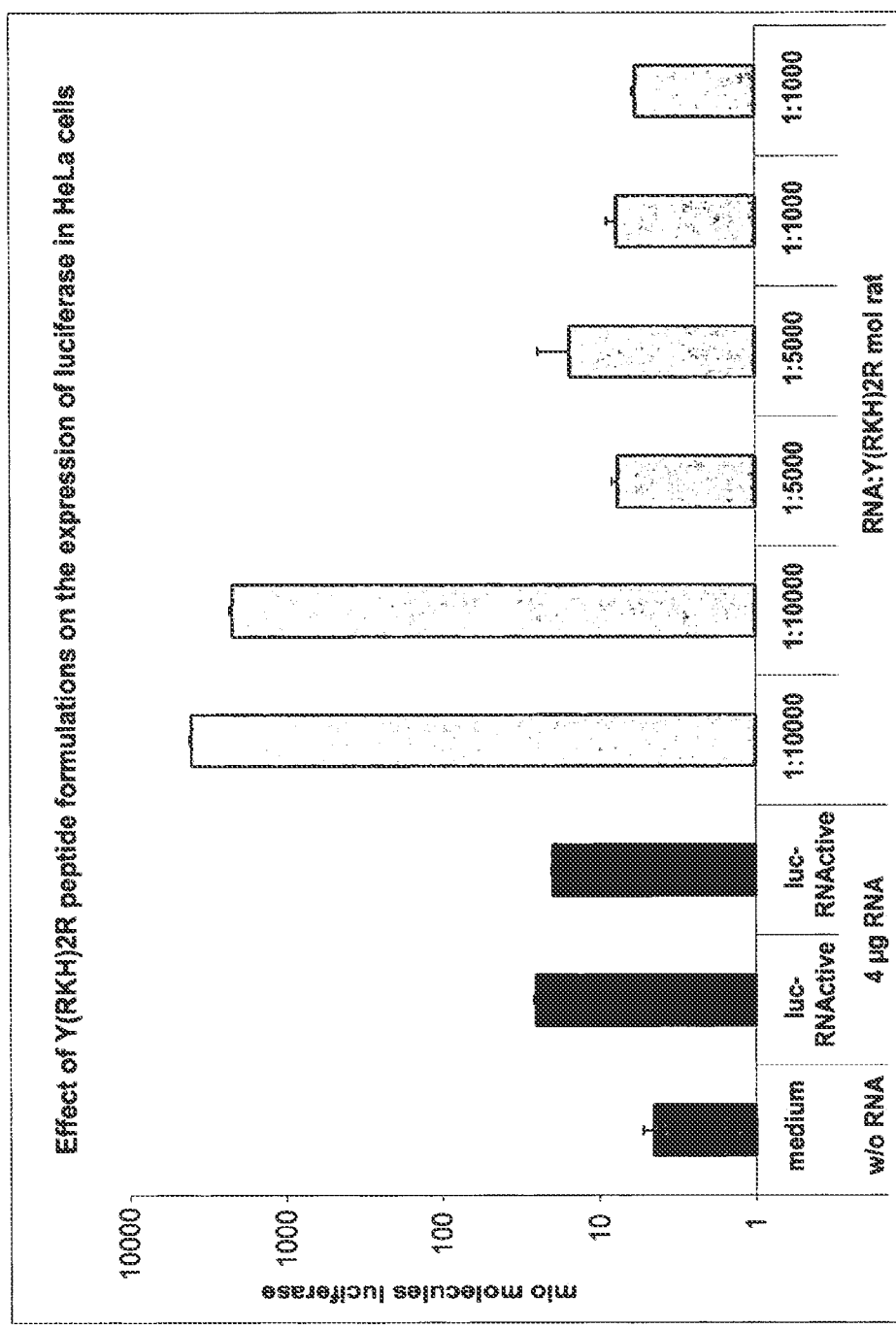

FIG. 18: shows the effect of RNA complexed with $Y(RKH)_2R$ peptide on the expression of luciferase in HeLa cells.

Figure 19:
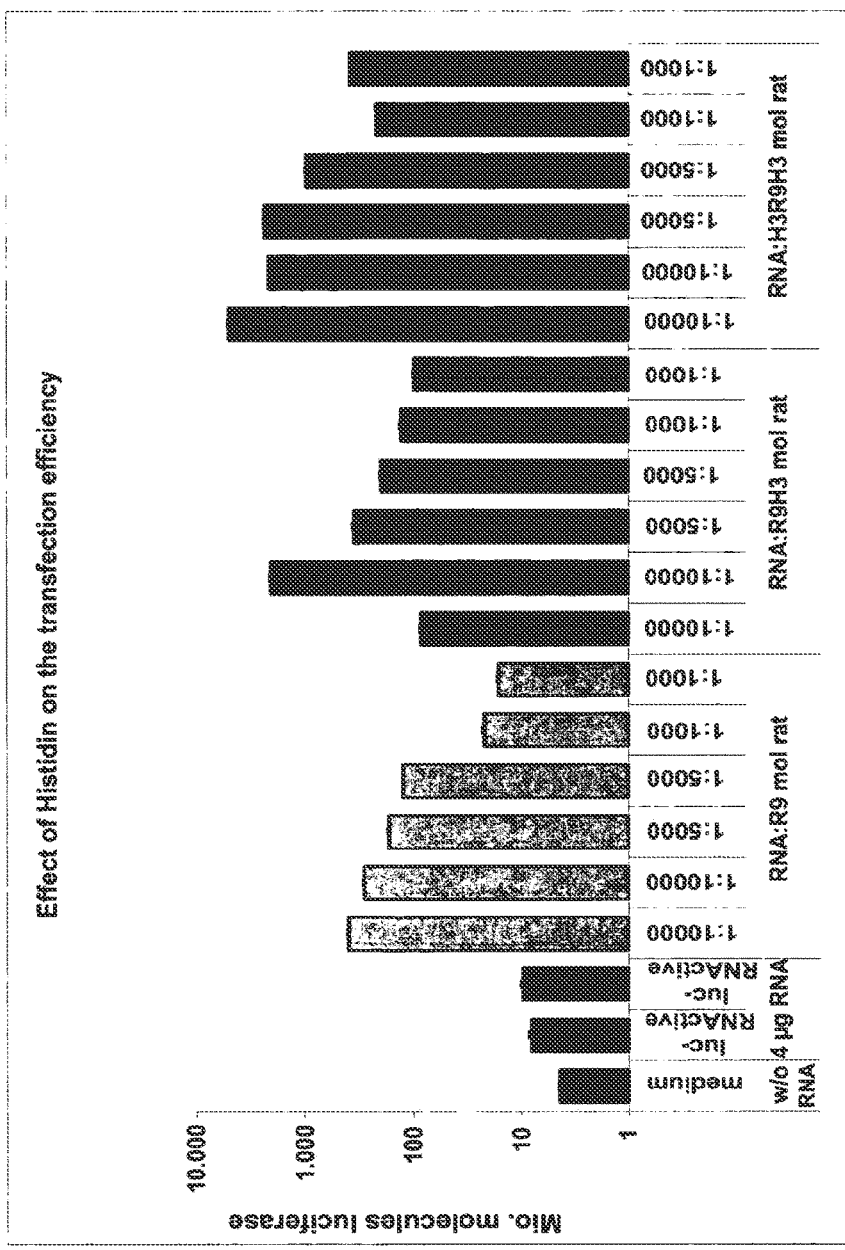

FIG. 19: shows the effect of Histidin in terminal positions on the transfection efficiacy.

Figure 20:
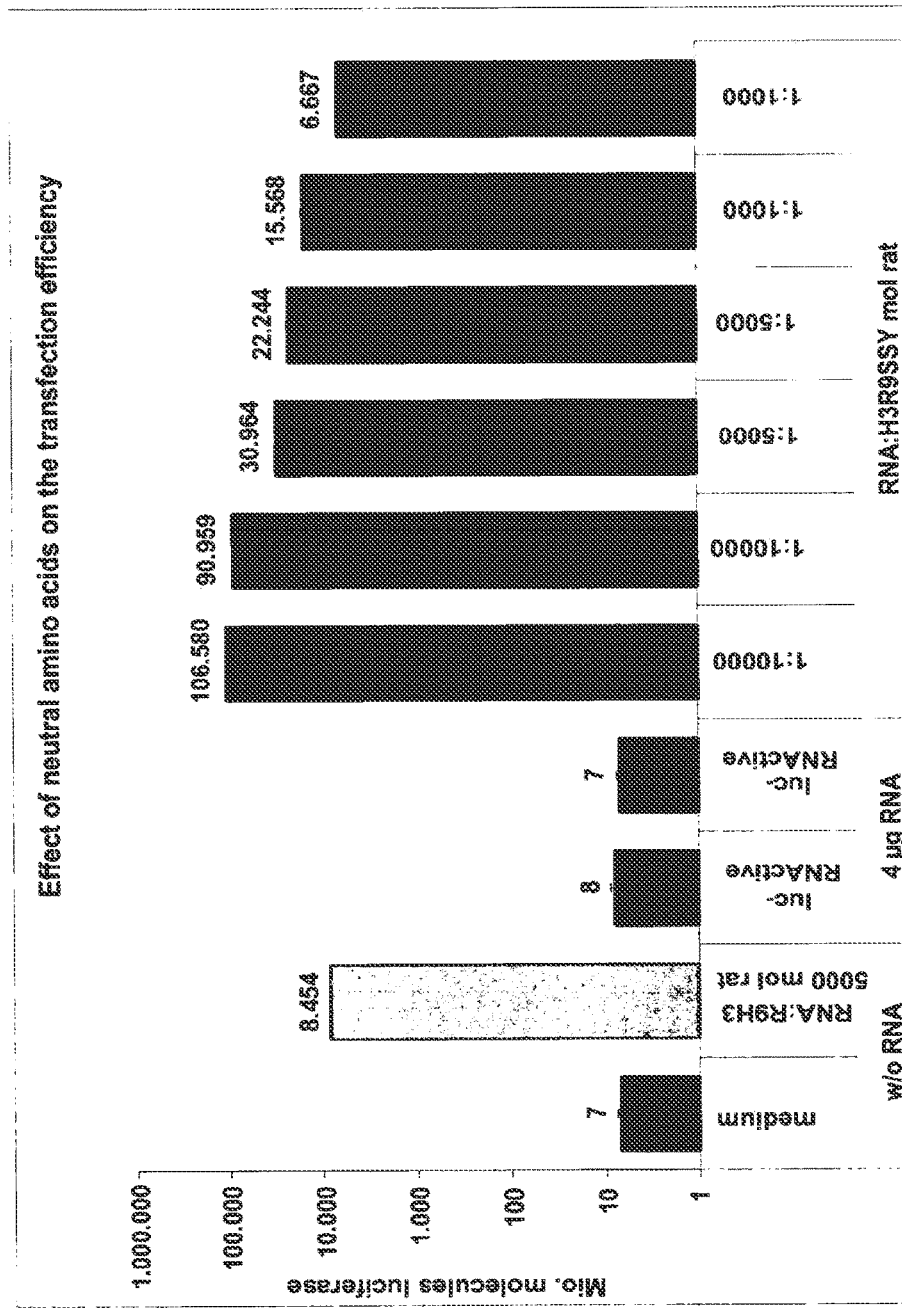

FIG. 20: shows the effect of neutral amino acids in terminal positions on the transfection efficiacy.

Figure 21:
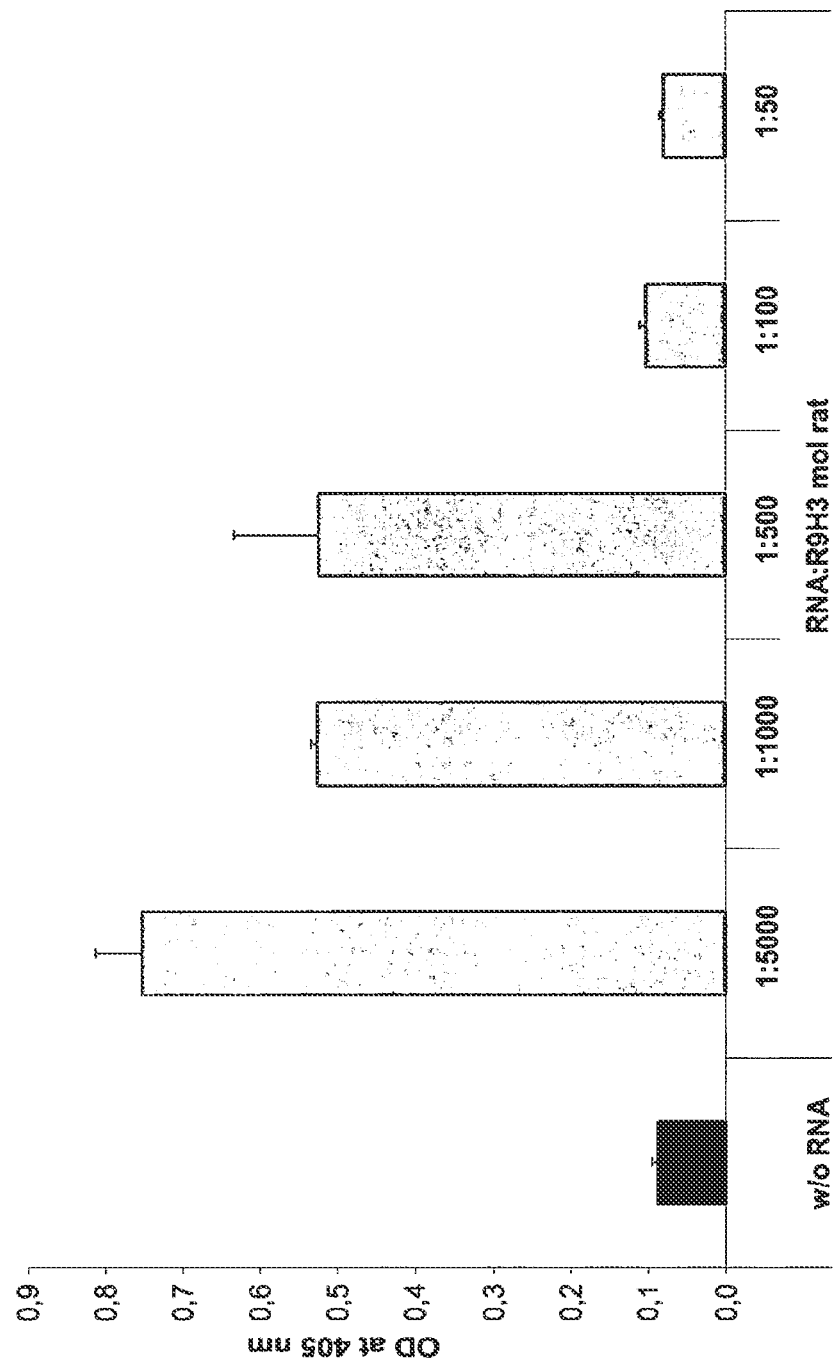

FIG. 21: shows the immunostimulatory effect of RNA complexed with R9H3 on secretion of TNFalpha in hPBMCs.

Figure 22:
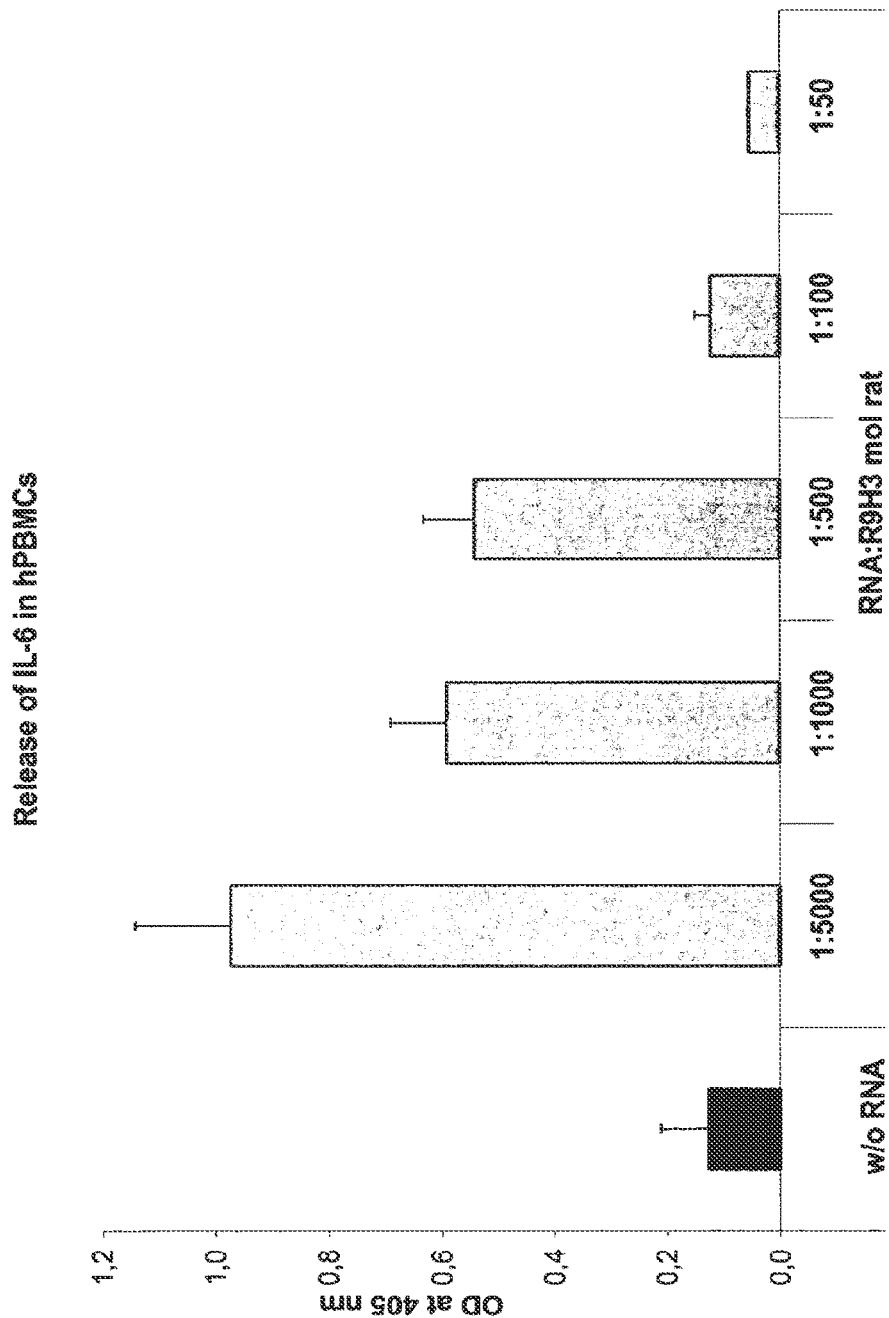

FIG. 22: shows the immunostimulatory effect of RNA complexed with R9H3 on secretion of IL-6 in hPBMCs.

EXAMPLES

The following examples are intended to illustrate the invention further. They are not intended to limit the subject matter of the invention thereto.

Example 1

Preparation of Luciferase mRNA Constructs

In the following experiments a stabilized luciferase mRNA sequence was prepared and used for transfection experiments, wherein the native luciferase encoding mRNA was modified with a poly-A/poly-C-tag (A70-C30) and was GC-optimized for a better codon-usage and further stabilized.

A first construct (construct CAP-Ppluc(wt)-muag-A70-C30, SEQ ID NO: 35) contained following sequence elements:
stabilizing sequences from the alpha-Globin gene
70 (Adenosin at the 3'-terminal end
30 (Cytosin at the 3'-terminal end The final construct (construct CAP-Ppluc(GC)-muag-A70-C30, SEQ ID NO: 36), as used herein for the following experiments, contained following sequence elements:
GC-optimized sequence for a better codon usage
stabilizing sequences from the alpha-Globin gene
70 (Adenosin at the 3'-terminal end
30 (Cytosin at the 3'-terminal end These sequences are also shown in FIGS. 1 and 2 (SEQ ID NOs: 35 and 36). The respective coding sequences are shown in FIGS. 3 and 4 (SEQ ID NOs: 35 and 36)

Example 2

In Vitro Transcription of Stabilized Luciferase mRNA

The stabilized luciferase mRNA according to SEQ ID NO: 35 or 36 (Luc-RNActive) was transcribed in vitro using T7-Polymerase (T7-Opti mRNA Kit, CureVac, Tübingen, Deutschland) following the manufactures instructions.

All mRNA-transkripts contained a 70 bases poly-A-tail and a 5'-Cap-structure. The 5'-Cap-structure was obtained by adding an excess of N7-Methyl-Guanosin-5'-Triphosphat-5'-Guanosin.

Example 3

Forming a Complex of RNA with Nona-Arginine ((Arg)), Poly-L-Arginine or Further Peptides Based on $(Arg)_9$, Respectively 15 µg RNA stabilized luciferase mRNA according to SEQ ID NO: 36 (Luc-RNActive) were mixed in different mass ratios with nona-arginine ($Arg_9$) or poly-L-arginine (Sigma-Aldrich; P4663; 5000-15000 g/mol), thereby forming a complex. Following mass ratios were used as shown exemplarily for (($Arg)_9$). Poly-L-arginine was used for comparative examples following the same instructions.

Additionally, further complexed RNAs based on $(Arg)_9$ were prepared above using the following peptides for complexation:

R9:
(SEQ ID NO: 2)
Arg-Arg-Arg-Arg-Arg-Arg-Arg-Arg-Arg

R9H3:
(SEQ ID NO: 39)
Arg-Arg-Arg-Arg-Arg-Arg-Arg-Arg-Arg-His-His-His

H3R9H3:
(SEQ ID NO: 40)
His-His-His-Arg-Arg-Arg-Arg-Arg-Arg-Arg-Arg-Arg-His-His-His

YSSR9SSY:
(SEQ ID NO: 41)
Tyr-Ser-Ser-Arg-Arg-Arg-Arg-Arg-Arg-Arg-Arg-Arg-Ser-Ser-Tyr

H3R9SSY:
(SEQ ID NO: 42)
His-His-His-Arg-Arg-Arg-Arg-Arg-Arg-Arg-Arg-Arg-Ser-Ser-Tyr (RKH)4:
(SEQ ID NO: 43)
Arg-Lys-His-Arg-Lys-His-Arg-Lys-His-Arg-Lys-His

Y(RKH)2R:
(SEQ ID NO: 44)
Tyr-Arg-Lys-His-Arg-Lys-His-Arg

For complexation, 4 µg stabilized luciferase mRNA according to SEQ ID NO: 36 (Luc-RNActive) were mixed in molar ratios with the respectively peptide (according to formula I), thereby forming a complex. Afterwards the resulting solution was adjusted with water to a final volume of 50 µl und incubated for 30 minutes at room temperature. The used ratios are indicated in the tables given below. HeLa-cells ($150\times10^3$/well) were then seeded 1 day prior to transfection on 24-well microtiter plates leading to a 70% confluence when transfection was carried out.

R9:

| Formulation -> N/P Molar ratio | | R9 Mass ratio | | |
|---|---|---|---|---|
| RNA | R9 | RNA µg | Peptid µg | N/P |
| 1.00 | 10000.00 | 1.00 | 23.72 | 50.00 |
| 1.00 | 5000.00 | 1.00 | 11.86 | 25.00 |
| 1.00 | 2500.00 | 1.00 | 5.93 | 12.50 |
| 1.00 | 1000.00 | 1.00 | 2.37 | 5.00 |

| | RNA | $(Arg)_9$ | $(Arg)_9$ µg | $(Arg)_9$ µg | RNA µl | $(Arg)_9$ µl | $H_2O$ µl | Concentration $(Arg)_9$ [µM] | Ratio $(Arg)_9$/RNA |
|---|---|---|---|---|---|---|---|---|---|
| 1 | Mock | | | | | | 70.0 | 0 | |
| 2 | $(Arg)_9$ alone | | | 150 | | 3 | 67.0 | 151.32 | |
| 3 | RNA alone | | 15 | | 3.8 | | 66.3 | 0.00 | |
| 4 | 1 | 10 | 15 | 150.0 | 3.8 | 3.0 | 63.3 | 151.32 | 10:1 |
| 5 | 1 | 8 | 15 | 120.0 | 3.8 | 2.4 | 63.9 | 121.06 | 8:1 |
| 6 | 1 | 5 | 15 | 75.0 | 3.8 | 1.5 | 64.8 | 75.66 | 5:1 |
| 7 | 1 | 2 | 15 | 30.0 | 3.8 | 0.6 | 65.7 | 30.26 | 2:1 |
| 8 | 1 | 1 | 15 | 15.0 | 3.8 | 15.0 | 51.3 | 15.13 | 1:1 |
| 9 | 2 | 1 | 15 | 7.5 | 3.8 | 7.5 | 58.8 | 7.57 | 1:2 |
| 10 | 5 | 1 | 15 | 3.0 | 3.8 | 3.0 | 63.3 | 3.03 | 1:5 |
| 11 | 8 | 1 | 15 | 1.9 | 3.8 | 1.9 | 64.4 | 1.89 | 1:8 |
| 12 | 10 | 1 | 15 | 1.5 | 3.8 | 1.5 | 64.8 | 1.51 | 1:10 |

-continued

R9:

| Formulation -> N/P Molar ratio | | R9 Mass ratio | | |
|---|---|---|---|---|
| RNA | R9 | RNA µg | Peptid µg | N/P |
| 1.00 | 500.00 | 1.00 | 1.19 | 2.50 |
| 1.00 | 100.00 | 1.00 | 0.24 | 0.50 |
| 1.00 | 10.00 | 1.00 | 0.02 | 0.05 |

R9H3:

| Formulation -> N/P Molar ratio | | R9H3 Mass ratio | | |
|---|---|---|---|---|
| RNA | R9H3 | RNA µg | Peptid µg | N/P |
| 1.00 | 10000.00 | 1.00 | 30.58 | 50.00 |
| 1.00 | 5000.00 | 1.00 | 15.29 | 25.00 |
| 1.00 | 2500.00 | 1.00 | 7.65 | 12.50 |
| 1.00 | 1000.00 | 1.00 | 3.06 | 5.00 |
| 1.00 | 500.00 | 1.00 | 1.53 | 2.50 |
| 1.00 | 100.00 | 1.00 | 0.31 | 0.50 |
| 1.00 | 10.00 | 1.00 | 0.03 | 0.05 |

H3R9H3:

| Formulation -> N/P Molar ratio | | H3R9H3 Mass ratio | | |
|---|---|---|---|---|
| RNA | H3R9H3 | RNA µg | Peptid µg | N/P |
| 1.00 | 10000.00 | 1.00 | 37.43 | 50.00 |
| 1.00 | 5000.00 | 1.00 | 18.72 | 25.00 |
| 1.00 | 2500.00 | 1.00 | 9.36 | 12.50 |
| 1.00 | 1000.00 | 1.00 | 3.74 | 5.00 |
| 1.00 | 500.00 | 1.00 | 1.87 | 2.50 |
| 1.00 | 100.00 | 1.00 | 0.37 | 0.50 |
| 1.00 | 10.00 | 1.00 | 0.04 | 0.05 |

YSSR9SSY:

| Formulation -> N/P Molar ratio | | YSSR9SSY Mass ratio | | |
|---|---|---|---|---|
| RNA | YSSR9SSY | RNA µg | Peptid µg | N/P |
| 1.00 | 10000.00 | 1.00 | 34.95 | 50.00 |
| 1.00 | 5000.00 | 1.00 | 17.48 | 25.00 |
| 1.00 | 2500.00 | 1.00 | 8.74 | 12.50 |
| 1.00 | 1000.00 | 1.00 | 3.50 | 5.00 |
| 1.00 | 500.00 | 1.00 | 1.75 | 2.50 |
| 1.00 | 100.00 | 1.00 | 0.35 | 0.50 |
| 1.00 | 10.00 | 1.00 | 0.03 | 0.05 |

H3R9SSY:

| Formulation -> N/P Molar ratio | | H3R9SSY Mass ratio | | |
|---|---|---|---|---|
| RNA | H3R9SSY | RNA µg | Peptid µg | N/P |
| 1.00 | 10000.00 | 1.00 | 36.18 | 50.00 |
| 1.00 | 5000.00 | 1.00 | 18.09 | 25.00 |
| 1.00 | 2500.00 | 1.00 | 9.05 | 12.50 |
| 1.00 | 1000.00 | 1.00 | 3.62 | 5.00 |
| 1.00 | 500.00 | 1.00 | 1.81 | 2.50 |
| 1.00 | 100.00 | 1.00 | 0.36 | 0.50 |
| 1.00 | 10.00 | 1.00 | 0.04 | 0.05 |

(RKH)4:

| Formulation -> N/P Molar ratio | | (RKH)4 Mass ratio | | |
|---|---|---|---|---|
| RNA | (RKH)4 | RNA µg | Peptid µg | N/P |
| 1.00 | 10000.00 | 1.00 | 28.38 | 44.44 |
| 1.00 | 5000.00 | 1.00 | 14.19 | 22.22 |
| 1.00 | 2500.00 | 1.00 | 7.10 | 11.11 |
| 1.00 | 1000.00 | 1.00 | 2.84 | 4.44 |
| 1.00 | 500.00 | 1.00 | 1.42 | 2.22 |
| 1.00 | 100.00 | 1.00 | 0.28 | 0.44 |
| 1.00 | 10.00 | 1.00 | 0.03 | 0.04 |

Y(RKH)2R:

| Formulation -> N/P Molar ratio | | YSSR9SSY Mass ratio | | |
|---|---|---|---|---|
| RNA | Y(RKH)2R | RNA µg | Peptid µg | N/P |
| 1.00 | 10000.00 | 1.00 | 19.67 | 27.78 |
| 1.00 | 5000.00 | 1.00 | 9.83 | 13.89 |
| 1.00 | 2500.00 | 1.00 | 4.92 | 6.94 |
| 1.00 | 1000.00 | 1.00 | 1.97 | 2.78 |
| 1.00 | 500.00 | 1.00 | 0.98 | 1.39 |
| 1.00 | 100.00 | 1.00 | 0.20 | 0.28 |
| 1.00 | 10.00 | 1.00 | 0.02 | 0.03 |

Example 4

Nona-arginine((Arg))-mediated Transfection and Expression of Stabilized Luciferase mRNA According to SEQ Id No: 35 or 36 (Luc-RNActive) in HeLa-Cells Hela-cells ($150 \times 10^3$/well) were seeded 1 day prior to transfection on 24-well microtiter plates leading to a 70% confluence when transfection was carried out. For transfection (40 µl) 50 µl of the RNA/(peptide)-solution as disclosed in Example 3 were mixed with 250 µl serum free medium and added to the cells (final RNA concentration: 13 µg/ml). Prior to addition of the transfection solution the HeLa-cells were washed gently and carefully 2 times with 1 ml Optimen (Invitrogen) per well. Then, the transfection solution (300 µl per well) was added to the cells and the cells were incubated for 4 h at 37° C. Subsequently 300 µl RPMI-medium (Camprex) containing 10% FCS was added per well and the cells were incubated for additional 20 h at 37° C. The transfection solution was sucked off 24 h after transfection and the cells were lysed in 300 µl lysis buffer (25 mM Tris-$PO_4$, 2 mM EDTA, 10% glycerol, 1% Triton-X 100, 2 mM DTT). The supernatants were then mixed with luciferin buffer (25 mM Glycylglycin, 15 mM $MgSO_4$, 5 mM ATP, 62.5 µM luciferin) and luminiscence was detected using a luminometer (Lumat LB 9507 (Berthold Technologies, Bad Wildbad, Germany)). The results of these experiments are shown in FIGS. 8 and 12 to 18.

Example 5

Immune Stimulation Upon Transfection of Complexes of RNA with Nona-Arginine ((Arg)9) or Poly-L-arginine (Comparative Example)

a) Transfection Experiments

HPBMC cells from peripheral blood of healthy donors were isolated using a Ficoll gradient and washed subsequently with 1×PBS (phosphate-buffered saline). The cells were then seeded on 96-well microtiter plates (200×103/well). The hPBMC cells were incubated for 24 h, as described under Example 4, supra, with 10 µl of the RNA/peptide complex (RNA final concentration: 6 µg/ml; the same amounts of RNA were used) in X-VIVO 15 Medium (BioWhittaker) (final RNA Concentration: 10 µg/ml). The immunostimulatory effect upon the hPBMC cells was measured by detecting the cytokine production (Interleukin-6 and Tumor necrose factor alpha). Therefore, ELISA microtiter plates (Nunc Maxisorb) were incubated over night (o/n) with binding buffer (0.02% NaN3, 15 mM Na2CO3, 15 mM NaHCO3, pH 9.7), additionally containing a specific cytokine antibody. Cells were then blocked with 1×PBS, containing 1% BSA (bovine serum albumin). The cell supernatant was added and incubated for 4 h at 37° C. Subsequently, the microtiter plate was washed with 1×PBS, 0.05% TWEEN®-20 surfactant and then incubated with a Biotin-labelled secondary antibody (BD Pharmingen, Heidelberg, Germany). Streptavidin-coupled horseraddish peroxidase was added to the plate. Then, the plate was again washed with 1×PBS, containing 0.05% TWEEN®-20 surfactant, and ABTS (2,2'-azino-bis(3-ethylbenzthiazoline-6-sulfonic acid) was added as a substrate. The amount of cytokine was determined by measuring the absorption at 405 nm (OD405) using a standard curve with recombinant Cytokines (BD Pharmingen, Heidelberg, Germany) with the Sunrise ELISA-Reader from Tecan (Crailsheim, Germany).

b) Results i) Immunostimulatory Effect of RNA Complexed with Nona-Arginine ($(Arg)_2$)

i1) HPBMC cells were incubated with RNA complexed with nona-arginine ($(Arg)_9$) for 24 h as disclosed above, wherein the mass ratio of RNA:$(Arg)_9$ was 1:1. Then, IL-6 production was measured in the cell supernatants using ELISA. As a result, HPBMC cells showed a significant IL-6 production, i.e. a significant immunostimulatory effect of RNA complexed with nona-arginine ($(Arg)_9$) (see FIG. 5).

i2) HPBMC cells were incubated with RNA complexed with nona-arginine ($(Arg)_9$) for 24 h as disclosed above, wherein the mass ratio of RNA:$(Arg)_9$ was 1:1. Then, THF-alpha production was measured in the cell supernatants using ELISA. As a result, HPBMC cells showed a significant TNF-alpha production, i.e. a significant immunostimulatory effect of RNA complexed with nona-arginine ($(Arg)_9$) (see FIG. 6).

ii) Comparison of Immunostimulatory Effect of RNA Complexed with Either Nona-Arginine ((Arg)) or Poly-L-Arginine, Respectively (Comparative Example)

hPBMCs were incubated in different mass ratios (RNA: nona-arginine 1:10; 1:8; 1:5; 1:2; 1:1; 2:1, 5:1; 8:1 and 10:1) with a complex of RNA and nona-arginine ($(Arg)_9$) or poly-L-arginine, etc., respectively, for 24 h. Subsequently TNF-alpha production was measured using ELISA.

Advantageously, a significant immunostimulatory effect can be observed for mass ratios lower than 5:1 (RNA: nona-arginine) (1:10; 1:8; 1:5; 1:2; 1:1; 2:1) (see FIG. 7). When using mass ratios of RNA:nona-arginine (5:1) no significant TNFalpha production can be observed. The same applies to stimulation experiments, using nona-arginine ($(Arg)_9$) or mRNA alone (see FIG. 7, left).

Furthermore, complexation of mRNA with poly-L-arginine leads to significantly lower induction of TNF-alpha production in comparison to nona-arginine ($(Arg)_9$) (see FIG. 7, right). Additionally, it was observed that higher concentrations of poly-L-arginine appear to be toxic for cells transfected therewith, particularly when using a mass ratio of 1:2 RNA:poly-L-arginine or lower, since the cells were lysed.

Example 6

Luciferase Expression Upon Transfection of Complexes of RNA with Nona-arginine ($(Arg)_9$) or Poly-L-Arginine, Respectively, in HeLa Cells (Comparative Example)

a) Luciferase expression upon transfection of complexes of RNA with nona-arginine ($(Arg)_9$) in HeLa cells. HeLa-Cells were transfected with RNActive encoding luciferase, which has been complexed with different ratios of nona-arginine or Poly-L-Arginine, respectively. 24 h later luciferase-activity was measured. Apparently, a mass ration of less than 2:1 (RNA:nona-arginine) appears to be advantageous (see FIG. 8).

b) In comparison, complexation with (high molecular mass) poly-L-arginine does not increase luciferase-activity at a significant level. Thus, (high molecular mass) poly-L-arginine does not appear to be suitable for transfection of mRNA (see FIG. 8).

Example 7

Luciferase Expression Upon Transfection of Complexes of RNA with Hepta-arginine ($(Arg)_Z$) in HeLa Cells (Comparative Example)

HeLa-Cells were transfected with RNActive encoding luciferase, which has been complexed with different ratios of hepta-arginine ($(Arg)_7$). 24 h later luciferase-activity was measured. Apparently, complexation with hepta-arginine ($(Arg)_7$) does not increase luciferase-activity at a significant level. Thus, hepta-arginine ($(Arg)_7$) does not appear to be suitable for transfection of mRNA (see FIG. 9).

Example 8

Immune Stimulation Upon Transfection of Complexes of RNA with Hepta-arginine ($(Arg)_Z$) (Comparative Example)

a) Transfection Experiments

Transfection Experiments were carried out for hepta-arginine ($(Arg)_7$) analogously to the experiments in Example 5 as shown above.

b) Results of Immunostimulatory Effect of RNA Complexed with Hepta-arginine ($(Arg)_7$))

i) HPBMC cells were incubated with RNA complexed with hepta-arginine ($(Arg)_7$) for 24 h as disclosed above, wherein the mass ratio of RNA:$(Arg)_7$ was 1:1. Then, IL-6 production was measured in the cell supernatants using ELISA. As a result, HPBMC cells showed a significant IL-6 production, i.e. a significant immunostimulatory effect of RNA complexed with hepta-arginine ($(Arg)_7$) (see FIG. 10).

ii) HPBMC cells were furthermore incubated with RNA complexed with hepta-arginine ($(Arg)_7$) for 24 h as disclosed above, wherein the mass ratio of RNA:$(Arg)_7$ was 1:1. Then, THF-alpha production was measured in the cell supernatants using ELISA. As a result, HPBMC cells also showed a significant TNF-alpha production, i.e. a significant immunostimulatory effect of RNA complexed with hepta-arginine ($(Arg)_7$) (see FIG. 11).

Example 9

Determination of the Effect of Histidin on the Transfection Efficiency

To determine the effect of Histidin on the transfection efficiency a transfection was carried out analogously to the transfection experiments above using peptides with different Histidine content. Therefore, 4 µg stabilized luciferase mRNA according to SEQ ID NO: 36 (Luc-RNActive) were mixed in molar ratios with the respectively peptide (according to formula I), particularly R9, R9H3 or H3R9H3, thereby forming a complex. Afterwards the resulting solution was adjusted with water to a final volume of 50 µl und incubated for 30 minutes at room temperature. The used ratios are in each experiment 1:10000, 1:5000 and 1:1000. HeLa-cells (150×10$^3$/well) were then seeded 1 day prior to transfection on 24-well microtiter plates leading to a 70% confluence when transfection was carried out. For transfection 50 µl of the RNA/(peptide)-solution were mixed with 250 µl serum free medium and added to the cells (final RNA concentration: 13 µg/ml). Prior to addition of the transfection solution the HeLa-cells were washed gently and carefully 2 times with 1 ml Optimen (Invitrogen) per well. Then, the transfection solution (300 µl per well) was added to the cells and the cells were incubated for 4 h at 37° C. Subsequently 300 µl RPMI-medium (Camprex) containing 10% FCS was added per well and the cells were incubated for additional 20 h at 37° C. The transfection solution was sucked off 24 h after transfection and the cells were lysed in 300 µl lysis buffer (25 mM Tris-PO$_4$, 2 mM EDTA, 10% glycerol, 1% Triton-X 100, 2 mM DTT). The supernatants were then mixed with luciferin buffer (25 mM Glycylglycin, 15 mM MgSO$_4$, 5 mM ATP, 62.5 µM luciferin) and luminiscence was detected using a luminometer (Lumat LB 9507 (Berthold Technologies, Bad Wildbad, Germany)).

The results are shown in FIG. 19. As can be seen, a stetch of 3 histidines at one terminal end already increases the transfection efficiacy of the complexed RNA, wherein a stetch of 3 histidines at both terminal ends significantly increases the transfection efficiacy of the complexed RNA.

Example 10

Determination of the Effect of Neutral Amino Acids on the Transfection Efficiency To determine the effect of neutral amino acids on the transfection efficiency a further transfection experiment was carried out analogously to the transfection experiments above in Example 9 using the peptide H3R9CCS. The results of this additional experiment are shown in FIG. 20.

Example 11

Immunostimulation Using R9H3 in hPBMCs

The effect of R9H3 on immunostimulation was tested in hPBMCs. Therefore, a complex of R9H3 and RNA as shown above in Example 3 was prepared. Furthermore, HPBMC cells from peripheral blood of healthy donors were isolated using a Ficoll gradient and washed subsequently with 1×PBS (phosphate-buffered saline). The cells were then seeded on 96-well microtiter plates (200×10$^3$/well). The hPBMC cells were incubated for 24 h, as described under Example 4, supra, with 10 µl of the RNA/peptide complex (RNA final concentration: 6 µg/ml; the same amounts of RNA were used) in X-VIVO 15 Medium (BioWhittaker). The immunostimulatory effect upon the hPBMC cells was measured by detecting the cytokine production (Interleukin-6 and Tumor necrose factor alpha). Therefore, ELISA microliter plates (Nunc Maxisorb) were incubated over night (o/n) with binding buffer (0.02% NaN3, 15 mM Na2CO3, 15 mM NaHCO3, pH 9.7), additionally containing a specific cytokine antibody. Cells were then blocked with 1×PBS, containing 1% BSA (bovine serum albumin). The cell supernatant was added and incubated for 4 h at 37° C. Subsequently, the microtiter plate was washed with 1×PBS, 0.05% TWEEN®-20 surfactant and then incubated with a Biotin-labelled secondary antibody (BD Pharmingen, Heidelberg, Germany). Streptavidin-coupled horseraddish peroxidase was added to the plate. Then, the plate was again washed with 1×PBS, containing 0.05% TWEEN®-20 surfactant, and ABTS (2,2'-azinobis(3-ethyl-benzthiazoline-6-sulfonic acid) was added as a substrate. The amount of cytokine was determined by measuring the absorption at 405 nm (OD405) using a standard curve with recombinant Cytokines (BD Pharmingen, Heidelberg, Germany) with the Sunrise ELISA-Reader from Tecan (Crailsheim, Germany). The results are seen in FIGS. 21 and 22. As can be seen, a significant immunostimulation was exhibited at a ratio of 1:5000 RNA:R9H3.

---

The invention claimed is:

1. A method of inducing or enhancing an innate immune response in a subject in need thereof, comprising administering to the subject a complexed ribonucleic acid (RNA) comprising at least one RNA molecule complexed with one or more oligopeptides, wherein the at least one RNA molecule is not covalently bound to the one or more oligopeptides, wherein the nitrogen/phosphate ratio (N/P-ratio) of the RNA to the one or more oligopeptides is in the range of 0.75-25, and wherein the oligopeptide is 8 to 15 amino acids in length and comprises the following formula:

$$(Arg)_l;(Lys)_m;(His)_n;(Orn)_o;(Xaa)_x \quad \text{(formula I)}$$

wherein
l+m+n+o+x=8-15, and
l, m, n or o independently of each other is any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and
Xaa is any amino acid selected from native or non-native amino acids except Arg, Lys, His or Orn; and
x is any number selected from 0, 1, 2, 3, 4, 5, 6, 7, or 8, provided, that the overall content of Xaa does not exceed 50% of all amino acids of the oligopeptide.

2. The method according to claim 1, wherein the at least one RNA molecule is a messenger RNA (mRNA).

3. The method according to claim 1, wherein the oligopeptide is 8 to 14 amino acids in length.

4. The method according to claim 1, wherein the overall content of Arg, Lys, His and Orn represents at least 60% of all amino acids of the oligopeptide of the complexed RNA.

5. The method according to claim 1, wherein Xaa in the formula $(Arg)_l;(Lys)_m;(His)_n;(Orn)_o;(Xaa)_x$ is selected from amino acids having a neutral side chain and amino acids having a neutral polar side chain.

6. The method according to claim 1, wherein the oligopeptide according to the formula $(Arg)_l; (Lys)_m; (His)_n; (Orn)_o;(Xaa)_x$ does not comprise amino acids having an acidic side chain at one or both terminal ends.

7. The method according to claim 1, wherein the oligopeptide according to the formula $(Arg)_l;(Lys)_m;(His)_n; (Orn)_o;(Xaa)_x$ comprises neutral or basic amino acids at one or both terminal ends.

8. The method according to claim 1, wherein the oligopeptide according to the formula $(Arg)_l;(Lys)_m;(His)_n; (Orn)_o;(Xaa)_x$ comprises a stretch of at least 3 contiguous basic amino acids within its sequence.

9. The method according to claim 1, wherein the oligopeptide according to the formula $(Arg)_l;(Lys)_m;(His)_n; (Orn)_o;(Xaa)_x$ comprises at least 1 non-cationic amino acid(s) at one or both terminal ends.

10. The method according to claim 2, wherein the mRNA codes for a therapeutically active protein or peptide, an immunostimulating protein or peptide, a tumor antigen, or an antibody.

11. The method according to claim 10, wherein the mRNA encodes an immunostimulating protein.

12. The method according to claim 1, wherein the RNA is a modified RNA with increased stability, compared to the RNA without modification.

13. The method according to claim 12, wherein the G/C content of the coding region of the modified RNA is increased compared with the G/C content of the coding region of the RNA without modification.

14. The method according to claim 1, wherein the mass ratio of the at least one RNA molecule of the complexed RNA to the one or more oligopeptides is in a range of 1:100 to 1:0.5.

15. The method according to claim 1, wherein the molar ratio of the at least one RNA molecule of the complexed RNA to the one or more oligopeptides is in a range of 1:20000 to 1:250.

16. The method according to claim 1, wherein the oligopeptide comprises an oligopeptide selected from the group consisting of:

Arg$_9$His$_3$ (SEQ ID NO: 39), His$_3$Arg$_9$His$_3$ (SEQ ID NO: 40), TyrSerSerArg$_9$SerSerTyr (SEQ ID NO: 41), His$_3$Arg$_9$SerSerTyr (SEQ ID NO: 42), (ArgLysHis)$_4$ (SEQ ID NO: 43) Tyr(ArgLysHis)$_2$Arg (SEQ ID NO: 44);

Arg$_8$ (SEQ ID NO: 1), Arg$_9$ (SEQ ID NO: 2), Arg$_{10}$ (SEQ ID NO: 3), Arg$_{11}$ (SEQ ID NO: 4), Arg$_{12}$ (SEQ ID NO: 5), Arg$_{13}$ (SEQ ID NO: 6), Arg$_{14}$ (SEQ ID NO: 7), Arg$_{15}$ (SEQ ID NO: 8);

Lys$_8$ (SEQ ID NO: 9), Lys$_9$ (SEQ ID NO: 10), Lys$_{10}$ (SEQ ID NO: 11), Lys$_{11}$ (SEQ ID NO: 12), Lys$_{12}$ (SEQ ID NO: 13), Lys$_{13}$ (SEQ ID NO: 14), Lys$_{14}$ (SEQ ID NO: 15), Lys$_{15}$ (SEQ ID NO: 16);

His$_8$ (SEQ ID NO: 17), His$_9$ (SEQ ID NO: 18), His$_{10}$ (SEQ ID NO: 19), His$_{11}$ (SEQ ID NO: 20), His$_{12}$ (SEQ ID NO: 21), His$_{13}$ (SEQ ID NO: 22), His$_{14}$ (SEQ ID NO: 23), His$_{15}$ (SEQ ID NO: 24); and Orn$_8$ (SEQ ID NO: 25), Orn$_9$ (SEQ ID NO: 26), Orn$_{10}$ (SEQ ID NO: 27), Orn$_{11}$ (SEQ ID NO: 28), Orn$_{12}$ (SEQ ID NO: 29), Orn$_{13}$ (SEQ ID NO: 30), Orn$_{14}$ (SEQ ID NO: 31), Orn$_{15}$ (SEQ ID NO: 32).

17. The method according to claim 1, wherein the subject is a mammal selected from the group consisting of humans, goat, cattle, swine, dog, cat, donkey, monkey, ape and rodents.

18. The method according to claim 1, wherein the subject has a disease selected from a tumour or cancer disease, a cardiovascular disease, an infectious disease, an autoimmune disease, a genetic disease, or an allergy.

19. The method according to claim 1, wherein the complexed RNA further induces or enhances an immune response to an antigen.

20. The method according to claim 19, wherein the antigen is a tumour antigen, an autoimmune antigen, an allergy antigen, or an infectious disease antigen.

21. The method according to claim 1, wherein the at least one RNA is a coding RNA.

22. The method according to claim 1, wherein the at least one RNA is single stranded.

23. The method according to claim 1, wherein the at least one RNA is double stranded.

24. The method according to claim 1, wherein the at least one RNA is an immunostimulatory RNA (isRNA).

25. The method according to claim 1, wherein the innate immune response comprises stimulation of at least one of toll-like receptor (TLR) 3, TLR7, TLR8, RIG-1, and Melanoma Differentiation-Associated protein 5 (MDA-5).

* * * * *

SEQUENCE LISTING

```
<160> NUMBER OF SEQ ID NOS: 401

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 1

Arg Arg Arg Arg Arg Arg Arg Arg
1               5
```

```
<210> SEQ ID NO 2
<211> LENGTH: 9
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 2

Arg Arg Arg Arg Arg Arg Arg Arg Arg
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 3

Arg Arg Arg Arg Arg Arg Arg Arg Arg Arg
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 4

Arg Arg Arg Arg Arg Arg Arg Arg Arg Arg Arg
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 5

Arg Arg Arg Arg Arg Arg Arg Arg Arg Arg Arg Arg
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 6

Arg Arg Arg Arg Arg Arg Arg Arg Arg Arg Arg Arg Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic peptide - Exemplary oligopeptide
      according to formula I
```

```
<400> SEQUENCE: 7

Arg Arg Arg Arg Arg Arg Arg Arg Arg Arg Arg Arg Arg
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 8

Arg Arg Arg Arg Arg Arg Arg Arg Arg Arg Arg Arg Arg Arg Arg
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 9

Lys Lys Lys Lys Lys Lys Lys Lys
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 10

Lys Lys Lys Lys Lys Lys Lys Lys Lys
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 11

Lys Lys Lys Lys Lys Lys Lys Lys Lys Lys
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 12

Lys Lys Lys Lys Lys Lys Lys Lys Lys Lys Lys
1               5                   10

<210> SEQ ID NO 13
<211> LENGTH: 12
<212> TYPE: PRT
```

<213> ORGANISM: Artificial Sequence
<220> FEATURE:
<223> OTHER INFORMATION: Synthetic peptide - Exemplary oligopeptide
      according to formula I

<400> SEQUENCE: 13

Lys Lys Lys Lys Lys Lys Lys Lys Lys Lys Lys Lys
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 14

Lys Lys Lys Lys Lys Lys Lys Lys Lys Lys Lys Lys Lys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 15

Lys Lys Lys Lys Lys Lys Lys Lys Lys Lys Lys Lys Lys Lys
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 16

Lys Lys Lys Lys Lys Lys Lys Lys Lys Lys Lys Lys Lys Lys Lys
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 17

His His His His His His His His
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 18

His His His His His His His His His
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 19

His His His His His His His His His His
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 20

His His His His His His His His His His His
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 21

His His His His His His His His His His His His
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 22

His His His His His His His His His His His His His
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 23

His His His His His His His His His His His His His His
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide - Exemplary oligopeptide
      according to formula I

<400> SEQUENCE: 24

His His His His His His His His His His His His His His His
1               5                   10                  15

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide - Exemplary oligopeptide
      according to formula I
<220> FEATURE:
<221> NAME/KEY: misc_feature
<222> LOCATION: (1)..(8)
<223> OTHER INFORMATION: Xaa is Ornithine

<400> SEQUENCE: 25

Xaa Xaa Xaa Xaa Xaa Xaa Xaa Xaa
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide - Exemplary oligopeptide
      according to formula I
<220> FEATURE:
<221> NAME/KEY: misc_feature
<222> LOCATION: (1)..(9)
<223> OTHER INFORMATION: Xaa is Ornithine

<400> SEQUENCE: 26

Xaa Xaa Xaa Xaa Xaa Xaa Xaa Xaa Xaa
1               5

<210> SEQ ID NO 27
<211> LENGTH: 10
<212> TYPE: PRT
<213> ORGANISM: Artificial Sequence
<220> FEATURE:
<223> OTHER INFORMATION: Synthetic peptide - Exemplary oligopeptide
      according to formula I
<220> FEATURE:
<221> NAME/KEY: misc_feature
<222> LOCATION: (1)..(10)
<223> OTHER INFORMATION: Xaa is Ornithine

<400> SEQUENCE: 27

Xaa Xaa Xaa Xaa Xaa Xaa Xaa Xaa Xaa Xaa
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic peptide - Exemplary oligopeptide
      according to formula I
<220> FEATURE:
<221> NAME/KEY: misc_feature
<222> LOCATION: (1)..(11)
<223> OTHER INFORMATION: Xaa is Ornithine

<400> SEQUENCE: 28

Xaa Xaa Xaa Xaa Xaa Xaa Xaa Xaa Xaa Xaa Xaa
1               5                   10

```
<210> SEQ ID NO 29
<211> LENGTH: 12
<212> TYPE: PRT
<213> ORGANISM: Artificial Sequence
<220> FEATURE:
<223> OTHER INFORMATION: Synthetic peptide - Exemplary oligopeptide
      according to formula I
<220> FEATURE:
<221> NAME/KEY: misc_feature
<222> LOCATION: (1)..(12)
<223> OTHER INFORMATION: Xaa is Ornithine

<400> SEQUENCE: 29

Xaa Xaa Xaa Xaa Xaa Xaa Xaa Xaa Xaa Xaa Xaa Xaa
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic peptide - Exemplary oligopeptide
      according to formula I
<220> FEATURE:
<221> NAME/KEY: misc_feature
<222> LOCATION: (1)..(13)
<223> OTHER INFORMATION: Xaa is ornithine

<400> SEQUENCE: 30

Xaa Xaa Xaa Xaa Xaa Xaa Xaa Xaa Xaa Xaa Xaa Xaa Xaa
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic peptide - Exemplary oligopeptide
      according to formula I
<220> FEATURE:
<221> NAME/KEY: misc_feature
<222> LOCATION: (1)..(14)
<223> OTHER INFORMATION: Xaa is ornithine

<400> SEQUENCE: 31

Xaa Xaa Xaa Xaa Xaa Xaa Xaa Xaa Xaa Xaa Xaa Xaa Xaa Xaa
1               5                   10

<210> SEQ ID NO 32
<211> LENGTH: 15
<212> TYPE: PRT
<213> ORGANISM: Artificial Sequence
<220> FEATURE:
<223> OTHER INFORMATION: Synthetic peptide - Exemplary oligopeptide
      according to formula I
<220> FEATURE:
<221> NAME/KEY: misc_feature
<222> LOCATION: (1)..(15)
<223> OTHER INFORMATION: Xaa is ornithine

<400> SEQUENCE: 32

Xaa Xaa Xaa Xaa Xaa Xaa Xaa Xaa Xaa Xaa Xaa Xaa Xaa Xaa Xaa
1               5                   10                  15

<210> SEQ ID NO 33
<211> LENGTH: 13
<212> TYPE: RNA
<213> ORGANISM: Artificial Sequence
<220> FEATURE:
<223> OTHER INFORMATION: Synthetic oligoribonucleotide - Kozak-Sequence
```

```
<400> SEQUENCE: 33
gccgccacca ugg                                                              13

<210> SEQ ID NO 34
<211> LENGTH: 22
<212> TYPE: RNA
<213> ORGANISM: Artificial Sequence
<220> FEATURE:
<223> OTHER INFORMATION: synthetic stabilizing sequence
<220> FEATURE:
<221> NAME/KEY: misc_feature
<222> LOCATION: (5)..(9)
<223> OTHER INFORMATION: N is A, U, C, or G and is either present or
      absent.
<220> FEATURE:
<221> NAME/KEY: misc_feature
<222> LOCATION: (14)..(17)
<223> OTHER INFORMATION: Y is either present or absent.

<400> SEQUENCE: 34
yccannnnnc cwyyyyucy cc                                                     22

<210> SEQ ID NO 35
<211> LENGTH: 1882
<212> TYPE: RNA
<213> ORGANISM: Artificial Sequence
<220> FEATURE:
<223> OTHER INFORMATION: Synthetic oligoribonucleotide - construct
      CAP-Ppluc(wt)-muag-A70-C30

<400> SEQUENCE: 35
gggagaaagc uuggcauucc gguacuguug guaaagccac cauggaagac gccaaaaaca           60 uaagaaagg  cccggcgcca uucuauccgc uggaagaugg aaccgcugga gagcaacugc          120
auaaggcuau gaagagauac gcccugguuc cuggaacaau gcuuuuaca gaugcacaua           180 ucgaggugga caucacuuac gcugaguacu cgaaauguc cguucgguug gcagaagcua           240
ugaaacgaua ugggcugaau acaaaucaca gaaucgucgu augcagugaa acucucuuc           300 aauucuuuau gccggugu ggcgcguuau uuaucggagu ugcaguugcg cccgcgaacg           360
acauuuauaa ugaacugaa uugcucaaca guaugggcau uucgcagccu accgugugu           420 ucguuuccaa aaagggguug caaaaaauuu ugaacgugca aaaaaagcuc ccaaucaucc          480
aaaaaauuau uaucauggau ucuaaaacgg auuaccaggg auuucagucg auguacacgu          540
ucgucacauc ucaucuaccu cccgguuuua ugaauacga uuuugugcca gagccuucg           600 auagggacaa gacaauugca cugaucauga acuccucugg aucuacuggu cugccuaag          660 gugucgcucu gccucauaga acugccugcg ugagauucuc gcaugccaga gauccuauuu          720
uuggcaauca aaucauuccg gauacugcga uuuuaagugu uguuccauuc caucacgguu          780
uuggaauguu uacuacacuc ggauauuuga uauggauu cgagcgucu uuaauguaua           840 gauuugaaga agagcuguuu cugaggagcc uucaggauua caagauucaa agugcgcugc          900
uggugccaac ccuauucucc uucuucgcca aaagcacucu gauugacaaa uacgauuuau          960
cuaauuuaca cgaaauugcu ucuggggcg cucccucuc uaaggaaguc ggggaagcgg          1020
uugccaagag guuccaucug ccagguauca ggcaaggaua uggcucacu gagacuacau          1080 cagcuauucu gauuacaccc gaggggggau auaaaccggg cgcggucggu aaaguuguuc          1140 cauuuuuga agcgaagguu guggaucugg uaccgggaa aacgcugggc guuaaucaaa          1200
gaggcgaacu gugugugaga gguccuauga uuaugccgg uuauguaaac aauccggaag          1260
cgaccaacgc cuugauugac aaggauggau ggcuacauuc uggagacaua gcuuacuggg          1320
```

-continued

```
acgaagacga acacuucuuc aucguugacc gccugaaguc ucugauuaag uacaaaggcu    1380 aucaggugge uccegcugaa uuggaaucca ucuugcucca acaccccaac aucuucgacg    1440
caggugucgc aggucuuccc gacgaugacg ccggugaacu ucccgccgcc guuguuguuu    1500
uggagcacgg aaagacgaug acggaaaaag agaucgugga uuacgucgcc agucaaguaa    1560
caaccgcgaa aaaguugcgc ggaggaguug uguuugugga cgaaguaccg aaaggucuua    1620
ccggaaaacu cgacgcaaga aaaucagag agauccucau aaaggccaag aagggcggaa    1680
agaucgccgu guaauucuag uuauaagacu gacuagcccg augggccucc aacgggccc    1740 uccucccuc cuugcaccga gauuaauaaa aaaaaaaaa aaaaaaaaaa aaaaaaaaa    1800 aaaaaaaaa aaaaaaaaaa aaaaaaaaaa auauuccccc cccccccccc ccccccccc    1860 cccccucuag acaauuggaa uu                                            1882
```

<210> SEQ ID NO 36
<211> LENGTH: 1857
<212> TYPE: RNA
<213> ORGANISM: Artificial Sequence
<220> FEATURE:
<223> OTHER INFORMATION: Synthetic oligoribonucleotide - construct
      CAP-Ppluc(GC)-muag-A70-C30

<400> SEQUENCE: 36

```
gggagaaagc uugaggaugg aggacgccaa gaacaucaag aagggcccgg cgcccuucua      60
cccgcuggag acgggaccg ccggcgagca gcuccacaag gccaugaagc gguacgcccu      120
ggugccgggc acgaucgccu ucaccgacgc ccacaucgag gucgacauca ccuacgcgga      180
guacuucgag augagcgugc gccuggccga ggccaugaag cgguacggcc ugaacaccaa      240
ccaccggauc guggugugcu cggagaacag ccugcaguuc uucaugccgg ugcugggcgc      300
ccucuucauc ggcguggccg ucgccccggc gaacgacauc uacaacgagc gggagcugcu      360
gaacagcaug gggaucagcc agccgaccgu ggguuucgug agcaagaagg gccugcagaa      420
gauccugaac gugcagaaga gcugcccau caaccagaag aucaucauca uggacagcaa      480
gaccgacuac cagggcuucc agucgaugua cacguucgug accagccacc ucccgccggg      540
cuucaacgag uacgacuucg uccggagag cuucgaccgg acaagacca ucgcccugau      600 caugaacagc agcggcagca ccggccugcc gaaggggguu gccccugccgc accgaccgc      660 cugcgugcgc uucucgcacg cccgggaccc caucuucggc aaccagauca uccggacac      720 cgccauccug agcguggugc cguuccacca cggcuucggc auguucacga cccugggcua      780
ccucaucugc ggcuuccggg ugguccugau guaccgguuc gaggaggagc uguuccugcg      840
gagccugcag gacuacaaga uccagagcgc gcucucgug ccgacccugu ucagcuucuu      900
cgccaagagc acccugaucg acaaguacga ccugucgaac cugcacgaga ucgccagcgg      960 gggcgcccg cugagcaagg aggugggcga ggccguggcc aagcgguucc accucccggg      1020
cauccgccag ggcuacggcc ugaccgagac cacgagcgcg auccugauca cccccgaggg      1080
ggacgacaag ccgggcgcc ugggcaaggu ggucccguuc uucgaggcca ggugguggaa      1140
ccuggacacc ggcaagaccc ugggcgugaa ccagcggggc gagcugugcg ugcggggcc      1200 gaugaucaug agcggcuacg ugaacaaccc ggaggccacc aacgcccuca ucgacaagga      1260 cggcuggcu cacagcggcg acaucgccua cuggacgag gacgagcacu ucuucaucgu      1320
cgaccggcug aagucgcuga ucaaguacaa gggcuaccag guggcgccgg ccgagcugga      1380
gagcauccug cuccagcacc ccaacaucuu cgacgccggc guggccgggc ugccggacga      1440
```
cgacgccggc gagcugccgg ccgcgguggu ggugcuggag cacgcaaga ccaugacgga    1500 gaaggagauc gucgacuacg uggccagcca ggugaccacc gccaagaagc ugcggggcgg    1560 cguggguguuc guggacgagg ucccgaaggg ccugaccggg aagcucgacg cccggaagau    1620
ccgcgagauc cugaucaagg ccaagaaggg cggcaagauc gccguguaag acuaguuaua    1680
agacugacua gcccgauggg ccucccaacg ggcccuccuc ccuccuugc accgagauua    1740 auaaaaaaaa aaaaaaaaaa aaaaaaaaaa aaaaaaaaaa aaaaaaaaaa aaaaaaaaaa    1800
aaaaaauauu ccccccccc cccccccc ccccccccc ucuagacaau uggaauu         1857

<210> SEQ ID NO 37
<211> LENGTH: 1653
<212> TYPE: RNA
<213> ORGANISM: Artificial Sequence
<220> FEATURE:
<223> OTHER INFORMATION: Synthetic oligoribonucleotide - coding sequence of construct CAP-Ppluc(wt)-muag-A70-C30

<400> SEQUENCE: 37
auggaagacg ccaaaaacau aaagaaaggc ccggcgccau ucuauccgcu ggaagaugga      60
accgcuggag agcaacugca uaaggcuaug aagagauacg cccugguucc uggaacaauu     120
gcuuuuacag augcacauau cgaggugac aucacuuacg cugaguacuu cgaaauguccc     180 guucgguugg cagaagcuau gaaacgauau gggcugaaua caaaucacag aaucgucgua     240
ugcagugaaa acucucuuca auucuuuaug ccgguguugg gcgcguuauu aucggaguu     300 gcaguugcgc ccgcgaacga cauuauauaau gaacgugaau ugcucaacag uaugggcauu   360
ucgcagccua ccguggug cguuuccaaa aggggguugc aaaaauuuu gaacgugcaa       420 aaaaagcucc caaucaucca aaaauuauu aucauggauu cuaaaacgga uuaccaggga    480
uuucagucga uguacacguu cgucacaucu caucuaccuc ccgguuuaa ugaauacgau    540 uuugugccag aguccuucga uaggacaag acaauugcac ugaucaugaa cucucugga     600 ucuacuggu ugccuaaagg ugucgcucug ccucauagaa cugccugcgu gagauucucg   660
caugccagag auccuauuu uggcaaucaa aucauuccgg auacugcgau uuuaagugu     720 guuccauuuc aucacgguuu ugaaauguuu acuacacucg gauauuugau augugauuu    780 cgagucgucu uaauguauag auuugaagaa gagcuguuc ugaggagcccu ucaggauuac    840 aagauucaaa gugcgcugcu ggugccaacc cuauucuccu ucuucgccaa aagcacucug    900
auugacaaau acgauuuauc uaauuuacac gaaauugcuu cuggugggcg ucccccucuc    960
aaggaagucg gggaagcggu ugccaagagg uuccaucug caggauacag gcaaggauaau   1020 ggcucacugg agacuacauc agcuauucug auuacacccg aggggauga uaaaaccgggc   1080 gcggucggua aaguuguucc auuuuugaa gcgaagguug uggaucugga uaccgggaaa    1140 acgcuggggcg uuaaucaaag aggcgaacug uguugagag uccuaugau auguccggu     1200 uauguaaca auccggaagc gaccaacgcc uugauugaca aggauggau gcuacauucu    1260 ggagacauag cuuacuggga cgaagacgaa cacuucuuca ucguugaccg ccugaagucu   1320
cugauuaagu acaaaggcua ucagguggcu cccgcugaau uggaauccau cuugcuccaa    1380
caccccaaca ucuucgacgc aggugucgca ggucuucccg acgaugacgc ggugaacuu    1440 cccgccgccg uuguuguuuu ggagcacgga aagacgauga cggaaaaaga gaucguggau   1500
uacgucgcca gucaaguaac aaccgcgaaa aaguugcgcg gaggagugu guuuggagac    1560 gaaguaccga aaggucuuac cggaaaacuc gacgcaagaa aaaucagaga gauccucaua   1620
aaggccaaga agggcggaaa gaucgccgug uaa    1653

<210> SEQ ID NO 38
<211> LENGTH: 1653
<212> TYPE: RNA
<213> ORGANISM: Artificial Sequence
<220> FEATURE:
<223> OTHER INFORMATION: GC-optimized coding sequence of construct
      CAP-Ppluc(GC)-muag-A70-C30

<400> SEQUENCE: 38
auggaggacg ccaagaacau caagaagggc ccggcgcccu ucuacccgcu ggaggacggg    60
accgccggcg agcagcucca caaggccaug aagcgguacg cccuggugcc gggcacgauc    120
gccuucaccg acgcccacau cgaggucgac aucaccuacg cggaguacuu cgagaugagc    180
gugcgccugg ccgaggccau gaagcgguac ggccugaaca ccaaccaccg gaucguggug    240
ugcucggaga acagccugca guucuucaug ccggugcugg cgccccucuu caucggcgug    300
gccgucgccc cggcgaacga caucuacaac gagcgggagc ugcugaacag caugggggauc    360
agccagccga ccguggucuu cgugagcaag aagggccugc agaagauccu gaacgugcag    420
aagaagcugc ccaucaucca agagaucauc aucauggaca gcaagaccga cuaccagggc    480
uuccagucga guacacgguu cgugaccagc caccucccgc cgggcuucaa cgaguacgac    540
uucgucccgg agagcuucga ccgggacaag accaucgccc ugaucaugaa cagcagcggc    600
agcaccggcc ugccgaaggg ggugggcccug ccgcaccgga ccgccugcgu gcgcuucucg    660
cacgcccggg accccaucuu cggcaaccag aucauccgg acaccgccau ccugagcgug    720
gugccguucc accacggcuu cggcauguuc acgacccugg gcuaccucau cugcggcuuc    780
cgggugguccc ugauguaccg guucgaggag gagcuguucc ugcggagccu gcaggacuac    840
aagauccaga gcgcgcugcu cgugccgacc cuguucagcu ucuucgccaa gagcacccug    900
aucgacaagu acgaccuguc gaaccugcac gagaucgcca gcgggggcgc cccgcugagc    960
aaggaggugg gcgaggccgu ggccaagcgg uuccaccucc cgggcaucog ccagggcuac    1020
ggccugaccg agaccacgag cgcgauccug aucacccccg aggggggacga caagccgggc    1080
gccgugggca aggugguccc guucuucgag gccaaggugg uggaccugga caccggcaag    1140
acccugggcg ugaaccagcg gggcgagcug ugcgugcggg gccgaugaau caugagcggc    1200
uacgugaaca acccggaggc caccaacgcc cucaucgaca aggacggcug gcugcacagc    1260
ggcgacaucg ccuacuggga cgaggacgag cacuucuuca ucgucgaccg gcugaagucg    1320
cugaucaagu acaagggcua ccagguggcg ccggccgagc uggagagcau ccugcuccag    1380
cacccccaaca ucuucgacgc cggcguggcc gggcugccgg acgacgacgc cggcgagcug    1440
ccggccgcgg uggugugucu ggagcacggc aagaccauga cggagaagga gaucgucgac    1500
uacgugggcca gccaggugac caccgccaag aagcugcggg gcggcguggu guucguggac    1560
gagguccccga agggccugac cgggaagcuc gacgcccgga gauccgcga gauccugauc    1620
aaggccaaga agggcggcaa gaucgccgug uaa    1653

<210> SEQ ID NO 39
<211> LENGTH: 12
<212> TYPE: PRT
<213> ORGANISM: Artificial Sequence
<220> FEATURE:
<223> OTHER INFORMATION: Synthetic oligopeptide - exemplary oligopeptide
      according to generic formula (I)

```
<400> SEQUENCE: 39

Arg Arg Arg Arg Arg Arg Arg Arg Arg His His His
1               5                   10

<210> SEQ ID NO 40
<211> LENGTH: 15
<212> TYPE: PRT
<213> ORGANISM: Artificial Sequence
<220> FEATURE:
<223> OTHER INFORMATION: Synthetic oligopeptide - exemplary oligopeptide
      according to generic formula (I)

<400> SEQUENCE: 40

His His His Arg Arg Arg Arg Arg Arg Arg Arg His His His
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic oligopeptide - exemplary oligopeptide
      according to generic formula (I)

<400> SEQUENCE: 41

Tyr Ser Ser Arg Arg Arg Arg Arg Arg Arg Arg Ser Ser Tyr
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic oligopeptide - exemplary oligopeptide
      according to generic formula (I)

<400> SEQUENCE: 42

His His His Arg Arg Arg Arg Arg Arg Arg Arg Ser Ser Tyr
1               5                   10                  15

<210> SEQ ID NO 43
<211> LENGTH: 12
<212> TYPE: PRT
<213> ORGANISM: Artificial Sequence
<220> FEATURE:
<223> OTHER INFORMATION: Synthetic oligopeptide - exemplary oligopeptide
      according to generic formula (I)

<400> SEQUENCE: 43

Arg Lys His Arg Lys His Arg Lys His Arg Lys His
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Synthetic oligopeptide - exemplary oligopeptide
      according to generic formula (I)

<400> SEQUENCE: 44

Tyr Arg Lys His Arg Lys His Arg
1               5

<210> SEQ ID NO 45
<211> LENGTH: 15
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent

<400> SEQUENCE: 45

Arg Arg Arg Arg Arg Arg Arg Arg Arg Arg Arg Arg Arg Arg Lys
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent

<400> SEQUENCE: 46

Arg Arg Arg Arg Arg Arg Arg Arg Arg Arg Arg Arg Arg Arg His
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 47

Arg Arg Arg Arg Arg Arg Arg Arg Arg Arg Arg Arg Arg Arg Xaa
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent

<400> SEQUENCE: 48

Lys Lys Lys Lys Lys Lys Lys Lys Lys Lys Lys Lys Lys Lys His
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
```

```
<220> FEATURE:
<221> NAME/KEY: MISC_FEATURE
<222> LOCATION: (15)..(15)
<223> OTHER INFORMATION: Xaa is Ornithine

<400> SEQUENCE: 49

Lys Lys Lys Lys Lys Lys Lys Lys Lys Lys Lys Lys Lys Lys Xaa
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 50

His His His His His His His His His His His His His His Xaa
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent

<400> SEQUENCE: 51

Arg Arg Arg Arg Arg Arg Arg Arg Arg Arg Arg Arg Arg Lys Lys
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent

<400> SEQUENCE: 52

Arg Arg Arg Arg Arg Arg Arg Arg Arg Arg Arg Arg Arg His His
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
```

<223> OTHER INFORMATION: Xaa is Ornithine

<400> SEQUENCE: 53

Arg Arg Arg Arg Arg Arg Arg Arg Arg Arg Arg Arg Arg Xaa Xaa
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent

<400> SEQUENCE: 54

Lys Lys Lys Lys Lys Lys Lys Lys Lys Lys Lys Lys Lys His His
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 55

Lys Lys Lys Lys Lys Lys Lys Lys Lys Lys Lys Lys Lys Xaa Xaa
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 56

His His His His His His His His His His His His His Xaa Xaa
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent

<400> SEQUENCE: 57

Arg Arg Arg Arg Arg Arg Arg Arg Arg Arg Arg Lys Lys Lys
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent

<400> SEQUENCE: 58

Arg Arg Arg Arg Arg Arg Arg Arg Arg Arg Arg Arg His His His
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 59

Arg Arg Arg Arg Arg Arg Arg Arg Arg Arg Arg Arg Xaa Xaa Xaa
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent

<400> SEQUENCE: 60

Lys Lys Lys Lys Lys Lys Lys Lys Lys Lys Lys Lys His His His
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 61

Lys Lys Lys Lys Lys Lys Lys Lys Lys Lys Lys Lys Xaa Xaa Xaa
1               5                   10                  15

```
<210> SEQ ID NO 62
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 62

His His His His His His His His His His His His Xaa Xaa Xaa
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent

<400> SEQUENCE: 63

Arg Arg Arg Arg Arg Arg Arg Arg Arg Arg Arg Lys Lys Lys Lys
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent

<400> SEQUENCE: 64

Arg Arg Arg Arg Arg Arg Arg Arg Arg Arg Arg His His His His
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 65

Arg Arg Arg Arg Arg Arg Arg Arg Arg Arg Arg Xaa Xaa Xaa Xaa
1               5                   10                  15

<210> SEQ ID NO 66
```

```
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent

<400> SEQUENCE: 66

Lys Lys Lys Lys Lys Lys Lys Lys Lys Lys Lys His His His His
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 67

Lys Lys Lys Lys Lys Lys Lys Lys Lys Lys Lys Xaa Xaa Xaa Xaa
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 68

His His His His His His His His His His His Xaa Xaa Xaa Xaa
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent

<400> SEQUENCE: 69

Arg Arg Arg Arg Arg Arg Arg Arg Arg Arg Lys Lys Lys Lys Lys
1               5                   10                  15

<210> SEQ ID NO 70
<211> LENGTH: 15
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent

<400> SEQUENCE: 70

Arg Arg Arg Arg Arg Arg Arg Arg Arg Arg His His His His His
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 71

Arg Arg Arg Arg Arg Arg Arg Arg Arg Arg Xaa Xaa Xaa Xaa Xaa
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent

<400> SEQUENCE: 72

Lys Lys Lys Lys Lys Lys Lys Lys Lys Lys His His His His His
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 73

Lys Lys Lys Lys Lys Lys Lys Lys Lys Lys Xaa Xaa Xaa Xaa Xaa
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 74

His His His His His His His His His His Xaa Xaa Xaa Xaa Xaa
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent

<400> SEQUENCE: 75

Arg Arg Arg Arg Arg Arg Arg Arg Arg Lys Lys Lys Lys Lys Lys
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent

<400> SEQUENCE: 76

Arg Arg Arg Arg Arg Arg Arg Arg Arg His His His His His His
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (10)..(15)
<223> OTHER INFORMATION: Xaa is Ornithine

<400> SEQUENCE: 77

Arg Arg Arg Arg Arg Arg Arg Arg Arg Xaa Xaa Xaa Xaa Xaa Xaa
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
```

<400> SEQUENCE: 78

Lys Lys Lys Lys Lys Lys Lys Lys Lys His His His His His His
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (10)..(15)
<223> OTHER INFORMATION: Xaa is Ornithine

<400> SEQUENCE: 79

Lys Lys Lys Lys Lys Lys Lys Lys Lys Xaa Xaa Xaa Xaa Xaa Xaa
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (10)..(15)
<223> OTHER INFORMATION: Xaa is Ornithine

<400> SEQUENCE: 80

His His His His His His His His His Xaa Xaa Xaa Xaa Xaa Xaa
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent

<400> SEQUENCE: 81

Arg Arg Arg Arg Arg Arg Arg Arg Lys Lys Lys Lys Lys Lys Lys
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent

<400> SEQUENCE: 82

```
Arg Arg Arg Arg Arg Arg Arg Arg His His His His His His His
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (9)..(15)
<223> OTHER INFORMATION: Xaa is Ornithine

<400> SEQUENCE: 83

Arg Arg Arg Arg Arg Arg Arg Arg Xaa Xaa Xaa Xaa Xaa Xaa Xaa
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent

<400> SEQUENCE: 84

Lys Lys Lys Lys Lys Lys Lys Lys His His His His His His His
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (9)..(15)
<223> OTHER INFORMATION: Xaa is Ornithine

<400> SEQUENCE: 85

Lys Lys Lys Lys Lys Lys Lys Lys Xaa Xaa Xaa Xaa Xaa Xaa Xaa
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (9)..(15)
<223> OTHER INFORMATION: Xaa is Ornithine

<400> SEQUENCE: 86
```

```
His His His His His His His His Xaa Xaa Xaa Xaa Xaa Xaa Xaa
1               5                   10                  15
```

<210> SEQ ID NO 87
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent

<400> SEQUENCE: 87

```
Arg Arg Arg Arg Arg Arg Arg Arg Arg Arg Arg Arg Arg Lys His
1               5                   10                  15
```

<210> SEQ ID NO 88
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 88

```
Arg Arg Arg Arg Arg Arg Arg Arg Arg Arg Arg Arg Arg Lys Xaa
1               5                   10                  15
```

<210> SEQ ID NO 89
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 89

```
Arg Arg Arg Arg Arg Arg Arg Arg Arg Arg Arg Arg Arg His Xaa
1               5                   10                  15
```

<210> SEQ ID NO 90
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent

<400> SEQUENCE: 90

```
Arg Lys Lys Lys Lys Lys Lys Lys Lys Lys Lys Lys Lys Lys His
1               5                   10                  15
```

```
<210> SEQ ID NO 91
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 91

Arg Lys Lys Lys Lys Lys Lys Lys Lys Lys Lys Lys Lys Lys Xaa
 1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 92

Lys Lys Lys Lys Lys Lys Lys Lys Lys Lys Lys Lys Lys His Xaa
 1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 93

Arg Lys His His His His His His His His His His His His His
 1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 94

Arg His His His His His His His His His His His His His Xaa
```

```
1               5                   10                  15
```

<210> SEQ ID NO 95
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 95

```
Lys His His His His His His His His His His His His His Xaa
1               5                   10                  15
```

<210> SEQ ID NO 96
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent

<400> SEQUENCE: 96

```
Arg Arg Arg Arg Arg Arg Arg Arg Arg Arg Arg Arg Lys Lys His
1               5                   10                  15
```

<210> SEQ ID NO 97
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent

<400> SEQUENCE: 97

```
Arg Arg Arg Arg Arg Arg Arg Arg Arg Arg Arg Arg Lys His His
1               5                   10                  15
```

<210> SEQ ID NO 98
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 98

```
Arg Arg Arg Arg Arg Arg Arg Arg Arg Arg Arg Arg Lys Lys Xaa
1               5                   10                  15
```

```
<210> SEQ ID NO 99
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 99

Arg Arg Arg Arg Arg Arg Arg Arg Arg Arg Arg Arg Lys Xaa Xaa
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 100

Arg Arg Arg Arg Arg Arg Arg Arg Arg Arg Arg Arg His His Xaa
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 101

Arg Arg Arg Arg Arg Arg Arg Arg Arg Arg Arg Arg His Xaa Xaa
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent

<400> SEQUENCE: 102

Arg Arg Lys Lys Lys Lys Lys Lys Lys Lys Lys Lys Lys Lys His
1               5                   10                  15
```

```
<210> SEQ ID NO 103
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent

<400> SEQUENCE: 103

Arg Lys Lys Lys Lys Lys Lys Lys Lys Lys Lys Lys Lys His His
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 104

Arg Arg Lys Lys Lys Lys Lys Lys Lys Lys Lys Lys Lys Lys Xaa
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 105

Arg Lys Lys Lys Lys Lys Lys Lys Lys Lys Lys Lys Lys Xaa Xaa
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 106

Lys Lys Lys Lys Lys Lys Lys Lys Lys Lys Lys Lys His His Xaa
1               5                   10                  15
```

```
<210> SEQ ID NO 107
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 107

Lys Lys Lys Lys Lys Lys Lys Lys Lys Lys Lys Lys His Xaa Xaa
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 108

Arg Arg Lys His His His His His His His His His His His His
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 109

Arg Lys Lys His His His His His His His His His His His His
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 110

Arg Arg His His His His His His His His His His His His Xaa
1               5                   10                  15

<210> SEQ ID NO 111
```

```
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 111

Arg His His His His His His His His His His His His Xaa Xaa
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 112

Lys Lys His His His His His His His His His His His His Xaa
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 113

Lys His His His His His His His His His His His His Xaa Xaa
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent

<400> SEQUENCE: 114

Arg Arg Arg Arg Arg Arg Arg Arg Arg Arg Arg Arg Lys Lys Lys His
1               5                   10                  15
```

```
<210> SEQ ID NO 115
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent

<400> SEQUENCE: 115

Arg Arg Arg Arg Arg Arg Arg Arg Arg Arg Arg Lys Lys His His
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent

<400> SEQUENCE: 116

Arg Arg Arg Arg Arg Arg Arg Arg Arg Arg Arg Lys His His His
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 117

Arg Arg Arg Arg Arg Arg Arg Arg Arg Arg Arg Lys Lys Lys Xaa
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 118

Arg Arg Arg Arg Arg Arg Arg Arg Arg Arg Arg Lys Lys Xaa Xaa
1               5                   10                  15

<210> SEQ ID NO 119
<211> LENGTH: 15
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 119

Arg Arg Arg Arg Arg Arg Arg Arg Arg Arg Arg Lys Xaa Xaa Xaa
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 120

Arg Arg Arg Arg Arg Arg Arg Arg Arg Arg Arg His His His Xaa
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 121

Arg Arg Arg Arg Arg Arg Arg Arg Arg Arg Arg His His Xaa Xaa
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 122

Arg Arg Arg Arg Arg Arg Arg Arg Arg Arg Arg His Xaa Xaa Xaa
1               5                   10                  15
```

```
<210> SEQ ID NO 123
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent

<400> SEQUENCE: 123

Arg Arg Arg Lys Lys Lys Lys Lys Lys Lys Lys Lys Lys Lys His
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent

<400> SEQUENCE: 124

Arg Arg Lys Lys Lys Lys Lys Lys Lys Lys Lys Lys Lys His His
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May or may not be present

<400> SEQUENCE: 125

Arg Lys Lys Lys Lys Lys Lys Lys Lys Lys Lys Lys His His His
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 126

Arg Arg Arg Lys Lys Lys Lys Lys Lys Lys Lys Lys Lys Lys Xaa
1               5                   10                  15

<210> SEQ ID NO 127
<211> LENGTH: 15
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 127

Arg Arg Lys Lys Lys Lys Lys Lys Lys Lys Lys Lys Lys Xaa Xaa
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 128

Arg Lys Lys Lys Lys Lys Lys Lys Lys Lys Lys Lys Xaa Xaa Xaa
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 129

Lys Lys Lys Lys Lys Lys Lys Lys Lys Lys Lys His His His Xaa
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 130

Lys Lys Lys Lys Lys Lys Lys Lys Lys Lys Lys His His Xaa Xaa
1               5                   10                  15
```

```
<210> SEQ ID NO 131
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 131

Lys Lys Lys Lys Lys Lys Lys Lys Lys Lys Lys His Xaa Xaa Xaa
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 132

Arg Arg Arg Lys His His His His His His His His His His His
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 133

Arg Arg Lys Lys His His His His His His His His His His His
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 134

Arg Lys Lys Lys His His His His His His His His His His His
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 135

Arg Arg Arg His His His His His His His His His His His Xaa
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 136

Arg Arg His His His His His His His His His His His Xaa Xaa
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 137

Arg His His His His His His His His His His His Xaa Xaa Xaa
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 138

Lys Lys Lys His His His His His His His His His His His Xaa
1               5                   10                  15

<210> SEQ ID NO 139
<211> LENGTH: 15
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 139

Lys Lys His His His His His His His His His His His Xaa Xaa
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 140

Lys His His His His His His His His His His His Xaa Xaa Xaa
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent

<400> SEQUENCE: 141

Arg Arg Arg Arg Arg Arg Arg Arg Arg Arg Lys Lys Lys Lys His
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent

<400> SEQUENCE: 142

Arg Arg Arg Arg Arg Arg Arg Arg Arg Arg Lys Lys Lys His His
1               5                   10                  15

<210> SEQ ID NO 143
<211> LENGTH: 15
<212> TYPE: PRT
<213> ORGANISM: Artificial Sequence
<220> FEATURE:
```

<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent

<400> SEQUENCE: 143

Arg Arg Arg Arg Arg Arg Arg Arg Arg Lys Lys His His His
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent

<400> SEQUENCE: 144

Arg Arg Arg Arg Arg Arg Arg Arg Arg Lys His His His His
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 145

Arg Arg Arg Arg Arg Arg Arg Arg Arg Lys Lys Lys Lys Xaa
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 146

Arg Arg Arg Arg Arg Arg Arg Arg Arg Lys Lys Lys Xaa Xaa
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE

```
<222> LOCATION: (4)..(10)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 147

Arg Arg Arg Arg Arg Arg Arg Arg Arg Arg Lys Lys Xaa Xaa Xaa
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 148

Arg Arg Arg Arg Arg Arg Arg Arg Arg Arg Lys Xaa Xaa Xaa Xaa
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 149

Arg Arg Arg Arg Arg Arg Arg Arg Arg Arg His His His His Xaa
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 150

Arg Arg Arg Arg Arg Arg Arg Arg Arg Arg His His His Xaa Xaa
1               5                   10                  15

<210> SEQ ID NO 151
<211> LENGTH: 15
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 151

Arg Arg Arg Arg Arg Arg Arg Arg Arg Arg His His Xaa Xaa Xaa
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 152

Arg Arg Arg Arg Arg Arg Arg Arg Arg Arg His Xaa Xaa Xaa Xaa
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent

<400> SEQUENCE: 153

Arg Arg Arg Arg Lys Lys Lys Lys Lys Lys Lys Lys Lys Lys His
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent

<400> SEQUENCE: 154

Arg Arg Arg Lys Lys Lys Lys Lys Lys Lys Lys Lys Lys His His
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (6)..(12)
<223> OTHER INFORMATION: May be present or absent

<400> SEQUENCE: 155

Arg Arg Lys Lys Lys Lys Lys Lys Lys Lys Lys His His His His
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent

<400> SEQUENCE: 156

Arg Lys Lys Lys Lys Lys Lys Lys Lys Lys Lys His His His His
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 157

Arg Arg Arg Arg Lys Lys Lys Lys Lys Lys Lys Lys Lys Lys Xaa
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 158

Arg Arg Arg Lys Lys Lys Lys Lys Lys Lys Lys Lys Lys Xaa Xaa
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
```

<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 159

Arg Arg Lys Lys Lys Lys Lys Lys Lys Lys Lys Lys Xaa Xaa Xaa
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 160

Arg Lys Lys Lys Lys Lys Lys Lys Lys Lys Lys Xaa Xaa Xaa Xaa
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 161

Lys Lys Lys Lys Lys Lys Lys Lys Lys Lys His His His His Xaa
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 162

Lys Lys Lys Lys Lys Lys Lys Lys Lys Lys His His His Xaa Xaa
1               5                   10                  15

<210> SEQ ID NO 163
<211> LENGTH: 15
<212> TYPE: PRT
<213> ORGANISM: Artificial Sequence

```
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 163

Lys Lys Lys Lys Lys Lys Lys Lys Lys Lys His His Xaa Xaa Xaa
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 164

Lys Lys Lys Lys Lys Lys Lys Lys Lys His Xaa Xaa Xaa Xaa
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 165

Arg Arg Arg Arg Lys His His His His His His His His His
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 166

Arg Arg Arg Lys Lys His His His His His His His His
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Synthetic peptide
<220> FEATURE:
```

-continued

```
<221> NAME/KEY: MISC_FEATURE
<222> LOCATION: (9)..(15)
<223> OTHER INFORMATION: May be present or absent

<400> SEQUENCE: 167

Arg Arg Lys Lys Lys His His His His His His His His His His
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 168

Arg Lys Lys Lys Lys His His His His His His His His His His
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 169

Arg Arg Arg Arg His His His His His His His His His His Xaa
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 170

Arg Arg Arg His His His His His His His His His His Xaa Xaa
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
```

```
<220> FEATURE:
<221> NAME/KEY: MISC_FEATURE
<222> LOCATION: (13)..(15)
<223> OTHER INFORMATION: Xaa is Ornithine

<400> SEQUENCE: 171

Arg Arg His His His His His His His His His Xaa Xaa Xaa
1               5                   10                  15

<210> SEQ ID NO 172
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 172

Arg His His His His His His His His His His Xaa Xaa Xaa Xaa
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 173

Lys Lys Lys Lys His His His His His His His His His His Xaa
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 174

Lys Lys Lys His His His His His His His His His Xaa Xaa
1               5                   10                  15

<210> SEQ ID NO 175
<211> LENGTH: 15
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 175

Lys Lys His His His His His His His His His His Xaa Xaa Xaa
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 176

Lys His His His His His His His His His His Xaa Xaa Xaa Xaa
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent

<400> SEQUENCE: 177

Arg Arg Arg Arg Arg Arg Arg Arg Arg Lys Lys Lys Lys Lys His
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent

<400> SEQUENCE: 178

Arg Arg Arg Arg Arg Arg Arg Arg Arg Lys Lys Lys Lys His His
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (3)..(9)
<223> OTHER INFORMATION: May be present or absent

<400> SEQUENCE: 179

Arg Arg Arg Arg Arg Arg Arg Arg Arg Lys Lys Lys His His His
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent

<400> SEQUENCE: 180

Arg Arg Arg Arg Arg Arg Arg Arg Arg Lys Lys His His His His
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent

<400> SEQUENCE: 181

Arg Arg Arg Arg Arg Arg Arg Arg Arg Lys His His His His His
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 182

Arg Arg Arg Arg Arg Arg Arg Arg Arg Lys Lys Lys Lys Lys Xaa
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine
```

<400> SEQUENCE: 183

Arg Arg Arg Arg Arg Arg Arg Arg Lys Lys Lys Lys Xaa Xaa
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 184

Arg Arg Arg Arg Arg Arg Arg Arg Lys Lys Lys Xaa Xaa Xaa
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 185

Arg Arg Arg Arg Arg Arg Arg Arg Lys Lys Xaa Xaa Xaa Xaa
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 186

Arg Arg Arg Arg Arg Arg Arg Arg Lys Xaa Xaa Xaa Xaa Xaa
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent

```
<220> FEATURE:
<221> NAME/KEY: MISC_FEATURE
<222> LOCATION: (15)..(15)
<223> OTHER INFORMATION: Xaa is Ornithine

<400> SEQUENCE: 187

Arg Arg Arg Arg Arg Arg Arg Arg Arg His His His His His Xaa
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 188

Arg Arg Arg Arg Arg Arg Arg Arg Arg His His His His Xaa Xaa
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 189

Arg Arg Arg Arg Arg Arg Arg Arg Arg His His His Xaa Xaa Xaa
1               5                   10                  15

<210> SEQ ID NO 190
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 190

Arg Arg Arg Arg Arg Arg Arg Arg Arg His His Xaa Xaa Xaa Xaa
1               5                   10                  15

<210> SEQ ID NO 191
<211> LENGTH: 15
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 191

Arg Arg Arg Arg Arg Arg Arg Arg Arg His Xaa Xaa Xaa Xaa Xaa
1               5                   10                  15

<210> SEQ ID NO 192
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent

<400> SEQUENCE: 192

Arg Arg Arg Arg Arg Lys Lys Lys Lys Lys Lys Lys Lys Lys His
1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent

<400> SEQUENCE: 193

Arg Arg Arg Arg Lys Lys Lys Lys Lys Lys Lys Lys Lys His His
1               5                   10                  15

<210> SEQ ID NO 194
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent

<400> SEQUENCE: 194

Arg Arg Arg Lys Lys Lys Lys Lys Lys Lys Lys Lys His His His
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent

<400> SEQUENCE: 195
```

Arg Arg Lys Lys Lys Lys Lys Lys Lys Lys His His His His His
1               5                   10                  15

<210> SEQ ID NO 196
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent

<400> SEQUENCE: 196

Arg Lys Lys Lys Lys Lys Lys Lys Lys Lys His His His His His
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 197

Arg Arg Arg Arg Arg Lys Lys Lys Lys Lys Lys Lys Lys Lys Xaa
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 198

Arg Arg Arg Arg Lys Lys Lys Lys Lys Lys Lys Lys Lys Xaa Xaa
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 199

Arg Arg Arg Lys Lys Lys Lys Lys Lys Lys Lys Xaa Xaa Xaa
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 200

Arg Arg Lys Lys Lys Lys Lys Lys Lys Lys Lys Xaa Xaa Xaa Xaa
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 201

Arg Lys Lys Lys Lys Lys Lys Lys Lys Lys Xaa Xaa Xaa Xaa Xaa
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 202

Lys Lys Lys Lys Lys Lys Lys Lys Lys His His His His His Xaa
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent

```
<220> FEATURE:
<221> NAME/KEY: MISC_FEATURE
<222> LOCATION: (14)..(15)
<223> OTHER INFORMATION: Xaa is Ornithine

<400> SEQUENCE: 203

Lys Lys Lys Lys Lys Lys Lys Lys Lys His His His His Xaa Xaa
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 204

Lys Lys Lys Lys Lys Lys Lys Lys Lys His His His Xaa Xaa Xaa
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 205

Lys Lys Lys Lys Lys Lys Lys Lys Lys His His Xaa Xaa Xaa Xaa
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 206

Lys Lys Lys Lys Lys Lys Lys Lys Lys His Xaa Xaa Xaa Xaa Xaa
1               5                   10                  15

<210> SEQ ID NO 207
<211> LENGTH: 15
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 207

Arg Arg Arg Arg Arg Lys His His His His His His His His His
1               5                   10                  15

<210> SEQ ID NO 208
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 208

Arg Arg Arg Arg Lys Lys His His His His His His His His His
1               5                   10                  15

<210> SEQ ID NO 209
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 209

Arg Arg Arg Lys Lys Lys His His His His His His His His His
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 210

Arg Arg Lys Lys Lys Lys His His His His His His His His His
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 211

Arg Lys Lys Lys Lys Lys His His His His His His His His His
1               5                   10                  15
```

```
<210> SEQ ID NO 212
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 212

Arg Arg Arg Arg Arg His His His His His His His His His Xaa
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 213

Arg Arg Arg Arg His His His His His His His His His Xaa Xaa
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 214

Arg Arg Arg His His His His His His His His His Xaa Xaa Xaa
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine
```

```
<400> SEQUENCE: 215

Arg Arg His His His His His His His His Xaa Xaa Xaa Xaa Xaa
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 216

Arg His His His His His His His His His Xaa Xaa Xaa Xaa Xaa
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 217

Lys Lys Lys Lys Lys His His His His His His His His His Xaa
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 218

Lys Lys Lys Lys His His His His His His His His His Xaa Xaa
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
```

```
<220> FEATURE:
<221> NAME/KEY: MISC_FEATURE
<222> LOCATION: (13)..(15)
<223> OTHER INFORMATION: Xaa is Ornithine

<400> SEQUENCE: 219

Lys Lys Lys His His His His His His His His Xaa Xaa Xaa
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 220

Lys Lys His His His His His His His His His Xaa Xaa Xaa Xaa
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 221

Lys His His His His His His His His His Xaa Xaa Xaa Xaa Xaa
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent

<400> SEQUENCE: 222

Arg Arg Arg Arg Arg Arg Arg Arg Lys Lys Lys Lys Lys Lys His
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
```

<223> OTHER INFORMATION: May be present or absent

<400> SEQUENCE: 223

Arg Arg Arg Arg Arg Arg Arg Lys Lys Lys Lys Lys His His
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent

<400> SEQUENCE: 224

Arg Arg Arg Arg Arg Arg Arg Lys Lys Lys Lys His His His
1               5                   10                  15

<210> SEQ ID NO 225
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent

<400> SEQUENCE: 225

Arg Arg Arg Arg Arg Arg Arg Arg Lys Lys Lys His His His His
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent

<400> SEQUENCE: 226

Arg Arg Arg Arg Arg Arg Arg Arg Lys Lys His His His His His
1               5                   10                  15

<210> SEQ ID NO 227
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent

<400> SEQUENCE: 227

Arg Arg Arg Arg Arg Arg Arg Arg Lys His His His His His His
1               5                   10                  15

<210> SEQ ID NO 228
<211> LENGTH: 15
<212> TYPE: PRT

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 228

Arg Arg Arg Arg Arg Arg Arg Arg Lys Lys Lys Lys Lys Lys Xaa
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 229

Arg Arg Arg Arg Arg Arg Arg Arg Lys Lys Lys Lys Lys Xaa Xaa
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 230

Arg Arg Arg Arg Arg Arg Arg Arg Lys Lys Lys Lys Xaa Xaa Xaa
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 231

Arg Arg Arg Arg Arg Arg Arg Arg Lys Lys Lys Xaa Xaa Xaa Xaa
1               5                   10                  15
```

```
<210> SEQ ID NO 232
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 232

Arg Arg Arg Arg Arg Arg Arg Arg Lys Lys Xaa Xaa Xaa Xaa Xaa
1               5                   10                  15

<210> SEQ ID NO 233
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (10)..(15)
<223> OTHER INFORMATION: Xaa is Ornithine

<400> SEQUENCE: 233

Arg Arg Arg Arg Arg Arg Arg Arg Lys Xaa Xaa Xaa Xaa Xaa Xaa
1               5                   10                  15

<210> SEQ ID NO 234
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 234

Arg Arg Arg Arg Arg Arg Arg Arg His His His His His His Xaa
1               5                   10                  15

<210> SEQ ID NO 235
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine
```

<400> SEQUENCE: 235

Arg Arg Arg Arg Arg Arg Arg His His His His His Xaa Xaa
1               5                   10                  15

<210> SEQ ID NO 236
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 236

Arg Arg Arg Arg Arg Arg Arg Arg His His His His Xaa Xaa Xaa
1               5                   10                  15

<210> SEQ ID NO 237
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 237

Arg Arg Arg Arg Arg Arg Arg Arg His His His Xaa Xaa Xaa Xaa
1               5                   10                  15

<210> SEQ ID NO 238
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 238

Arg Arg Arg Arg Arg Arg Arg Arg His His Xaa Xaa Xaa Xaa Xaa
1               5                   10                  15

<210> SEQ ID NO 239
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)

```
<223> OTHER INFORMATION: May be present or absent
<220> FEATURE:
<221> NAME/KEY: MISC_FEATURE
<222> LOCATION: (10)..(15)
<223> OTHER INFORMATION: Xaa is Ornithine

<400> SEQUENCE: 239

Arg Arg Arg Arg Arg Arg Arg Arg His Xaa Xaa Xaa Xaa Xaa Xaa
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent

<400> SEQUENCE: 240

Arg Arg Arg Arg Arg Arg Lys Lys Lys Lys Lys Lys Lys His
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent

<400> SEQUENCE: 241

Arg Arg Arg Arg Arg Lys Lys Lys Lys Lys Lys Lys His His
1               5                   10                  15

<210> SEQ ID NO 242
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent

<400> SEQUENCE: 242

Arg Arg Arg Arg Lys Lys Lys Lys Lys Lys Lys His His His
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent

<400> SEQUENCE: 243

Arg Arg Arg Lys Lys Lys Lys Lys Lys Lys His His His His
1               5                   10                  15
```

<210> SEQ ID NO 244
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent

<400> SEQUENCE: 244

Arg Arg Lys Lys Lys Lys Lys Lys Lys His His His His His His
1               5                   10                  15

<210> SEQ ID NO 245
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent

<400> SEQUENCE: 245

Arg Lys Lys Lys Lys Lys Lys Lys Lys His His His His His His
1               5                   10                  15

<210> SEQ ID NO 246
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 246

Arg Arg Arg Arg Arg Arg Lys Lys Lys Lys Lys Lys Lys Lys Xaa
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 247

Arg Arg Arg Arg Arg Lys Lys Lys Lys Lys Lys Lys Lys Xaa Xaa
1               5                   10                  15

<210> SEQ ID NO 248
<211> LENGTH: 15

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 248

Arg Arg Arg Arg Lys Lys Lys Lys Lys Lys Lys Lys Xaa Xaa Xaa
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 249

Arg Arg Arg Lys Lys Lys Lys Lys Lys Lys Lys Xaa Xaa Xaa Xaa
1               5                   10                  15

<210> SEQ ID NO 250
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 250

Arg Arg Lys Lys Lys Lys Lys Lys Lys Lys Xaa Xaa Xaa Xaa Xaa
1               5                   10                  15

<210> SEQ ID NO 251
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (10)..(15)
<223> OTHER INFORMATION: Xaa is Ornithine

<400> SEQUENCE: 251

Arg Lys Lys Lys Lys Lys Lys Lys Lys Xaa Xaa Xaa Xaa Xaa Xaa
```

<210> SEQ ID NO 252
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 252

Lys Lys Lys Lys Lys Lys Lys Lys His His His His His His Xaa
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 253

Lys Lys Lys Lys Lys Lys Lys Lys His His His His His Xaa Xaa
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 254

Lys Lys Lys Lys Lys Lys Lys Lys His His His His Xaa Xaa Xaa
1               5                   10                  15

<210> SEQ ID NO 255
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (12)..(15)

```
<223> OTHER INFORMATION: Xaa is Ornithine

<400> SEQUENCE: 255

Lys Lys Lys Lys Lys Lys Lys Lys His His His Xaa Xaa Xaa Xaa
1               5                   10                  15

<210> SEQ ID NO 256
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 256

Lys Lys Lys Lys Lys Lys Lys His His Xaa Xaa Xaa Xaa Xaa
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(8)
<223> OTHER INFORMATION: May be present or absent
<220> FEATURE:
<221> NAME/KEY: MISC_FEATURE
<222> LOCATION: (10)..(15)
<223> OTHER INFORMATION: Xaa is Ornithine

<400> SEQUENCE: 257

Lys Lys Lys Lys Lys Lys Lys Lys His Xaa Xaa Xaa Xaa Xaa Xaa
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 258

Arg Arg Arg Arg Arg Arg Lys His His His His His His His His
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 259
```

Arg Arg Arg Arg Arg Lys Lys His His His His His His His His
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 260

Arg Arg Arg Arg Lys Lys Lys His His His His His His His His
1               5                   10                  15

<210> SEQ ID NO 261
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 261

Arg Arg Arg Lys Lys Lys Lys His His His His His His His His
1               5                   10                  15

<210> SEQ ID NO 262
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 262

Arg Arg Lys Lys Lys Lys Lys His His His His His His His His
1               5                   10                  15

<210> SEQ ID NO 263
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(15)
<223> OTHER INFORMATION: May be present or absent

<400> SEQUENCE: 263

Arg Lys Lys Lys Lys Lys Lys His His His His His His His His
1               5                   10                  15

<210> SEQ ID NO 264
<211> LENGTH: 15
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 264

Arg Arg Arg Arg Arg His His His His His His His His His Xaa
1               5                   10                  15

<210> SEQ ID NO 265
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 265

Arg Arg Arg Arg Arg His His His His His His His His Xaa Xaa
1               5                   10                  15

<210> SEQ ID NO 266
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 266

Arg Arg Arg Arg His His His His His His His His Xaa Xaa Xaa
1               5                   10                  15

<210> SEQ ID NO 267
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 267

Arg Arg Arg His His His His His His His Xaa Xaa Xaa Xaa
1               5                   10                  15

<210> SEQ ID NO 268
```

<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 268

Arg Arg His His His His His His His His Xaa Xaa Xaa Xaa Xaa
1               5                   10                  15

<210> SEQ ID NO 269
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (10)..(15)
<223> OTHER INFORMATION: Xaa is Ornithine

<400> SEQUENCE: 269

Arg His His His His His His His His Xaa Xaa Xaa Xaa Xaa Xaa
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 270

Lys Lys Lys Lys Lys Lys His His His His His His His His Xaa
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 271

Lys Lys Lys Lys Lys His His His His His His His Xaa Xaa
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 272

Lys Lys Lys Lys His His His His His His His Xaa Xaa Xaa
1               5                   10                  15

<210> SEQ ID NO 273
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 273

Lys Lys Lys His His His His His His His Xaa Xaa Xaa Xaa
1               5                   10                  15

<210> SEQ ID NO 274
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 274

Lys Lys His His His His His His His Xaa Xaa Xaa Xaa Xaa
1               5                   10                  15

<210> SEQ ID NO 275
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE

```
<222> LOCATION: (10)..(15)
<223> OTHER INFORMATION: Xaa is Ornithine

<400> SEQUENCE: 275

Lys His His His His His His His His Xaa Xaa Xaa Xaa Xaa Xaa
1               5                   10                  15

<210> SEQ ID NO 276
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 276

Arg Arg Arg Arg Arg Arg Arg Arg Arg Arg Arg Arg Lys His Xaa
1               5                   10                  15

<210> SEQ ID NO 277
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 277

Arg Lys Lys Lys Lys Lys Lys Lys Lys Lys Lys Lys Lys His Xaa
1               5                   10                  15

<210> SEQ ID NO 278
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 278

Arg Lys His His His His His His His His His His His His Xaa
1               5                   10                  15

<210> SEQ ID NO 279
<211> LENGTH: 15
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (4)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 279

Arg Lys His Xaa Xaa Xaa Xaa Xaa Xaa Xaa Xaa Xaa Xaa Xaa Xaa
1               5                   10                  15

<210> SEQ ID NO 280
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 280

Arg Arg Arg Arg Arg Arg Arg Arg Arg Arg Arg Lys Lys His Xaa
1               5                   10                  15

<210> SEQ ID NO 281
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 281

Arg Arg Arg Arg Arg Arg Arg Arg Arg Arg Arg Lys His His Xaa
1               5                   10                  15

<210> SEQ ID NO 282
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 282

Arg Arg Arg Arg Arg Arg Arg Arg Arg Arg Lys His Xaa Xaa
1               5                   10                  15

<210> SEQ ID NO 283
<211> LENGTH: 15
```

<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 283

Arg Arg Lys Lys Lys Lys Lys Lys Lys Lys Lys Lys Lys His Xaa
1               5                   10                  15

<210> SEQ ID NO 284
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 284

Arg Lys Lys Lys Lys Lys Lys Lys Lys Lys Lys Lys His His Xaa
1               5                   10                  15

<210> SEQ ID NO 285
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 285

Arg Lys Lys Lys Lys Lys Lys Lys Lys Lys Lys Lys His Xaa Xaa
1               5                   10                  15

<210> SEQ ID NO 286
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 286

Arg Arg Lys His His His His His His His His His His His Xaa

```
<210> SEQ ID NO 287
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 287

Arg Lys Lys His His His His His His His His His His His Xaa
1               5                   10                  15

<210> SEQ ID NO 288
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 288

Arg Lys His His His His His His His His His His His Xaa Xaa
1               5                   10                  15

<210> SEQ ID NO 289
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 289

Arg Arg Lys His Xaa Xaa Xaa Xaa Xaa Xaa Xaa Xaa Xaa Xaa Xaa
1               5                   10                  15

<210> SEQ ID NO 290
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(15)
<223> OTHER INFORMATION: Xaa is Ornithine
<220> FEATURE:
<221> NAME/KEY: MISC_FEATURE
<222> LOCATION: (9)..(15)
```

<223> OTHER INFORMATION: May be present or absent

<400> SEQUENCE: 290

Arg Lys Lys His Xaa Xaa Xaa Xaa Xaa Xaa Xaa Xaa Xaa Xaa Xaa
1               5                   10                  15

<210> SEQ ID NO 291
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 291

Arg Lys His His Xaa Xaa Xaa Xaa Xaa Xaa Xaa Xaa Xaa Xaa Xaa
1               5                   10                  15

<210> SEQ ID NO 292
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 292

Arg Arg Arg Arg Arg Arg Arg Arg Arg Arg Lys Lys Lys His Xaa
1               5                   10                  15

<210> SEQ ID NO 293
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 293

Arg Arg Arg Arg Arg Arg Arg Arg Arg Lys Lys His His Xaa
1               5                   10                  15

<210> SEQ ID NO 294
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE

```
<222> LOCATION: (4)..(10)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 294

Arg Arg Arg Arg Arg Arg Arg Arg Arg Arg Lys Lys His Xaa Xaa
1               5                   10                  15

<210> SEQ ID NO 295
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 295

Arg Arg Arg Arg Arg Arg Arg Arg Arg Arg Lys His His Xaa Xaa
1               5                   10                  15

<210> SEQ ID NO 296
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 296

Arg Arg Arg Arg Arg Arg Arg Arg Arg Arg Lys His Xaa Xaa Xaa
1               5                   10                  15

<210> SEQ ID NO 297
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 297

Arg Arg Arg Lys Lys Lys Lys Lys Lys Lys Lys Lys Lys His Xaa
1               5                   10                  15

<210> SEQ ID NO 298
<211> LENGTH: 15
<212> TYPE: PRT
```

-continued

<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 298

Arg Arg Lys Lys Lys Lys Lys Lys Lys Lys Lys His His Xaa
1               5                   10                  15

<210> SEQ ID NO 299
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 299

Arg Arg Lys Lys Lys Lys Lys Lys Lys Lys Lys His Xaa Xaa
1               5                   10                  15

<210> SEQ ID NO 300
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 300

Arg Lys Lys Lys Lys Lys Lys Lys Lys Lys His His Xaa Xaa
1               5                   10                  15

<210> SEQ ID NO 301
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 301

Arg Lys Lys Lys Lys Lys Lys Lys Lys Lys Lys His Xaa Xaa Xaa
1               5                   10                  15

<210> SEQ ID NO 302
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 302

Arg Arg Arg Lys His His His His His His His His His His Xaa
1               5                   10                  15

<210> SEQ ID NO 303
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 303

Arg Arg Lys Lys His His His His His His His His His His Xaa
1               5                   10                  15

<210> SEQ ID NO 304
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 304

Arg Arg Lys His His His His His His His His His His Xaa Xaa
1               5                   10                  15

<210> SEQ ID NO 305
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 305

Arg Lys Lys His His His His His His His His His Xaa Xaa
1               5                   10                  15

<210> SEQ ID NO 306
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 306

Arg Lys His His His His His His His His His Xaa Xaa Xaa
1               5                   10                  15

<210> SEQ ID NO 307
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 307

Arg Arg Arg Lys His Xaa Xaa Xaa Xaa Xaa Xaa Xaa Xaa Xaa Xaa
1               5                   10                  15

<210> SEQ ID NO 308
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 308

Arg Arg Lys Lys His Xaa Xaa Xaa Xaa Xaa Xaa Xaa Xaa Xaa Xaa
1               5                   10                  15

<210> SEQ ID NO 309
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(15)

```
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 309

Arg Arg Lys His His Xaa Xaa Xaa Xaa Xaa Xaa Xaa Xaa Xaa Xaa
1               5                   10                  15

<210> SEQ ID NO 310
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 310

Arg Lys Lys His His Xaa Xaa Xaa Xaa Xaa Xaa Xaa Xaa Xaa Xaa
1               5                   10                  15

<210> SEQ ID NO 311
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 311

Arg Lys His His His Xaa Xaa Xaa Xaa Xaa Xaa Xaa Xaa Xaa Xaa
1               5                   10                  15

<210> SEQ ID NO 312
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 312

Arg Arg Arg Arg Arg Arg Arg Arg Arg Lys Lys Lys Lys His Xaa
1               5                   10                  15

<210> SEQ ID NO 313
<211> LENGTH: 15
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 313

Arg Arg Arg Arg Arg Arg Arg Arg Arg Lys His His His His Xaa
1               5                   10                  15

<210> SEQ ID NO 314
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 314

Arg Arg Arg Arg Arg Arg Arg Arg Arg Lys His Xaa Xaa Xaa Xaa
1               5                   10                  15

<210> SEQ ID NO 315
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 315

Arg Arg Arg Arg Arg Arg Arg Arg Arg Lys Lys Lys His His Xaa
1               5                   10                  15

<210> SEQ ID NO 316
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 316

Arg Arg Arg Arg Arg Arg Arg Arg Arg Lys Lys Lys His Xaa Xaa
1               5                   10                  15
```

<210> SEQ ID NO 317
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 317

Arg Arg Arg Arg Arg Arg Arg Arg Arg Lys Lys His His His Xaa
1               5                   10                  15

<210> SEQ ID NO 318
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 318

Arg Arg Arg Arg Arg Arg Arg Arg Arg Lys Lys His Xaa Xaa Xaa
1               5                   10                  15

<210> SEQ ID NO 319
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 319

Arg Arg Arg Arg Arg Arg Arg Arg Arg Lys His His Xaa Xaa Xaa
1               5                   10                  15

<210> SEQ ID NO 320
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

```
<400> SEQUENCE: 320

Arg Arg Arg Arg Arg Arg Arg Arg Lys His His His Xaa Xaa
1               5                   10                  15

<210> SEQ ID NO 321
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(9)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 321

Arg Arg Arg Arg Arg Arg Arg Arg Lys Lys His His Xaa Xaa
1               5                   10                  15

<210> SEQ ID NO 322
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 322

Arg Arg Arg Arg Lys Lys Lys Lys Lys Lys Lys Lys His Xaa
1               5                   10                  15

<210> SEQ ID NO 323
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 323

Arg Lys Lys Lys Lys Lys Lys Lys Lys Lys His His His His Xaa
1               5                   10                  15

<210> SEQ ID NO 324
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
```

<220> FEATURE:
<221> NAME/KEY: MISC_FEATURE
<222> LOCATION: (12)..(15)
<223> OTHER INFORMATION: Xaa is Ornithine

<400> SEQUENCE: 324

Arg Lys Lys Lys Lys Lys Lys Lys Lys Lys His Xaa Xaa Xaa Xaa
1               5                   10                  15

<210> SEQ ID NO 325
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 325

Arg Arg Arg Lys Lys Lys Lys Lys Lys Lys Lys Lys His His Xaa
1               5                   10                  15

<210> SEQ ID NO 326
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 326

Arg Arg Arg Lys Lys Lys Lys Lys Lys Lys Lys Lys His Xaa Xaa
1               5                   10                  15

<210> SEQ ID NO 327
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 327

Arg Arg Lys Lys Lys Lys Lys Lys Lys Lys Lys His His His Xaa
1               5                   10                  15

<210> SEQ ID NO 328
<211> LENGTH: 15
<212> TYPE: PRT
<213> ORGANISM: Artificial Sequence
<220> FEATURE:

```
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 328

Arg Arg Lys Lys Lys Lys Lys Lys Lys Lys Lys His Xaa Xaa Xaa
1               5                   10                  15

<210> SEQ ID NO 329
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 329

Arg Lys Lys Lys Lys Lys Lys Lys Lys Lys His His Xaa Xaa Xaa
1               5                   10                  15

<210> SEQ ID NO 330
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 330

Arg Arg Arg Lys Lys Lys Lys Lys Lys Lys Lys Lys His Xaa Xaa
1               5                   10                  15

<210> SEQ ID NO 331
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 331

Arg Arg Lys Lys Lys Lys Lys Lys Lys Lys Lys His His Xaa Xaa
1               5                   10                  15
```

```
<210> SEQ ID NO 332
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 332

Arg Arg Arg Arg Lys His His His His His His His His His Xaa
1               5                   10                  15

<210> SEQ ID NO 333
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(10)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 333

Arg Lys Lys Lys Lys His His His His His His His His His Xaa
1               5                   10                  15

<210> SEQ ID NO 334
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 334

Arg Lys His His His His His His His His His Xaa Xaa Xaa Xaa
1               5                   10                  15

<210> SEQ ID NO 335
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 335
```

Arg Arg Arg Lys Lys His His His His His His His His His Xaa
1               5                   10                  15

<210> SEQ ID NO 336
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 336

Arg Arg Arg Lys His His His His His His His His His Xaa Xaa
1               5                   10                  15

<210> SEQ ID NO 337
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 337

Arg Arg Arg Lys Lys His His His His His His His His His Xaa
1               5                   10                  15

<210> SEQ ID NO 338
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 338

Arg Arg Lys Lys Lys His His His His His His His His His Xaa
1               5                   10                  15

<210> SEQ ID NO 339
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:

```
<221> NAME/KEY: MISC_FEATURE
<222> LOCATION: (13)..(15)
<223> OTHER INFORMATION: Xaa is Ornithine

<400> SEQUENCE: 339

Arg Arg Lys His His His His His His His His Xaa Xaa Xaa
1               5                   10                  15

<210> SEQ ID NO 340
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 340

Arg Lys Lys His His His His His His His His His Xaa Xaa Xaa
1               5                   10                  15

<210> SEQ ID NO 341
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 341

Arg Lys Lys Lys His His His His His His His His His Xaa Xaa
1               5                   10                  15

<210> SEQ ID NO 342
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 342

Arg Arg Lys Lys His His His His His His His His His Xaa Xaa
1               5                   10                  15

<210> SEQ ID NO 343
<211> LENGTH: 15
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (7)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 343

Arg Arg Arg Arg Lys His Xaa Xaa Xaa Xaa Xaa Xaa Xaa Xaa Xaa
1               5                   10                  15

<210> SEQ ID NO 344
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 344

Arg Lys Lys Lys Lys His Xaa Xaa Xaa Xaa Xaa Xaa Xaa Xaa Xaa
1               5                   10                  15

<210> SEQ ID NO 345
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 345

Arg Lys His His His His Xaa Xaa Xaa Xaa Xaa Xaa Xaa Xaa Xaa
1               5                   10                  15

<210> SEQ ID NO 346
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 346

Arg Arg Arg Lys Lys His Xaa Xaa Xaa Xaa Xaa Xaa Xaa Xaa Xaa
1               5                   10                  15

<210> SEQ ID NO 347
```

```
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 347

Arg Arg Arg Lys His His Xaa Xaa Xaa Xaa Xaa Xaa Xaa Xaa Xaa
1               5                   10                  15

<210> SEQ ID NO 348
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 348

Arg Arg Lys Lys Lys His Xaa Xaa Xaa Xaa Xaa Xaa Xaa Xaa Xaa
1               5                   10                  15

<210> SEQ ID NO 349
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 349

Arg Arg Lys His His His Xaa Xaa Xaa Xaa Xaa Xaa Xaa Xaa Xaa
1               5                   10                  15

<210> SEQ ID NO 350
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 350
```

```
Arg Lys Lys His His His Xaa Xaa Xaa Xaa Xaa Xaa Xaa Xaa Xaa
1               5                   10                  15

<210> SEQ ID NO 351
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 351

Arg Lys Lys Lys His His Xaa Xaa Xaa Xaa Xaa Xaa Xaa Xaa Xaa
1               5                   10                  15

<210> SEQ ID NO 352
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(15)
<223> OTHER INFORMATION: Xaa is Ornithine
<220> FEATURE:
<221> NAME/KEY: MISC_FEATURE
<222> LOCATION: (9)..(15)
<223> OTHER INFORMATION: May be present or absent

<400> SEQUENCE: 352

Arg Arg Lys Lys His His Xaa Xaa Xaa Xaa Xaa Xaa Xaa Xaa Xaa
1               5                   10                  15

<210> SEQ ID NO 353
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 353

Arg Arg Arg Arg Arg Arg Arg Arg Lys Lys Lys Lys Lys His Xaa
1               5                   10                  15

<210> SEQ ID NO 354
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: May be present or absent
<220> FEATURE:
<221> NAME/KEY: MISC_FEATURE
```

```
<222> LOCATION: (15)..(15)
<223> OTHER INFORMATION: Xaa is Ornithine

<400> SEQUENCE: 354

Arg Arg Arg Arg Arg Arg Arg Arg Lys His His His His His Xaa
1               5                   10                  15

<210> SEQ ID NO 355
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 355

Arg Arg Arg Arg Arg Arg Arg Arg Lys His Xaa Xaa Xaa Xaa Xaa
1               5                   10                  15

<210> SEQ ID NO 356
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 356

Arg Arg Arg Arg Arg Arg Arg Arg Lys Lys Lys Lys His His Xaa
1               5                   10                  15

<210> SEQ ID NO 357
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 357

Arg Arg Arg Arg Arg Arg Arg Arg Lys Lys His His His His Xaa
1               5                   10                  15

<210> SEQ ID NO 358
<211> LENGTH: 15
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (1)..(8)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 358

Arg Arg Arg Arg Arg Arg Arg Arg Lys Lys His Xaa Xaa Xaa Xaa
1               5                   10                  15

<210> SEQ ID NO 359
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 359

Arg Arg Arg Arg Arg Arg Arg Arg Lys His His Xaa Xaa Xaa Xaa
1               5                   10                  15

<210> SEQ ID NO 360
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 360

Arg Arg Arg Arg Arg Arg Arg Arg Lys His His His His Xaa Xaa
1               5                   10                  15

<210> SEQ ID NO 361
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 361

Arg Arg Arg Arg Arg Arg Arg Arg Lys Lys Lys Lys His Xaa Xaa
1               5                   10                  15

<210> SEQ ID NO 362
<211> LENGTH: 15
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 362

Arg Arg Arg Arg Arg Arg Arg Arg Lys Lys Lys His His His Xaa
1               5                   10                  15

<210> SEQ ID NO 363
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 363

Arg Arg Arg Arg Arg Arg Arg Arg Lys Lys Lys His Xaa Xaa Xaa
1               5                   10                  15

<210> SEQ ID NO 364
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 364

Arg Arg Arg Arg Arg Arg Arg Arg Lys His His His Xaa Xaa Xaa
1               5                   10                  15

<210> SEQ ID NO 365
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(13)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 365

Arg Arg Arg Arg Arg Lys Lys Lys Lys Lys Lys Lys Lys His Xaa
```

```
1               5                   10                  15
```

<210> SEQ ID NO 366
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(9)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 366

```
Arg Lys Lys Lys Lys Lys Lys Lys Lys His His His His His Xaa
1               5                   10                  15
```

<210> SEQ ID NO 367
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(9)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 367

```
Arg Lys Lys Lys Lys Lys Lys Lys Lys His Xaa Xaa Xaa Xaa Xaa
1               5                   10                  15
```

<210> SEQ ID NO 368
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(12)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 368

```
Arg Arg Arg Arg Lys Lys Lys Lys Lys Lys Lys Lys His His Xaa
1               5                   10                  15
```

<210> SEQ ID NO 369
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(10)
<223> OTHER INFORMATION: May be present or absent
<220> FEATURE:
<221> NAME/KEY: MISC_FEATURE
<222> LOCATION: (15)..(15)

```
<223> OTHER INFORMATION: Xaa is Ornithine

<400> SEQUENCE: 369

Arg Arg Lys Lys Lys Lys Lys Lys Lys His His His His Xaa
1               5                   10                  15

<210> SEQ ID NO 370
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(10)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 370

Arg Arg Lys Lys Lys Lys Lys Lys Lys His Xaa Xaa Xaa Xaa
1               5                   10                  15

<210> SEQ ID NO 371
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(9)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 371

Arg Lys Lys Lys Lys Lys Lys Lys His His Xaa Xaa Xaa Xaa
1               5                   10                  15

<210> SEQ ID NO 372
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(9)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 372

Arg Lys Lys Lys Lys Lys Lys Lys His His His His Xaa Xaa
1               5                   10                  15

<210> SEQ ID NO 373
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (5)..(12)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 373

Arg Arg Arg Arg Lys Lys Lys Lys Lys Lys Lys His Xaa Xaa
1               5                   10                  15

<210> SEQ ID NO 374
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(11)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 374

Arg Arg Arg Lys Lys Lys Lys Lys Lys Lys His His His Xaa
1               5                   10                  15

<210> SEQ ID NO 375
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(11)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 375

Arg Arg Arg Lys Lys Lys Lys Lys Lys Lys His Xaa Xaa Xaa
1               5                   10                  15

<210> SEQ ID NO 376
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(9)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 376

Arg Lys Lys Lys Lys Lys Lys Lys Lys His His His Xaa Xaa Xaa
1               5                   10                  15

<210> SEQ ID NO 377
<211> LENGTH: 15
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 377

Arg Arg Arg Arg Arg Lys His His His His His His His His Xaa
1               5                   10                  15

<210> SEQ ID NO 378
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 378

Arg Lys Lys Lys Lys Lys His His His His His His His His Xaa
1               5                   10                  15

<210> SEQ ID NO 379
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(10)
<223> OTHER INFORMATION: May be present or absent
<220> FEATURE:
<221> NAME/KEY: MISC_FEATURE
<222> LOCATION: (11)..(15)
<223> OTHER INFORMATION: Xaa is Ornithine

<400> SEQUENCE: 379

Arg Lys His His His His His His His His Xaa Xaa Xaa Xaa Xaa
1               5                   10                  15

<210> SEQ ID NO 380
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 380

Arg Arg Arg Arg Lys Lys His His His His His His His His Xaa
1               5                   10                  15
```

```
<210> SEQ ID NO 381
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 381

Arg Arg Lys Lys Lys Lys His His His His His His His His Xaa
1               5                   10                  15

<210> SEQ ID NO 382
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 382

Arg Arg Lys His His His His His His His His Xaa Xaa Xaa Xaa
1               5                   10                  15

<210> SEQ ID NO 383
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(11)
<223> OTHER INFORMATION: May be present or absent
<220> FEATURE:
<221> NAME/KEY: MISC_FEATURE
<222> LOCATION: (12)..(15)
<223> OTHER INFORMATION: Xaa is Ornithine

<400> SEQUENCE: 383

Arg Lys Lys His His His His His His His His Xaa Xaa Xaa Xaa
1               5                   10                  15

<210> SEQ ID NO 384
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine
```

```
<400> SEQUENCE: 384

Arg Lys Lys Lys Lys His His His His His His His His Xaa Xaa
1               5                   10                  15

<210> SEQ ID NO 385
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(13)
<223> OTHER INFORMATION: May be present or absent
<220> FEATURE:
<221> NAME/KEY: MISC_FEATURE
<222> LOCATION: (14)..(15)
<223> OTHER INFORMATION: Xaa is Ornithine

<400> SEQUENCE: 385

Arg Arg Arg Arg Lys His His His His His His His His Xaa Xaa
1               5                   10                  15

<210> SEQ ID NO 386
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(14)
<223> OTHER INFORMATION: May be present or absent
<220> FEATURE:
<221> NAME/KEY: MISC_FEATURE
<222> LOCATION: (15)..(15)
<223> OTHER INFORMATION: Xaa is Ornithine

<400> SEQUENCE: 386

Arg Arg Arg Lys Lys Lys His His His His His His His His Xaa
1               5                   10                  15

<210> SEQ ID NO 387
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(12)
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 387

Arg Arg Arg Lys His His His His His His His His Xaa Xaa Xaa
1               5                   10                  15

<210> SEQ ID NO 388
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(12)
```

```
<223> OTHER INFORMATION: May be present or absent
<220> FEATURE:
<221> NAME/KEY: MISC_FEATURE
<222> LOCATION: (13)..(15)
<223> OTHER INFORMATION: Xaa is Ornithine

<400> SEQUENCE: 388

Arg Lys Lys Lys His His His His His His His Xaa Xaa Xaa
1               5                   10                  15

<210> SEQ ID NO 389
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(15)
<223> OTHER INFORMATION: May be present or absent
<220> FEATURE:
<221> NAME/KEY: MISC_FEATURE
<222> LOCATION: (8)..(15)
<223> OTHER INFORMATION: Xaa is Ornithine

<400> SEQUENCE: 389

Arg Arg Arg Arg Arg Lys His Xaa Xaa Xaa Xaa Xaa Xaa Xaa Xaa
1               5                   10                  15

<210> SEQ ID NO 390
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(15)
<223> OTHER INFORMATION: May be present or absent
<220> FEATURE:
<221> NAME/KEY: MISC_FEATURE
<222> LOCATION: (8)..(15)
<223> OTHER INFORMATION: Xaa is Ornithine

<400> SEQUENCE: 390

Arg Lys Lys Lys Lys Lys His Xaa Xaa Xaa Xaa Xaa Xaa Xaa Xaa
1               5                   10                  15

<210> SEQ ID NO 391
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(15)
<223> OTHER INFORMATION: May be present or absent
<220> FEATURE:
<221> NAME/KEY: MISC_FEATURE
<222> LOCATION: (8)..(15)
<223> OTHER INFORMATION: Xaa is Ornithine

<400> SEQUENCE: 391

Arg Lys His His His His His Xaa Xaa Xaa Xaa Xaa Xaa Xaa Xaa
1               5                   10                  15

<210> SEQ ID NO 392
<211> LENGTH: 15
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (8)..(15)
<223> OTHER INFORMATION: May be present or absent
<220> FEATURE:
<221> NAME/KEY: MISC_FEATURE
<222> LOCATION: (8)..(15)
<223> OTHER INFORMATION: Xaa is Ornithine

<400> SEQUENCE: 392

Arg Arg Arg Arg Lys Lys His Xaa Xaa Xaa Xaa Xaa Xaa Xaa Xaa
1               5                   10                  15

<210> SEQ ID NO 393
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(15)
<223> OTHER INFORMATION: May be present or absent
<220> FEATURE:
<221> NAME/KEY: MISC_FEATURE
<222> LOCATION: (8)..(15)
<223> OTHER INFORMATION: Xaa is Ornithine

<400> SEQUENCE: 393

Arg Arg Lys Lys Lys Lys His Xaa Xaa Xaa Xaa Xaa Xaa Xaa Xaa
1               5                   10                  15

<210> SEQ ID NO 394
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(15)
<223> OTHER INFORMATION: May be present or absent
<220> FEATURE:
<221> NAME/KEY: MISC_FEATURE
<222> LOCATION: (8)..(15)
<223> OTHER INFORMATION: Xaa is Ornithine

<400> SEQUENCE: 394

Arg Arg Lys His His His His Xaa Xaa Xaa Xaa Xaa Xaa Xaa Xaa
1               5                   10                  15

<210> SEQ ID NO 395
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(15)
<223> OTHER INFORMATION: May be present or absent
<220> FEATURE:
<221> NAME/KEY: MISC_FEATURE
<222> LOCATION: (8)..(15)
<223> OTHER INFORMATION: Xaa is Ornithine

<400> SEQUENCE: 395

Arg Lys Lys His His His His Xaa Xaa Xaa Xaa Xaa Xaa Xaa Xaa
1               5                   10                  15
```

```
<210> SEQ ID NO 396
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(15)
<223> OTHER INFORMATION: May be present or absent
<220> FEATURE:
<221> NAME/KEY: MISC_FEATURE
<222> LOCATION: (8)..(15)
<223> OTHER INFORMATION: Xaa is Ornithine

<400> SEQUENCE: 396

Arg Lys Lys Lys Lys His His Xaa Xaa Xaa Xaa Xaa Xaa Xaa Xaa
1               5                   10                  15

<210> SEQ ID NO 397
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(15)
<223> OTHER INFORMATION: May be present or absent
<220> FEATURE:
<221> NAME/KEY: MISC_FEATURE
<222> LOCATION: (8)..(15)
<223> OTHER INFORMATION: Xaa is Ornithine

<400> SEQUENCE: 397

Arg Arg Arg Arg Lys His His Xaa Xaa Xaa Xaa Xaa Xaa Xaa Xaa
1               5                   10                  15

<210> SEQ ID NO 398
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(15)
<223> OTHER INFORMATION: May be present or absent
<220> FEATURE:
<221> NAME/KEY: MISC_FEATURE
<222> LOCATION: (8)..(15)
<223> OTHER INFORMATION: Xaa is Ornithine

<400> SEQUENCE: 398

Arg Arg Arg Lys Lys Lys His Xaa Xaa Xaa Xaa Xaa Xaa Xaa Xaa
1               5                   10                  15

<210> SEQ ID NO 399
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(15)
<223> OTHER INFORMATION: May be present or absent
<220> FEATURE:
<221> NAME/KEY: MISC_FEATURE
<222> LOCATION: (8)..(15)
<223> OTHER INFORMATION: Xaa is Ornithine
```

```
<400> SEQUENCE: 399

Arg Arg Arg Lys His His His Xaa Xaa Xaa Xaa Xaa Xaa Xaa Xaa
1               5                   10                  15

<210> SEQ ID NO 400
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(15)
<223> OTHER INFORMATION: May be present or absent
<220> FEATURE:
<221> NAME/KEY: MISC_FEATURE
<222> LOCATION: (8)..(15)
<223> OTHER INFORMATION: Xaa is Ornithine

<400> SEQUENCE: 400

Arg Lys Lys Lys His His His Xaa Xaa Xaa Xaa Xaa Xaa Xaa Xaa
1               5                   10                  15

<210> SEQ ID NO 401
<211> LENGTH: 15
<212> TYPE: PRT
<213> ORGANISM: Artificial Sequence
<220> FEATURE:
<223> OTHER INFORMATION: Synthetic peptide

<400> SEQUENCE: 401

Tyr Tyr Tyr Arg Arg Arg Arg Arg Arg Arg Arg Ser Ser Tyr
1               5                   10                  15
```

UNITED STATES PATENT AND TRADEMARK OFFICE
CERTIFICATE OF CORRECTION

PATENT NO. : 10,111,967 B2
APPLICATION NO. : 13/904868
DATED : October 30, 2018
INVENTOR(S) : Fotin-Mleczek et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 397 days.

Signed and Sealed this
Eighteenth Day of June, 2019

Andrei Iancu
*Director of the United States Patent and Trademark Office*